United States Patent
Sakai et al.

(10) Patent No.: US 10,100,070 B2
(45) Date of Patent: Oct. 16, 2018

(54) BORATE-BASED BASE GENERATOR, AND BASE-REACTIVE COMPOSITION COMPRISING SUCH BASE GENERATOR

(71) Applicant: FUJIFILM Wako Pure Chemical Corporation, Osaka-shi, Osaka (JP)

(72) Inventors: Nobuhiko Sakai, Kawagoe (JP); Kosuke Yanaba, Kawagoe (JP)

(73) Assignee: FUJIFILM Wako Pure Chemical Corporation, Tokyo (JP)

( * ) Notice: Subject to any disclaimer, the term of this patent is extended or adjusted under 35 U.S.C. 154(b) by 0 days.

(21) Appl. No.: 15/114,048

(22) PCT Filed: Jan. 22, 2015

(86) PCT No.: PCT/JP2015/051593
§ 371 (c)(1),
(2) Date: Jul. 25, 2016

(87) PCT Pub. No.: WO2015/111640
PCT Pub. Date: Jul. 30, 2015

(65) Prior Publication Data
US 2016/0340374 A1    Nov. 24, 2016

(30) Foreign Application Priority Data

Jan. 24, 2014  (JP) ................. 2014-011774

(51) Int. Cl.

| | | |
|---|---|---|
| *G03F 7/004* | (2006.01) | |
| *C07C 279/02* | (2006.01) | |
| *C07C 279/04* | (2006.01) | |
| *C07C 279/16* | (2006.01) | |
| *C07C 279/18* | (2006.01) | |
| *C07F 5/02* | (2006.01) | |
| *C07F 9/22* | (2006.01) | |
| *C07C 229/26* | (2006.01) | |
| *C07F 9/53* | (2006.01) | |
| *C07F 9/572* | (2006.01) | |
| *C07F 9/6584* | (2006.01) | |
| *C07F 9/06* | (2006.01) | |
| *C07C 279/26* | (2006.01) | |
| *C07D 233/50* | (2006.01) | |
| *C07D 487/04* | (2006.01) | |

(52) U.S. Cl.
CPC .............. *C07F 9/22* (2013.01); *C07C 229/26* (2013.01); *C07C 279/02* (2013.01); *C07C 279/04* (2013.01); *C07C 279/16* (2013.01); *C07C 279/18* (2013.01); *C07C 279/26* (2013.01); *C07D 233/50* (2013.01); *C07D 487/04* (2013.01); *C07F 5/027* (2013.01); *C07F 9/065* (2013.01); *C07F 9/5337* (2013.01); *C07F 9/5721* (2013.01); *C07F 9/6584* (2013.01); *C07F 9/65848* (2013.01); *G03F 7/0045* (2013.01); *C07C 2601/14* (2017.05)

(58) Field of Classification Search
CPC ... G03F 7/0382; C07C 279/02; C07C 279/04; C07C 279/16; C07C 279/18; C07F 5/027
USPC .............. 430/270.1, 919, 920, 280.1; 564/8; 568/1, 6
See application file for complete search history.

(56) References Cited

U.S. PATENT DOCUMENTS

| | | | |
|---|---|---|---|
| 2,768,205 | A | 10/1956 | Hechenbleikner et al. |
| 3,261,809 | A | 7/1966 | Sherr |
| 2013/0164656 | A1 | 6/2013 | Lee et al. |
| 2014/0329926 | A1 | 11/2014 | Kirino |
| 2016/0122292 | A1 | 5/2016 | Sakai et al. |

FOREIGN PATENT DOCUMENTS

| | | |
|---|---|---|
| EP | 2792694 | 10/2014 |
| JP | 09278738 | 10/1997 |
| JP | 09292712 | 11/1997 |
| JP | 2010138234 | 6/2010 |
| JP | 2011236416 | 11/2011 |
| JP | 2012131936 | 7/2012 |
| JP | 2012250969 | 12/2012 |
| JP | 2013137489 | 7/2013 |
| WO | 2010095390 | 8/2010 |
| WO | 2012142126 | 10/2012 |
| WO | 2013089100 | 6/2013 |

OTHER PUBLICATIONS

Robertson, KatherineN.; Knop, Osvald; Cameron, T. Stanley, C—H Organoammonium tatraphenylborates; Another Look At Dihydrogen Bonds, Canadian Journal of Chemistry (2003), 81(6), 727-743. (Abstract).*

Scherer, Alexander; Mukerherjee, Tathagata; Hampel, Frank; Gladysz, John., Metal-Templated Hydrogen Bond Donors as "Organocatalysts" for Carbon-Carbon Bond Forming Reactions: Syntheses, Structures, and Reaactivities of 2-Guanidinobenzimidazole Cyclopentadienyl Ruthemium Complexes Organometallics (2014), 33(23), 6709-6722. (Abstract).*

Ken-Ichi Ito, et al., "Thermal Crosslinking of Poly(glycidyl methacrylate) Films and Epoxy Resin Films Using Amines Formed by Photolysis of O-acyloximes," Journal of Polymer Science: Part A: Polymer Chemistry, 1994, vol. 32, p. 1793-1796.

(Continued)

*Primary Examiner* — John S Chu
(74) *Attorney, Agent, or Firm* — Hamre, Schumann, Mueller & Larson, P.C.

(57) ABSTRACT

A compound capable of providing a composition having high storage stability without reacting with a base-reactive compound, even when stored in a mixed state with the base-reactive compound, as well as capable of generating a strong base by irradiation of light (active energy rays) or heating. A base generator comprises the compound and a base-reactive composition comprises the base generator and the base-reactive compound. The compound is represented by the general formula (A).

10 Claims, No Drawings

(56) References Cited

OTHER PUBLICATIONS

S. Hassoon, et al., "Photochemistry of (Benzophenonylmethyl)-tri-n-butylammonium Triphenylbutylborate: Inter- and Intra-Ion-Pair Electron Transfer Photoreduction," J. Am. Chem. Soc., 1995, vol. 117, p. 11369-11370.

Roman Popielarz, et al., "Applicability of Tetraphenylborate Salts as Free Radical Initiators," Macromolecules, 1998, vol. 31, No. 4, p. 951-954.

Shengkui Hu, et a;., "Reactivities of Chromophore-Containing Methyl Tri-n-butylammonium Organoborate Salts as Free Radical Photoinitiators: Dependence on the Chromophore and Borate Counterion," Macromolecules, 1998, vol. 31, No. 19, p. 6476-6480.

Oleg Grinevich, "Relative Activity of Possible Initiating Species Produced from Photolysis of Tetraphenyl and Triphenylbutyl Borates As Measured by Fluorescence Probe Techniques," Macromolecules, 1999, vol. 32, No. 2, p. 328-330.

Xun Sun, et al., "Bicyclic Guanidinium Tetraphenylborate: A Photobase Generator and A Photocatalyst for Living Anionic Ring-Opening Polymerization and Cross-Linking of Polymeric Materials Containing Ester and Hydroxy Groups," J. Am. Chem. Soc., 2008, vol. 130, p. 8130-8131.

Yuji Shibasaki, et al., "Synthesis of Photobase Generators Based on Proazaphosphatrane—Tetraarylborate Complex for i-Line Photopatterning," Journal of Photopolymer Science and Technology, 2012, vol. 25, No. 4, p. 497-499.

Georges Gelbard, et al., "Polynitrogen Strong Bases: 1—New Syntheses of Biguanides and their Catalytic Properties in Transesterification Reactions," Tetrahedron Letters, 1998, vol. 39, p. 2743-2746.

Johannes C. Jochims, et al., "Amino-substituted 2-Azaallenium Salts," Chem. Ber., 1984, vol. 117, p. 1900-1912.

Reinhard Schwesinger, et al., "Extremely Base-Resistant Organic Phosphazenium Cations," Chem. Eur. J., 2006, vol. 12, p. 429-437.

Alfred Schmidpeter, et al., "Zur Ammonolyse von Chlorphosphoranen," Z. Naturforschg, 1969, vol. 24 b, p. 799-810.

International Search Report for PCT/JP2015/051593, dated Apr. 21, 2015, 5 pages including English translation.

Schmidpeter, Alfred, et al. On the ammonolysis of chlorophosphoranes. Zeitschrift fur Naturforschung [journal for natural sciences]. vol. 24 b, 1969, 21 pages.

\* cited by examiner

BORATE-BASED BASE GENERATOR, AND BASE-REACTIVE COMPOSITION COMPRISING SUCH BASE GENERATOR

TECHNICAL FIELD

The present invention relates to a base generator and the like to be used in a resist field and the like, and more particularly relates to a borate-based compound having a property to generate a strong base, such as guanidines, biguanides, phosphazenes and phosphoniums, a base generator comprising these, and a base-reactive composition comprising the base generator.

BACKGROUND ART

A polymer (resin) has been used, for example, in molding materials, layer forming materials or adhesives of electronics parts, optical products, optical parts, and the like. The polymer (resin) is formed by a polymerization reaction of forming a polymer chain by bonding polymer precursors (monomers) or by a cross-linking reaction of linking polymer chains, by using a polymerization initiator, and physical and chemical properties thereof are different from those of the polymer precursors (monomers) in many cases.

To form a structure, where molecules are linked two-dimensionally or three-dimensionally by this polymerization reaction or cross-linking reaction is named curing, and there has been known curing by a polymerization initiator which is sensitive to light (active energy rays) such as infrared rays, visible rays, UV rays and X-rays (hereafter it may be abbreviated as photo-curing), curing by a polymerization initiator which is sensitive to heat (hereafter it may be abbreviated as thermal-curing), and the like.

The polymerization initiators to be used in curing are classified largely into three groups; a radical generator, an acid generator and a base generator, depending on active species generated. The radical generator is a polymerization initiator generating radical species by irradiation of light (active energy rays) or by heating, which has conventionally been used widely, however, it has the drawbacks that the radical species are inactivated by oxygen in air, and then the polymerization reaction is inhibited and suppressed. Accordingly, in using the radical generator, special devise is needed, such as interception of oxygen in air. The acid generator is a polymerization initiator generating an acid by irradiation of light (active energy rays) or by heating, and does not receive inhibition by oxygen, therefore a wide variety of acid generators have been provided practically since the latter half of 1990's. However, there may be the case where the acid generated may remain inside a system even after curing, and thus there has been pointed out a problem such as decreasing film performance caused by denaturation of a cured film by influence of the remaining acid after curing a curing composition containing the acid generator, or a problem of corrosion by the acid to a metal wiring on a semiconductor substrate. On the other hand, the base generator is a generator which generates a base by irradiation of light (active energy rays) or by heating, and does not receive inhibition by oxygen in air, and the problem of corrosion or denaturation of a cured film in the case of using an acid generator is hardly occurred, and thus research and development thereof have been carried out actively in recent years.

Recently, the technology of applying a photosensitive composition containing a photo-base generator to a photo-resist material, a photo-curing material, and the like, has been investigated. For example, there has been proposed a method for generating amines within an epoxy resin by irradiation of light (active energy rays), and then curing the epoxy resin by heating treatment, by utilization of the fact that, for example, a compound having an epoxy group is cured by generation of a cross-linking reaction by an action of a base (for example, NON PATENT LITERATURE 1).

In the case of curing an epoxy-based compound by amines generated from a base generator, a weak base, such as a primary amine and a secondary amine, requires a long period of time in reaction with an epoxy group, and thus it has required heating treatment at high temperature and the like to increase curing speed. In addition, although it is possible to increase curing speed by increasing cross-linking density using a multi-functionalized primary amine or secondary amine, it is necessary for all amines to be made latescent (protection) by carrying out salt formation to all amines, and it could have been to decrease solubility significantly. In this way, in the case where a base generated from a base generator is a weak base, there was a problem that curing of an epoxy-based compound cannot be carried out simply, conveniently and efficiently.

On the contrary, it has been reported that in the case of a base generator which generates strongly basic amines, such as a tertiary amine, an amidine, a guanidine and a phosphazene, these amines are easy to function as catalysts, therefore it is capable of curing an epoxy-based compound even in relatively small amount, and particularly in the case where a cross-linking agent having an acidic proton (for example, a multifunctional carboxylic acid, a multifunctional phenol, a multifunctional thiol, a multifunctional β-keto-ester, and the like) is used in combination, the epoxy-based compound can be cured rapidly under low temperature condition.

As the base generator of such amines, there have conventionally been known a photo-base generator, such as an amineimide-based compound which generates a tertiary amine, an amidine [such as 1,5-diazabicyclo[4.3.0]-5-nonene (DBN), 1,8-diazabicyclo[5.4.0]-7-undecene (DBU)], imidazole, pyridine, and the like, by irradiation of light (active energy rays) (for example, PATENT LITERATURE 1); and an ammonium borate-based compound (for example, PATENT LITERATURE 2, NON-PATENT LITERATURE 2, NON-PATENT LITERATURE 3, NON-PATENT LITERATURE 4, NON-PATENT LITERATURE 5). In addition, there have also been known examples of a compound composed of a carboxylic acid which is decarboxylated by irradiation of light (active energy rays) and amines (for example, PATENT LITERATURE 3); a benzoic acid-based compound which is circularly esterified by irradiation of light (active energy rays) (for example, PATENT LITERATURE 4); a tetraphenylborate-based compound which generates a strong base, such as guanidine, for example, 1,1,3,3-tetramethylguanidine (TMG), 1,5,7-triazabicyclo[4.4.0]deca-5-ene (TBD), 7-methyl-1,5,7-triazabicyclo[4.4.0]deca-5-ene (MTBD), and the like, and phosphazene, by irradiation of light (active energy rays) (for example, NON-PATENT LITERATURE 6); a tetraarylborate-based compound which generates a proazaphosphatrane which is a strong base, such as 2,8,9-triisopropyl-2,5,8,9-tetraaza-1-phosphabicyclo[3.3.3]undecane, by irradiation of light (active energy rays) (for example, NON-PATENT LITERATURE 7). Still more, there has also been known a compound which generates biguanides, as an organic strong base having higher basicity than amidines or guanidines (for example, PATENT LITERATURE 5, NON-PATENT LITERATURE 8, NON-PATENT LITERATURE 9), and there has also been reported an example of using a compound which generates such biguanides for curing an epoxy (for example, PATENT LITERATURE 6). In addition, there has also been known an example of applying a compound which is obtained by forming a salt by a pyrolytic compound together with biguanides, as a thermal-curing catalyst (for example, PATENT LITERATURE 7, PATENT LITERATURE 8).

However, although the base generators are capable of generating strong bases, they are generally solids in many cases, and most of them had a problem of having insufficient solubility to an organic solvent. In addition, in the case of a base generator composed of, for example, a carboxylic acid and amines, there are some oil-like compounds not having the problem of solubility in an organic solvent, depending on a combination thereof, however, such a base generator generally has a problem that heat resistance is inferior.

Under such a circumstance, the present inventors have reported a base generator composed of a carboxylic acid having a specific structure and biguanides as a base generator which is capable of generating strong bases (biguanides), having high solubility in various organic solvents and base-reactive compounds, and having high heat resistance (PATENT LITERATURE 9).

CITATION LIST

Patent Literature

PATENT LITERATURE

[PATENT LITERATURE 1] JP-A-2012-131936
[PATENT LITERATURE 2] WO2010-095390
[PATENT LITERATURE 3] JP-A-2011-236416
[PATENT LITERATURE 4] JP-A-2012-250969
[PATENT LITERATURE 5] U.S. Pat. No. 2,768,205
[PATENT LITERATURE 6] U.S. Pat. No. 3,261,809
[PATENT LITERATURE 7] JP A 9 278378 JP-A-9-278738
[PATENT LITERATURE 8] JP-A-9-292712
[PATENT LITERATURE 9] JP-A-2013-137489

Non Patent Literature

[NON PATENT LITERATURE 1] J. Polym. Sci., Part A: Polym. Chem., 32, 1793 (1994)
[NON PATENT LITERATURE 2] J. Am. Chem. Soc., 117, 11369-11370 (1995)
[NON PATENT LITERATURE 3] Macromolecules, 31, 951-954 (1998)
[NON PATENT LITERATURE 4] Macromolecules, 31, 6476-6480 (1998)
[NON PATENT LITERATURE 5] Macromolecules, 32, 328-330 (1999)
[NON PATENT LITERATURE 6] J. Am. Chem. Soc., 130, 8130 (2008)
[NON PATENT LITERATURE 7] J. Photopolym. Sci. Tech., 25, 497-499 (2012)
[NON PATENT LITERATURE 8] Tetrahedron Lett., 39, 2743 (1998)
[NON PATENT LITERATURE 9] Chem. Ber., 117, 1900-1912 (1984)

SUMMARY OF INVENTION

Technical Problem

However, because an anion part of a base generator described in PATENT LITERATURE 9 is a carboxylic acid, due to nucleophilicity of the carboxylic acid, when the base generator is stored in a mixed state with a base-reactive compound, such as an epoxy-based compound, there was the case where the carboxylic acid part of the base generator reacted with the base-reactive compound. Accordingly, a base-reactive composition, which is obtained by mixing the base generator and a base-reactive compound such as an epoxy-based compound in advance, has a problem that stable storage thereof for a long period of time is difficult, due to start of curing during storage. In addition, in the case where the base generator and the base-reactive compound were stored separately to prevent curing during this storage, both components should be combined just before curing operation and be used quickly, which poses a problem of inferior convenience. Under such a circumstance, development of such a base generator has been desired that is capable of providing a composition having high storage stability without decreasing performance thereof, even in storage for a long period of time in a mixed state of a base generator and a base-reactive compound.

The present invention has been made in view of the circumstances, and an object of the present invention is to provide a compound which generates a strong base (guanidines, biguanides, phosphazenes or phosphoniums) by operation of irradiation of light (active energy rays), heating, and the like, as well as which has high storage stability without reacting with a base-reactive compound, even in the case of storage for a long period of time in a mixed state with a base-reactive compound such as an epoxy-based compound; a base generator comprising the compound; and a base-reactive composition comprising the base generator and a base-reactive compound.

Solution to Problem

The present invention is composed of the following constitutions:

(1) A compound represented by the general formula (A) (hereafter, it may be abbreviated as the compound of the present invention).

(A)

(wherein $R^1$ represents an alkyl group having 1 to 12 carbon atoms; an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms; an alkenyl group having 2 to 12 carbon atoms; a 2-furylethynyl group; a 2-thiophenylethynyl group; or a 2,6-dithianyl group; $R^2$ to $R^4$ each independently represent an alkyl group having 1 to 12 carbon atoms; an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms; an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms; a furanyl group; a thienyl group; or an N-alkyl-substituted pyrrolyl group; and $Z^+$ represents an ammonium cation having a guanidinium group, a biguanidium group or a phosphazenium group, or a phosphonium cation.)

(2) A base generator comprising the compound represented by the general formula (A) (hereafter, it may be abbreviated as the base generator of the present invention).

(3) A base-reactive composition comprising the base generator comprising the compound represented by the general formula (A), and a base-reactive compound (hereafter, it may be abbreviated as the base-reactive composition of the present invention).

Advantageous Effects of Invention

The compound of the present invention is a compound by formation of a salt between a borate-based anion having a specific structure and a cation having strong basicity, such as guanidines, biguanides, phosphazenes, phosphoniums, and it is capable of generating a strong base by operation of irradiation of light (active energy rays), heating, and the like. Because of low nucleophilicity of the borate part of the anion, these compounds react poorly with a base-reactive compound, such as an epoxy-based compound. Accordingly, the base generator comprising the compound of the present invention exerts such effect as having high storage stability without reacting with a base-reactive compound, even in the case of storage for a long period of time in a mixed state with a base-reactive compound, such as an epoxy-based compound.

The base-reactive composition of the present invention exerts such effect as being capable of storage in a stable state without decreasing performance as the base-reactive composition, even in storage for a long period of time, as well as, in carrying out curing operation, capable of effectively advancing curing of the base-reactive compound in the composition, using the strong base (guanidines, biguanides, phosphazenes or phosphoniums) generated from the base generator, as an initiator.

DESCRIPTION OF EMBODIMENTS

In the present invention, active energy rays include, excluding the case when a wavelength is specified, not only an electromagnetic wave having a wavelength of a visible region (visible rays), but also, for example, an electromagnetic wave having a wavelength of an ultraviolet region (UV rays), an electromagnetic wave having a wavelength of an infrared region (infrared rays), and an electromagnetic wave having a wavelength of a non-visible ray region such as X-rays. In the present invention, a base generator sensitive to active energy rays (a base generator generating a base by irradiation of active energy rays) may be abbreviated as a photo-base generator. In addition, active energy rays having a wavelength of 365 nm, 405 nm and 436 nm may be described as i-rays, h-rays, and g-rays, respectively.

The Compound of the Present Invention

The compound of the present invention is a compound represented by the following general formula (A).

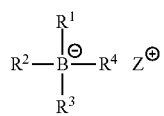

(A)

(wherein $R^1$ represents an alkyl group having 1 to 12 carbon atoms; an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms; an alkenyl group having 2 to 12 carbon atoms; a 2-furylethynyl group; a 2-thiophenylethynyl group; or a 2,6-dithianyl group; $R^2$ to $R^4$ each independently represent an alkyl group having 1 to 12 carbon atoms; an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms; an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms; a furanyl group; a thienyl group; or an N-alkyl-substituted pyrrolyl group; and $Z^+$ represents an ammonium cation having a guanidinium group, a biguanidium group or a phosphazenium group, or a phosphonium cation.)

The alkyl group having 1 to 12 carbon atoms represented by $R^1$ in the general formula (A), may be any of a straight chained, a branched, or a cyclicone, and among these, the straight chained one is preferable. In addition, among the alkyl group having 1 to 12 carbon atoms, an alkyl group having 1 to 8 carbon atoms is preferable, an alkyl group having 1 to 6 carbon atoms is more preferable, and an alkyl group having 1 to 4 carbon atoms is still more preferable. A specific example of the alkyl group includes, for example, a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, a norbornyl group (a norbornane-x-yl group), a bornyl group (a bornane-x-yl group), a menthyl group (a mentha-x-yl group), an adamantyl group, a decahydronaphthyl group, and the like. Among these alkyl groups, an alkyl group having 1 to 8 carbon atoms is preferable, among these, an alkyl group having 1 to 6 carbon atoms is more preferable, among these, an alkyl group having 1 to 4 carbon atoms is still more preferable, among these, a straight chained alkyl group having 1 to 4 carbon atoms is particularly preferable, and among these, an n-butyl group is most preferable.

The alkyl group having 1 to 12 carbon atoms represented by $R^2$ to $R^4$ in the general formula (A), may be any of a straight chained, a branched, or a cyclic one, and among these, the straight chained one is preferable. In addition, among the alkyl groups having 1 to 12 carbon atoms, an alkyl group having 4 to 12 carbon atoms is preferable, an alkyl group having 4 to 8 carbon atoms is more preferable, and an alkyl group having 4 to 6 carbon atoms is still more preferable. A specific example of the alkyl group includes the same as the specific example of the alkyl group having 1 to 12 carbon atoms represented by $R^2$ to $R^4$ in the general formula (A). Among such alkyl groups, an alkyl group having 4 to 12 carbon atoms is preferable, among these, an alkyl group having 4 to 8 carbon atoms is more preferable, among these, an alkyl group having 4 to 6 carbon atoms is still more preferable, and among these, a straight chained alkyl group having 4 to 6 carbon atoms is particularly preferable, and among these, an n-butyl group is most preferable.

The arylalkynyl group having 8 to 16 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), is a group where an aryl group moiety may be any of a monocyclic or a condensed polycyclic group, and among these, the monocyclic group is preferable. In addition, the alkynyl group moiety may be any of a straight chained or a branched one, and among these, the straight chained one is preferable. A specific example of the arylalkynyl group includes, for example, a phenylethynyl group, a 3-phenyl-1-propyne-1-yl group, a 3-phenyl-2-propyne-1-yl group (a 3-phenylpropargyl group), a 4-phenyl-1-butyne-1-yl group, a 4-phenyl-2-butyne-1-yl group, a 4-phenyl-3-butyne-1-yl group, a 3-phenyl-1-butyne-1-yl group, a 4-phenyl-3-butyne-2-yl group, a 5-phenyl-1-pentyne-1-yl group, a 5-phenyl-2-pentyne-1-yl group, a 5-phenyl-3-pentyne-1-yl group, a 5-phenyl-4-pentyne-1-yl group, a 4-phenyl-1-pentyne-1-yl group, a 4-phenyl-2-pentyne-1-yl group, a 3-phenyl-1-pentyne-1-yl group, a 5-phenyl-3-pentyne-2-yl group, a 5-phenyl-4-pentyne-2-yl group, a 5-phenyl-4-pentyne-3-yl group, a 4-phenyl-3-methyl-1-butyne-1-yl group, a 4-phenyl-2-methyl-3-butyne-1-yl group, a 3-phenyl-3-methyl-1-butyne-1-yl group, a 6-phenyl-1-hexyne-1-yl group, a 6-phenyl-2-hexyne-1-yl group, a 6-phenyl-3-hexyne-1-yl group, a 6-phenyl-4-hexyne-1-yl group, a 6-phenyl-5-hexyne-1-yl group, a 5-phenyl-1-hexyne-1-yl group, a 5-phenyl-2-hexyne-1-yl group, a 5-phenyl-3-hexyne-1-yl group, a 5-phenyl-4-hexyne-1-yl group, a 5-phenyl-3-hexyne-2-yl group, a 3-phenyl-1-hexyne-1-yl group, a 3-phenyl-2-hexyne-1-yl group, a 6-phenyl-3-hexyne-2-yl group, a 6-phenyl-4-hexyne-2-yl group, a 6-phenyl-4-hexyne-3-yl group, a 6-phenyl-5-hexyne-2-yl group, a 6-phenyl-5-hexyne-3-yl group, a 6-phenyl-5-hexyne-4-yl group, a 5-phenyl-3-hexyne-2-yl group, a 4-phenyl-4-methyl-1-pentyne-1-yl group, a 4-phenyl-3-methyl-1-pentyne-1-yl group, a 4-phenyl-4-methyl-2-pentyne-1-yl group, a 3-phenyl-3-methyl-2-pentyne-1-yl group, a 4-phenyl-3-methyl-1-pentyne-1-yl group, a 1-naphthylethynyl group, a 2-naphthylethynyl group, a 3-(1-naphthyl)-1-propyne-1-yl group, a 3-(2-naphthyl)-1-propyne-1-yl group, a 4-(1-naphthyl)-1-butyne-1-yl group, a 4-(2-naphthyl)-1-butyne-1-yl group, a 5-(1-naphthyl)-1-pentyne-1-yl group, a 5-(2-naphthyl)-1-pentyne-1-yl group, a 6-(1-naphthyl)-1-hexyne-1-yl group, a 6-(2-naphthyl)-1-hexyne-1-yl group, a 9-anthracenylethynyl group, and the like. Among such arylalkynyl groups, a phenylalkynyl group having 8 to 12 carbon atoms is more preferable, and among these, a phenylalkynyl group having 8 to 12 carbon atoms, in which the alkynyl group moiety is a straight chained one, and a phenyl group is bonded at the terminal thereof, for example, a phenylethynyl group, a 3-phenyl-1-propyne-1-yl group, a 3-phenyl-2-propyne-1-yl group (a 3-phenylpropargyl group), a 4-phenyl-1-butyne-1-yl group, a 4-phenyl-2-butyne-1-yl group, a 4-phenyl-3-butyne-1-yl group, a 5-phenyl-1-pentyne-1-yl group, a 5-phenyl-2-pentyne-1-yl group, a 5-phenyl-3-pentyne-1-yl group, a 5-phenyl-4-pentyne-1-yl group, a 6-phenyl-1-hexyne-1-yl group, a 6-phenyl-2-hexyne-1-yl group, a 6-phenyl-3-hexyne-1-yl group, a 6-phenyl-4-hexyne-1-yl group, a 6-phenyl-5-hexyne-1-yl group, and the like, is more preferable, and among these, a phenylethynyl group is still more preferable. It should be noted that number of carbon atoms in the arylalkynyl group shown here means number of carbon atoms constituting the arylalkynyl group, and number of carbon atoms constituting a substituent should not be included in number of carbon atoms shown as "8 to 16 carbon atoms" in the arylalkynyl group having 8 to 16 carbon atoms.

The halogen atom in "an arylalkynyl group having 8 to 16 carbon atoms, which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in general formula (A), specifically includes, for example, a fluorine atom, a chlorine atom, a bromine atom, an iodine atom, and the like.

The alkyl group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), may be any of a straight chained, a branched, or a cyclic one, and among these, the straight chained one is preferable. In addition, among the alkyl groups having 1 to 6 carbon atoms, an alkyl group having 1 to 4 carbon atoms is preferable, and an alkyl group having 1 to 2 carbon atoms is more preferable. A specific example of the alkyl group includes, for example, a methyl group, an ethyl group, a n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, and the like. Among these alkyl groups, an alkyl group having 1 to 4 carbon atoms is preferable, among these, an alkyl group having 1 to 2 carbon atoms is more preferable, and among these, a methyl group is still more preferable.

The alkoxy group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), may be any of a straight chained, a branched, or a cyclic one, among these, the straight chained one is preferable. In addition, among the alkoxy groups having 1 to 6 carbon atoms, an alkoxy group having 1 to 4 carbon atoms is preferable, and an alkoxy group having 1 to 2 carbon atoms is more preferable. A specific example of the alkoxy group includes, for example, a methoxy group, an ethoxy group, an n-propoxy group, an isopropoxy group, an n-butoxy group, an isobutoxy group, a sec-butoxy group, a tert-butoxy group, a cyclobutoxy group, an n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, an n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, and the like. Among these alkoxy groups, an alkoxy group having 1 to 4 carbon atoms is preferable, among these, an alkoxy group having 1 to 2 carbon atoms is more preferable, and among these, a methoxy group is still more preferable.

The alkylthio group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), may be any of a straight chained, a branched, or a cyclic one, and among these, the straight chained one is preferable. In addition, among the alkylthio groups having 1 to 6 carbon atoms, an alkylthio group having 1 to 4 carbon atoms is preferable, an alkylthio group having 1 to 2 carbon atoms is more preferable. A specific example of the alkylthio group includes, for example, a methylthio group, an ethylthio group, an n-propylthio group, an isopropylthio group, an n-butylthio group, an isobutylthio group, a sec-butylthio group, a tert-butylthio group, a cyclobutylthio group, an n-pentylthio group, an isopentylthio group, a sec-pentylthio group, a tert-pentylthio group, a neopentylthio group, a 2-methylbutylthio group, a 1,2-dimethylpropylthio group, a 1-ethylpropylthio group, a cyclopentylthio group, an n-hexylthio group, an isohexylthio group, a sec-hexylthio group, a tert-hexylthio group, a neohexylthio group, a 2-methylpentylthio group, a 1,2-dimethylbutylthio group, a 2,3-dimethylbutylthio group, a 1-ethylbutylthio group, a cyclohexylthio group, and the like. Among these alkylthio groups, an alkylthio group having 1 to 4 carbon atoms is preferable, among these, an alkylthio group having 1 to 2 carbon atoms is more preferable, and among these, a methylthio group is still more preferable.

The substituent (a halogen atom, an alkyl group having 1 to 6 carbon atoms, an alkoxy group having 1 to 6 carbon atoms, or an alkylthio group having 1 to 6 carbon atoms) substituting the arylalkynyl group having 8 to 16 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), substitutes only an aryl group moiety on the arylalkynyl group.

Number of substituents, on the arylalkynyl group having 8 to 16 carbon atoms, includes an integer of 0 (non-substitution) to 9, and 0 (non-substitution) to 5 is preferable, 1 to 3 is more preferable, and 1 is still more preferable.

A binding site of a substituent on the arylalkynyl group having 8 to 16 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), is different depending on whether the arylalkynyl group is a phenylalkynyl group, a naphthylalkynyl group or an anthracenylalkynyl group, and a specific example of a preferable arylalkynyl group is also different.

In the case where the arylalkynyl group having 8 to 16 carbon atoms is a phenylalkynyl group, in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), the binding site of a substituent may be any of ortho position, meta position or para position, and among these, ortho position or para position is more preferable, and among these, para position is still more preferable.

In the case where the arylalkynyl group having 8 to 16 carbon atoms is a naphthylalkynyl group, in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), a binding site of the alkynyl group may be any of the first or the second binding site.

The binding site of a substituent on the naphthylalkynyl group may be any of the first to the eighth binding sites, and among these, the first to the fourth binding sites are preferable.

In the case where the arylalkynyl group having 8 to 16 carbon atoms is an anthracenylalkynyl group, in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), a binding site of the alkynyl group may be any of the first, the second or the ninth binding site, and among these, the ninth binding site is preferable.

In the case where the binding site of the alkynyl group on the anthracenylalkynyl group is the first or the second binding site, the binding site of a substituent on the anthracenylalkynyl group may be any of the first to the tenth binding sites, and among these, the first to the fourth binding sites are preferable.

In the case where the binding site of the alkynyl group on the anthracenylalkynyl group is the ninth binding site, the binding site of a substituent on the anthracenylalkynyl group may be any of the first to the eighth or the tenth binding site, and among these, the tenth binding site is preferable.

The alkenyl group having 2 to 12 carbon atoms represented by $R^1$ in the general formula (A) may be any of a straight chained, a branched, or a cyclic one, and among these, the straight chained one is preferable. In addition, among the alkenyl group having 2 to 12 carbon atoms, an alkenyl group having 2 to 6 carbon atoms is preferable, and an alkenyl group having 2 to 3 carbon atoms is more preferable. A specific example of the alkenyl group includes, for example, a vinyl group, a 1-propenyl group, a 2-propenyl group (an allyl group), an isopropenyl group, a 1-butenyl group, a 2-butenyl group, a 3-butenyl group, an isobutenyl group, a methallyl group (a 2-methylallyl group), a prenyl group (a dimethylallyl group), an isopentenyl group, a cyclopentenyl group, an n-hexenyl group, a cyclohexenyl group, an n-heptenyl group, an n-octenyl group, an n-nonenyl group, an n-decenyl group, an n-undecenyl group, an n-dodecenyl group, and the like, among these, an alkenyl group having 2 to 6 carbon atoms is preferable, and among these, an alkenyl group having 2 to 3 carbon atoms is more preferable.

The aryl group having 6 to 14 carbon atoms in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), specifically includes, for example, a phenyl group, a naphthyl group, an anthracenyl group, and the like, and among these, a phenyl group is preferable. It should be noted that number of carbon atoms in the aryl group shown here means number of carbon atoms constituting the aryl group, and number of carbon atoms constituting a substituent should not be included in number of carbon atoms shown by "6 to 14 carbon atoms" in the aryl group having 6 to 14 carbon atoms.

A specific example of the halogen atom in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), includes the same as the specific example of the halogen atom in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A).

A specific example of the alkyl group having 1 to 6 carbon atoms in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), includes the same as the specific example of the alkyl group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), and a specific example of a preferable alkyl group also includes the same.

A specific example of the alkoxy group having 1 to 6 carbon atoms in "an aryl group having 6 to 14 carbon atoms, which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), includes the same as the specific example of the alkoxy group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), and a specific example of a preferable alkoxy group also includes the same.

A specific example of the alkylthio group having 1 to 6 carbon atoms in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), includes the same as the specific example of the alkylthio group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), and a specific example of a preferable alkylthio group also includes the same.

Number of substituents on the aryl group having 6 to 14 carbon atoms in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), includes an integer of 0 (non-substitution) to 9, 0 (non-substitution) to 5 is preferable, 1 to 3 is more preferable, 0 (non-substitution) to 1 is still more preferable, and 0 (non-substitution) is particularly preferable.

A binding site of a substituent on the aryl group having 6 to 14 carbon atoms in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), is different depending on whether the aryl group is a phenyl group, a naphthyl group or an anthracenyl group, and a specific example of a preferable aryl group is also different.

In the case where the aryl group having 6 to 14 carbon atoms is a phenyl group, in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), the binding site of a substituent may be any of ortho position, meta position or para position, and among these, ortho position or para position is more preferable, and among these, para position is still more preferable.

In the case where the aryl group having 6 to 14 carbon atoms is a naphthyl group, in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), a binding site of the atomic bonding may be any of the first or the second binding site.

The binding site of a substituent on the naphthyl group may be any of the first to the eighth binding sites, and among these, the first to the fourth binding sites are preferable.

In the case where the aryl group having 6 to 14 carbon atoms is a anthracenyl group, in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^2$ to $R^4$ in the general formula (A), a binding site of the atomic bonding may be any of the first, the second or the ninth binding site, and among these, the ninth binding site is preferable.

In the case where a binding site of the atomic bonding on the anthracenyl group is the first or the second binding site, the binding site of a substituent on the anthracenyl group may be any of the first to the tenth binding sites, and among these, the first to the fourth binding sites are preferable.

In the case where a binding site of the atomic bonding on the anthracenyl group is the ninth binding site, the binding site of a substituent on the anthracenyl group may be any of the first to the eighth binding sites or the tenth binding site, and among these, the tenth binding site is preferable.

The N-alkyl substituted pyrrolyl group represented by $R^2$ to $R^4$ in general formula (A) represents a group where a nitrogen atom in the pyrrolyl group is substituted with an alkyl group, and the alkyl group may be any of a straight chained, a branched, or a cyclic one, and among these, the straight chained one is preferable. In addition, a specific example of the alkyl group includes the same as the specific example of the alkyl group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), and a specific example of a preferable alkyl group also includes the same.

A specific example of the N-alkyl substituted pyrrolyl group, represented by $R^2$ to $R^4$ in the general formula (A), includes, for example, an N-methylpyrrolyl group, an N-ethylpyrrolyl group, an N-n-propylpyrrolyl group, an N-isopropylpyrrolyl group, an N-n-butylpyrrolyl group, an N-isobutylpyrrolyl group, an N-sec-butylpyrrolyl group, an N-tert-butylpyrrolyl group, an N-cyclobutylpyrrolyl group, an N-n-pentylpyrrolyl group, an N-isopentylpyrrolyl group, an N-sec-pentylpyrrolyl group, an N-tert-pentylpyrrolyl group, an N-neopentylpyrrolyl group, an N-2-methylbutylpyrrolyl group, an N-1,2-dimethylpropylpyrrolyl group, an N-1-ethylpropylpyrrolyl group, an N-cyclopentylpyrrolyl group, an N-n-hexylpyrrolyl group, an N-isohexylpyrrolyl group, an N-sec-hexylpyrrolyl group, an N-tert-hexylpyrrolyl group, an N-neohexylpyrrolyl group, an N-2-methylpentylpyrrolyl group, an N-1,2-dimethylbutylpyrrolyl group, an N-2,3-dimethylbutylpyrrolyl group, an N-1-ethylbutylpyrrolyl group, an N-cyclohexylpyrrolyl group, and the like. Among these N-alkyl substituted pyrrolyl groups, an N-alkyl substituted pyrrolyl group, substituted with an alkyl group having 1 to 4 carbon atoms, is preferable, among these, an N-alkyl substituted pyrrolyl group, substituted with a straight chained alkyl group having 1 to 4 carbon atoms, is more preferable, and among these, an N-methylpyrrolyl group is still more preferable.

As the arylalkynyl group having 8 to 16 carbon atoms in "an arylalkynyl group having 8 to 16 carbon atoms, which may be substituted with a halogen atom, an alkyl group having 1 to 6 carbon atoms an alkoxy group having 1 to 6 carbon atoms, or an alkylthio group having 1 to 6 carbon atoms", represented by $R^1$ and $R^2$ to $R^4$ in the general formula (A), an arylalkynyl group substituted with one or more substituents (a halogen atom, an alkyl group having 1 to 6 carbon atoms, an alkoxy group having 1 to 6 carbon atoms, or an alkylthio group having 1 to 6 carbon atoms) is preferable, among these, an arylalkynyl group substituted with any one of a halogen atom, an alkyl group having 1 to 6 carbon atoms, an alkoxy group having 1 to 6 carbon atoms, or an alkylthio group having 1 to 6 carbon atoms, at one binding site is more preferable, and among these, an arylalkynyl group substituted with an alkyl group having 1 to 6 carbon atoms at one binding site is still more preferable.

Among "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), a phenylalkynyl group having 8 to 12 carbon atoms which may be substituted with any of a substituent selected from the group consisting of a halogen atom, an alkyl group having 1 to 6 carbon atoms, an alkoxy group having 1 to 6 carbon atoms, and an alkylthio group having 1 to 6 carbon atoms, is preferable, among these, a phenylethynyl group which may be substituted with any of a substituent selected from the substituents is more preferable, among these, a phenylethynyl group which is substituted with any one of a substituent selected from the substituents at one binding site is still more preferable, and among these, a phenylethynyl group which is substituted with an alkyl group having 1 to 6 carbon atoms at one binding site is particularly preferable. A specific example of the arylalkynyl group includes an unsubstituted arylalkynyl group having 8 to 16 carbon atoms, such as a phenylethynyl group, a 3-phenylpropynyl group, a 4-phenylbutynyl group, a 5-phenylpentynyl group, a 6-phenylhexynyl group; an arylalkynyl group having 8 to 16 carbon atoms substituted with a halogen atom, such as an o-fluorophenylethynyl group, a m-fluorophenylethynyl group, a p-fluorophenylethynyl group, an o-chlorophenylethynyl group, a m-chlorophenylethynyl group, a p-chlorophenylethynyl group, an o-bromophenylethynyl group, a m-bromophenylethynyl group, a p-bromophenylethynyl group, an o-iodophenylethynyl group, a m-iodophenylethynyl group, a p-iodophenylethynyl group, a 2,3-difluorophenylethynyl group, a 3,4-difluorophenylethynyl group, a 2,4-difluorophenylethynyl group, a 2,6-difluorophenylethynyl group, a 2,3-dichlorophenylethynyl group, a 3,4-dichlorophenylethynyl group a 2,4-dichlorophenylethynyl group, a 2,6-dichlorophenylethynyl group, a 2,3-dibromophenylethynyl group, a 3,4-dibromophenylethynyl group, a 2,4-dibromophenylethynyl group, a 2,6-dibromophenylethynyl group, a 2,3-diiodophenylethynyl group, a 3,4-diiodophenylethynyl group, a 2,4-diiodophenylethynyl group, a 2,6-diiodophenylethynyl group, a 2,3,4-trifluorophenylethynyl group, a 2,3,5-trifluorophenylethynyl group, a 2,3,6-trifluorophenylethynyl group, a 2,4,5-trifluorophenylethynyl group, a 2,4,6-trifluorophenylethynyl group, a 2,5,6-trifluorophenylethynyl group, a 2,3,4-trichlorophenylethynyl group, a 2,3,5-trichlorophenylethynyl group, a 2,3,6-trichlorophenylethynyl group, a 2,4,5-trichlorophenylethynyl group, a 2,4,6-trichlorophenylethynyl group, a 2,5,6-trichlorophenylethynyl group, a 2,3,4-tribromophenylethynyl group, a 2,3,5-tribromophenylethynyl group, a 2,3,6-tribromophenylethynyl group, a 2,4,5-tribromophenylethynyl group, a 2,4,6-tribromophenylethynyl group, a 2,5,6-tribromophenylethynyl group, a 2,3,4-triiodophenylethynyl group, a 2,3,5-triiodophenylethynyl group, a 2,3,6-triiodophenylethynyl group, a 2,4,5-triiodophenylethynyl group, a 2,4,6-triiodophenylethynyl group, a 2,5,6-triiodophenylethynyl group, a 2,3,4,5-tetrafluorophenylethynyl group, a 2,3,4,5-tetrachlorophenylethynyl group, a 2,3,4,5-tetrabromophenylethynyl group, a 2,3,4,5-tetraiodophenylethynyl group, a pentafluorophenylethynyl group, a pentachlorophenylethynyl group, a pentabromophenylethynyl group, a pentaiodophenylethynyl group, a 3-(p-fluorophenyl)propynyl group, a 3-(p-chlorophenyl)propynyl group, a 3-(p-bromophenyl)propynyl group, a 3-(p-iodophenyl)propynyl group, a 4-(p-fluorophenyl)butynyl group, a 4-(p-chlorophenyl)butynyl group, a 4-(p-bromophenyl)butynyl group, a 4-(p-iodophenyl)butynyl group, a 5-(p-fluorophenyl)pentynyl group, a 5-(p-chlorophenyl)pentynyl group, a 5-(p-bromophenyl)pentynyl group, a 5-(p-iodophenyl)pentynyl group, a 6-(p-fluorophenyl)hexynyl group, a 6-(p-chlorophenyl)hexynyl group, a 6-(p-bromophenyl)hexynyl group, a 6-(p-iodophenyl)hexynyl group, a 1-(2-fluoro)naphthylethynyl group, a 1-(2-chloro)naphthylethynyl group, a 1-(2-bromo)naphthylethynyl group, a 1-(2-iodo)naphthylethynyl group, a 2-(1-fluoro)naphthylethynyl group, a 2-(1-chloro)naphthylethynyl group, a 2-(1-bromo)naphthylethynyl group, a 2-(1-iodo)naphthylethynyl group, a 3-{1-(2-fluoro)naphthyl}propynyl group, a 3-{1-(2-chloro)naphthyl}propynyl group, a 3-{1-(2-bromo)naphthyl}propynyl group, a 3-{1-(2-iodo)naphthyl}propynyl group, a 3-{2-(1-fluoro)

naphthyl}propynyl group, a 3-{2-(1-chloro)naphthyl}propynyl group, a 3-{2-(1-bromo)naphthyl}propynyl group, a 3-{2-(1-iodo)naphthyl}propynyl group, a 4-{1-(2-fluoro)naphthyl}butynyl group, a 4-{1-(2-chloro)naphthyl}butynyl group, a 4-{1-(2-bromo)naphthyl}butynyl group, a 4-{1-(2-iodo)naphthyl}butynyl group, a 4-{2-(1-fluoro)naphthyl}butynyl group, a 4-{2-(1-chloro)naphthyl}butynyl group, a 4-{2-(1-bromo)naphthyl}butynyl group, a 4-{2-(1-iodo)naphthyl}butynyl group, a 5-{1-(2-fluoro)naphthyl}pentynyl group, a 5-{1-(2-chloro)naphthyl}pentynyl group, a 5-{1-(2-bromo)naphthyl}pentynyl group, a 5-{1-(2-iodo)naphthyl}pentynyl group, a 5-{2-(1-fluoro)naphthyl}pentynyl group, a 5-{2-(1-chloro)naphthyl}pentynyl group, a 5-{2-(1-bromo)naphthyl}pentynyl group, a 5-{2-(1-iodo)naphthyl}pentynyl group, a 6-{1-(2-fluoro)naphthyl}hexynyl group, a 6-{1-(2-chloro)naphthyl}hexynyl group, a 6-{1-(2-bromo)naphthyl}hexynyl group, a 6-{1-(2-iodo)naphthyl}hexynyl group, a 6-{2-(1-fluoro)naphthyl}hexynyl group, a 6-{2-(1-chloro)naphthyl}hexynyl group, a 6-{2-(1-bromo)naphthyl}hexynyl group, a 6-{2-(1-iodo)naphthyl}hexynyl group, a 9-(10-fluoro)anthracenylethynyl group, a 9-(10-chloro)anthracenylethynyl group, a 9-(10-bromo)anthracenylethynyl group, a 9-(10-iodo)anthracenylethynyl group; an arylalkynyl group having 8 to 16 carbon atoms substituted with an alkyl group having 1 to 6 carbon atoms, such as an o-methylphenylethynyl group, a m-methylphenylethynyl group, a p-methylphenylethynyl group, a p-ethylphenylethynyl group, a p-propylphenylethynyl group, a p-butylphenylethynyl group, a p-pentylphenylethynyl group, a p-hexylphenylethynyl group, a 2,3-dimethylphenylethynyl group, a 3,4-dimethylphenylethynyl group, a 2,4-dimethylphenylethynyl group, a 2,6-dimethylphenylethynyl group, a 2,3,4-trimethylphenylethynyl group, a 2,3,5-trimethylphenylethynyl group, a 2,3,6-trimethylphenylethynyl group, a 2,4,5-trimethylphenylethynyl group, a 2,4,6-trimethylphenylethynyl group, a 2,5,6-trimethylphenylethynyl group, a 2,3,4,5-tetramethylphenylethynyl group, a pentamethylphenylethynyl group, a 3-(p-methylphenyl)propynyl group, a 4-(p-methylphenyl)butynyl group, a 5-(p-methylphenyl)pentynyl group, a 6-(p-methylphenyl)hexynyl group, a 1-(2-methyl)naphthylethynyl group, a 2-(1-methyl)naphthylethynyl group, a 3-{1-(2-methyl)naphthyl}propynyl group, a 3-{2-(1-methyl)naphthyl}propynyl group, a 4-{1-(2-methyl)naphthyl}butynyl group, a 4-{2-(1-methyl)naphthyl}butynyl group, a 5-{1-(2-methyl)naphthyl}pentynyl group, a 5-{2-(1-methy)naphthyl)pentynyl group, a 6-{1-(2-methyl)naphthyl}hexynyl group, a 6-{2-(1-methyl)naphthyl}hexynyl group, a 9-(10-methyl)anthracenylethynyl group; an arylalkynyl group having 8 to 16 carbon atoms substituted with an alkoxy group having 1 to 6 carbon atoms, such as an o-methoxyphenylethynyl group, a m-methoxyphenylethynyl group, a p-methoxyphenylethynyl group, a p-ethoxyphenylethynyl group, a p-propoxyphenylethynyl group, a p-butoxyphenylethynyl group, a p-pentyloxyphenylethynyl group, a p-hexyloxyphenylethynyl group, a 2,3-dimethoxyphenylethynyl group, a 3,4-dimethoxyphenylethynyl group, a 2,4-dimethoxyphenylethynyl group, a 2,6-dimethoxyphenylethynyl group, a 2,3,4-trimethoxyphenylethynyl group, a 2,3,5-trimethoxyphenylethynyl group, a 2,3,6-trimethoxyphenylethynyl group, a 2,4,5-trimethoxyphenylethynyl group, a 2,4,6-trimethoxyphenylethynyl group, a 2,5,6-trimethoxyphenylethynyl group, a 2,3,4,5-tetramethoxyphenylethynyl group, a pentamethoxyphenylethynyl group, a 3-(p-methoxyphenyl)propynyl group, a 4-(p-methoxyphenyl)butynyl group, a 5-(p-methoxyphenyl)pentynyl group, a 6-(p-methoxyphenyl)hexynyl group, a 1-(2-methoxy)naphthylethynyl group, a 2-(1-methoxy)naphthylethynyl group, a 3-{1-(2-methoxy)naphthyl}propynyl group, a 3-{2-(1-methoxy)naphthyl}propynyl group, a 4-{1-(2-methoxy)naphthyl}butynyl group, a 4-{2-(1-methoxy)naphthyl}butynyl group, a 5-{1-(2-methoxy)naphthyl}pentynyl group, a 5-{2-(1-methoxy)naphthyl}pentynyl group, a 6-{1-(2-methoxy)naphthyl}hexynyl group, a 6-{2-(1-methoxy)naphthyl}hexynyl group, a 9-(10-methoxy)anthracenylethynyl group; an arylalkynyl group having 8 to 16 carbon atoms substituted with an alkylthio group having 1 to 6 carbon atoms, such as an o-methylthiophenylethynyl group, a m-methylthiophenylethynyl group, a p-methylthiophenylethynyl group, a p-ethylthiophenylethynyl group, a p-propylthiophenylethynyl group, a p-butylthiophenylethynyl group, a p-pentylthiophenylethynyl group, a p-hexylthiophenylethynyl group, a 2,3-dimethylthiophenylethynyl group, a 3,4-dimethylthiophenylethynyl group, a 2,4-dimethylthiophenylethynyl group, a 2,6-dimethylthiophenylethynyl group, a 2,3,4-trimethylthiophenylethynyl group, a 2,3,5-trimethylthiophenylethynyl group, a 2,3,6-trimethylthiophenylethynyl group, a 2,4,5-trimethylthiophenylethynyl group, a 2,4,6-trimethylthiophenylethynyl group, a 2,5,6-trimethylthiophenylethynyl group, a 2,3,4,5-tetramethylthiophenylethynyl group, a pentamethylthiophenylethynyl group, a 3-(p-methylthiophenyl)propynyl group, a 4-(p-methylthiophenyl)butynyl group, a 5-(p-methylthiophenyl)pentynyl group, a 6-(p-methylthiophenyl)hexynyl group, a 1-(2-methylthio)naphthylethynyl group, a 2-(1-methylthio)naphthylethynyl group, a 3-{1-(2-methylthio)naphthyl}propynyl group, a 3-{2-(1-methylthio)naphthyl}propynyl group, a 4-{1-(2-methylthio)naphthyl}butynyl group, a 4-{2-(1-methylthio)naphthyl}butynyl group, a 5-{1-(2-methylthio)naphthyl}pentynyl group, a 5-{2-(1-methylthio)naphthyl}pentynyl group, a 6-{1-(2-methylthio)naphthyl}hexynyl group, a 6-{2-(1-methylthio)naphthyl}hexynyl group, a 9-(10-methylthio)anthracenylethynyl group. It should be noted that, in the specific example, the alkyl group having 1 to 6 carbon atoms, the alkoxy group having 1 to 6 carbon atoms, and the alkylthio group having 1 to 6 carbon atoms, substituting the arylalkynyl group having 8 to 16 carbon atoms, are not limited to a normal-form, and the specific example also includes a branched-type one such as sec-form, tert-form, iso-form, neo-form, or a ring-type one such as cyclo-form.

As the aryl group having 6 to 14 carbon atoms, in "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^2$ to $R^4$ in the general formula (A), an aryl group having no substitutional group is preferable.

Among "an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ and $R^2$ to $R^4$ in the general formula (A), a phenyl group which may be substituted with any of a substituent selected from the group consisting of a halogen atom, an alkyl group having 1 to 6 carbon atoms, an alkoxy group having 1 to 6 carbon atoms, and an alkylthio group having 1 to 6 carbon atoms, is preferable, and among these, an unsubstituted phenyl group is more preferable. A specific example of the aryl group includes an unsubstituted aryl group having 6 to 14 carbon atoms, such as a phenyl group, a naphthyl group, an anthracenyl group; an aryl group having 6 to 14 carbon atoms substituted with a halogen atom, for example, an o-fluorophenyl group, a m-fluorophenyl group, a p-fluorophenyl group, an o-chlorophenyl group, a m-chlorophenyl group, a p-chlorophenyl group, an o-bromophenyl group, a m-bromophenyl group, a p-bromophenyl group, an o-iodophenyl group, a m-iodophenyl group, a p-iodophenyl group, a 2,3-difluorophenyl group, a 3,4-difluorophenyl group, a 2,4-difluorophenyl group, a 2,6-difluorophenyl group, a 2,3-dichlorophenyl group, a 3,4-dichlorophenyl group, a 2,4-dichlorophenyl group, a 2,6-dichlorophenyl group, a 2,3-dibromophenyl group, a 3,4-dibromophenyl group, a 2,4-dibromophenyl group, a 2,6-dibromophenyl group, a 2,3-diiodophenyl group, a 3,4-diiodophenyl group, a 2,4-diiodophenyl group, a 2,6-diiodophenyl group, a 2,3,4-trifluorophenyl group, a 2,3,5-trifluorophenyl group, a 2,3,6-trifluorophenyl group, a 2,4,5-trifluorophenyl group, a 2,4,6-trifluorophenyl group, a 2,5,6-trifluorophenyl group, a 2,3,4-trichlorophenyl group, a 2,3,5-trichlorophenyl group, a 2,3,6-trichlorophenyl group, a 2,4,5-trichlorophenyl group, a 2,4,6-trichlorophenyl group, a 2,5,6-trichlorophenyl group, a 2,3,4-tribromophenyl group, a 2,3,5-tribromophenyl group, a 2,3,6-tribromophenyl group, a 2,4,5-tribromophenyl group, a 2,4,6-tribromophenyl group, a 2,5,6-tribromophenyl group, a 2,3,4-triiodophenyl group, a 2,3,5-triiodophenyl group, a 2,3,6-triiodophenyl group, a 2,4,5-triiodophenyl group, a 2,4,6-triiodophenyl group, a 2,5,6-triiodophenyl group, a 2,3,4,5-tetrafluorophenyl group, a 2,3,4,5-tetrachlorophenyl group, a 2,3,4,5-tetrabromophenyl group, a 2,3,4,5-tetraiodophenyl group, a pentafluorophenyl group, a pentachlorophenyl group, a pentabromophenyl group, a pentaiodophenyl group, a 1-(2-fluoro)naphthyl group, a 1-(2-chloro)naphthyl group, a 1-(2-bromo)naphthyl group, a 1-(2-iodo)naphthyl group, a 2-(1-fluoro)naphthyl group, a 2-(1-chloro)naphthyl group, a 2-(1-bromo)naphthyl group, a 2-(1-iodo)naphthyl group, a 9-(10-fluoro)anthracenyl group, a 9-(10-chloro)anthracenyl group, a 9-(10-bromo)anthracenyl group, a 9-(10-iodo)anthracenyl group; an aryl group having 6 to 14 carbon atoms substituted with an alkyl group having 1 to 6 carbon atoms, such as an o-methylphenyl group, a m-methylphenyl group, a p-methylphenyl group, a p-ethylphenyl group, a p-propylphenyl group, a p-butylphenyl group, a p-pentylphenyl group, a p-hexylphenyl group, a 2,3-dimethylphenyl group, a 3,4-dimethylphenyl group, a 2,4-dimethylphenyl group, a 2,6-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 2,5,6-trimethylphenyl group, a 2,3,4,5-tetramethylphenyl group, a pentamethylphenyl group, a 1-(2-methyl)naphthyl group, a 2-(1-methyl)naphthyl group, a 9-(10-methyl)anthracenyl group; an aryl group having 6 to 14 carbon atoms substituted with an alkoxy group having 1 to 6 carbon atoms, such as an o-methoxyphenyl group, a m-methoxyphenyl group, a p-methoxyphenyl group, a p-ethoxyphenyl group, a p-propoxyphenyl group, a p-butoxyphenyl group, a p-pentyloxyphenyl group, a p-hexyloxyphenyl group, a 2,3-dimethoxyphenyl group, a 3,4-dimethoxyphenyl group, a 2,4-dimethoxyphenyl group, a 2,6-dimethoxyphenyl group, a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, a 2,5,6-trimethoxyphenyl group, a 2,3,4,5-tetramethoxyphenyl group, a pentamethoxyphenyl group, a 1-(2-methoxy)naphthyl group, a 2-(1-methoxy)naphthyl group, a 9-(10-methoxy)anthracenyl group; an aryl group having 6 to 14 carbon atoms substituted with an alkylthio group having 1 to 6 carbon atoms, such as an o-methylthiophenyl group, a m-methylthiophenyl group, a p-methylthiophenyl group, a p-ethylthiophenyl group, a p-propylthiophenyl group, a p-butylthiophenyl group, a p-pentylthiophenyl group, a p-hexylthiophenyl group, a 2,3-di(methylthio)phenyl group, a 3,4-di(methylthio)phenyl group, a 2,4-di(methylthio)phenyl group, a 2,6-di(methylthio)phenyl group, a 2,3,4-tri(methylthio)phenyl group, a 2,3,5-tri(methylthio)phenyl group, a 2,3,6-tri(methylthio)phenyl group, a 2,4,5-tri(methylthio)phenyl group, a 2,4,6-tri(methylthio)phenyl group, a 2,5,6-tri(methylthio)phenyl group, a 2,3,4,5-tetra(methylthio)phenyl group, a penta(methylthio)phenyl group, a 1-(2-methylthio)naphthyl group, a 2-(1-methylthio)naphthyl group, a 9-(10-methylthio)anthracenyl group. It should be noted that, in the specific example, the alkyl group having 1 to 6 carbon atoms, the alkoxy group having 1 to 6 carbon atoms, and the alkylthio group having 1 to 6 carbon atoms, substituting the aryl group having 6 to 14 carbon atoms, are not limited to a normal-form, and the specific example also includes a branched-type one such as sec-form, tert-form, iso-form, neo-form, or a ring-type one such as cyclo-form.

As $R^1$ in the general formula (A), an alkyl group having 1 to 12 carbon atoms, and a phenylalkynyl group having 8 to 12 carbon atoms which may be substituted with a halogen atom, an alkyl group having 1 to 6 carbon atoms, an alkoxy group having 1 to 6 carbon atoms, or an alkylthio group having 1 to 6 carbon atoms, are preferable. Still more, among these, an alkyl group having 1 to 12 carbon atoms, and a phenylethynyl group which may be substituted with a halogen atom, an alkyl group having 1 to 6 carbon atoms, an alkoxy group having 1 to 6 carbon atoms, or an alkylthio group having 1 to 6 carbon atoms, is more preferable, and among these, an alkyl group having 1 to 6 carbon atoms, and a phenylethynyl group substituted with any one of a halogen atom, an alkyl group having 1 to 6 carbon atoms, an alkoxy group having 1 to 6 carbon atoms, an alkylthio group having 1 to 6 carbon atoms, at one binding site, is still more preferable.

As $R^2$ to $R^4$ in the general formula (A), it is preferable that all of $R^2$ to $R^4$ are the same group, which is an alkyl group having 4 to 12 carbon atoms; a phenylalkynyl group having 8 to 12 carbon atoms which may be substituted with a halogen atom, an alkyl group having 1 to 6 carbon atoms, an alkoxy group having 1 to 6 carbon atoms, or an alkylthio group having 1 to 6 carbon atoms; a phenyl group which may be substituted with a halogen atom, an alkyl group having 1 to 6 carbon atoms, an alkoxy group having 1 to 6 carbon atoms, or an alkylthio group having 1 to 6 carbon atoms; a furanyl group; a thienyl group; or an N-alkyl substituted pyrrolyl group. Still more, among these, it is more preferable that all of $R^2$ to $R^4$ are the same group, which is an phenyl group which may be substituted with a halogen atom, an alkyl group having 1 to 6 carbon atoms, an alkoxy group having 1 to 6 carbon atoms or an alkylthio group having 1 to 6 carbon atoms; a furanyl group; a thienyl group; and an N-alkyl substituted pyrrolyl group, and among these, it is still more preferable that all of $R^2$ to $R^4$ are the same phenyl group which may be substituted with a halogen atom, an alkyl group having 1 to 6 carbon atoms, an alkoxy group having 1 to 6 carbon atoms or an alkylthio group having 1 to 6 carbon atoms, and among these, it is particularly preferable that all of $R^2$ to $R^4$ are the same unsubstituted phenyl group.

Combinations of $R^1$ to $R^4$ in the general formula (A) include those described in the following Table 1.

TABLE 1

| R¹ | R² | R³ | R⁴ |
|---|---|---|---|
| alkyl group having 1 to 12 carbon atoms | | functional group B | |
| | | franyl group | |
| | | thienyl group | |
| | | N-alkyl substitutd pyrrolyl group | |
| | alkyl group having 1 to 12 carbon atoms | functional group B | |
| | alkyl group having 1 to 12 carbon atoms | functional group B | alkyl group having 1 to 12 carbon atoms |
| functional group A | | functional group B | |
| | functional group A | functional group B | |
| | functional group A | functional group B | |
| | | functional group A | |
| alkenyl group having 2 to 12 carbon atoms | | functional group B | |
| 2,6-dithianyl group | | functional group B | |
| 2-furylethynyl group | | functional group B | |
| 2-thiophenylethynyl group | | functional group B | |

In the Table, the functional group A represents an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms, and the functional group B represents an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms.

A specific example of "an ammonium cation having a guanidinium group, a biguanidium group or a phosphazenium group, or a phosphonium cation", represented by Z⁺ in the general formula (A), includes, for example, an ammonium cation having a guanidinium group represented by the following general formula ($B_1$), an ammonium cation having a biguanidium group represented by the following general formula ($B_2$), an ammonium cation having a phosphazenium group represented by the following general formula ($B_3$) or ($B_4$), or a phosphonium cation represented by the following general formula ($B_5$) or ($B_6$).

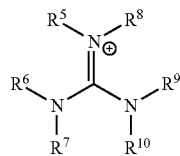
($B_1$)

(wherein $R^5$ to $R^8$ and $R^{10}$ each independently represent a hydrogen atom, an alkyl group having 1 to 12 carbon atoms or an amino group, $R^9$ represents a hydrogen atom, an alkyl group having 1 to 12 carbon atoms, an amino group or a group represented by the following formula ($b_1$):

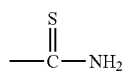
($b_1$)

$R^5$ together with $R^6$ and/or $R^7$ together with $R^{10}$ may form an alkylene group having 2 to 4 carbon atoms, and number of hydrogen atoms among $R^5$ to $R^{10}$ is 0 to 2.)

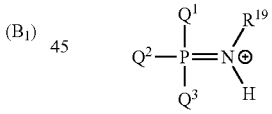
($B_2$)

(wherein $R^{11}$ to $R^{15}$ and $R^{18}$ each independently represent a hydrogen atom or an alkyl group having 1 to 12 carbon atoms, $R^{16}$ and $R^{17}$ each independently represent a hydrogen atom, an alkyl group having 1 to 12 carbon atoms, or the aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 1 to 12 carbon atoms; $R^{16}$ together with $R^{17}$ may form an alkylene group having 2 to 4 carbon atoms, and number of hydrogen atoms among $R^{11}$ to $R^{18}$ is 0 to 2.)

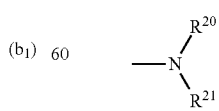
($B_3$)

{wherein $R^{19}$ represents a hydrogen atom or an alkyl group having 1 to 12 carbon atoms, $Q^1$ to $Q^3$ each independently represent a group represented by the following general formula ($b_2$) or ($b_3$), or $Q^1$ together with $Q^2$ represent a cyclic structure represented by the following general formula ($b_4$), and number of hydrogen atoms bonding to the nitrogen atoms in the formula is 1 to 5.

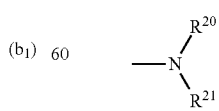
($b_2$)

(wherein $R^{20}$ and $R^{21}$ each independently represent a hydrogen atom or an alkyl group having 1 to 6 carbon atoms, and $R^2$ together with $R^{21}$ may form an alkylene group having 2 to 4 carbon atoms.)

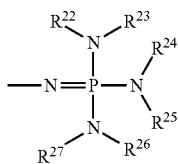

(b₃)

(wherein $R^{22}$ to $R^{27}$ each independently represent a hydrogen atom or an alkyl group having 1 to 6 carbon atoms.)

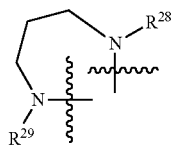

(b₄)

(wherein $R^2$ and $R^{29}$ each independently represent a hydrogen atom or an alkyl group having 1 to 6 carbon atoms.)}

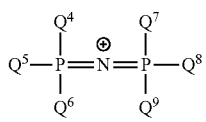

(B₄)

(wherein $Q^4$ to $Q^9$ each independently represent a group represented by the general formula (b₂) or (b₃), and number of hydrogen atoms bonding to the nitrogen atoms in the formula is 0 to 4.)

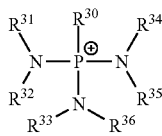

(B₅)

(wherein $R^{30}$ represents a hydrogen atom or a group represented by the general formula (b₂) or (b₃), $R^{31}$ to $R^{36}$ each independently represent a hydrogen atom or an alkyl group having 1 to 6 carbon atoms; or $R^{31}$ together with $R^{32}$, $R^{32}$ together with $R^{33}$, $R^{34}$ together with $R^{35}$, $R^{35}$ together with $R^{36}$, and/or, $R^{33}$ together with $R^{36}$ may form an alkylene group having 2 to 4 carbon atoms; $R^{32}$, $R^{33}$ together with $R^{35}$ may form an alkylene group having 3 to 10 carbon atoms which may contain a nitrogen atom, and number of hydrogen atoms bonding to the nitrogen atoms in the formula is 0 to 4.)

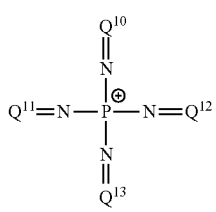

(B₆)

{wherein $Q^{10}$ to $Q^{13}$ each independently represent a group represented by the following general formula (b₅) or (b₆), and number of hydrogen atoms bonding to the nitrogen atoms in the formula is 0 to 4.

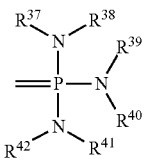

(b₅)

(wherein $R^{37}$ to $R^{42}$ each independently represent a hydrogen atom or an alkyl group having 1 to 6 carbon atoms.)

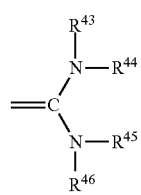

(b₆)

(wherein $R^{43}$ to $R^{46}$ each independently represent a hydrogen atom or an alkyl group having 1 to 6 carbon atoms.)}

The alkyl group having 1 to 12 carbon atoms represented by $R^5$ to $R^{10}$ in the general formula (B₁) may be any of a straight chained, a branched, or a cyclic one, and among these, the straight chained one is preferable. In addition, among the alkyl group having 1 to 12 carbon atoms, an alkyl group having 1 to 6 carbon atoms is preferable, and an alkyl group having 1 to 4 carbon atoms is more preferable. A specific example of the alkyl group includes the same as the specific example of the alkyl group having 1 to 12 carbon atoms, represented by $R^1$ in the general formula (A), among these, an alkyl group having 1 to 6 carbon atoms is preferable, among these, an alkyl group having 1 to 4 carbon atoms is more preferable, among these, a straight chained alkyl group having carbon atom of 1 to 4 carbon atoms is still more preferable, and among these, a methyl group is particularly preferable.

The alkylene group having 2 to 4 carbon atoms in the case where "$R^5$ together with $R^6$ and/or $R^7$ together with $R^{10}$ form an alkylene group having 2 to 4 carbon atoms" in the general formula (B₁), may be any of a straight chained or a branched one, and specifically includes, for example, an ethylene group, a trimethylene group, a propylene group, a tetramethylene group, a 1-methyltrimethylene group, a 2-methyltrimethylene group, a 1,2-dimethylethylene group, a 1,1-dimethylethylene group, an ethylethylene group, and the like, and among these, a trimethylene group is preferable.

In the case where $R^5$ together with $R^6$ form an alkylene group having 2 to 4 carbon atoms, in the general formula (B), the alkylene group together with an —N=C—N— group bonding to the alkylene group form a cyclic structure of a 5 to 7 membered ring.

A specific example of the cyclic structure includes, for example, an imidazoline ring, a 1,4,5,6-tetrahydropyrimidine ring, a 4-methylimidazoline ring, a 5-methylimidazoline ring, a 1,3-diaza-2-cycloheptene ring, a 1,5,6-trihydro-4-methylpyrimidine ring, a 1,4,6-trihydro-5-methylpyrimidine ring, a 1,4,5-trihydro-6-methylpyrimidine ring, a 4-ethylimidazoline ring, 5-ethylimidazoline ring, a 4,4-dimethylimidazoline ring, a 4,5-dimethylimidazoline ring, a 5,5-dimethylimidazoline ring, and among these, the 1,4,5,6-tetrahydropyrimidine ring is preferable.

In the case where $R^7$ together with $R^{10}$ form an alkylene group having 2 to 4 carbon atoms, in the general formula ($B_1$), the alkylene group together with an —N—C—N— group bonding to the alkylene group form a cyclic structure of a 5 to 7 membered ring.

A specific example of the cyclic structure includes, for example, an imidazolidine ring, a hexahydropyrimidine ring, a 4-methylimidazolidine ring, a 1,3-diazacyclohexane ring, a 1,3,5,6-tetrahydro-4-methylpyrimidine ring, a 1,3,4,6-tetrahydro-5-methylpyrimidine ring, a 4-ethylimidazolidine ring, a 4,4-dimethylimidazolidine ring, 4,5-dimethylimidazolidine ring, and among these, a hexahydropyrimidine ring is still more preferable.

"Number of hydrogen atoms among $R^5$ to $R^{10}$ is 0 to 2" in the general formula (B) means that, among $R^5$ to $R^{10}$, number of R, where the group represented by $R^5$ to $R^{10}$ is a hydrogen atom, is 0 to 2.

Number of hydrogen atoms among $R^5$ to $R^{10}$ in the general formula ($B_1$), is an integer of 0 to 2, 1 to 2 is preferable, and 1 is more preferable.

A specific example of the alkyl group having 1 to 12 carbon atoms, represented by $R^{11}$ to $R^{15}$ and $R^{18}$ in the general formula ($B_2$), includes the same as the specific example of the alkyl group having 1 to 12 carbon atoms, represented by $R^5$ to $R^{12}$ in the general formula ($B_1$), and a specific example of a preferable alkyl group also includes the same.

The alkyl group having 1 to 12 carbon atoms, represented by $R^{16}$ and $R^{17}$ in the general formula ($B_2$), may be any of a straight chained, branched or a cyclic one, and among these, the branched or the cyclic one is preferable. In addition, among the alkyl group having 1 to 12 carbon atoms, an alkyl group having 1 to 8 carbon atoms is preferable, and an alkyl group having 1 to 6 carbon atoms is more preferable. A specific example of the alkyl group includes the same as the specific example of the alkyl group having 1 to 12 carbon atoms, represented by $R^1$ in the general formula (A), and among these, an alkyl group having 1 to 8 carbon atoms is preferable, and among these, an alkyl group having 1 to 6 carbon atoms is more preferable, and among these, an isopropyl group and a cyclohexyl group are still more preferable.

The aryl group having 6 to 14 carbon atoms, in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$), includes specifically, for example, a phenyl group, a naphthyl group, an anthracenyl group, and the like, and among these, a phenyl group is preferable. It should be noted that number of carbon atoms in the aryl group shown here means number of carbon atoms composing the aryl group, and number of carbon atoms composing the substituent should not be included in number of carbon atoms shown by "6 to 14 carbon atoms" in the aryl group having 6 to 14 carbon atoms.

A specific example of the alkyl group having 1 to 6 carbon atoms, in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$) includes the same as the specific example of the alkyl group having 1 to 6 carbon atoms, in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$, and $R^2$ to $R^4$ in the general formula (A), and among these, a straight chained or a branched alkyl group having 1 to 6 carbon atoms is preferable, a straight chained or a branched alkyl group having 1 to 4 carbon atoms is preferable, and an isopropyl group is particularly preferable.

A specific example of the alkoxy group having 1 to 6 carbon atoms, in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms", represented by $R^{16}$ and $R^{17}$ in the general formula ($B_2$), includes the same as the specific example of the alkoxy group having 1 to 6 carbon atoms, in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$, and $R^2$ to $R^4$ in the general formula (A), and a specific example of the preferable alkoxy group also includes the same.

A specific example of the alkylthio group having 1 to 6 carbon atoms, in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$) includes the same as the specific example of the alkylthio group having 1 to 6 carbon atoms, in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$, and $R^2$ to $R^4$ in the general formula (A), and a specific example of the preferable alkylthio group also includes the same.

In the dialkylamino group having 2 to 12 carbon atoms in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$), 2 to 12 carbon atoms of the dialkylamino group shown here means total number of carbon atoms in the two alkyl groups composing the dialkylamino group, and number of carbon atoms in each alkyl group is both 1 to 6. That is, "a dialkylamino group having 2 to 12 carbon atoms" represents an amino group having, as a substituent, two alkyl groups having 1 to 6 carbon atoms which may be the same or different.

A specific example of the alkyl group having 1 to 6 carbon atoms composing the dialkylamino group having 2 to 12 carbon atoms, in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms", represented by $R^{16}$ and $R^{17}$ in the general formula ($B_2$), includes the same as the specific example of the alkyl group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$ and $R^2$ to $R^4$ in the general formula (A), and a specific example of a preferable alkyl group also includes the same.

As the dialkylamino group having 2 to 12 carbon atoms in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or dialkylamino group having 2 to 12 carbon atoms", represented by $R^{16}$ and $R^{17}$ in the general formula ($B_2$), a dialkylamino group, where the two alkyl groups having 1 to 6 carbon atoms constituting the dialkylamino group are the same, is preferable. Specifically, it includes, for example, an N,N-dimethylamino group, an N,N-ethylmethylamino group, an N,N-diethylamino group, an N,N-methylpropylamino group, an N,N-ethylpropylamino group, an N,N-butylmethylamino group, an N,N-dipropylamino group, an N,N-butylethylamino group, an N,N-methylpentylamino group, an N,N-butylpropylamino group, an N,N-ethylpentylamino group, an N,N-hexylmethylamino group, an N,N-dibutylamino group, an N,N-propylpentylamino group, an N,N-ethylhexylamino group, an N,N-butylpentylamino group, an N,N-hexylpropylamino group, an N,N-dipentylamino group, an N,N-butylhexylamino group, an N,N-hexylpentylamino group, an N,N-dihexylamino group, and the like. Among these dialkylamino groups, a dialkylamino group having the same alkyl groups having 1 to 6 carbon atoms as the substituents is preferable, a dialkylamino group having the same alkyl groups having 1 to 4 carbon atoms as the substituents is more preferable, and a dialkylamino group having the same straight chained alkyl groups having 1 to 4 carbon atoms, as the substituents is still more preferable, and an N,N-dimethylamino group and an N,N-diethylamino group are particularly preferable. It should be noted that, in the specific example, the alkyl group as the substituent in the dialkylamino group is not limited to a normal-form, and the specific example also includes a branched-type one such as sec-form, tert-form, iso-form, neo-form, or a ring-type one such as cyclo-form, as the substituent.

Number of substituents on the aryl group having 6 to 14 carbon atoms in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$) includes an integer of 0 (non-substitution) to 9, 1 to 5 is preferable, 1 to 3 is more preferable, and 1 to 2 is particularly preferable.

A binding site of a substituent on the aryl group having 6 to 14 carbon atoms in "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$), includes the same as the binding site of a substituent on "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^2$ to $R^4$ in the general formula (A), and a preferable binding site of the substituent also includes the same.

As "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$), a substituted aryl group is preferable. As the substituted aryl group having 6 to 14 carbon atoms, an aryl group may be substituted with at least one kind of the substituents, and may be substituted with two or more kinds of the substituents, selected from a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms, however, an aryl group substituted with only one kind of the substituents is preferable, and among these, an aryl group substituted with only a nitro group or only an alkyl group having 1 to 6 carbon atoms is more preferable.

Among the "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$), a phenyl group which may be substituted with either of substituents selected from the group consisting of a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms, is preferable, and among these, a phenyl group which is substituted with either one kind of substituents selected from the above groups, is more preferable, and among these, a phenyl group which is substituted with only a nitro group or only an alkyl group having 1 to 6 carbon atoms, at 1 to 2 binding sites, is still more preferable.

A specific example of "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or dialkylamino group having 2 to 12 carbon atoms", represented by $R^{16}$ and $R^{17}$ in the general formula ($B_2$), includes an unsubstituted aryl group having 6 to 14 carbon atoms, such as a phenyl group, a naphthyl group, an anthracenyl group; an aryl group having 6 to 14 carbon atoms which is substituted with a nitro group, such as an o-nitrophenyl group, a m-nitrophenyl group, a p-nitrophenyl group, a 2,4-dinitrophenyl group, a 2,6-dinitrophenyl group, a 1-(2-nitro)naphthyl group, a 2-(1-nitro)naphthyl group, a 9-(10-nitro)anthracenyl group; an aryl group having 6 to 14 carbon atoms which is substituted with an alkyl group having 1 to 6 carbon atoms, such as an o-methylphenyl group, a m-methylphenyl group, a p-methylphenyl group, a p-ethylphenyl group, a p-propylphenyl group, a p-butylphenyl group, a p-pentylphenyl group, a p-hexylphenyl group, a 2,3-dimethylphenyl group, a 3,4-dimethylphenyl group, a 2,4-dimethylphenyl group, a 2,6-dimethylphenyl group, a 2,3-diethylphenyl group, a 3,4-diethylphenyl group, a 2,4-diethylphenyl group, a 2,6-diethylphenyl group, a 2,3-dipropylphenyl group, a 3,4-dipropylphenyl group, a 2,4-dipropylphenyl group, a 2,6-dipropylphenyl group, a 2,3-dibutylphenyl group, a 3,4-dibutylphenyl group, a 2,4-dibutylphenyl group, a 2,6-dibutylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 2,5,6-trimethylphenyl group, a 2,3,4,5-tetramethylphenyl group, a pentamethylphenyl group, a 1-(2-methyl)naphthyl group, a 2-(1-methyl)

naphthyl group, a 9-(10-methyl)anthracenyl group; an aryl group having 6 to 14 carbon atoms which is substituted with an alkoxy group having 1 to 6 carbon atoms, such as an o-methoxyphenyl group, a m-methoxyphenyl group, a p-methoxyphenyl group, a p-ethoxyphenyl group, a p-propoxyphenyl group, a p-butoxyphenyl group, a p-pentyloxyphenyl group, a p-hexyloxyphenyl group, a 2,3-dimethoxyphenyl group, a 3,4-dimethoxyphenyl group, a 2,4-dimethoxyphenyl group, a 2,6-dimethoxyphenyl group, a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, a 2,5,6-trimethoxyphenyl group, a 2,3,4,5-tetramethoxyphenyl group, a pentamethoxyphenyl group, a 1-(2-methoxy)naphthyl group, a 2-(1-methoxy)naphthyl group, a 9-(10-methoxy)anthracenyl group; an aryl group having 6 to 14 carbon atoms which is substituted with an alkylthio group having 1 to 6 carbon atoms, such as an o-methylthiophenyl group, a m-methylthiophenyl group, a p-methylthiophenyl group, a p-ethylthiophenyl group, a p-propylthiophenyl group, a p-butylthiophenyl group, a p-pentylthiophenyl group, a p-hexylthiophenyl group, a 2,3-di(methylthio)phenyl group, a 3,4-di(methylthio)phenyl group, a 2,4-di(methylthio)phenyl group, a 2,6-di(methylthio)phenyl group, a 2,3,4-tri(methylthio)phenyl group, a 2,3,5-tri(methylthio) phenyl group, a 2,3,6-tri(methylthio)phenyl group, a 2,4,5-tri(methylthio)phenyl group, a 2,4,6-tri(methylthio)phenyl group, a 2,5,6-tri(methylthio)phenyl group, a 2,3,4,5-tetra (methylthio)phenyl group, a penta(methylthio)phenyl group, a 1-(2-methylthio)naphthyl group, a 2-(1-methylthio) naphthyl group, a 9-(10-methylthio)anthracenyl group; an aryl group having 6 to 14 carbon atoms which is substituted with a dialkylamino group having 2 to 12 carbon atoms, such as an o-(N,N-dimethylamino)phenyl group, a m-(N,N-dimethylamino)phenyl group, a p-(N,N-dimethylamino) phenyl group, a p-(N,N-diethylamino)phenyl group, a p-(N,N-dipropylamino)phenyl group, a p-(N,N-dibutylamino) phenyl group, a p-(N,N-dipentylamino)phenyl group, a p-(N,N-dihexylamino)phenyl group, a 2,4-di(N,N-dimethylamino)phenyl group, a 2,6-di(N,N-dimethylamino)phenyl group, a 1-[2-(N,N-dimethylamino)]naphthyl group, a 2-[1-(N,N-dimethylamino)]naphthyl group, a 9-[10-(N,N-dimethylamino)]anthracenyl group. It should be noted that, in the specific example, the alkyl group having 1 to 6 carbon atoms, the alkoxy group having 1 to 6 carbon atoms, and the alkylthio group having 1 to 6 carbon atoms, substituting the aryl group having 6 to 14 carbon atoms, as well as the two alkyl groups having 1 to 6 carbon atoms in the dialkylamino group having 2 to 12 carbon atoms, substituting the aryl group having 6 to 14 carbon atoms, are not limited to a normal-form, and the specific example also includes a branched-type one such as sec-form, tert-form, iso-form, neo-form, or a ring-type one such as cyclo-form.

A specific example of the alkylene group having 2 to 4 carbon atoms, in the case where "$R^{16}$ together with $R^{17}$ form an alkylene group having 2 to 4 carbon atoms" in the general formula ($B_2$), includes the same as the specific example of the alkylene group having 2 to 4 carbon atoms in the case where "$R^5$ together with $R^6$ and/or $R^7$ together with $R^{10}$ form an alkylene group having 2 to 4 carbon atoms" in the general formula ($B_1$), and among these, an ethylene group, which is a straight chained alkylene group having 2 carbon atoms, is preferable.

In the case where $R^{16}$ together with $R^{17}$ form an alkylene group having 2 to 4 carbon atoms in the general formula ($B_2$), the alkylene group together with an —N=C—N— group bonding to the alkylene group form a cyclic structure of a 5 to 7 membered ring.

A specific example of the cyclic structure includes, for example, an imidazoline ring, a 1,4,5,6-tetrahydropyrimidine ring, a 4-methylimidazoline ring, a 5-methylimidazoline ring, a 1,3-diaza-2-cycloheptene ring, a 1,5,6-trihydro-4-methylpyrimidine ring, a 1,4,6-trihydro-5-methylpyrimidine ring, a 1,4,5-trihydro-6-methylpyrimidine ring, a 4-ethylimidazoline ring, 5-ethylimidazoline ring, a 4,4-dimethylimidazoline ring, a 4,5-dimethylimidazoline ring, a 5,5-dimethylimidazoline ring, and among these, an imidazoline ring is preferable.

"Number of hydrogen atoms among $R^{11}$ to $R^{18}$ is 0 to 2", in the general formula ($B_2$), means that, among $R^{11}$ to $R^{18}$, number of R, where the group represented by $R^{11}$ to $R^{18}$ is a hydrogen atom, is 0 to 2.

Number of hydrogen atoms among $R^{11}$ to $R^{18}$ in the general formula ($B_2$), is an integer of 0 to 2, and 0 or 2 is more preferable.

The alkyl group having 1 to 12 carbon atoms, represented by $R^{19}$ in the general formula ($B_3$), may be any of a straight chained, branched or a cyclic one, and among these, the branched or the cyclic one is preferable. In addition, among the alkyl group having 1 to 12 carbon atoms, an alkyl group having 1 to 8 carbon atoms is preferable, and an alkyl group having 1 to 4 carbon atoms is more preferable. A specific example of the alkyl group includes the same as the specific example of the alkyl group having 1 to 12 carbon atoms, represented by $R^1$ in the general formula (A), and among these, the alkyl group having 1 to 8 carbon atoms is preferable, and among these, the alkyl group having 1 to 4 carbon atoms is preferable, and among these, a tert-butyl group is still more preferable.

In general the formula ($B_3$), number of hydrogen atoms bonding to the nitrogen atoms in the formula is an integer of 1 to 5, 1 to 3 is preferable, and 1 is more preferable. It should be noted that number of hydrogen atoms shown here is always 1 or larger, because the nitrogen atom in the general formula ($B_3$) already has one hydrogen atom.

A specific example of the alkyl group having 1 to 6 carbon atoms, represented by $R^{20}$ to $R^{29}$ in the general formulae ($b_2$), ($b_3$), and ($b_4$), includes the same as the specific example of the alkyl group having 1 to 6 carbon atoms, in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$, and $R^2$ to $R^4$ in the general formula (A), and a specific example of a preferable alkyl group also includes the same.

A specific example of the alkylene group having 2 to 4 carbon atoms, in the case where "$R^{20}$ together with $R^{21}$ form an alkylene group having 2 to 4 carbon atoms", in the general formula ($b_2$), includes the same as the specific example of the alkylene group having 2 to 4 carbon atoms, in the case where "$R^5$ together with $R^6$ and/or $R^7$ together with $R^{10}$ form an alkylene group having 2 to 4 carbon atoms", in the general formula ($B_1$), and among these, a tetramethylene group is preferable.

In the case where $R^{20}$ together with $R^{21}$ form an alkylene group having 2 to 4 carbon atoms, in the general formula ($b_2$), the alkylene group together with a nitrogen atom bonding to the alkylene group form a cyclic structure of a 3 to 5 membered ring.

A specific example of the cyclic structure includes, for example, an aziridine ring, an azetidine ring, a 2-methylaziridine ring, a pyrrolidine ring, a 2-methylazetidine ring, a 3-methylazetidine ring, a 2-ethylaziridine ring, a 2,2-dimethylaziridine ring, a 2,3-dimethylaziridine ring, and among these, a pyrrolidine ring is preferable.

In the general formula ($B_4$), number of hydrogen atoms bonding to the nitrogen atoms in the formula, is an integer of 0 to 4, 0 to 2 is preferable, and 0 is more preferable.

A specific example of the alkyl group having 1 to 6 carbon atoms, represented by $R^{31}$ to $R^{36}$ in the general formula ($B_5$), includes the same as the specific example of the alkyl group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$ and $R^2$ to $R^4$ in the general formula (A), and a specific example of a preferable alkyl group also includes the same.

A specific example of the alkylene group having 2 to 4 carbon atoms, in the case where $R^{31}$ together with $R^{32}$, $R^{34}$ together with $R^{35}$ and/or $R^{35}$ together with $R^{36}$ form an alkylene group having 2 to 4 carbon atoms, among the case "where $R^{31}$ together with $R^{32}$, $R^{32}$ together with $R^{33}$, $R^{34}$ together with $R^{35}$, $R^{35}$ together with $R^{36}$ and/or $R^{33}$ together with $R^{36}$ form an alkylene group having 2 to 4 carbon atoms", in the general formula ($B_5$), includes the same as the specific example of the alkylene group having 2 to 4 carbon atoms in the case "where $R^{20}$ together with $R^{21}$ form an alkylene group having 2 to 4 carbon atoms in the general formula ($b_2$)", and a specific example of a preferable alkylene group also includes the same.

A specific example of the alkylene group having 2 to 4 carbon atoms, in the case where $R^{32}$ together with $R^{33}$ and/or $R^{35}$ together with $R^{36}$ form an alkylene group having 2 to 4 carbon atoms, among the case "where $R^{31}$ together with $R^{32}$, $R^{32}$ together with $R^{33}$, $R^{34}$ together with $R^{35}$, $R^{35}$ together with $R^{36}$ and/or $R^{33}$ together with $R^{36}$ form an alkylene group having 2 to 4 carbon atoms, in the general formula ($B_5$)", includes the same as the specific example of the alkylene group having 2 to 4 carbon atoms in the case "where $R^5$ together with $R^6$ and/or $R^7$ together with $R^{10}$ form an alkylene group having 2 to 4 carbon atoms, in the general formula ($B_1$)", and a specific example of a preferable alkyl group also includes the same.

In the case where $R^{31}$ together with $R^{32}$ form an alkylene group having 2 to 4 carbon atoms, in the general formula ($B_5$), the alkylene group together with a nitrogen atom bonding to the alkylene group form a cyclic structure of a 3 to 5 membered ring.

A specific example of the cyclic structure includes, for example, an aziridine ring, an azetidine ring, a 2-methylaziridine ring, a pyrrolidine ring, a 2-methylazetidine ring, a 3-methylazetidine ring, a 2-ethylaziridine ring, a 2,2-dimethylaziridine ring, a 2,3-dimethylaziridine ring, and among these, a pyrrolidine ring is preferable.

In the case where $R^{32}$ together with $R^{33}$ form an alkylene group having 2 to 4 carbon atoms in the general formula (Br), the alkylene group together with an —N—P—N— group bonding to the alkylene group form a cyclic structure of a 5 to 7 membered ring.

A specific example of the cyclic structure includes, for example, a tetrahydro-2H-1,3,2-diazaphosphol ring (a 1,3-diaza-2-phosphacyclopentane ring), a hexahydro-1,3,2-diazaphosphorine ring (a 1,3-diaza-2-phosphacyclohexane ring), a 1,3-diaza-4-methyl-2-phosphacyclopentane ring, a 1,3-diaza-2-phosphacycloheptane ring, a 1,3-diaza-4-methyl-2-phosphacyclohexane ring, a 1,3-diaza-5-methyl-2-phosphacyclohexane ring, a 1,3-diaza-4-ethyl-2-phosphacyclopentane ring, a 1,3-diaza-4,4-dimethyl-2-phosphacyclopentane ring, a 1,3-diaza-4,5-dimethyl-2-phosphacyclopentane ring, and among these, a hexahydro-1,3,2-diazaphosphorine ring is preferable.

In the case where $R^{34}$ together with $R^{35}$ form an alkylene group having 2 to 4 carbon atoms, in the general formula ($B_5$), the alkylene group together with a nitrogen atom bonding to the alkylene group form a cyclic structure of a 3 to 5 membered ring.

A specific example of the cyclic structure includes the same as the specific example of the cyclic structure of a 3 to 5 membered ring, formed by the alkylene group together with the nitrogen atom bonding to the alkylene group, in the case where $R^{31}$ together with $R^{32}$ form an alkylene group having 2 to 4 carbon atoms in the general formula ($B_5$), and also a specific example of a preferable cyclic structure includes the same.

In the case where $R^{35}$ together with $R^{36}$ form an alkylene group having 2 to 4 carbon atoms in the general formula ($B_5$), the alkylene group together with an —N—P—N— group bonding to the alkylene group form a cyclic structure of a 5 to 7 membered ring.

A specific example of the cyclic structure includes the same as the specific example of the cyclic structure of a 5 to 7 membered ring, formed by the alkylene group together with the —N—P—N— group bonding to the alkylene group, in the case where $R^{32}$ together with $R^{33}$ form an alkylene group having 2 to 4 carbon atoms in the general formula ($B_5$), and also a specific example of a preferable cyclic structure includes the same.

In the case where $R^{33}$ together with $R^{36}$ form an alkylene group having 2 to 4 carbon atoms in the general formula ($B_5$), the alkylene group together with a nitrogen atom bonding to the alkylene group form a cyclic structure of a 3 to 5 membered ring.

A specific example of the cyclic structure includes the same as the specific example of the cyclic structure of a 3 to 5 membered ring, formed by the alkylene group together with the nitrogen atom bonding to the alkylene group, in the case where $R^{31}$ together with $R^{32}$ form an alkylene group having 2 to 4 carbon atoms in the general formula ($B_5$), and also a specific example of a preferable cyclic structure includes the same.

A specific example of the alkylene group having 3 to 10 carbon atoms which may contain a nitrogen atom, in the case where "$R^{32}$, $R^{33}$ together with $R^{35}$ form an alkylene group having 3 to 10 carbon atoms which may contain a nitrogen atom", in the general formula ($B_5$), includes an alkylene group represented by the following general formula ($b_7$).

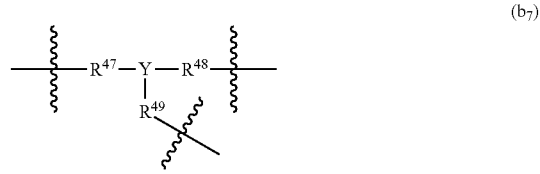

($b_7$)

(wherein $R^{47}$ to $R^{49}$ each independently represent an alkylene group having 1 to 3 carbon atoms, and Y represents a carbon atom or a nitrogen atom.)

The alkylene group having 1 to 3 carbon atoms, represented by $R^{47}$ to $R^{49}$ in the general formula ($b_7$), includes a methylene group, an ethylene group, a trimethylene group, a propylene group, and among these, an ethylene group is preferable.

It is preferable that all of $R^{47}$ to $R^{49}$ in the general formula ($b_7$) are the same alkylene group having 1 to 3 carbon atoms.

Y in the general formula ($b_7$) is preferably a nitrogen atom.

A preferable combination of $R^{47}$ to $R^{49}$ and Y in the general formula ($b_7$) is the one where all of $R^{47}$ to $R^{49}$ are the same alkylene group having 1 to 3 carbon atoms, and Y is a nitrogen atom.

In the case where $R^{32}$, $R^{33}$ together with $R^{35}$ form an alkylene group having 3 to 10 carbon atoms which may contain a nitrogen atom, in the general formula ($B_5$), the alkylene group together with the group represented by the following formula ($b_8$) bonding to the alkylene group form a bicycloalkane ring.

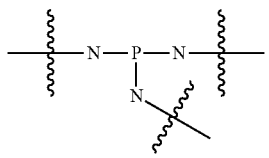
($b_8$)

A specific example of the bicycloalkane ring includes, for example, a 2,4,6,7-tetraaza-1-phosphabicyclo[2.2.2]octane ring, a 2,5,7,8-tetraaza-1-phosphabicyclo[3.2.2]nonane ring, a 2,6,7-triaza-1-phosphabicyclo[2.2.2]octane ring, a 2,5,8,9-tetraaza-1-phosphabicyclo[3.3.2]decane ring, a 2,5,8,9-tetraaza-1-phosphabicyclo[3.3.3]undecane ring, a 2,6,9,10-tetraaza-1-phosphabicyclo[4.3.3]dodecane ring, a 2,8,9-triaza-1-phosphabicyclo[3.3.3]undecane ring, a 2,6,10,11-tetraaza-1-phosphabicyclo[4.4.3]tridecane ring, a 2,6,10,11-tetraaza-1-phosphabicyclo[4.4.4]tetradecane ring, a 2,10,11-triaza-1-phosphabicyclo[4.4.4]tetradecane ring, and among these, a 2,5,8,9-tetraaza-1-phosphabicyclo[3.3.3]undecane ring is preferable.

In the general formula ($B_5$), number of hydrogen atoms bonding to the nitrogen atoms in the formula, is an integer of 0 to 4, 0 to 2 is preferable, and 0 is more preferable.

In the general formula ($B_6$), number of hydrogen atoms bonding to the nitrogen atoms in the formula, is an integer of 0 to 4, 0 to 2 is preferable, and 0 is more preferable.

A specific example of the alkyl group having 1 to 6 carbon atoms, represented by $R^{37}$ to $R^{46}$ in the general formula ($b_5$) or ($b_6$), includes the same as the specific example of the alkyl group having 1 to 6 carbon atoms in "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$ and $R^2$ to $R^4$ in the general formula (A), and a specific example of a preferable alkyl group also includes the same.

As the ammonium cation having the guanidinium group, the biguanidium group or the phosphazenium group, or the phosphonium cation, represented by $Z^+$ in the general formula (A), the ammonium cation having the guanidinium group represented by the general formula ($B_1$), the ammonium cation having the biguanidium group represented by the general formula ($B_2$), the ammonium cation having the phosphazenium group represented by the general formula ($B_3$) or ($B_4$), and the phosphonium cation represented by the general formula ($B_5$) or ($B_6$) are more preferable, and among these, the ammonium cation having the guanidinium group represented by the general formula ($B_1$), the ammonium cation having the biguanidium group represented by the general formula ($B_2$), and the phosphonium cation represented by the general formula ($B_6$) are still more preferable.

As $R^6$ in the general formula ($B_1$), a hydrogen atom, an alkyl group having 1 to 12 carbon atoms, and the one where R together with $R^6$ form an alkylene group having 2 to 4 carbon atoms are more preferable, and among these, the one where $R^6$ together with $R^6$ form an alkylene group having 2 to 4 carbon atoms, is still more preferable.

As $R^6$ in the general formula ($B_1$), an alkyl group having 1 to 12 carbon atoms, and the one where $R^5$ together with $R^6$ form an alkylene group having 2 to 4 carbon atoms are more preferable, and among these, the one where $R^5$ together with $R^6$ form the alkylene group having 2 to 4 carbon atoms is still more preferable.

As $R^7$ and $R^{10}$ in the general formula ($B_1$), an alkyl group having 1 to 12 carbon atoms, and the one where $R^7$ together with $R^{10}$ form an alkylene group having 2 to 4 carbon atoms are more preferable, and among these, the one where $R^7$ together with $R^{10}$ form an alkylene group having 2 to 4 carbon atoms is still more preferable.

As $R^8$ in the general formula ($B_1$), a hydrogen atom and an alkyl group having 1 to 12 carbon atoms are more preferable, and among these, a hydrogen atom is still more preferable.

As $R^9$ in the general formula ($B_1$), a hydrogen atom and an alkyl group having 1 to 12 carbon atoms are more preferable.

A combination of $R^5$ to $R^9$ in the general formula ($B_1$) includes a combination where $R^5$ to $R^7$ and $R^9$ each independently represent an alkyl group having 1 to 12 carbon atoms, and $R^8$ represents a hydrogen atom; a combination where $R^5$ to $R^7$ each independently represent an alkyl group having 1 to 12 carbon atoms, and $R^8$ and $R^9$ represent a hydrogen atom; a combination where $R^5$ together with $R^6$ as well as $R^7$ together with $R^{10}$ each independently form an alkylene group having 2 to 4 carbon atoms, $R^8$ represents a hydrogen atom, and $R^9$ represents an alkyl group having 1 to 12 carbon atoms; as well as a combination where $R^5$ and $R^6$ as well as $R^7$ and $R^{10}$ each independently form an alkylene group having 2 to 4 carbon atoms, and $R^8$ and $R^9$ represent a hydrogen atom; and among these, a combination where $R^5$ together with $R^6$ as well as $R^7$ together with $R^{10}$ each independently form an alkylene group having 2 to 4 carbon atoms, $R^8$ represents a hydrogen atom, and $R^9$ represents an alkyl group having 1 to 12 carbon atoms; as well as a combination where $R^5$ together with $R^6$ as well as $R^7$ together with $R^{10}$ each independently form an alkylene group having 2 to 4 carbon atoms, and $R^8$ and $R^9$ represent a hydrogen atom are preferable.

As $R^{11}$ to $R^{14}$ in the general formula ($B_2$), an alkyl group having 1 to 12 carbon atoms is more preferable.

As $R^{15}$ and $R^{18}$ in the general formula ($B_2$), a hydrogen atom or an alkyl group having 1 to 6 carbon atoms is more preferable.

As $R^{16}$ and $R^{17}$ in the general formula ($B_2$), an alkyl group having 1 to 12 carbon atoms; a phenyl group which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms; and the one where $R^{16}$ together with $R^{17}$ form an alkylene group having 2 to 4 carbon atoms, are more preferable, and among these, an alkyl group having 1 to 12 carbon atoms, a phenyl group which is substituted with a nitro group or an alkyl group having 1 to 6 carbon atoms, and the one where $R^{16}$ together with $R^{17}$ form an alkylene group having 2 to 4 carbon atoms, are still more preferable.

A combination of $R^{11}$ to $R^{18}$ in the general formula ($B_2$) includes a combination where $R^{11}$ to $R^{14}$, $R^{16}$ and $R^{17}$ each independently represent an alkyl group having 1 to 12 carbon atoms, and $R^{15}$ and $R^{18}$ represents a hydrogen atom; a combination where $R^{11}$ to $R^{15}$ and $R^{18}$ each independently represent an alkyl group having 1 to 12 carbon atoms, and $R^{16}$ together with $R^{17}$ form an alkylene group having 2 to 4 carbon atoms; a combination where $R^{11}$ to $R^{14}$ each independently represent an alkyl group having 1 to 12 carbon atoms, $R^{15}$ and $R^{18}$ represent a hydrogen atom, and $R^{16}$ and $R^{17}$ each independently represent the aryl group having 6 to 14 carbon atoms, which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms; as well as a combination where $R^{11}$ to $R^{14}$ each independently represent an alkyl group having 1 to 12 carbon atoms, $R^{15}$ and $R^{18}$ represent a hydrogen atom, either one of $R^{16}$ or $R^{17}$ represents an alkyl group having 1 to 12 carbon atoms, and the other one represents an aryl group having 6 to 14 carbon atoms, which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms.

As $R^{19}$ in the general formula ($B_3$), an alkyl group having 1 to 12 carbon atoms is more preferable.

As $Q^1$ to $Q^3$ in the general formula ($B_3$), the one where all of $Q^1$ to $Q^3$ represent the same group represented by the general formula ($b_2$) or ($b_3$), as well as the one where $Q^1$ together with $Q^2$ represent a cyclic structure represented by the general formula ($b_4$), and $Q^3$ represents the group represented by the general formula ($b_2$) or ($b_4$) are preferable, and among these, the one where all of $Q^1$ to $Q^3$ represent the same group represented by the general formula ($b_2$) or ($b_3$) is still more preferable.

As $R^{20}$ and $R^{21}$ in the general formula ($b_2$), an alkyl group having 1 to 6 carbon atoms, and the one where $R^{21}$ together with $R^{21}$ form an alkylene group having 2 to 4 carbon atoms are more preferable.

As $R^{22}$ to $R^{29}$ in the general formula ($b_3$) or ($b_4$), an alkyl group having 1 to 6 carbon atoms is more preferable.

A combination of $R^{19}$ and $Q^1$ to $Q^3$ in the general formula ($B_3$) includes a combination where $R^{19}$ represents an alkyl group having 1 to 12 carbon atoms, and all of $Q^1$ to $Q^3$ represent the group represented by the general formula ($b_3$); a combination where $R^{19}$ represents an alkyl group having 1 to 12 carbon atoms, and all of $Q^1$ to $Q^3$ represent the group represented by the general formula ($b_3$); a combination where $R^{19}$ represents an alkyl group having 1 to 12 carbon atoms, $Q^1$ together with $Q^2$ represent a cyclic structure represented by the general formula ($b_4$), and $Q^3$ represents the group represented by the general formula ($b_2$); and a combination where $R^{19}$ represents an alkyl group having 1 to 12 carbon atoms, $Q^1$ together with $Q^2$ represent a cyclic structure represented by the general formula ($b_4$), and $Q^3$ represents the group represented by the general formula ($b_3$).

As $Q^4$ to $Q^9$ in the general formula ($B_4$), the one where all of $Q^4$ to $Q^9$ represent the same group represented by the general formula (b) is preferable.

A combination of $Q^4$ to $Q^9$ in the general formula ($B_4$) includes a combination where all of $Q^4$ to $Q^9$ represent the group represented by the general formula ($b_2$); and a combination where all of $Q^4$ to $Q^9$ represent the group represented by the general formula ($b_3$), and among these, a combination where all of $Q^4$ to $Q^9$ represent the group represented by the general formula ($b_2$) is preferable.

As $R^{30}$ in the general formula ($B_5$), a hydrogen atom and the group represented by the general formula ($b_3$) are more preferable.

As $R^{31}$, $R^{34}$ and $R^{36}$ in the general formula ($B_5$), a hydrogen atom and an alkyl group having 1 to 6 carbon atoms are more preferable.

As $R^{32}$, $R^{33}$ and $R^{35}$ in the general formula ($B_5$), the one where $R^{32}$ together with $R^{33}$ form an alkylene group having 2 to 4 carbon atoms, and $R^{35}$ represents an alkyl group having 1 to 6 carbon atoms, as well as the one where $R^{32}$, $R^{33}$ together with $R^{35}$ form an alkylene group having 3 to 10 carbon atoms which may contain a nitrogen atom, are more preferable.

A combination of $R^{30}$ to $R^{36}$ in the general formula ($B_5$) includes a combination where $R^{30}$ represents a hydrogen atom, and $R^{31}$, $R^{34}$ and $R^{36}$ each independently represent an alkyl group having 1 to 12 carbon atoms, and $R^{32}$, $R^{33}$ together with $R^{35}$ form an alkylene group having 3 to 10 carbon atoms which may contain a nitrogen atom; as well as a combination where $R^{30}$ represents the group represented by the general formula ($b_3$), $R^{31}$ and $R^{35}$ each independently represent an alkyl group having 1 to 6 carbon atoms, $R^{32}$ together with $R^{33}$ form an alkylene group having 2 to 4 carbon atoms, and $R^{34}$ and $R^{36}$ represents a hydrogen atom.

As $Q^{10}$ to $Q^{13}$ in the general formula ($B_6$), the one where all of $Q^{10}$ to $Q^{13}$ represent the same group represented by the general formula ($b_5$) or ($b_6$) is more preferable, and among these, the one where all of $Q^{10}$ to $Q^{13}$ represent the same group represented by the general formula ($b_5$) is still more preferable.

As $R^{37}$ to $R^{46}$ in the general formula ($b_5$) or ($b_6$), an alkyl group having 1 to 6 carbon atoms is more preferable.

A combination of $Q^{10}$ to $Q^{13}$ in the general formula ($B_6$) includes a combination where all of $Q^{10}$ to $Q^{13}$ represent the group represented by the general formula ($b_5$); and a combination where all of $Q^{10}$ to $Q^{13}$ represent the group represented by the general formula ($b_6$), and among these, a combination where all of $Q^{10}$ to $Q^{13}$ represent the group represented by the general formula ($b_6$) is preferable.

A specific example of the borate-based anion in the compound represented by the general formula (A) of the present invention includes the anions represented by the following formulae (A-1) to (A-32). It should be noted that "the borate-based anion" represents an anion part composed of a boron anion and groups represented by $R^1$ to $R^4$ which bond to the boron anion, in the compound represented by the general formula (A).

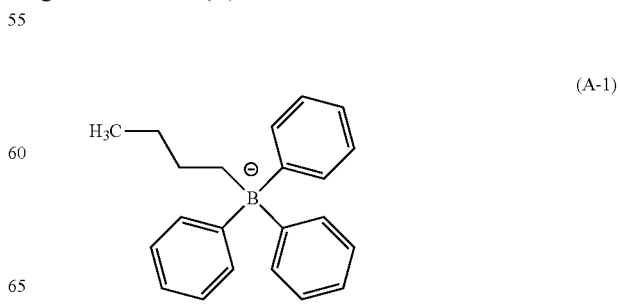

(A-1)

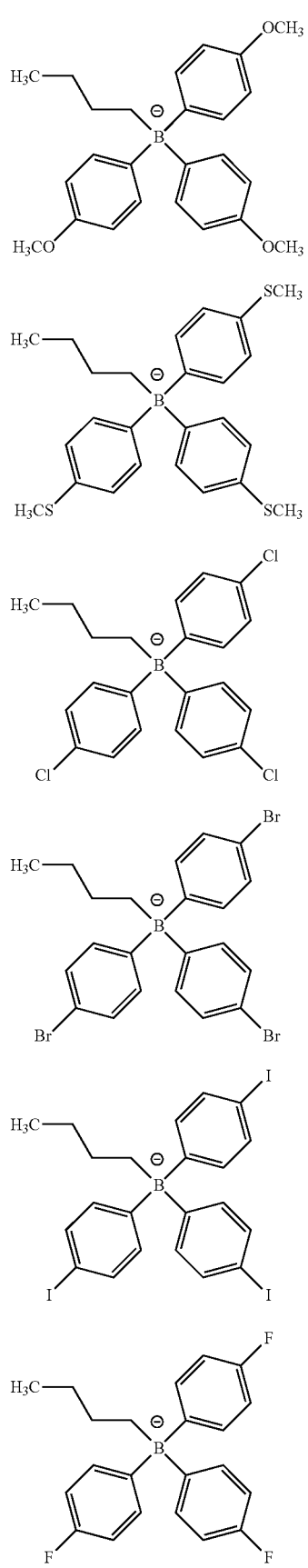
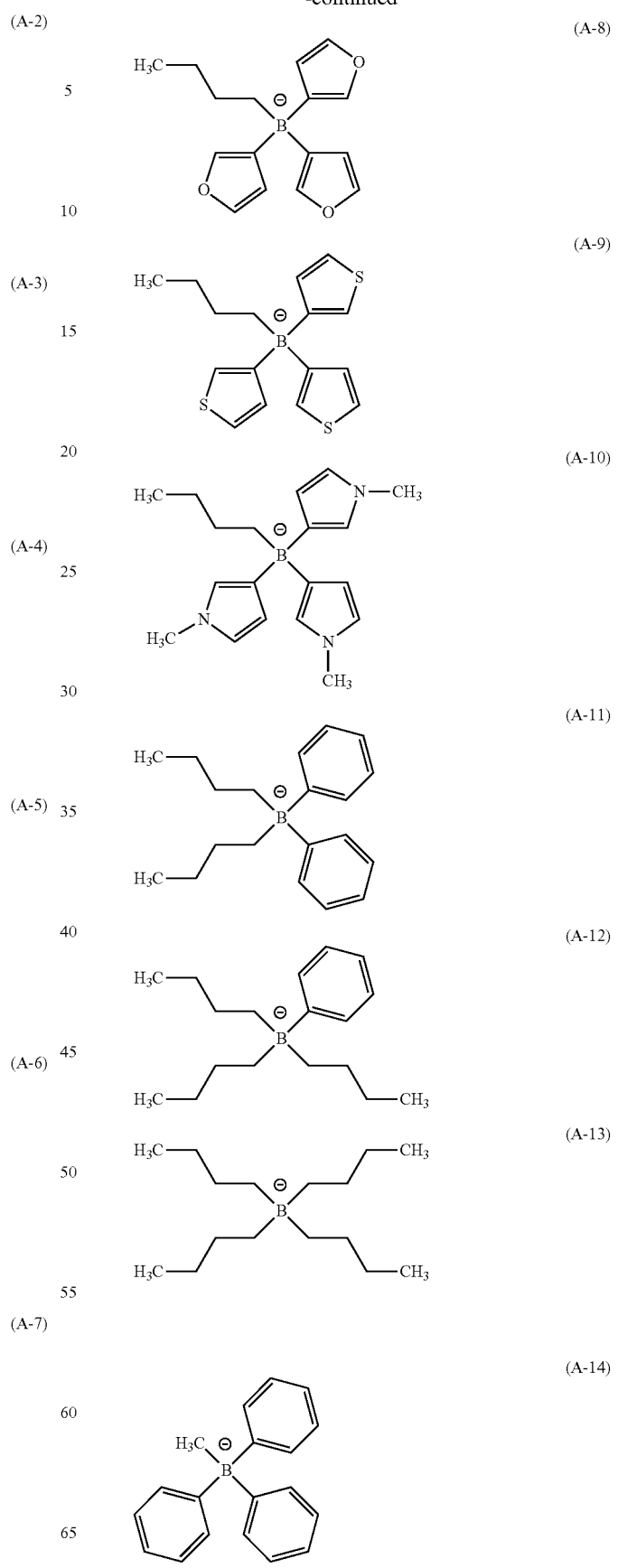

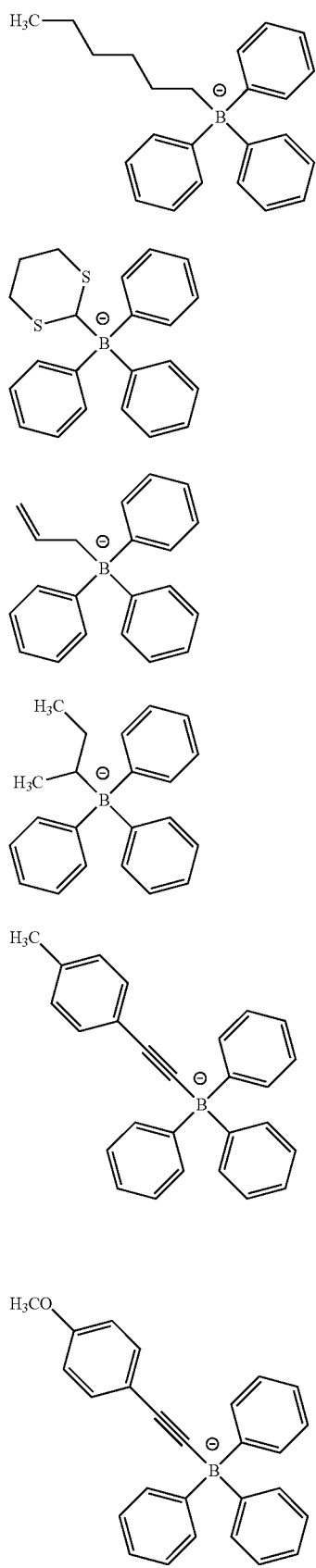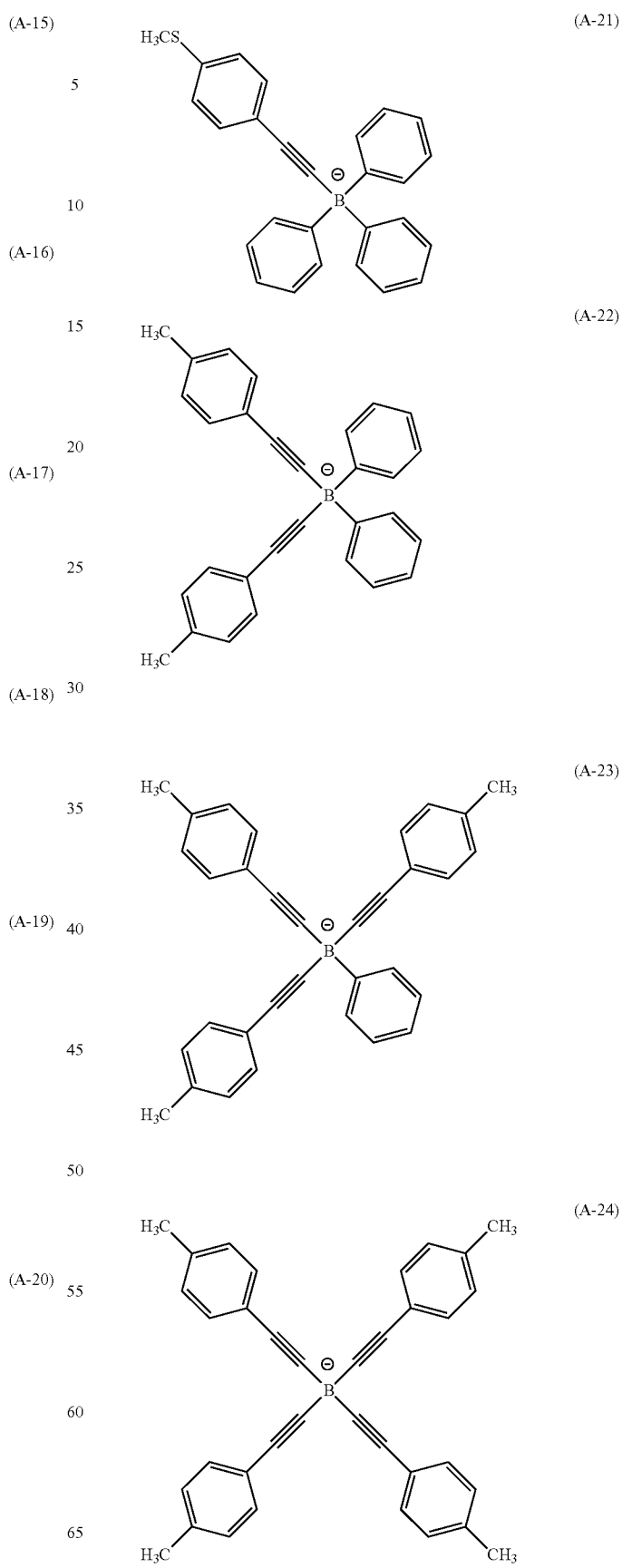

(A-25) 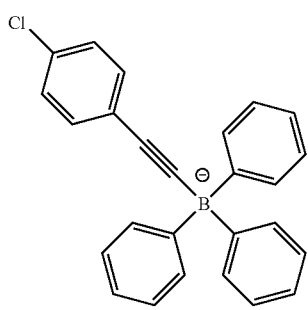
(A-26) 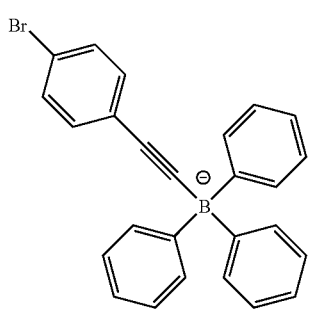
(A-27) 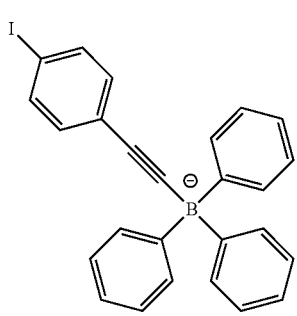
(A-28) 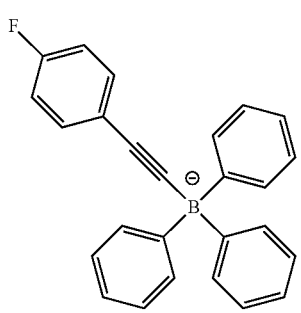
(A-29) 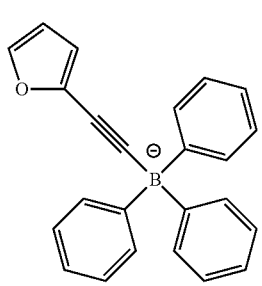
(A-30) 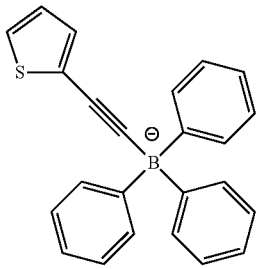
(A-31) 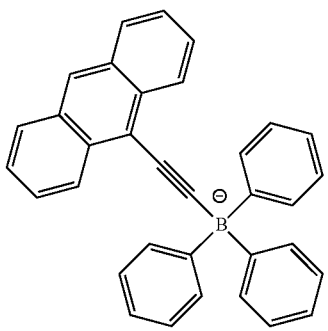
(A-32) 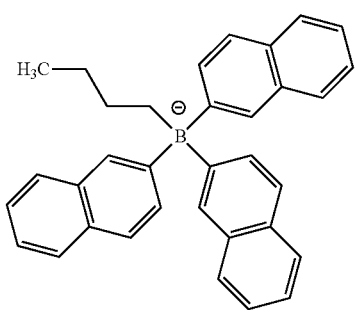
A specific example of the ammonium cation having the guanidinium group, the biguanidium group or the phosphazenium group, or the phosphonium cation represented by $Z^+$ in the general formula (A), includes the cations represented by the following formulae (B-1) to (B-18).
(B-1) 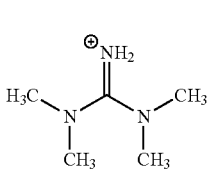
(B-2) 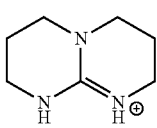
(B-3) 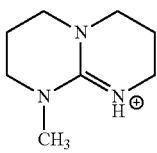

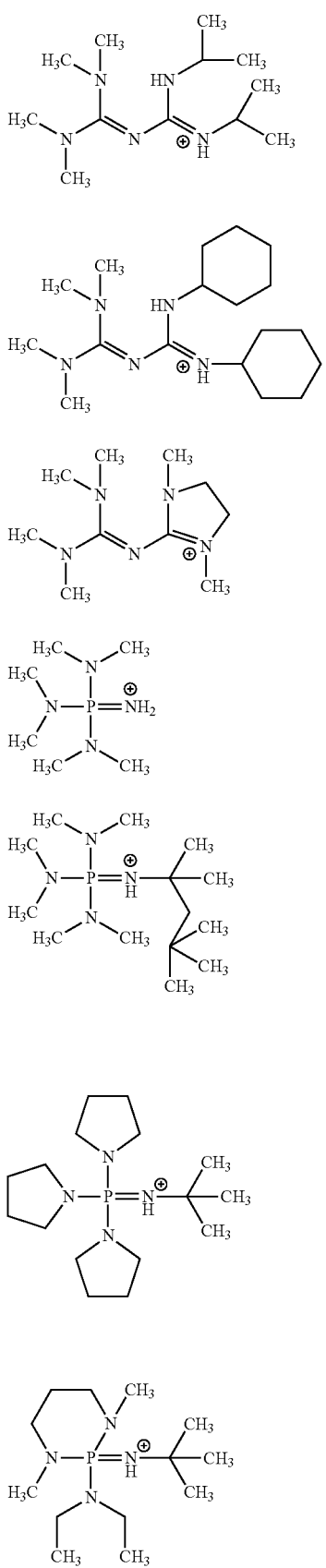

-continued

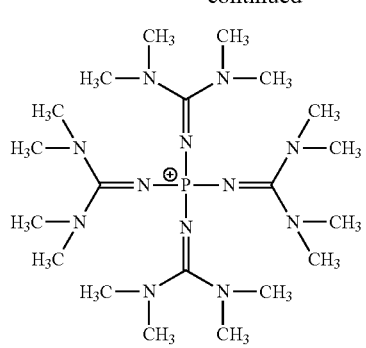
(B-16)

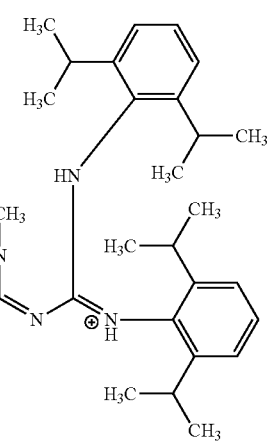
(B-17)

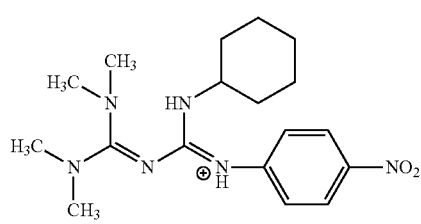
(B-18)

A more preferable specific example of the compound, represented by the general formula (A) of the present invention, includes the compound represented by the following general formula (A')

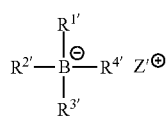
(A')

[wherein $R^{1\prime}$ represents an alkyl group having 1 to 12 carbon atoms; a phenylalkynyl group which may be substituted with a halogen atom, an alkyl group having 1 to 6 carbon atoms, an alkoxy group having 1 to 6 carbon atoms, or an alkylthio group having 1 to 6 carbon atoms; an alkenyl group having 2 to 12 carbon atoms; 2-furylethynyl group; 2-thiophenyl-ethynyl group; or 2,6-dithianyl group; all of $R^{2\prime}$ to $R^{4\prime}$ represent the same phenyl group which may be substituted with a halogen atom, an alkyl group having 1 to 6 carbon atoms, an alkoxy group having 1 to 6 carbon atoms, or an alkylthio group having 1 to 6 carbon atoms; a furanyl group; a thienyl group; or an N-alkyl-substituted pyrrolyl group; $Z^+$ represents an ammonium cation having a guanidinium group represented by the following general formula ($B_1'$), an ammonium cation having a biguanidium group represented by the following general formula ($B_2'$), an ammonium cation having a phosphazenium group represented by the general formula ($B_3'$) or ($B_4'$), or a phosphonium cation represented by the following general formula ($B_5'$) or ($B_6'$).

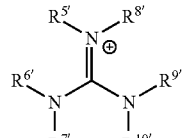
($B_1'$)

(wherein $R^{5\prime}$ to $R^{10\prime}$ each independently represent a hydrogen atom or an alkyl group having 1 to 12 carbon atoms, and $R^{5\prime}$ together with $R^{6\prime}$ and/or $R^{7\prime}$ together with $R^{10\prime}$ may form an alkylene group having 2 to 4 carbon atoms, and number of hydrogen atoms among $R^{5\prime}$ to $R^{10\prime}$ is 1 or 2.)

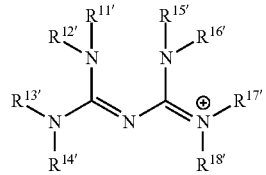
($B_2'$)

(wherein $R^{11\prime}$ to $R^{14\prime}$ each independently represent an alkyl group having 1 to 12 carbon atoms, $R^{15\prime}$ and $R^{18\prime}$ each independently represent a hydrogen atom or an alkyl group having 1 to 12 carbon atoms, and $R^{16\prime}$ and $R^{17\prime}$ each independently represent an alkyl group having 1 to 12 carbon atoms, or a phenyl group which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms, and $R^{16\prime}$ together with $R^{17\prime}$ may form an alkylene group having 2 to 4 carbon atoms.)

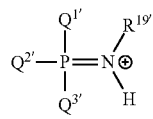
($B_3'$)

{wherein $R^{19\prime}$ represents a hydrogen atom or an alkyl group having 1 to 12 carbon atoms, all of $Q^{1\prime}$ to $Q^{3\prime}$ represent the same group represented by the following general formula ($b_2'$) or ($b_3'$), or $Q^{1\prime}$ together with $Q^{2\prime}$ represent a cyclic structure represented by the following general formula ($b_4'$), and number of hydrogen atoms bonding to the nitrogen atoms in the formula is 1 to 3.

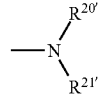
($b_2'$)

(wherein $R^{20'}$ and $R^{21'}$ each independently represent a hydrogen atom or an alkyl group having 1 to 6 carbon atoms, and $R^{20'}$ together with $R^{21'}$ may form an alkylene group having 2 to 4 carbon atoms.)

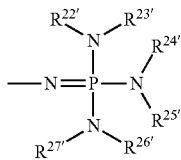

(b$_3$')

(wherein $R^{22'}$ to $R^{27'}$ each independently represent a hydrogen atom or an alkyl group having 1 to 6 carbon atoms.)

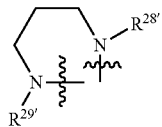

(b$_4$')

(wherein $R^{28'}$ and $R^{29'}$ each independently represent a hydrogen atom or an alkyl group having 1 to 6 carbon atoms.)}

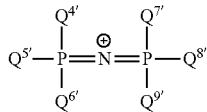

(B$_4$')

(wherein all of $Q^{4'}$ to $Q^{9'}$ represent the same group represented by the general formula (b$_2$') or (b$_3$'), and number of hydrogen atoms bonding to the nitrogen atoms in the formula is 0 to 2.)

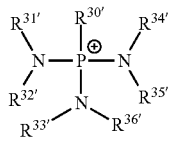

(B$_5$')

(wherein $R^{30'}$ represents a hydrogen atom or a group represented by the general formula (b$_2$') or (b$_3$'), $R^{31'}$ to $R^{36'}$ each independently represent a hydrogen atom or an alkyl group having 1 to 6 carbon atoms; or $R^{31'}$ together with $R^{32'}$, $R^{32'}$ together with $R^{33'}$, $R^{34'}$ together with $R^{35'}$, $R^{35'}$ together with $R^{36'}$ and/or $R^{33'}$ together with $R^{36'}$ may form an alkylene group having 2 to 4 carbon atoms; and $R^{32'}$, $R^{33'}$ together with $R^{35'}$ may form an alkylene group having 3 to 10 carbon atoms which may contain a nitrogen atom, and number of hydrogen atoms bonding to the nitrogen atoms in the formula is 0 to 2.)

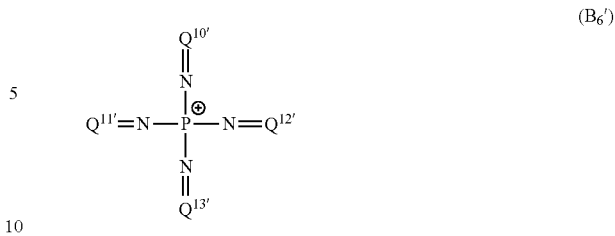

(B$_6$')

{wherein $Q^{10'}$ to $Q^{13'}$ each independently represent a group represented by the general formula (b$_5$') or (b$_6$'), and number of hydrogen atoms bonding to the nitrogen atoms in the formula is 0 to 2.

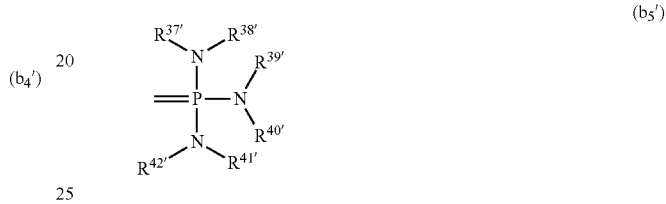

(b$_5$')

(wherein $R^{37'}$ to $R^{42'}$ each independently represent a hydrogen atom or an alkyl group having 1 to 6 carbon atoms.)

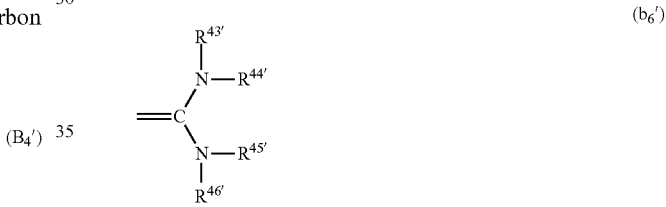

(b$_6$')

(wherein $R^{43'}$ to $R^{46'}$ each independently represent a hydrogen atom or an alkyl group having 1 to 6 carbon atoms.)}]

A specific example of each functional group ($R^{1'}$ to $R^{46'}$ and $Q^{1'}$ to $Q^{13'}$) in the general formulae (A') to (b$_6$') includes the same as the specific example of corresponding each functional group ($R^1$ to $R^{46}$ and $Q^1$ to $Q^{13}$) described in the general formulae (A) to (b$_6$), and a preferable specific example also includes the same. It should be noted that each functional group to be described below is different from each functional group corresponding to the one described in the general formulae (A) to (b$_6$).

The phenylalkynyl group having 8 to 12 carbon atoms in "a phenylalkynyl group having 8 to 12 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^{1'}$ in the general formula (A'), is a group where the alkynyl group moiety may be any of a straight chained or a branched one, and among these, the straight chained one is preferable. A specific example of the phenylalkynyl group includes, for example, a phenylethynyl group, a 3-phenyl-1-propyne-1-yl group, a 3-phenyl-2-propyne-1-yl group (a 3-phenylpropargyl group), a 4-phenyl-1-butyne-1-yl group, a 4-phenyl-2-butyne-1-yl group, a 4-phenyl-3-butyne-1-yl group, a 3-phenyl-1-butyne-1-yl group, a 4-phenyl-3-butyne-2-yl group, a 5-phenyl-1-pentyne-1-yl group, a 5-phenyl-2-pentyne-1-yl group, a 5-phenyl-3-pentyne-1-yl group, a 5-phenyl-4-pentyne-1-yl group, a 4-phenyl-1-pentyne-1-yl group, a 4-phenyl-2-pentyne-1-yl group, a 3-phenyl-1-pentyne-1-yl group, a 5-phenyl-3-pentyne-2-yl group, a 5-phenyl-4-pentyne-2-yl group, a 5-phenyl-4-pentyne-3-yl group, a 4-phenyl-3-methyl-1-butyne-1-yl group, a 4-phenyl-2-methyl-3-butyne-1-yl group, a 3-phenyl-3-methyl-1-butyne-1-yl group, a 6-phenyl-1-hexyne-1-yl group, a 6-phenyl-2-hexyne-1-yl group, a 6-phenyl-3-hexyne-1-yl group, a 6-phenyl-4-hexyne-1-yl group, a 6-phenyl-5-hexyne-1-yl group, a 5-phenyl-1-hexyne-1-yl group, a 5-phenyl-2-hexyne-1-yl group, a 5-phenyl-3-hexyne-1-yl group, a 5-phenyl-3-hexyne-2-yl group, a 3-phenyl-1-hexyne-1-yl group, a 3-phenyl-2-hexyne-1-yl group, a 6-phenyl-3-hexyne-2-yl group, a 6-phenyl-4-hexyne-2-yl group, a 6-phenyl-4-hexyne-3-yl group, a 6-phenyl-5-hexyne-2-yl group, a 6-phenyl-5-hexyne-3-yl group, a 6-phenyl-5-hexyne-4-yl group, a 5-phenyl-3-hexyne-2-yl group, a 4-phenyl-4-methyl-1-pentyne-1-yl group, a 4-phenyl-3-methyl-1-pentyne-1-yl group, a 4-phenyl-4-methyl-2-pentyne-1-yl group, a 3-phenyl-3-methyl-2-pentyne-1-yl group, a 4-phenyl-3-methyl-1-butyne-1-yl group, and the like. Among these phenylalkynyl groups, a phenylalkynyl group having 8 to 12 carbon atoms in which the alkynyl group moiety is a straight chained one, and a phenyl group is bonded at the terminal thereof, for example, a phenylethynyl group, a 3-phenyl-1-propyne-1-yl group, a 3-phenyl-2-propyne-1-yl group (a 3-phenylpropargyl group), 4-phenyl-1-butyne-1-yl group, a 4-phenyl-2-butyne-1-yl group, a 4-phenyl-3-butyne-1-yl group, a 5-phenyl-1-pentyne-1-yl group, a 5-phenyl-2-pentyne-1-yl group, a 5-phenyl-3-pentyne-1-yl group, a 5-phenyl-4-pentyne-1-yl group, a 6-phenyl-1-hexyne-1-yl group, a 6-phenyl-2-hexyne-1-yl group, a 6-phenyl-3-hexyne-1-yl group, a 6-phenyl-4-hexyne-1-yl group, a 6-phenyl-5-hexyne-1-yl group, and the like, is preferable, and among these, a phenylethynyl group is still more preferable. It should be noted that number of carbon atoms in the phenylalkynyl group shown here means number of carbon atoms constituting the phenylalkynyl group, and number of carbon atoms constituting a substituent should not be included in number of carbon atoms represented by "8 to 12 carbon atoms" in the phenylalkynyl group having 8 to 12 carbon atoms.

As the phenylalkynyl group having 8 to 12 carbon atoms, in "a phenylalkynyl group having 8 to 12 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^{1'}$ in the general formula (A'), a phenylalkynyl group substituted with one or more substituents (a halogen atom, an alkyl group having 1 to 6 carbon atoms, an alkoxy group having 1 to 6 carbon atoms, or an alkylthio group having 1 to 6 carbon atoms) is preferable, and among these, a phenylalkynyl group substituted with either one of a halogen atom, an alkyl group having 1 to 6 carbon atoms, an alkoxy group having 1 to 6 carbon atoms, or an alkylthio group having 1 to 6 carbon atoms, at one binding site, is more preferable, and among these, a phenylalkynyl group substituted with an alkyl group having 1 to 6 carbon atoms, at one binding site, is still more preferable.

A specific example of "a phenylalkynyl group having 8 to 12 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^{1'}$ in the general formula (A) includes the same as the specific example of "a phenylalkynyl group having 8 to 12 carbon atoms which may be substituted with a halogen atom, an alkyl group having 1 to 6 carbon atoms, an alkoxy group having 1 to 6 carbon atoms, or an alkylthio group having 1 to 6 carbon atoms", described in the specific example of "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$ in the general formula (A).

A preferable specific example among the phenylalkynyl groups includes the same as the specific example of "a phenylethynyl group which may be substituted with a halogen atom, an alkyl group having 1 to 6 carbon atoms, an alkoxy group having 1 to 6 carbon atoms, or an alkylthio group having 1 to 6 carbon atoms", described in the specific example of "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$ in the general formula (A).

A more preferable specific example among the phenylalkynyl groups includes the same as the specific example of "a phenylethynyl group which is substituted with either one of a halogen atom, an alkyl group having 1 to 6 carbon atoms, an alkoxy group having 1 to 6 carbon atoms, or an alkylthio group having 1 to 6 carbon atoms, at one binding site", described in the specific example of "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$ in the general formula (A).

A still more preferable specific example among the phenylalkynyl groups includes the same as the specific example of "a phenylethynyl group which is substituted with an alkyl group having 1 to 6 carbon atoms, at one binding site", described in the specific example of "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^1$ in the general formula (A).

As $R^{1'}$ in the general formula (A'), an alkyl group having 1 to 12 carbon atoms, and a phenylalkynyl group having 8 to 12 carbon atoms which may be substituted with a halogen atom, an alkyl group having 1 to 6 carbon atoms, an alkoxy group having 1 to 6 carbon atoms, or an alkylthio group having 1 to 6 carbon atoms is more preferable, and among these, an alkyl group having 1 to 12 carbon atoms, and a phenylethynyl group which may be substituted with a halogen atom, an alkyl group having 1 to 6 carbon atoms, an alkoxy group having 1 to 6 carbon atoms, or an alkylthio group having 1 to 6 carbon atoms is still more preferable, and among these, an alkyl group having 1 to 12 carbon atoms, and a phenylethynyl group which is substituted with either one of a halogen atom, an alkyl group having 1 to 6 carbon atoms, an alkoxy group having 1 to 6 carbon atoms, or an alkylthio group having 1 to 6 carbon atoms, at one binding site, is particularly preferable.

As $R^{2'}$ to $R^{4'}$ in the general formula (A'), it is preferable that all of $R^{2'}$ to $R^{4'}$ are the same phenyl group which may be substituted with a halogen atom, an alkyl group having 1 to 6 carbon atoms, an alkoxy group having 1 to 6 carbon atoms, and an alkylthio group having 1 to 6 carbon atoms, and among these, it is still more preferable that all of $R^{2'}$ to $R^{4'}$ are the same unsubstituted phenyl group.

As the phenyl group in "a phenyl group which may be substituted with a halogen atom, an alkyl group having 1 to 6 carbon atoms, an alkoxy group having 1 to 6 carbon atoms, or an alkylthio group having 1 to 6 carbon atoms", represented by $R^{2'}$ to $R^{4'}$ in the general formula (A'), an unsubstituted phenyl group is preferable.

A specific example of "a phenyl group which may be substituted with a halogen atom, an alkyl group having 1 to 6 carbon atoms, an alkoxy group having 1 to 6 carbon atoms, or an alkylthio group having 1 to 6 carbon atoms", represented by $R^{2'}$ to $R^{4'}$ in the general formula (A), includes the same as the specific example of "a phenyl group which may be substituted with a halogen atom, an alkyl group having 1 to 6 carbon atoms, an alkoxy group having 1 to 6 carbon atoms, or an alkylthio group having 1 to 6 carbon atoms", described in the specific example of "an aryl group having 8 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms" represented by $R^2$ to $R^4$ in the general formula (A).

Among the phenyl groups, an unsubstituted phenyl group is preferable.

Combinations of $R^{1'}$ to $R^{4'}$ in the general formula (A') include the combinations described in the following Table 2.

TABLE 2

| $R^1$ | $R^2$ | $R^3$ | $R^4$ |
|---|---|---|---|
| alkyl group having 1 to 12 carbon atoms | | functional group D furanyl group thienyl group N-alkyl-substituted pyrollyl group | |
| functional group C | | functional group D | |
| alkenyl group having 2 to 12 carbon atoms | | functional group D | |
| 2,6-dithianyl group | | functional group D | |
| 2-furylthienyl group | | functional group D | |
| 2-thiophenylethynyl group | | functional group D | |

In the Table, the functional group C represents a phenylalkynyl group having 8 to 12 carbon atoms which may be substituted with a halogen atom, an alkyl group having 1 to 6 carbon atoms, an alkoxy group having 1 to 6 carbon atoms, or an alkylthio group having 1 to 6 carbon atoms, and the functional group D represents a phenyl group which may be substituted with a halogen atom, an alkyl group having 1 to 6 carbon atoms, an alkoxy group having 1 to 6 carbon atoms, or an alkylthio group having 1 to 6 carbon atoms.

"Number of hydrogen atoms among $R^{5'}$ to $R^{10'}$ is 1 or 2" in the general formula ($B_1'$) means that, among $R^{5'}$ to $R^{10'}$, number of R, where the group represented by $R^{5'}$ to $R^{10'}$ is a hydrogen atom, is 1 or 2.

Number of hydrogen atoms among $R^{5'}$ to $R^{10'}$ in the general formula ($B_1'$), is 1 or 2, and 1 is preferable.

A specific example of "a phenyl group which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms", represented by $R^{16'}$ and $R^{17'}$ in the general formula ($B_2'$), includes the same as the specific example of "a phenyl group which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms", described in the specific example of "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$).

A preferable specific example among the phenyl groups, includes the same as the specific example of "a phenyl group which is substituted with at least one kind of substituents selected from a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms", described in the specific example of "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$).

A more preferable specific example among the phenyl groups, includes the same as the specific example of "a phenyl group which is substituted with only a nitro group or only an alkyl group having 1 to 6 carbon atoms", described in the specific example of "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$).

In the general formula ($B_3'$), number of hydrogen atoms bonding to the nitrogen atoms in the formula, is an integer of 1 to 3, and 1 is preferable. It should be noted that number of hydrogen atoms shown here is always 1 or larger, because the nitrogen atom in the general formula ($B_3'$) already has one hydrogen atom.

In the general formula ($B_4'$), number of hydrogen atoms bonding to the nitrogen atoms in the formula, is an integer of 0 to 2, and 0 is preferable.

In the general formula ($B_5'$), number of hydrogen atoms bonding to the nitrogen atoms in the formula, is an integer of 0 to 2, and 0 is preferable.

In the general formula ($B_6'$), number of hydrogen atoms bonding to the nitrogen atoms in the formula, is an integer of 0 to 2, and 0 is preferable.

As the ammonium cation having the guanidinium group represented by the general formula ($B_1'$), the ammonium cation having the biguanidium group represented by the general formula ($B_2'$), the ammonium cation having the phosphazenium group represented by the general formula ($B_3'$) or ($B_4'$), or the phosphonium cation represented by the general formula ($B_5'$) or ($B_6'$), represented by $Z'^+$ in the general formula (A'), the ammonium cation having the guanidinium group represented by the general formula ($B_1'$), the ammonium cation having the biguanidium group represented by the general formula ($B_2'$), and the phosphonium cation represented by the general formula ($B_6'$) are more preferable.

As $R^{5'}$ and $R^{6'}$ in the general formula ($B_1'$), the one where $R^{5'}$ together with $R^{6'}$ form an alkylene group having 2 to 4 carbon atoms is more preferable.

As $R^{7'}$ and $R^{10'}$ in the general formula ($B_1'$), the one where $R^{7'}$ together with $R^{10'}$ form an alkylene group having 2 to 4 carbon atoms is more preferable.

As $R^{8'}$ in the general formula ($B_1'$), a hydrogen atom is more preferable.

As $R^{9'}$ in the general formula ($B_1'$), a hydrogen atom and an alkyl group having 1 to 6 carbon atoms are more preferable.

A combination of $R^{5'}$ to $R^{9'}$ in the general formula ($B_1'$) includes a combination where $R^{5'}$ to $R^{7'}$ and $R^{9'}$ each independently represent an alkyl group having 1 to 12 carbon atoms, and $R^8$ represents a hydrogen atom; a combination where $R^{5'}$ to $R^7$ each independently represent an alkyl group having 1 to 12 carbon atoms, and $R^8$ and $R^{9'}$ represent a hydrogen atom; a combination where $R^{5'}$ together with $R^{6'}$ and $R^{7'}$ together with $R^{ill}$ each independently form an alkylene group having 2 to 4 carbon atoms, $R^{8'}$ represents a hydrogen atom, and $R^{9'}$ represents an alkyl group having 1 to 12 carbon atoms; as well as a combination where $R^{5'}$ together with $R^{6'}$ and $R^7$ together with $R^{10'}$ each independently form an alkylene group having 2 to 4 carbon atoms, and $R^8$ and $R^{9'}$ represent a hydrogen atom; and among these, a combination where $R^{5'}$ together with $R^{6'}$ and $R^{7'}$ together with $R^{10'}$ each independently form an alkylene group having 2 to 4 carbon atoms, $R^{8'}$ represents a hydrogen atom, and $R^{9'}$ represents an alkyl group having 1 to 12 carbon atoms; as well as a combination where $R^{5'}$ together with $R^{6'}$ and $R^7$ together with $R^{10'}$ each independently form an alkylene group having 2 to 4 carbon atoms, $R^{8'}$ and $R^{9'}$ represent a hydrogen atom are preferable.

As $R^{11'}$ to $R^{14'}$ in the general formula ($B_2'$), an alkyl group having 1 to 6 carbon atoms is more preferable.

As $R^{15'}$ to $R^{18'}$ in the general formula ($B_2'$), a hydrogen atom or an alkyl group having 1 to 6 carbon atoms is more preferable.

As $R^{16'}$ and $R^{17'}$ in the general formula ($B_2'$), an alkyl group having 1 to 6 carbon atoms, a phenyl group which is substituted with only a nitro group or only an alkyl group having 1 to 6 carbon atoms, and the one where $R^{16'}$ together with $R^{17'}$ form an alkylene group having 2 to 4 carbon atoms, are more preferable.

A combination of $R^{11'}$ to $R^{18'}$ in the general formula ($B_2'$) includes a combination where $R^{11'}$ to $R^{14'}$, $R^{16'}$ and $R^{17'}$ each independently represent an alkyl group having 1 to 12 carbon atoms, and $R^{15'}$ and $R^{18'}$ represent a hydrogen atom; a combination where $R^{11'}$ to $R^{15'}$, and $R^{18'}$ each independently represent an alkyl group having 1 to 12 carbon atoms, and $R^{16'}$ together with $R^{17'}$ form an alkylene group having 2 to 4 carbon atoms; a combination where $R^{11'}$ to $R^{14'}$ each independently represent an alkyl group having 1 to 12 carbon atoms, $R^{15'}$ and $R^{18'}$ represent a hydrogen atom, and $R^{16'}$ and $R^{17'}$ each independently represent a phenyl group which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms; as well as a combination where $R^{11'}$ to $R^{14'}$ each independently represent an alkyl group having 1 to 12 carbon atoms, $R^{15'}$ and $R^{18'}$ represent a hydrogen atom, either one of $R^{16'}$ and $R^{17'}$ represents an alkyl group having 1 to 12 carbon atoms, and the other one represents a phenyl group which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms.

As $R^{19'}$ in the general formula ($B_3'$), a hydrogen atom and an alkyl group having 1 to 8 carbon atoms are more preferable, and among these, an alkyl group having 1 to 8 carbon atoms is more preferable.

As $Q^{1'}$ to $Q^{3'}$ in the general formula ($B_3'$), the one where all of $Q^{1'}$ to $Q^{3'}$ represent the same group represented by the general formula ($b_2'$) or ($b_3'$) is more preferable.

As $R^{20'}$ and $R^{21'}$ in the general formula ($b_2'$), an alkyl group having 1 to 6 carbon atoms, and the one where $R^{20'}$ together with $R^{21'}$ form an alkylene group having 2 to 4 carbon atoms are more preferable.

As $R^{22'}$ to $R^{29'}$ in the general formula ($b_3'$) or ($b_4'$), an alkyl group having 1 to 6 carbon atoms is more preferable.

A combination of $R^{19'}$ and $Q^{1'}$ to $Q^{3'}$ in the general formula ($B_3'$) includes a combination where $R^{19'}$ represents an alkyl group having 1 to 12 carbon atoms, and all of $Q^{1'}$ to $Q^{3'}$ represent the group represented by the general formula ($b_2'$); a combination where $R^{19'}$ represents an alkyl group having 1 to 12 carbon atoms, and all of $Q^{1'}$ to $Q^{3'}$ represent the group represented by the general formula ($b_3'$); a combination where $R^{19'}$ represents an alkyl group having 1 to 12 carbon atoms, and $Q^{1'}$ together with $Q^{2'}$ represent a cyclic structure represented by the general formula ($b_4$), and $Q^{3'}$ represents the group represented by the general formula ($b_2$); and a combination where $R^{19'}$ represents an alkyl group having 1 to 12 carbon atoms, and $Q^{1'}$ together with $Q^{2'}$ represent a cyclic structure represented by the general formula ($b_4'$), and $Q^{3'}$ represents the group represented by the general formula ($b_3'$).

As $Q^{4'}$ to $Q^{9'}$ in the general formula ($B_4'$), the one where all of $Q^{4'}$ to $Q^{9'}$ represent the same group represented by the general formula ($b_2'$) is more preferable.

A combination of $Q^{4'}$ to $Q^{9'}$ in the general formula ($B_4'$) includes a combination where all of $Q^{4'}$ to $Q^{9'}$ represent the group represented by the general formula ($b_2$); and a combination where all of $Q^{4'}$ to $Q^{9'}$ represent the group represented by the general formula ($b_3$); and among these, a combination where all of $Q^{4'}$ to $Q^{9'}$ represent the group represented by the general formula ($b_2$) is preferable.

As $R^{30'}$ in the general formula ($B_5'$), a hydrogen atom and the group represented by the general formula ($b_3'$) are more preferable.

As $R^{31'}$, $R^{34'}$ and $R^{36'}$ in the general formula ($B_5'$), a hydrogen atom and an alkyl group having 1 to 6 carbon atoms are more preferable.

As $R^{32'}$, $R^{33'}$ and $R^{35'}$ in the general formula ($B_5'$), the one where $R^{32'}$ together with $R^{33'}$ form an alkylene group having 2 to 4 carbon atoms, $R^{35'}$ represents an alkyl group having 1 to 6 carbon atoms; as well as the one where $R^{32'}$, $R^{33'}$ together with $R^{35'}$ form an alkylene group having 3 to 10 carbon atoms which may contain a nitrogen atom; are more preferable.

A combination of $R^{30'}$ to $R^{36'}$ in the general formula ($B_5'$) includes a combination where $R^{30'}$ represents a hydrogen atom, $R^{31'}$, $R^{34'}$ and $R^{36'}$ each independently represent an alkyl group having 1 to 12 carbon atoms, and $R^{32'}$, $R^{33'}$ together with $R^{35'}$ form an alkylene group having 3 to 10 carbon atoms which may contain a nitrogen atom; as well as a combination where $R^{30'}$ represents the group represented by the general formula ($b_3'$), $R^{31'}$ and $R^{35'}$ each independently represent an alkyl group having 1 to 6 carbon atoms, $R^{32'}$ together with $R^{33'}$ form an alkylene group having 2 to 4 carbon atoms, and $R^{34'}$ and $R^{35'}$ represent a hydrogen atom.

As $Q^{10'}$ to $Q^{3'}$ in the general formula ($B_6'$), a combination where all of $Q^{10'}$ to $Q^{13'}$ represent the same group represented by the general formula ($b_5'$) or ($b_6'$) is more preferable, and among these, a combination where all of $Q^{10'}$ to $Q^{13'}$ represent the same group represented by the general formula ($b_6'$) is still more preferable.

As $R^{37'}$ to $R^{46'}$ in the general formula ($b_5'$) or ($b_6'$), an alkyl group having 1 to 6 carbon atoms is more preferable.

A combination of $Q^{10'}$ to $Q^{13'}$ in the general formula ($B_6'$) includes a combination where all of $Q^{10'}$ to $Q^{13'}$ represent the group represented by the general formula ($b_5'$); and a combination where all of $Q^{10'}$ to $Q^{13'}$ represent the group represented by the general formula ($b_6'$); and among these, a combination where all of $Q^{10'}$ to $Q^{13'}$ represent the group represented by the general formula ($b_6'$) is preferable.

A specific example of the borate-based anion in the compound represented by the general formula (A') includes the anions represented by the formulae (A-1), (A-2), (A-3), (A-4), (A-5), (A-6), (A-7), (A-8), (A-9), (A-10), (A-14), (A-15), (A-18), (A-19), (A-20), (A-21), (A-25), (A-26), (A-27) and (A-28).

A specific example of the ammonium cation having the guanidinium group represented by the general formula ($B_1'$), the ammonium cation having the biguanidium group represented by the general formula ($B_2'$), the ammonium cation having the phosphazenium group represented by the general formula ($B_3'$) or ($B_4'$), or the phosphonium cation represented by the general formula ($B_5'$) or ($B_6'$), represented by $Z^+$ in the compound represented by the general formula (A'), includes the cations represented by the formulae (B-1) to (B-18).

A more preferable specific example of the compound represented by the general formula (A') of the present invention includes the compound represented by the following general formula (A").

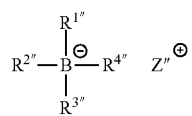

(A")

[wherein $R^{1''}$ represents an alkyl group having 1 to 12 carbon atoms, or a phenylethynyl group which may be substituted with a halogen atom, an alkyl group having 1 to 6 carbon atoms, an alkoxy group having 1 to 6 carbon atoms, or an alkylthio group having 1 to 6 carbon atoms; all of $R^{2''}$ to $R^{4''}$ represent the same phenyl group which may be substituted with a halogen atom, an alkyl group having 1 to 6 carbon atoms, an alkoxy group having 1 to 6 carbon atoms, or an alkylthio group having 1 to 6 carbon atoms; $Z''^+$ represents an ammonium cation having a guanidinium group represented by the following general formula ($B_1''$), an ammonium cation having a biguanidium group represented by the following general formula ($B_2''$), or a phosphonium cation represented by the following general formula ($B_6''$).

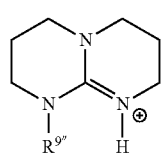

($B_1''$)

(wherein $R^{9''}$ represents a hydrogen atom or an alkyl group having 1 to 12 carbon atoms.)

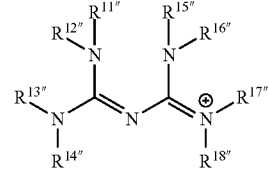

($B_2''$)

(wherein $R^{11''}$ to $R^{14''}$ each independently represent an alkyl group having 1 to 12 carbon atoms, $R^{15''}$ and $R^{18''}$ each independently represent a hydrogen atom or an alkyl group having 1 to 12 carbon atoms, $R^{16''}$ and $R^{17''}$ each independently represent an alkyl group having 1 to 12 carbon atoms, or a phenyl group substituted with only a nitro group or only an alkyl group having 1 to 6 carbon atoms, and $R^{16''}$ together with $R^{17''}$ may form an alkylene group having 2 to 4 carbon atoms.)

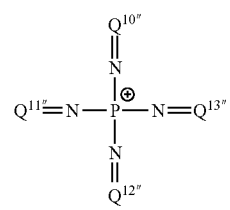

($B_6''$)

{wherein all of $Q^{10''}$ to $Q^{13''}$ represent the same group represented by the following general formula ($b_5''$) or ($b_6''$).

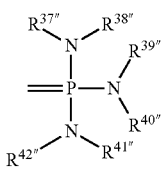

($b_5''$)

(wherein $R^{37''}$ to $R^{42''}$ each independently represent an alkyl group having 1 to 6 carbon atoms.)

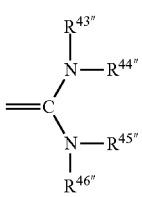

($b_6''$)

(wherein $R^{43''}$ to $R^{46''}$ each independently represent an alkyl group having 1 to 6 carbon atoms.)}]

A specific example of each functional group ($R^{1''}$ to $R^{46''}$ and $Q^{10''}$ to $Q^{13''}$) in the general formulae (A") to ($b_6''$) includes the same as the specific example of corresponding each functional group ($R^1$ to $R^{46}$ and $Q^1$ to $Q^{13}$) described in the general formulae (A) to ($b_6$), and a preferable specific example also includes the same.

As the phenylethynyl group in "a phenylethynyl group which may be substituted with a halogen atom, an alkyl group having 1 to 6 carbon atoms, an alkoxy group having 1 to 6 carbon atoms, or an alkylthio group having 1 to 6 carbon atoms", represented by $R^{1''}$ in the general formula (A"), a phenylethynyl group substituted with a substituent (a halogen atom, an alkyl group having 1 to 6 carbon atoms, an alkoxy group having 1 to 6 carbon atoms, or an alkylthio group having 1 to 6 carbon atoms) is preferable, and among these, a phenylethynyl group substituted with any one of a halogen atom, an alkyl group having 1 to 6 carbon atoms, an alkoxy group having 1 to 6 carbon atoms, or an alkylthio group having 1 to 6 carbon atoms, at one binding site, is more preferable, and among these, a phenylethynyl group substituted with an alkyl group having 1 to 6 carbon atoms, at one binding site, is still more preferable A specific example of "a phenylethynyl group which may be substituted with a halogen atom, an alkyl group having 1 to 6 carbon atoms, an alkoxy group having 1 to 6 carbon atoms, or an alkylthio group having 1 to 6 carbon atoms", represented by $R^{1''}$ in the general formula (A"), includes the same as the specific example of "a phenylethynyl group which may be substituted with a halogen atom, an alkyl group having 1 to 6 carbon atoms, an alkoxy group having 1 to 6 carbon atoms, or an alkylthio group having 1 to 6 carbon atoms" described in the specific example of "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ in the general formula (A).

A preferable specific example among the phenylalkynyl groups includes the same as the specific example of "a phenylethynyl group which is substituted with any one of a halogen atom, an alkyl group having 1 to 6 carbon atoms, an alkoxy group having 1 to 6 carbon atoms, or an alkylthio group having 1 to 6 carbon atoms, at one binding site" described in the specific example of "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms", represented by $R^1$ in the general formula (A).

A more preferable specific example among the phenylalkynyl groups includes the same as the specific example of "a phenylethynyl group substituted with an alkyl group having 1 to 6 carbon atoms at one binding site" described in the specific example of "an arylalkynyl group having 8 to 16 carbon atoms, which may be substituted with a halogen atom, an alkyl group having 1 to 6 carbon atoms, an alkoxy group having 1 to 6 carbon atoms, or an alkylthio group having 1 to 6 carbon atoms", represented by $R^1$ in the general formula (A).

As the phenyl group in "a phenyl group which may be substituted with a halogen atom, an alkyl group having 1 to 6 carbon atoms, an alkoxy group having 1 to 6 carbon atoms, or an alkylthio group having 1 to 6 carbon atoms", represented by $R^{2''}$ to $R^{4''}$ in the general formula (A"), an unsubstituted phenyl group is preferable.

A specific example of "a phenyl group which may be substituted with a halogen atom, an alkyl group having 1 to 6 carbon atoms, an alkoxy group having 1 to 6 carbon atoms, or an alkylthio group having 1 to 6 carbon atoms", represented by $R^{2''}$ to $R^{4''}$ in the general formula (A") includes the same as the specific example of "a phenyl group which may be substituted with a halogen atom, an alkyl group having 1 to 6 carbon atoms, an alkoxy group having 1 to 6 carbon atoms, or an alkylthio group having 1 to 6 carbon atoms", represented by $R^{2'}$ to $R^{4'}$ in the general formula (A'), and a preferable specific example also includes the same.

As $R^{1''}$ in general formula (A"), an alkyl group having 1 to 6 carbon atoms, and a phenylethynyl group substituted with either one of a halogen atom, an alkyl group having 1 to 6 carbon atoms, an alkoxy group having 1 to 6 carbon atoms, or an alkylthio group having 1 to 6 carbon atoms at one binding site are more preferable.

As $R^{2''}$ to $R^{4''}$ in the general formula (A"), the one where all of $R^{2''}$ to $R^{4''}$ are the same unsubstituted phenyl groups is preferable.

A combination of $R^{1''}$ to $R^{4''}$ in the general formula (A") includes a combination where $R^{1''}$ represents an alkyl group having 1 to 12 carbon atoms, and all of $R^{2''}$ to $R^{4''}$ represent the same phenyl group which may be substituted with a halogen atom, an alkyl group having 1 to 6 carbon atoms, an alkoxy group having 1 to 6 carbon atoms, or an alkylthio group having 1 to 6 carbon atoms; and a combination where $R^{1''}$ represents a phenylethynyl group which may be substituted with a halogen atom, an alkyl group having 1 to 6 carbon atoms, an alkoxy group having 1 to 6 carbon atoms, or an alkylthio group having 1 to 6 carbon atoms, and all of $R^{2''}$ to $R^{4''}$ are the same phenyl group, which may be substituted with a halogen atom, an alkyl group having 1 to 6 carbon atoms, an alkoxy group having 1 to 6 carbon atoms, or an alkylthio group having 1 to 6 carbon atoms.

As $R^{9''}$ in the general formula ($B_1''$), a hydrogen atom or an alkyl group having 1 to 6 carbon atoms are more preferable.

As $R^{11''}$ to $R^{14''}$ in the general formula ($B_2''$), an alkyl group having 1 to 6 carbon atoms is more preferable.

As $R^{15''}$ and $R^{18''}$ in the general formula ($B_2''$), a hydrogen atom or an alkyl group having 1 to 6 carbon atoms are more preferable.

As $R^{16''}$ and $R^{17''}$ in the general formula ($B_2''$), an alkyl group having 1 to 6 carbon atoms, a phenyl group, which is substituted with only a nitro group or only an alkyl group having 1 to 6 carbon atoms, at 1 to 2 binding sites, and the one where $R^{11''}$ together with $R^{12''}$ form an alkylene group having 2 to 4 carbon atoms are more preferable.

A combination of $R^{11''}$ to $R^{18''}$ in the general formula ($B_2''$) includes a combination where $R^{11''}$ to $R^{14''}$, $R^{16''}$ and $R^{17''}$ each independently represent an alkyl group having 1 to 12 carbon atoms, and $R^{15''}$ and $R^{18''}$ represents a hydrogen atom; as well as a combination where $R^{11''}$ to $R^{15''}$, and $R^{18''}$ each independently represent an alkyl group having 1 to 12 carbon atoms, and $R^{16''}$ together with $R^{17''}$ form an alkylene group having 2 to 4 carbon atoms; a combination where $R^{11''}$ to $R^{14''}$ each independently represent an alkyl group having 1 to 12 carbon atoms, $R^{15''}$ and $R^{18''}$ represents a hydrogen atom, and $R^{16''}$ and $R^{17''}$ each independently represent the phenyl group which is substituted with only a nitro group or only an alkyl group having 1 to 6 carbon atoms; as well as a combination where $R^{11''}$ to $R^{14''}$ each independently represent an alkyl group having 1 to 12 carbon atoms, and $R^{15''}$ and $R^{18''}$ represent a hydrogen atom, either one of $R^{16''}$ and $R^{17''}$ represents an alkyl group having 1 to 12 carbon atoms, and the other one represents the phenyl group which is substituted with only a nitro group or only an alkyl group having 1 to 6 carbon atoms.

As $Q^{10''}$ to $Q^{13''}$ in the general formula ($B_6''$), the one where all of $Q^{10''}$ to $Q^{13''}$ are the same group represented by the general formula ($b_6''$) is preferable.

As $R^{37''}$ to $R^{46''}$ in the general formula ($b_5''$) or ($b_6''$), an alkyl group having 1 to 6 carbon atoms is more preferable.

A preferable combination of $Q^{10''}$ to $Q^{13''}$ in the general formula ($B_6''$) includes a combination where all of $Q^{10''}$ to $Q^{13"}$ represent the group represented by the general formula ($b_5"$); and a combination where all of $Q^{10"}$ to $Q^{13"}$ represent the group represented by the general formula ($b_6"$); and among these, a combination where all of $Q^{10"}$ to $Q^{13"}$ represent the group represented by the general formula ($b_6"$) is preferable.

A specific example of the borate-based anion in the compound represented by the general formula (A") includes the anions represented by the formulae (A-1), (A-2), (A-3), (A-4), (A-5), (A-6), (A-7), (A-14), (A-15), (A-18), (A-19), (A-20), (A-21), (A-25), (A-26), (A-27), and (A-28), and among these, the anions represented by the formulae (A-1) and (A-19) are preferable.

A specific example of the ammonium cation having the guanidinium group represented by the general formula ($B_1"$), the ammonium cation having the biguanidium group represented by the general formula ($B_2"$), or the phosphonium cation represented by the general formula ($B_6"$), which are represented by $Z^{"+}$ in the compound represented by the general formula (A"), includes the cations represented by the formulae (B-2), (B-3), (B-4), (B-5), (B-6), (B-15), (B-16), (B-17), and (B-18), and among these, the cations represented by the formulae (B-2), (B-4), (B-5), (B-6), (B-16), (B-17), and (B-18) are preferable.

As the ammonium cation having the guanidinium group, the biguanidium group or the phosphazenium group, or the phosphonium cation, to be combined with the anion selected from the formulae (A-1) to (A-30), in the compound represented by the general formula (A), a cation selected from the cations represented by the formulae (B-1) to (B-18) are preferable, and among these, the cations represented by the formulae (B-1), (B-2), (B-3), (B-4), (B-5), (B-6), (B-15), (B-16), (B-17), and (B-18) are more preferable, and among these, the cations represented by the formulae (B-2), (B-4), (B-5), (B-6), (B-16), (B-17), and (B-18) are still more preferable.

Still more, a specific example of the compound represented by the general formula (A), where the ammonium cation having the guanidinium group, the biguanidium group or the phosphazenium group, or the phosphonium cation, to be combined with an anion selected from the formulae (A-1) to (A-30), is a cation selected from the formulae (B-1) to (B-18), includes the compounds, for example, represented by the following formulae (1), (2), (3), (4), (5), (6), (7), (8), and (9).

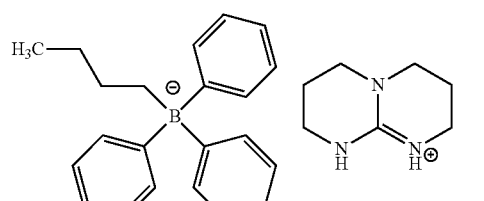

(1)

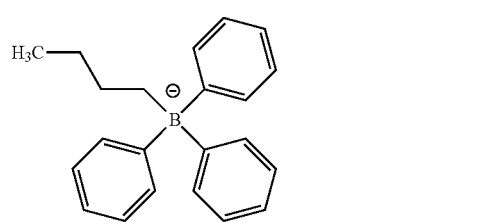

(2)

-continued

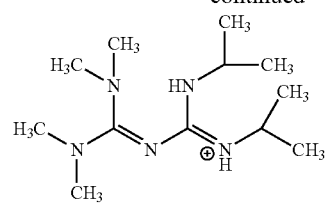

(3)

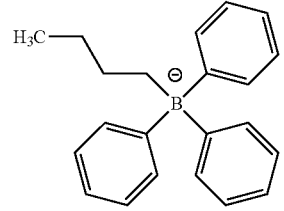

(4)

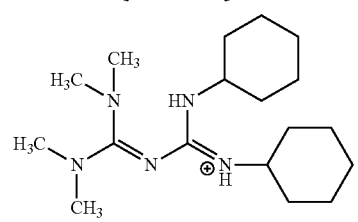

(5)

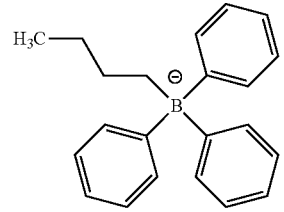

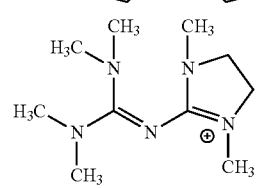

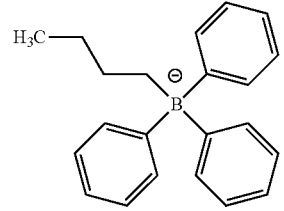

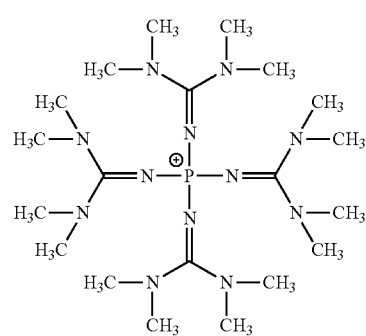

-continued (6)
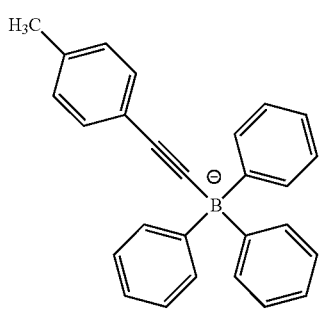

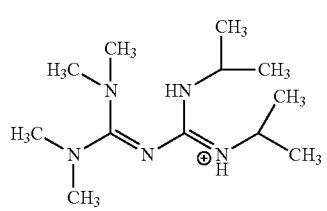

(7)
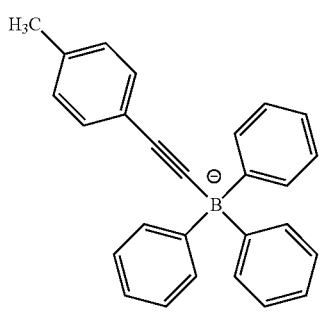

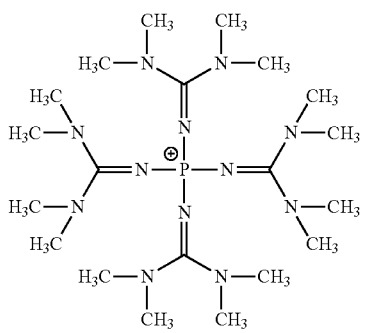

(8)
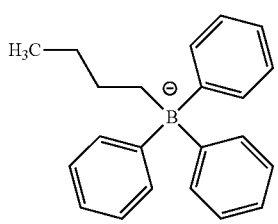

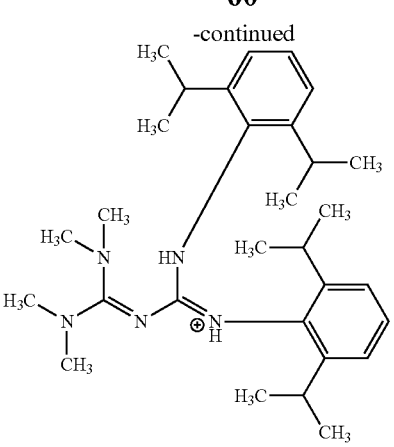

(9)
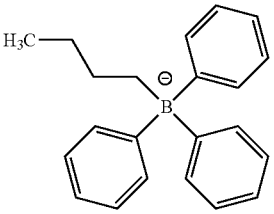

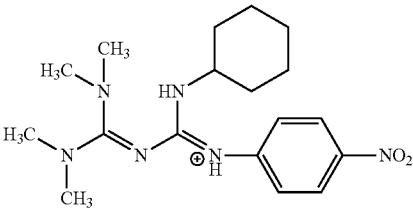

The Production Method for the Compound of the Present Invention

The compound of the present invention can be produced, for example, by a method shown in the following scheme [i]. That is, the compound represented by the general formula (A) may be synthesized, for example, by a reaction of an organoborane compound represented by the general formula (I) and an organolithium compound represented by the general formula (II), to obtain a compound represented by the general formula (III), and then by a reaction of the compound represented by the general formula (III) and a compound represented by the general formula (IV).

[i]
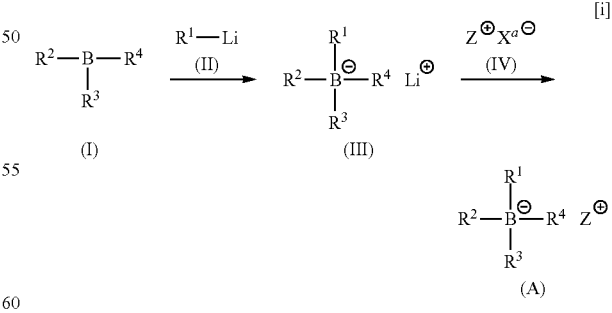

(in the scheme, $X^{a-}$ represents a halide ion, $R^2$ to $R^4$ and $Z^+$ are the same as described above.)

The halide ion represented by $X^{a-}$ in the general formula (IV) includes, for example, a chloride ion, a bromide ion, an iodide ion, and the like, and among these, a chloride ion is preferable.

As the organoborane compound represented by the general formula (I), pertaining to the production method for the compound represented by the general formula (A) of the present invention, the commercially available one, or the one synthesized as appropriate by a method known per se may be used. A specific example of the organoborane compound represented by the general formula (I) includes a triarylborane, such as triphenylborane, trinaphthylborane, trianthracenylborane, tri(p-fluorophenyl)borane, tri(p-chlorophenyl)borane, tri(p-bromophenyl)borane, tri(p-iodophenyl)borane, tri(p-methylphenyl)borane, tri(p-ethylphenyl)borane, tri(p-(n-propyl)phenyl)borane, tri(p-isopropylphenyl)borane, tri(p-(n-butyl)phenyl)borane, tri(p-isobutylphenyl)borane, tri(p-(sec-butyl)phenyl)borane, tri(p-(tert-butyl)phenyl)borane, tri(p-methoxyphenyl)borane, tri(p-ethoxyphenyl)borane, tri(p-(n-propoxy)phenyl)borane, tri(p-isopropoxyphenyl)borane, tri(p-(n-butoxy)phenyl)borane, tri(p-isobutoxyphenyl)borane, tri(p-(sec-butoxy)phenyl)borane, tri(p-(tert-butoxy)phenyl)borane, tri(p-methylthiophenyl)borane, tri(p-ethylthiophenyl)borane, tri(p-(n-propylthio)phenyl)borane, tri(p-isopropylthiophenyl)borane, tri(p-(n-butylthio)phenyl)borane, tri(p-isobutylthiophenyl)borane, tri(p-(sec-butylthio)phenyl)borane, tri(p-(tert-butylthio)phenyl)borane; an alkyl diarylborane, such as n-butyl diphenylborane; a dialkyl arylborane, such as di-n-butyl phenylborane; a trialkylborane, such as tri-n-butylborane, tri-n-pentylborane, tri-n-hexylborane; an arylalkynyl diarylborane, such as phenylethynyl diphenylborane; a diarylalkynyl arylborane, such as diphenylethynyl phenylborane; a triarylalkynylborane, such as triphenylethynylborane; trifuranylborane; trithienylborane; tri(N-methylpyrrolyl)borane; and the like.

As the organolithium compound represented by the general formula (II), pertaining to the production method for the compound represented by the general formula (A) of the present invention, the commercially available one, or the one synthesized as appropriate by a method known per se may be used. A specific example of the organolithium compound represented by the general formula (II) includes an alkyllithium, such as methyllithium, ethyllithium, n-propyllithium, isopropyllithium, n-butyllithium, isobutyllithium, sec-butyllithium, tert-butyllithium, cyclobutyllithium, n-pentyllithium, isopentyllithiumn, sec-pentyllithium, tert-pentyllithium, neopentyllithium, 2-methylbutyllithium, 1,2-dimethylpropyllithium, 1-ethylpropyllithium, cyclopentyllithium, n-hexyllithium, isohexyllithium, sec-hexyllithium, tert-hexyllithium, neohexyllithium, 2-methylpentyllithium, 1,2-dimethylbutyllithium, 2,3-dimethylbutyllithium, 1-ethylbutyllithium, cyclohexyllithium; an arylalkynyllithium, such as p-fluorophenylethynyllithium, p-chlorophenylethynyllithium, p-bromophenylethynyllithium, p-iodophenylethynyllithium, p-methylphenylethynyllithium, p-ethylphenylethynyllithium, p-(n-propyl)phenylethynyllithium, p-isopropylphenylethynyllithium, p-(n-butyl)phenylethynyllithium, p-isobutylphenylethynyllithium, p-(sec-butyl)phenylethynyllithium, p-(tert-butyl)phenylethynyllithium, p-methoxyphenylethynyllithium, p-ethoxyphenylethynyllithium, p-(n-propoxy)phenylethynyllithium, p-isopropoxyphenylethynyllithium, p-(n-butoxy)phenylethynyllithium, p-isobutoxyphenylethynyllithium, p-(sec-butoxy)phenylethynyllithium, p-(tert-butoxy)phenylethynyllithium, p-methylthiophenylethynyllithium, p-ethylthiophenylethynyllithium, p-(n-propylthio)phenylethynyllithium, p-isopropylthiophenylethynyllithium, p-(n-butylthio)phenylethynyllithium, p-isobutylthiophenylethynyllithium, p-(sec-butylthio)phenylethynyllithiumn, p-(tert-butylthio)phenylethynyllithium; an alkenyllithium, such as vinyllithium, 1-propenyllithium, 2-propenyllithium, isopropenyllithium, 1-butenyllithium, 2-butenyllithium, 3-butenyllithium, isobutenyllithium, methallyllithium, prenyllithium, isopentenyllithium, cyclopentenyllithium, n-hexenyllithium, cyclohexenyllithium; 2-furylethynyllithium; 2-thiophenylethynyllithium; 2,6-dithianyllithium; and the like.

A specific example of the compound represented by the general formula (IV), pertaining to the production method for the compound represented by the general formula (A) of the present invention, includes, for example, an ammonium salt having a guanidinium group represented by the following general formula ($B_1$, an ammonium salt having a biguanidium group represented by the following general formula ($B_2$), an ammonium salt having a phosphazenium group represented by the following general formula ($B_3$) or ($B_4$), a phosphonium salt represented by the following general formula ($B_5$) or ($B_6$).

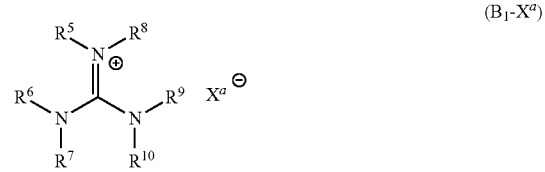

(wherein $R^5$ to $R^{10}$ and $X^{a-}$ are the same as described above, and number of hydrogen atoms among $R^5$ to $R^{10}$ is 0 to 2.)

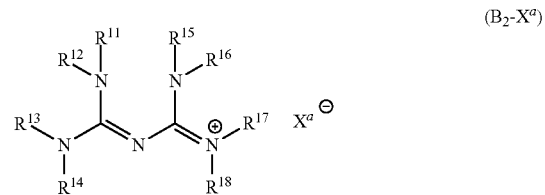

(wherein $R^{11}$ to $R^{18}$ and $X^{a-}$ are the same as described above, and number of hydrogen atoms among $R^{11}$ to $R^{18}$ is 0 to 2.)

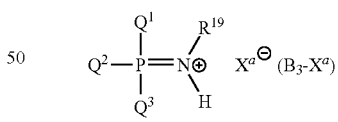

(wherein $Q^1$ to $Q^3$, $R^{19}$ and $X^{a-}$ are the same as described above, and number of hydrogen atoms bonding to the nitrogen atoms in the formula is 1 to 5.)

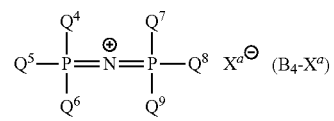

(wherein $Q^4$ to $Q^9$, and $X^{a-}$ are the same as described above, and number of hydrogen atoms bonding to the nitrogen atoms in the formula is 0 to 4.)

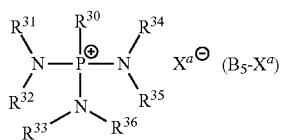

(wherein $R^{30}$ to $R^{36}$, and $X^{a-}$ are the same as described above, and number of hydrogen atoms bonding to the nitrogen atoms in the formula is 0 to 4.)

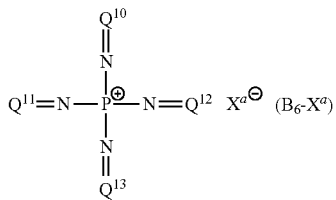

(wherein $Q^{10}$ to $Q^{13}$, and $X^{a-}$ are the same as described above, and number of hydrogen atoms bonding to the nitrogen atoms in the formula is 0 to 4.)

Number of hydrogen atoms among $R^5$ to $R^{10}$ in the general formula ($B_1$—$X^a$), is an integer of 0 to 2, 1 to 2 is preferable, and 1 is more preferable.

Number of hydrogen atoms among $R^{11}$ to $R^{18}$ in the general formula ($B_2$—$X^a$), is an integer of 0 to 2, and 0 or 2 is more preferable.

In the general formula ($B_3$—$X^a$), number of hydrogen atoms bonding to the nitrogen atoms in the formula, is an integer of 1 to 5, 1 to 3 is preferable, and 1 is more preferable. It should be noted that number of hydrogen atoms shown here is always 1 or larger, because the nitrogen atoms in the general formula ($B_3$—$X^a$) already has one hydrogen atom.

In the general formula ($B_4$—$X^a$), number of hydrogen atoms bonding to the nitrogen atoms in the formula, is an integer of 0 to 4, and 0 to 2 is preferable, and 0 is more preferable.

In the general formula ($B_5$—$X^a$), number of hydrogen atoms bonding to the nitrogen atoms in the formula, is an integer of 0 to 4, and 0 to 2 is preferable, and 0 is more preferable.

In the general formula ($B_6$—$X^a$), number of hydrogen atoms bonding to the nitrogen atoms in the formula, is an integer of 0 to 4, and 0 to 2 is preferable, and 0 is more preferable.

As the ammonium salt having the guanidinium group represented by the general formula ($B_1$—$X^a$), the commercially available one, or the one synthesized as appropriate by a method known per se may be used. A specific example of the ammonium cation in the ammonium salt having the guanidinium group represented by the general formula ($B_1$—$X^a$) includes the cations represented by the formulae (B-1) to (B-3), and the like.

As the ammonium salt having the biguanidium group represented by the general formula ($B_2$—$X^a$), the one synthesized as appropriate by a method to be described later may be used. A specific example of the ammonium cation in the ammonium salt having the biguanidium group represented by the general formula ($B_2$—$X^a$) includes the cations represented by the formulae (B-4) to (B-6), (B-17) and (B-18), and the like.

As the ammonium salt having the phosphazenium group represented by the general formula ($B_3$—$X^a$), the one synthesized as appropriate by a method to be described later may be used. A specific example of the ammonium cation in the ammonium salt having the phosphazenium group represented by the general formula ($B_3$—$X^a$) includes the cations represented by the formulae (B-7) to (B-11), and the like.

As the ammonium salt having the phosphazenium group represented by the general formula ($B_4$—$X^a$), the one synthesized as appropriate by a method to be described later may be used. A specific example of the ammonium cation in the ammonium salt having the phosphazenium group represented by the general formula ($B_4$—$X^a$) includes the cation represented by the formula (B-12), and the like.

As the phosphonium salt represented by the general formula ($B_5$—$X^a$), the one synthesized as appropriate by a method to be described later may be used. A specific example of the phosphonium cation in the phosphonium salt represented by the general formula ($B_5$—$X^a$) includes the cations represented by the formulae (B-13) and (B-14), and the like.

As the phosphonium salt represented by the general formula ($B_6$—$X^a$), the one synthesized as appropriate by a method to be described later may be used. A specific example of the phosphonium cation in the phosphonium salt represented by the general formula ($B_6$—$X^a$) includes the cations represented by the formulae (B-15) and (B-16), and the like.

Use amount of the organolithium compound represented by the general formula (II), in the production method for the compound represented by the general formula (A) of the present invention, is not especially limited, as long as being a generally use amount in this field usually, and is, for example, usually 0.8 to 10 equivalents, preferably 0.9 to 5 equivalents, and more preferably 1 to 2 equivalents, relative to mole number of organoborane compounds represented by the general formula (I). When the use amount of the organolithium compound is extremely low, yield of the compound represented by the general formula (III) could decrease. On the other hand, when the use amount of the organolithium compound is extremely high, a problem such as impairing economic performance occurs.

Use amount of the compound represented by the general formula (IV), in the production method for the compound represented by the general formula (A) of the present invention, is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (III). When the use amount of the compound represented by the general formula (IV) is extremely low, yield of the compound represented by the general formula (V) could decrease. On the other hand, when the use amount of the compound represented by the general formula (IV) is extremely high, a problem such as impairing economic performance occurs.

A series of reactions represented by the scheme [i] may be carried out under solvent-free condition, or may be carried out in an organic solvent or in water. A specific example of the organic solvent is not especially limited, as long as it is an organic solvent which does not react with the organoborane compound, the organolithium compound, the compounds represented by the general formulae (III) and (IV), and includes an aliphatic hydrocarbon-based solvent, such as hexane, heptan, octane; an aromatic hydrocarbon-based solvent, such as benzene, toluene, ethynyltoluene, xylene; a halogen-based solvent, such as dichloromethane, trichloromethane (chloroform), tetrachloromethane (carbon tetrachloride); an ether-based solvent, such as diethyl ether, diisopropyl ether, methyl tert-butyl ether, cyclopentyl methyl ether, tetrahydrofuran, 2-methyltetrahydrofuran, 1,4-dioxane; a glycol ether-based solvent, such as ethylene glycol dimethyl ether, propylene glycol dimethyl ether, ethylene glycol diethyl ether, propylene glycol diethyl ether, diethylene glycol dimethyl ether, dipropylene glycol dimethyl ether, dipropylene glycol diethyl ether; a glycol ether acetate-based solvent, such as ethylene glycol monoethyl ether acetate, diethylene glycol monoethyl ether acetate, diethylene glycol monobutyl ether acetate, propylene glycol monomethyl ether acetate, propylene glycol monoethyl ether acetate, dipropylene glycol monomethyl ether acetate, dipropylene glycol monoethyl ether acetate; a ketone-based solvent, such as 2-propanone (acetone), 2-butanone (ethyl methyl ketone), 4-methyl-2-pentanone (methyl isobutyl ketone); an ester-based solvent, such as ethyl acetate, n-propyl acetate, isopropyl acetate, isobutyl acetate, sec-butyl acetate, tert-butyl acetate, ethyl butyrate, isoamyl butyrate; an amide-based solvent, such as N,N-dimethylformamide, N,N-dimethylacetamide, 1-methyl-2-pyrrolidinone (N-methylpyrrolidone), 1,3-dimethyl-2-imidazolidinone (dimethylethyleneurea); a nitrile-based solvent, such as acetonitrile; and the like. It should be noted that such an organic solvent may be used alone as one kind of the organic solvent, or may be used in combination of two or more kinds of the organic solvents. In addition, as such an organic solvent, the commercially available one may be used.

Use amount of the organic solvent is not especially limited, as long as being a generally use amount in this field usually, and is, for example, usually 0.01 to 500 mL, and preferably 0.1 to 100 mL, relative to 1 mmol of the organoborane compound represented by the general formula (I) or the compound represented by the general formula (III).

It is desirable that a series of reactions represented by the scheme [i] are carried out under the following conditions (reaction temperature, pressure, reaction time).

It is desirable that temperature in the reaction (reaction temperature) of the organoborane compound represented by the general formula (I) and the organolithium compound represented by the general formula (II), is set at temperature where the organoborane compound and the organolithium compound react in good efficiency, and the compound represented by the general formula (III) can be obtained in good yield. Specifically, the reaction temperature is, for example, usually −20 to 150° C., and preferably 0 to 80° C.

It is desirable that temperature in the reaction (reaction temperature) of the compound represented by the general formula (III) and the compound represented by the general formula (IV), is set at temperature where the compound represented by the general formula (III) and the compound represented by the general formula (IV) react in good efficiency, and the compound represented by the general formula (A) can be obtained in good yield. Specifically, the reaction temperature is, for example, usually −20 to 150° C., and preferably 0 to 80° C.

Pressure in a series of reactions represented by the scheme [i] is not especially limited, as long as the series of reactions is carried out without delay, and the series of reactions may be carried out, for example, under normal pressure.

Reaction time in a series of reactions represented by the scheme [i] may be influenced in some cases, by kinds of the organoborane compound, the organolithium compound and the compounds represented by the general formulae (III) and (IV), use amount of such compounds, presence or absence of the organic solvent and kinds thereof, reaction temperature, pressure in the reaction, and the like. Accordingly, desirable reaction time cannot be said unconditionally, however, it is, for example, usually 1 minute to 24 hours, and preferably 3 minutes to 12 hours.

A series of products after the reaction, in the production method of the compound represented by the general formula (A) of the present invention, can be isolated by a general post-treatment operation and purification operation usually carried out in this field. As a specific example of the isolation method, the product can be isolated, for example, as needed, by extraction of an aqueous layer with the addition of a polar solvent such as water into a reaction system, in the reaction of the organoborane compound represented by the general formula (I) and the organolithium compound represented by the general formula (II); by extraction of an organic layer with the addition of a non-polar solvent such as ethyl acetate into a reaction system, in the reaction of the compound represented by the general formula (III) and the compound represented by the general formula (IV); and after the extraction, by vacuum concentration of the resulting reaction solution. In addition, the product may be isolated by filtration or washing of the reaction solution, as needed, and by carrying out recrystallization, distillation, column chromatography, and the like, of the residue obtained by concentration of the reaction solution.

The compound represented by the general formula ($B_2$—$X^a$), pertaining to the production method for the compound represented by the general formula (A) of the present invention, can be produced, for example, by a method shown in the following scheme [ii]. That is, among the compounds represented by the general formula ($B_2$—$X^a$), a compound where $R^{15}$ and $R^{18}$ in the general formula ($B_2$—$X^a$) are hydrogen atoms, and $R^{16}$ together with $R^{17}$ do not form the alkylene group having 2 to 4 carbon atoms (a compound represented by the following general formula ($B_{2a}$—$X^a$)), may be synthesized, for example, by a reaction of a guanidine or a guanidine derivative represented by the general formula (V), and a carbodiimide derivative represented by the general formula (VI), to obtain a compound represented by the general formula (VII), and then by a reaction of the compound represented by the general formula (VII) and a hydrogen halide represented by the general formula (VIII). In addition, among the compounds represented by the general formula ($B_2$—$X^a$), a compound where either one of $R^{15}$ or $R^{18}$ in the general formula ($B_2$—$X^a$) is other than a hydrogen atom, and the other one is a hydrogen atom, and $R^{16}$ together with $R^{17}$ do not form the alkylene group having 2 to 4 carbon atoms (a compound represented by the following general formula ($B_{2b}$—$X^a$)), may be synthesized, for example, by a reaction of the compound represented by the general formula (VII), synthesized by the method, and an alkyl halide represented by the general formula (IX), under the presence of a base, to obtain a compound represented by the general formula (X), and then by a reaction of the compound represented by the general formula (X) and the hydrogen halide represented by the general formula (VIII). In addition, among the compounds represented by the general formula ($B_2$—$X^a$), (i) a compound where $R^{15}$ and $R^{18}$ in the general formula ($B_2$—$X_a$) are other than hydrogen atoms, or (ii) a compound where $R^{16}$ together with $R^{17}$ in the general formula ($B_2$—$X_a$) form an alkylene group having 2 to 4 carbon atoms (a compound represented by the following general formula ($B_{2c}$—$X^a$)), may be synthesized, for example, by a reaction of the guanidine or the guanidine derivative represented by the general formula (V) and a compound represented by the general formula (XI).

gen atom, or an alkyl group having 1 to 12 carbon atoms, and $R^{16c}$ together with $R^{17c}$ form an alkylene group having 2 to

[ii]

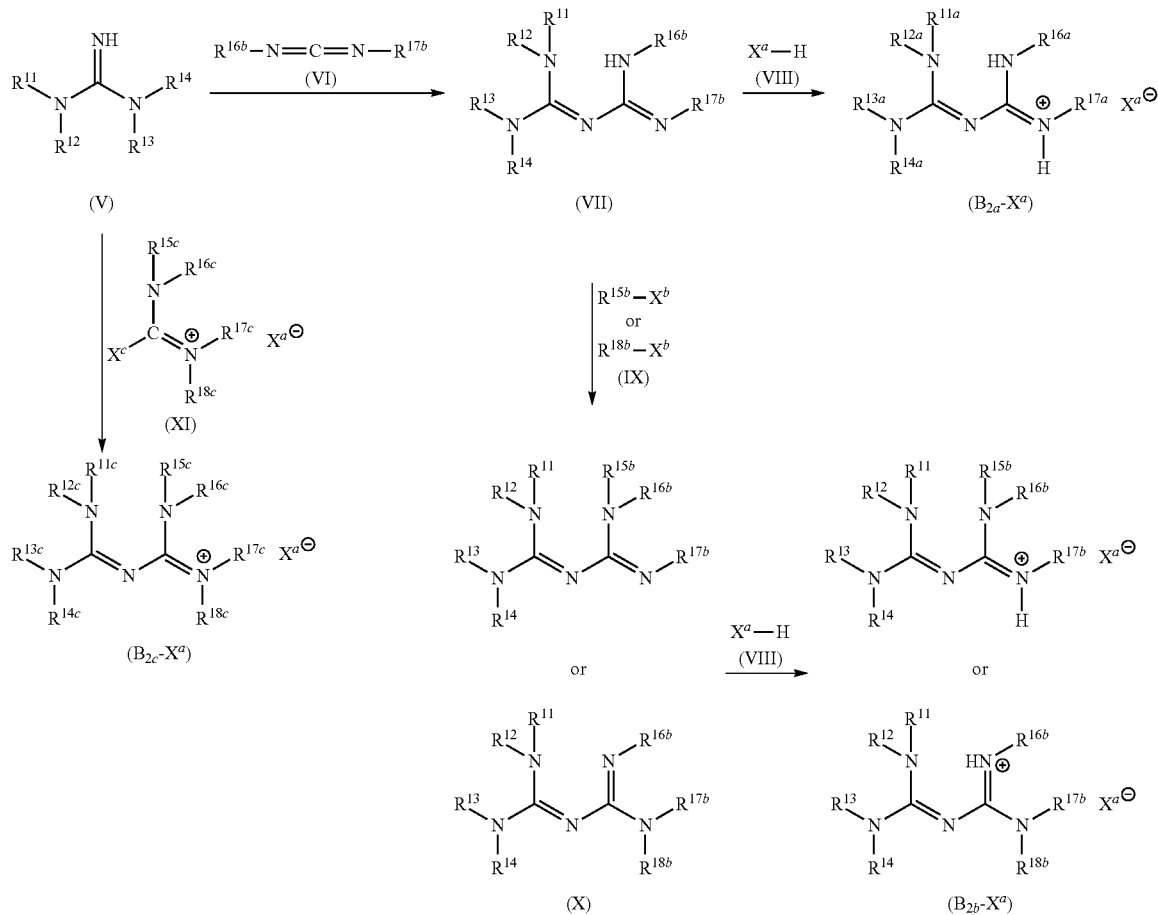

(in the scheme, $R^{11a}$ to $R^{14a}$ each independently represent an alkyl group having 1 to 12 carbon atoms; $R^{16a}$ and $R^{17a}$ each independently represent an alkyl group having 1 to 12 carbon atoms, or an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms; $R^{15b}$ and $R^{18b}$ each independently represent an alkyl group having 1 to 12 carbon atoms; $R^{16b}$ and $R^{17b}$ each independently represent a hydrogen atom, an alkyl group having 1 to 12 carbon atoms, or an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms; (i) $R^{15c}$ and $R^{18c}$ each independently represent an alkyl group having 1 to 12 carbon atoms, and $R^{16c}$ and $R^{17c}$ each independently represent an alkyl group having 1 to 12 carbon atoms, or an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms; or (ii) $R^{15c}$ and $R^{18c}$ each independently represent a hydro- 4 carbon atoms; $X^a$ and $X^b$ each independently represent a halogen atom; and $R^{11}$ to $R^{14}$ and $X^a$ are the same as described above, and number of hydrogen atoms, among $R^{11}$ to $R^{14}$, $R^{16b}$ and $R^{17b}$ in the general formulae (VII), (X) and ($B_{2b}$—$X^a$), is 0 to 1, and number of hydrogen atoms, among $R^{11c}$ to $R^{15c}$ and $R^{18c}$ in the general formula ($B_{2c}$—$X^a$), is 0 to 2.)

A specific example of each functional group ($R^{11a}$ to $R^{14a}$, $R^{16a}$, $R^{17a}$, $R^{15b}$ to $R^{18b}$, and $R^{15c}$ to $R^{18c}$) in the general formulae (V) to (XI) and ($B_{2a}$—$X^a$) to ($B_{2c}$—$X^a$) includes the same as the specific example of corresponding each functional group ($R^{11}$ to $R^{18}$) described in the general formula ($B_2$), and a preferable specific example also includes the same.

Number of hydrogen atoms, among $R^{11}$ to $R^{14}$, $R^{16b}$ and $R^{17b}$ in the general formula (VII), is an integer of 0 to 1, and 0 is preferable.

The halogen atom represented by $X^a$ in the general formula (VIII) specifically includes, for example, a chlorine atom, a bromine atom, an iodine atom, and the like, and among these, a chlorine atom is preferable.

The halogen atom represented by $X^b$ in the general formula (IX) specifically includes, for example, a chlorine atom, a bromine atom, an iodine atom, and the like, and among these, an iodine atom is preferable.

Number of hydrogen atoms, among $R^{11}$ to $R^{14}$, $R^{16b}$ and $R^{17b}$ in the general formula (X), is an integer of 0 to 1, and 0 is preferable.

Number of hydrogen atoms, among R to $R^{11}$, $R^{16b}$ and $R^{17b}$ in the general formula ($B_{2b}$—$X^a$), is an integer of 0 to 1, and 0 is preferable.

Number of hydrogen atoms, among $R^{11c}$ to $R^{15c}$, and $R^{18c}$ in the general formula ($B_{2c}$—$X^a$), is an integer of 0 to 2, 0 to 1 is preferable, and 0 is more preferable.

In the case where $R^{15}$ in the general formula ($B_2$—$X^a$) is other than a hydrogen atom, and $R^{18}$ is a hydrogen atom, a reaction proceeds in a structure represented by the upper part in the general formulae (IX), (X) and ($B_{2b}$—$X^a$). On the other hand, in the case where $R^{15}$ in the general formula ($B_2$—$X^a$) is a hydrogen atom, and $R^{18}$ is other than a hydrogen atom, a reaction proceeds in a structure represented by the lower part in the general formulae (IX), (X) and ($B_{2b}$—$X^a$).

As the guanidine derivative represented by the general formula (V), pertaining to the production method for the compound represented by the general formula ($B_2$—$X^a$), the commercially available one, or the one synthesized as appropriate by a method known per se may be used. A specific example of the guanidine derivative represented by the general formula (V) includes, for example, 1,1,3,3-tetramethylguanidine, 1,1,3,3-tetraethylguanidine, 1,1,3,3-tetra-n-propylguanidine, 1,1,3,3-tetraisopropylguanidine, 1,1,3,3-tetra-n-butylguanidine, 1,1,3,3-tetraisobutylguanidine, 1,1,3,3-tetra-sec-butylguanidine, 1,1,3,3-tetra-tert-butylguanidine, 1,1,3,3-tetracyclobutylguanidine, 1,1,3,3-tetra-n-pentylguanidine, 1,1,3,3-tetraisopentylguanidine, 1,1,3,3-tetra-sec-pentylguanidine, 1,1,3,3-tetra-tert-pentylguanidine, Ill 1,1,3,3-tetraneopentylguanidine, 1,1,3,3-tetracyclopentylguanidine, 1,1,3,3-tetra-n-hexylguanidine, 1,1,3,3-tetraisohexylguanidine, 1,1,3,3-tetra-sec-hexylguanidine, 1,1,3,3-tetra-tert-hexylguanidine, 1,1,3,3-tetraneohexylguanidine, 1,1,3,3-tetracyclohexylguanidine, 1,1,3,3-tetra-n-heptylguanidine, 1,1,3,3-tetraisoheptylguanidine, 1,1,3,3-tetra-sec-heptylguanidine, 1,1,3,3-tetra-tert-heptylguanidine, 1,1,3,3-tetraneoheptylguanidine, 1,1,3,3-tetracycloheptylguanidine, 1,1,3,3-tetra-n-octylguanidine, 1,1,3,3-tetraisooctylguanidine, 1,1,3,3-tetra-sec-octylguanidine, 1,1,3,3-tetra-tert-octylguanidine, 1,1,3,3-tetraneooctylguanidine, 1,1,3,3-tetracyclooctylguanidine, 1,1,3,3-tetra-n-nonylguanidine, 1,1,3,3-tetraisononylguanidine, 1,1,3,3-tetra-sec-nonylguanidine, 1,1,3,3-tetra-tert-nonylguanidine, 1,1,3,3-tetraneononylguanidine, 1,1,3,3-tetracyclononylguanidine, 1,1,3,3-tetra-n-decylguanidine, 1,1,3,3-tetraisodecylguanidine, 1,1,3,3-tetra-sec-decylguanidine, 1,1,3,3-tetra-tert-decylguanidine, 1,1,3,3-tetraneodecylguanidine, 1,1,3,3-tetracyclodecylguanidine, 1,1,3,3-tetra-n-undecylguanidine, 1,1,3,3-tetracycloundecylguanidine, 1,1,3,3-tetra-n-dodecylguanidine, 1,1,3,3-tetracyclododecylguanidine, 1,1,3,3-tetranorbornylguanidine, 1,1,3,3-tetrabornylguanidine, 1,1,3,3-tetramenthylguanidine, 1,1,3,3-tetraadamantylguanidine, 1,1,3,3-tetra(decahydronaphthyl)guanidine, and the like.

As the carbodiimide derivative represented by the general formula (VI), pertaining to the production method for the compound represented by the general formula ($B_2$—$X^a$), the commercially available one, or the one synthesized as appropriate by a method known per se may be used. Such a carbodiimide derivative represented by the general formula (VI) includes, for example, a N,N'-dialkylcarbodiimide, a N,N'-diarylcarbodiimide which may have a substituent on the aryl group, a N-alkyl-N'-arylcarbodiimide which may have a substituent on the aryl group, and the like.

A specific example of the N,N'-dialkylcarbodiimide includes, for example, N,N'-dimethylcarbodiimide, N,N'-diethylcarbodiimide, N,N'-di(n-propyl)carbodiimide, N,N'-diisopropylcarbodiimide, N-tert-butyl-N'-ethylcarbodiimide, N,N'-di(n-butyl)carbodiimide, N,N'-diisobutylcarbodiimide, N,N'-di(sec-butyl)carbodiimide, N,N'-di(tert-butyl)carbodiimide, N,N'-dicyclobutylcarbodiimide, N,N'-di(n-pentyl)carbodiimide, N,N'-diisopentylcarbodiimide, N,N'-di(sec-pentyl)carbodiimnide, N,N'-di(tert-pentyl)carbodiimide, N,N'-dineopentylcarbodiimide, N,N'-di(2-methylbutyl)carbodiimide, N,N'-di(1,2-dimethylpropyl)carbodiimide, N,N'-di(1-ethylpropyl)carbodiimide, N,N'-dicyclopentylcarbodiimide, N,N'-di(n-hexyl)carbodiimide, N,N'-diisohexylcarbodiimide, N,N'-di(sec-hexyl)carbodiimide, N,N'-di(tert-hexyl)carbodiimide, N,N'-dineohexylcarbodiimide, N,N'-di(2-methylpentyl)carbodiimide, N,N'-di(1,2-dimethylbutyl)carbodiimide, N,N'-di(2,3-dimethylbutyl)carbodiimide, N,N'-di(1-ethylbutyl)carbodiimide, N,N'-dicyclohexylcarbodiimide, and the like.

A specific example of the N,N'-diarylcarbodiimide which may have a substituent on the aryl group, includes, for example, N,N'-diphenylcarbodiimide, N,N'-bis(2-nitrophenyl)carbodiimide, N,N'-bis(3-nitrophenyl)carbodiimide, N,N'-bis(4-nitrophenyl)carbodiimide, N,N'-bis(2,4-dinitrophenyl)carbodiimide, N,N'-bis(2,6-dinitrophenyl)carbodiimide, N,N'-bis(2-methylphenyl)carbodiimide, N,N'-bis(3-methylphenyl)carbodiimide, N,N'-bis(4-methylphenyl)carbodiimide, N,N'-bis(4-ethylphenyl)carbodiimide, N,N'-bis(4-n-propylphenyl)carbodiimide, N,N'-bis(4-isopropylphenyl)carbodiimide, N,N'-bis(4-n-butylphenyl)carbodiimide, N,N'-bis(4-n-pentylphenyl)carbodiimide, N,N'-bis(4-n-hexylphenyl)carbodiimide, N,N'-bis(2,3-dimethylphenyl)carbodiimide, N,N'-bis(3,4-dimethylphenyl)carbodiimide, N,N'-bis(2,4-dimethylphenyl)carbodiimide, N,N'-bis(2,6-dimethylphenyl)carbodiimide, N,N'-bis(2,3-diethylphenyl)carbodiimide, N,N'-bis(3,4-diethylphenyl)carbodiimide, N,N'-bis(2,4-diethylphenyl)carbodiimide, N,N'-bis(2,6-diethylphenyl)carbodiimide, N,N'-bis{2,3-di(n-propyl)phenyl}carbodiimnide, N,N'-bis{2,4-di(n-propyl)phenyl}carbodiimide, N,N'-bis{3,4-di(n-propyl)phenyl}carbodiimide, N,N-bis{2,6-di(n-propyl)phenyl}carbodiimide, N,N'-bis(2,3-diisopropylphenyl)carbodiimide, N,N'-bis(3,4-diisopropylphenyl)carbodiimide, N,N'-bis(2,4-diisopropylphenyl)carbodiimide, N,N'-bis(2,6-diisopropylphenyl)carbodiimide, N,N'-bis{2,3-di(n-butyl)phenyl}carbodiimide, N,N'-bis{2,4-di(n-butyl)phenyl}carbodiimide, N,N'-bis{3,4-di(n-butyl)phenyl}carbodiimide, N,N'-bis{2,6-di(n-butyl)phenyl}carbodiimide, N,N'-bis(2,3-diisobutylphenyl)carbodiimide, N,N'-bis(3,4-diisobutylphenyl)carbodiimide, N,N'-bis(2,4-diisobutylphenyl)carbodiimide, N,N'-bis(2,6-diisobutylphenyl)carbodiimide, N,N'-bis{2,3-di(sec-butyl)phenyl}carbodiimide, N,N'-bis{2,4-di(sec-butyl)phenyl}carbodiimide, N,N'-bis{3,4-di(sec-butyl)phenyl}carbodiimide, N,N'-bis{2,6-di(sec-butyl)phenyl}carbodiimide, N,N'-bis{2,3-di(tert-butyl)phenyl}carbodiimide, N,N'-bis{2,4-di(tert-butyl)phenyl}carbodiimide, N,N'-bis{3,4-di(tert-butyl)phenyl}carbodiimide, N,N'-bis{2,6-di(tert-butyl)phenyl}carbodiimide, N,N'-bis(2,3-dicyclobutylphenyl)carbodiimide, N,N'-bis(3,4-dicyclobutylphenyl)carbodiimide, N,N'-bis(2,4-dicyclobutylphenyl)carbodiimide, N,N'-bis(2,6-dicyclobutylphenyl)carbodiimide, N,N'-bis(4-methoxyphenyl)carbodiimide, N,N'-bis(4-methylthiophenyl)carbodiimide, N,N'-bis{4-(N,N-dimethylamino)phenyl}carbodiimide, and the like.

A specific example of the N-alkyl-N'-arylcarbodiimide which may have a substituent on the aryl group includes, for example, a compound represented by the following general formula (VI-d).

(wherein either one of $R^{16d}$ or $R^{17d}$ represents an alkyl group having 1 to 12 carbon atoms, and the other one represents an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms.)

A specific example of the alkyl group having 1 to 12 carbon atoms represented by $R^{16d}$ and $R^{17d}$ in the general formula (VI-d) includes the same as the specific example of the alkyl group having 1 to 12 carbon atoms represented by $R^{16}$ and $R^{17}$ in the general formula ($B_2$), and a preferable specific example also includes the same.

A specific example of "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms", represented by $R^{16d}$ and $R^{17d}$ in the general formula (VI-d), includes the same as the specific example of "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms", represented by $R^{16}$ and $R^{17}$ in the general formula ($B_2$), and a preferable specific example also includes the same.

As $R^{16d}$ and $R^{17d}$ in the general formula (VI-d), an alkyl group having 1 to 12 carbon atoms, and a phenyl group which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms, are more preferable, and among these, an alkyl group having 1 to 12 carbon atoms, and a phenyl group which is substituted with only a nitro group or only an alkyl group having 1 to 6 carbon atoms is still more preferable.

A specific example of the compound represented by the general formula (VI-d) includes, for example, N-hexyl-N'-phenylcarbodiimide, N-hexyl-N'-(2-nitrophenyl)carbodiimide, N-hexyl-N'-(3-nitrophenyl)carbodiimide, N-methyl-N'-(4-nitrophenyl)carbodiimide, N-ethyl-N'-(4-nitrophenyl)carbodiimide, N-propyl-N'-(4-nitrophenyl)carbodiimide, N-butyl-N'-(4-nitrophenyl)carbodiimide, N-pentyl-N'-(4-nitrophenyl)carbodiimide, N-hexyl-N'-(4-nitrophenyl)carbodiimide, N-hexyl-N'-(2,4-dinitrophenyl)carbodiimide, N-hexyl-N'-(2,6-dinitrophenyl)carbodiimide, N-hexyl-N'-(2-methylphenyl)carbodiimide, N-hexyl-N'-(3-methylphenyl)carbodiimide, N-methyl-N'-(4-methylphenyl)carbodiimide, N-ethyl-N'-(4-methylphenyl)carbodiimide, N-propyl-N'-(4-methylphenyl)carbodiimide, N-butyl-N'-(4-methylphenyl)carbodiimide, N-pentyl-N'-(4-methylphenyl)carbodiimide, N-hexyl-N'-(4-methylphenyl)carbodiimide, N-hexyl-N'-(4-ethylphenyl)carbodiimide, N-hexyl-N'-(4-propylphenyl)carbodiimide, N-hexyl-N'-(4-butylphenyl)carbodiimide, N-hexyl-N'-(4-pentylphenyl)carbodiimide, N-hexyl-N'-(4-hexylphenyl)carbodiimide, N-hexyl-N'-(2,3-dipropylphenyl)carbodiimide, N-hexyl-N'-(2,4-dipropylphenyl)carbodiimide, N-hexyl-N'-(3,4-dipropylphenyl)carbodiimide, N-hexyl-N'-(2,6-dipropylphenyl)carbodiimide, N-hexyl-N'-(4-methoxyphenyl)carbodiimide, N-hexyl-N'-(4-methylthiophenyl)carbodiimide, N-hexyl-N'-{4-(N,N-dimethylamino)phenyl}carbodiimide. It should be noted that, in the specific example, the alkyl group in the N-alkyl-N'-arylcarbodiimide, and the alkyl group which is a substituent on the aryl group in the N-alkyl-N'-arylcarbodiimide are not limited to a normal-form, and the specific example also includes a branched-type one such as sec-form, tert-form, iso-form, neo-form, or a ring-type one such as cyclo-form.

As the hydrogen halide represented by the general formula (VIII), pertaining to the production method for the compound represented by the general formula ($B_2$—$X^a$), the commercially available one, or the one synthesized as appropriate by a method known per se may be used. A specific example of the hydrogen halide represented by the general formula (VIII) includes hydrogen chloride, hydrogen bromide, hydrogen iodide, and the like.

As the alkyl halide represented by the general formula (IX), pertaining to the production method for the compound represented by the general formula ($B_2$—$X^a$), the commercially available one, or the one synthesized as appropriate by a method known per se may be used. A specific example of the alkyl halide represented by the general formula (IX) includes methyl chloride, methyl bromide, methyl iodide, ethyl chloride, ethyl bromide, ethyl iodide, propyl chloride, propyl bromide, propyl iodide, butyl chloride, butyl bromide, butyl iodide, pentyl chloride, pentyl bromide, pentyl iodide, hexyl chloride, hexyl bromide, hexyl iodide, heptyl chloride, heptyl bromide, heptyl iodide, octyl chloride, octyl bromide, octyl iodide, nonyl chloride, nonyl bromide, nonyl iodide, decyl chloride, decyl bromide, decyl iodide, undecyl chloride, undecyl bromide, undecyl iodide, dodecyl chloride, dodecyl bromide, dodecyl iodide, norbornyl chloride, norbornyl bromide, norbornyl iodide, bornyl chloride, bornyl bromide, bornyl iodide, menthyl chloride, menthyl bromide, menthyl iodide, adamantyl chloride, adamantyl bromide, adamantyl iodide, decahydronaphthyl chloride, decahydronaphthyl bromide, decahydronaphthyl iodide, and the like. It should be noted that, in the specific example, the alkyl group in the alkyl halide is not limited to a normal-form, and the specific example also includes a branched-type one such as sec-form, tert-form, iso-form, neo-form, or a ring-type one such as cyclo-form.

As the compound represented by the general formula (XI), pertaining to the production method for the compound represented by the general formula ($B_2$—$X^a$), the commercially available one, or the one synthesized as appropriate by a method known per se may be used. A specific example of the compound represented by the general formula (XI) includes 1-chloro-N,N,N',N'-tetramethylaminoimine chloride, 1-chloro-N,N,N',N'-tetraethylaminoimine chloride, 1-chloro-N,N,N',N'-tetra-n-propylaminoimine chloride, 1-chloro-N,N'-diisopropyl-N,N'-dimethylaminoimine chloride, 1-chloro-N,N'-diethyl-N,N'-diisopropylaminoimine chloride, 1-chloro-N,N,N',N'-tetraisopropylaminoimine chloride, 1-chloro-N,N'-di-tert-butyl-N,N'-dimethylaminoimine chloride, 1-chloro-N,N'-diethyl-N,N'-di-tert-butylaminoimine chloride, 1-chloro-N,N,N',N'-tetra-n-butylaminoimine chloride, 1-chloro-N,N'-dicyclohexyl-N,N'-dimethylaminoimine chloride, 1-chloro-N,N'-diethyl-N,N'-dicyclohexylaminoimine chloride, 2-chloro-1,3-dimethylimidazolinium chloride, 2-chloro-1,3-diethylimidazolinium chloride, 2-chloro-1,3-di-n-propylimidazolinium chloride, 2-chloro-1,3-diisopropylimidazolinium chloride, 2-chloro-1,3-di-n-butylimidazolinium chloride, 2-chloro-1,3-dimethyl-4,5,6- trihydropyrimidinium chloride, 2-chloro-1,3-dimethyl-(1,3-diaza-1-cycloheptene)chloride, and the like.

A specific example of the base to be used in a reaction to obtain the compound represented by the general formula (X) by a reaction of the compound represented by the general formula (VII) and the alkyl halide represented by the general formula (IX) includes, an alkali metal hydride, such as sodium hydride, potassium hydride; an alkali metal alkoxide, such as sodium methoxide, potassium methoxide, sodium ethoxide, potassium ethoxide, lithium tert-butoxide, sodium tert-butoxide, potassium tert-butoxide; an organolithium compound, such as n-butyl lithium, sec-butyl lithium, tert-butyl lithium, n-hexyl lithium; an alkali metal hydroxide, such as sodium hydroxide, potassium hydroxide; an alkali metal salt of a carbonic acid, such as sodium carbonate, potassium carbonate, cesium carbonate; a tertiary amine, such as triethylamine, pyridine, 1,8-diazabicyclo[5.4.0]undeca-7-ene (DBU), 1,5-diazabicyclo[4.3.0]nona-5-ene (DBN); a metal amide, such as lithium diisopropylamide (LDA), lithium hexamethyldisilazane (LHMDS), sodium hexamethyldisilazane (NaHMDS), potassium hexamethyldisilazane (KHMDS); and the like; and among these, an alkali metal hydride, such as sodium hydride, potassium hydride is preferable. It should be noted that such a base may be used alone as one kind of the base, or may be used in combination of two or more kinds of the bases. In addition, as such a base, the one commercially available may be used.

Use amount of the carbodiimide derivative represented by the general formula (VI), in the production method for the compound represented by the general formula ($B_2$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of guanidines or guanidine derivatives represented by the general formula (V). When the use amount of the carbodiimides is extremely low, yield of the compound represented by the general formula (VII) could decrease. On the other hand, when the use amount of the carbodiimide is extremely high, a problem such as impairing economic performance occurs.

Use amount of the hydrogen halide represented by the general formula (VIII), in the production method for the compound represented by the general formula ($B_2$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (VII) or the general formula (X). When the use amount of the hydrogen halide is extremely low, yield of the compound represented by the general formula ($B_{2a}$—$X^a$) or the general formula ($B_{2b}$—$X^a$) could decrease. On the other hand, when the use amount of the hydrogen halide is extremely high, a problem such as impairing economic performance occurs.

Use amount of the alkyl halide represented by the general formula (IX), in the production method for the compound represented by the general formula ($B_2$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (VII). When the use amount of the alkyl halide is extremely low, yield of the compound represented by the general formula (X) could decrease. On the other hand, when the use amount of the alkyl halide is extremely high, a problem such as impairing economic performance occurs.

Use amount of the base to be used in a reaction to obtain the compound represented by the general formula (X), in the production method for the compound represented by the general formula ($B_2$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (VII). When the use amount of the base is extremely low, yield of the compound represented by the general formula (X) could decrease. On the other hand, when the use amount of the base is extremely high, a problem such as impairing economic performance occurs.

Use amount of the compound represented by the general formula (XI), in the production method for the compound represented by the general formula ($B_2$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of guanidines or guanidine derivatives represented by the general formula (V). When the use amount of the compound represented by the general formula (XI) is extremely low, yield of the compound represented by the general formula ($B_{2c}$—$X^a$) could decrease. On the other hand, when the use amount of the compound represented by the general formula (XI) is extremely high, a problem such as impairing economic performance occurs.

A series of reactions represented by the scheme [ii] may be carried out under solvent-free condition, or may be carried out in an organic solvent. A specific example of the organic solvent is not especially limited, as long as it is an organic solvent which does not react with the guanidine or the guanidine derivative, the carbodiimide derivative, the hydrogen halide, the alkyl halide, the compounds represented by the general formulae (VII), 00 and (XI), as well as the base, and includes the same as the specific example of the organic solvent represented by the scheme [i]. It should be noted that such an organic solvent may be used alone as one kind of the organic solvent, or may be used in combination of two or more kinds of the organic solvents. In addition, as such an organic solvent, the commercially available one may be used.

Use amount of the organic solvent is not especially limited, as long as being a generally use amount in this field usually, and is, for example, usually 0.01 to 500 mL, and preferably 0.1 to 100 mL, relative to 1 mmol of the guanidine or the the guanidine derivative represented by the general formula (V), the compound represented by the general formula (XII), or the compound represented by the general formula (X).

It is desirable that a series of reactions represented by the scheme [ii] are carried out under the following conditions (reaction temperature, pressure, reaction time).

It is desirable that temperature in the reaction (reaction temperature) of the guanidine or the guanidine derivative represented by the general formula (V) and the carbodiimide derivative represented by the general formula (VI), is set at temperature where the guanidine or the guanidine derivative and the carbodiimide derivative react in good efficiency, and the compound represented by the general formula (VII) can be obtained in good yield. Specifically, the reaction temperature is, for example, usually 0 to 200° C., and preferably 20 to 150° C.

It is desirable that temperature in the reaction (reaction temperature) of the compound represented by the general formula (VII) or the general formula (X), and the hydrogen halide represented by the general formula (VIII), is set at temperature where the compound represented by the general formula (VII) or the general formula (X), and the hydrogen halide react in good efficiency, and the compound represented by the general formula ($B_{2a}$—$X^a$) or the general formula ($B_{2b}$—$X^a$) can be obtained in good yield. Specifically, the reaction temperature is, for example, usually −20 to 150° C., and preferably 0 to 80° C.

It is desirable that temperature in the reaction (reaction temperature) of the compound represented by the general formula (VII) and the alkyl halide represented by the general formula (IX), is set at temperature where the compound represented by the general formula (VII) and the alkyl halide react in good efficiency, and the compound represented by the general formula (X) can be obtained in good yield. Specifically, the reaction temperature is, for example, usually −20 to 150° C., and preferably 0 to 80° C.

It is desirable that temperature in the reaction (reaction temperature) of the guanidine or the guanidine derivative represented by the general formula (V) and the compound represented by the general formula (XI), is set at temperature where the guanidine or the guanidine derivative and the compound represented by the general formula (XI) react in good efficiency, and the compound represented by the general formula ($B_{2c}$—$X^a$) can be obtained in good yield. Specifically, the reaction temperature is, for example, usually 0 to 200° C., and preferably 20 to 150° C.

Pressure in a series of reactions represented by the scheme [ii] is not especially limited, as long as the series of reactions is carried out without delay, and the series of reactions may be carried out, for example, under normal pressure.

Reaction time in a series of reactions represented by the scheme [ii] may be influenced in some cases, by kinds of the guanidine or the guanidine derivative, the carbodiimide derivative, the hydrogen halide, the alkyl halide, the compounds represented by the general formulae (VII), (X) and (XI) and the base, use amount of such compounds and the base, presence or absence of the organic solvent and kinds thereof, reaction temperature, pressure in the reaction, and the like. Accordingly, desirable reaction time cannot be said unconditionally, however, it is, for example, usually 1 minute to 24 hours, and preferably 3 minutes to 12 hours.

A series of products after the reaction represented by the scheme [ii] can be isolated by a general post-treatment operation and purification operation usually carried out in this field. As a specific example of the isolation method, the product can be isolated, for example, as needed, by the addition of a non-polar solvent such as hexane into a reaction system, and after cooling, by filtration of the resulting crystal, in the reaction of the guanidine or the guanidine derivative represented by the general formula (V) and the carbodiimide derivative represented by the general formula (VI), or in the reaction of the compound represented by the general formula (VII) and the alkyl halide represented by the general formula (IV). In addition, in the reaction of the guanidine or the guanidine derivative represented by the general formula (V) and the compound represented by the general formula (XI), the product can be isolated by the addition of a polar solvent such as acetone into a reaction system, by removal of a salt deposited and by vacuum concentration of an organic layer. Still more, the product may be isolated by filtration or washing of the reaction solution, as needed, and by carrying out recrystallization, distillation, column chromatography, and the like, of the residue obtained by concentration of the reaction solution.

It should be noted that the compound represented by the general formula (VI-d), which is one of the specific examples of the compound represented by the general formula (VI), in the scheme [ii], can be produced by a method, for example, shown in the following scheme [ii-i]. That is, it may be synthesized, for example, by a reaction of an alkylamine represented by the general formula (VI-a) and an aryl isothiocyanate represented by the general formula (VI-b), to obtain an thiourea derivative represented by the general formula (VI-c), and then by carrying out a desulfurization reaction.

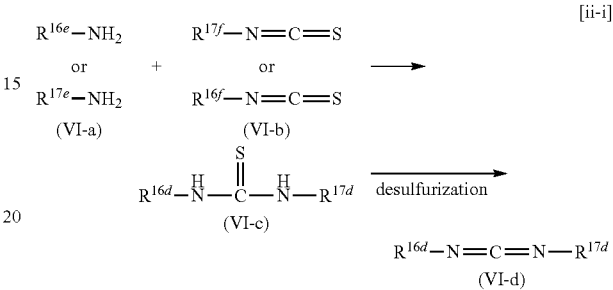

(wherein $R^{16e}$ and $R^{17e}$ each independently represent an alkyl group having 1 to 12 carbon atoms, $R^{16f}$ and $R^{17f}$ each independently represent an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms; $R^{16d}$ and $R^{17d}$ are the same as described above.)

A specific example of $R^{16e}$ and $R^{17e}$ in the general formula (VI-d) includes the same as the specific example of the alkyl group having 1 to 12 carbon atoms, represented by $R^{16}$ and $R^{17}$ in the general formula ($B_2$), and a preferable specific example also includes the same.

A specific example of $R^{16f}$ and $R^{17f}$ in the general formula (VI-d) includes the same as the specific example of "an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms" represented by $R^{16}$ and $R^{17}$ in the general formula ($B_2$), and a preferable specific example also includes the same.

In the case where $R^{16d}$ in the general formula (VI-d) is an alkyl group having 1 to 12 carbon atoms, and $R^{17d}$ is an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms, a reaction proceeds in a structure represented by the upper part in the general formulae (VI-a) and (VI-b). In this case, $R^{16d}$ in the general formulae (VI-c) and (VI-d) is $R^{16e}$ in the general formula (VI-a), and $R^{17d}$ in the general formulae (VI-c) and (VI-d) is $R^{17f}$ in the general formula (VI-a).

On the other hand, in the case where $R^{16d}$ in the general formula (VI-d) is an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 2 to 12 carbon atoms, and $R^{17d}$ is an alkyl group having 1 to 12 carbon atoms, a reaction proceeds in a structure represented by the lower part in the general formulae (VI-a) and (VI-b). In this case, $R^{16d}$ in the general formulae (VI-c) and (VI-d) is $R^{16f}$ in the general formula (VI-a), and $R^{17d}$ in the general formulae (VI-c) and (VI-d) is $R^{17e}$ in the general formula (VI-a).

As the alkylamine represented by the general formula (VI-a), pertaining to the production method for the compound represented by the general formula (VI-d), the commercially available one, or the one synthesized as appropriate by a method known per se may be used. A specific example of the alkylamine represented by the general formula (VI-a) includes, for example, methylamine, ethylamine, n-propylamine, isopropylamine, n-butylamine, isobutylamine, sec-butylamine, tert-butylamine, cyclobutylamine, n-pentylamine, isopentylamine, sec-pentylamine, tert-pentylamine, neopentylamine, (2-methylbutyl)amine, (1,2-dimethylpropyl)amine, (1-ethylpropyl)amine, cyclopentylamine, n-hexylamine, isohexylamine, sec-hexylamine, tert-hexylamine, neohexylamine, (2-methylpentyl)amine, (1,2-dimethylbutyl)amine, (2,3-dimethylbutyl)amine, (1-ethylbutyl)amine, cyclohexylamine, and the like.

As the aryl isothiocyanate represented by the general formula (VI-b), pertaining to the production method for the compound represented by the general formula (VI-d), the commercially available one, or the one synthesized as appropriate by a method known per se may be used. A specific example of the aryl isothiocyanate represented by the general formula (VI-b) includes, for example, phenyl isothiocyanate, 2-nitrophenyl isothiocyanate, 3-nitrophenyl isothiocyanate, 4-nitrophenyl isothiocyanate, 2,4-dinitrophenyl isothiocyanate, 2,6-dinitrophenyl isothiocyanate, 2-methylphenyl isothiocyanate, 3-methylphenyl isothiocyanate, 4-methylphenyl isothiocyanate, 4-ethylphenyl isothiocyanate, 4-n-propylphenyl isothiocyanate, 4-isopropylphenyl isothiocyanate, 4-n-butylphenyl isothiocyanate, 4-n-pentylphenyl isothiocyanate, 4-n-hexylphenyl isothiocyanate, 2,3-dimethylphenyl isothiocyanate, 3,4-dimethylphenyl isothiocyanate, 2,4-dimethylphenyl isothiocyanate, 2,6-dimethylphenyl isothiocyanate, 2,3-diethylphenyl isothiocyanate, 3,4-diethylphenyl isothiocyanate, 2,4-diethylphenyl isothiocyanate, 2,6-diethylphenyl isothiocyanate, 2,3-di(n-propyl)phenyl isothiocyanate, 2,4-di(n-propyl)phenyl isothiocyanate, 3,4-di(n-propyl)phenyl isothiocyanate, 2,6-di(n-propyl)phenyl isothiocyanate, 2,3-diisopropylphenyl isothiocyanate, 3,4-diisopropylphenyl isothiocyanate, 2,4-diisopropylphenyl isothiocyanate, 2,6-diisopropylphenyl isothiocyanate, 2,3-di(n-butyl)phenyl isothiocyanate, 2,4-di(n-butyl)phenyl isothiocyanate, 3,4-di(n-butyl)phenyl isothiocyanate, 2,6-di(n-butyl)phenyl isothiocyanate, 2,3-diisobutylphenyl isothiocyanate, 3,4-diisobutylphenyl isothiocyanate, 2,4-diisobutylphenyl isothiocyanate, 2,6-diisobutylphenyl isothiocyanate, 2,3-di(sec-butyl)phenyl isothiocyanate, 2,4-di(sec-butyl)phenyl isothiocyanate, 3,4-di(sec-butyl)phenyl isothiocyanate, 2,6-di(sec-butyl)phenyl isothiocyanate, 2,3-di(tert-butyl)phenyl isothiocyanate, 2,4-di(tert-butyl)phenyl isothiocyanate, 3,4-di(tert-butyl)phenyl isothiocyanate, 2,6-di(tert-butyl)phenyl isothiocyanate, 2,3-dicyclobutylphenyl isothiocyanate, 3,4-dicyclobutylphenyl isothiocyanate, 2,4-dicyclobutylphenyl isothiocyanate, 2,6-dicyclobutylphenyl isothiocyanate, 4-methoxyphenyl isothiocyanate, 4-methylthiophenyl isothiocyanate, 4-(N,N-dimethylamino)phenyl isothiocyanate, and the like.

Use amount of the aryl isothiocyanate represented by the general formula (VI-b) is not especially limited, as long as being a generally use amount in this field usually, and is, for example, usually 0.8 to 10 equivalents, preferably 0.9 to 5 equivalents, and more preferably 1 to 2 equivalents, relative to mole number of alkylamines represented by the general formula (VI-a). When the use amount of the aryl isothiocyanate is extremely low, yield of the thiourea derivative represented by the general formula (VI-c) could decrease. On the other hand, when the use amount of the aryl isothiocyanate is extremely high, a problem such as impairing economic performance occurs.

The desulfurization reaction in the production method for the compound represented by the general formula (VI-d) may be carried out as appropriate by a method known per se, and specifically, for example, the compound represented by the general formula (VI-d) may be obtained by a reaction of the thiourea derivative represented by the general formula (VI-c) with an amine, such as triethylamine, and a halogen atom, such as iodine.

Use amount of the amine in the desulfurization reaction is not especially limited, as long as being a generally use amount in this field usually, and is, for example, usually 0.8 to 10 equivalents, preferably 0.9 to 5 equivalents, and more preferably 2 to 3 equivalents, relative to mole number of thiourea derivatives represented by the general formula (VI-c). When the use amount of the amine is extremely low, yield of the compound represented by the general formula (VI-d) could decrease. On the other hand, when the use amount of the amine is extremely high, a problem such as impairing economic performance occurs.

Use amount of the halogen atom in the desulfurization reaction is not especially limited, as long as being a generally use amount in this field usually, and is, for example, usually 0.8 to 10 equivalents, preferably 0.9 to 5 equivalents, and more preferably 1 to 2 equivalents, relative to mole number of thiourea derivatives represented by the general formula (VI-c). When the use amount of the halogen atom is extremely low, yield of the compound represented by the general formula (VI-d) could decrease. On the other hand, when the use amount of the halogen atom is extremely high, a problem such as impairing economic performance occurs.

A series of reactions represented by the scheme [ii-i] may be carried out under solvent-free condition, or may be carried out in an organic solvent. A specific example of the organic solvent is not especially limited, as long as it is an organic solvent which does not react with the alkylamine, the aryl isothiocyanate, the thiourea derivative, and the compound represented by the general formula (VI-d), and includes the same as the specific example of the organic solvent represented by the scheme [i]. It should be noted that such an organic solvent may be used alone as one kind of the organic solvent, or may be used in combination of two or more kinds of the organic solvents. In addition, as such an organic solvent, the commercially available one may be used.

Use amount of the organic solvent is not especially limited, as long as being a generally use amount in this field usually, and is, for example, usually 0.01 to 500 mL, and preferably 0.1 to 100 mL, relative to 1 mmol of the alkylamine represented by the general formula (VI-a) or the thiourea derivative represented by the general formula (VI-c).

It is desirable that a series of reactions represented by the scheme [ii-i] are carried out under the following conditions (reaction temperature, pressure, reaction time).

It is desirable that temperature in the reaction (reaction temperature) of the alkylamine represented by the general formula (VI-a) and the aryl isothiocyanate represented by the general formula (VI-b), is set at temperature where the alkylamine and the aryl isothiocyanate react in good efficiency, and the thiourea derivative represented by the general formula (VI-c) can be obtained in good yield. Specifically, the reaction temperature is, for example, usually 0 to 200° C., and preferably 20 to 150° C.

It is desirable that temperature in the reaction (reaction temperature), in the desulfurization reaction for the thiourea derivative represented by the general formula (VI-c), is set at temperature where the compound represented by the general formula (VI-c) can be obtained in good yield. Specifically, the reaction temperature is, for example, usually 0 to 200° C., and preferably 20 to 150° C.

Pressure in a series of reactions represented by the scheme [ii-i] is not especially limited, as long as the series of reactions is carried out without delay, and the series of reactions may be carried out, for example, under normal pressure.

Reaction time in a series of reactions represented by the scheme [ii-i] may be influenced in some cases, by kinds of the alkylamine, the aryl isothiocyanate, the thiourea derivative and the compounds represented by the general formula (VI-d), use amount thereof, presence or absence of the organic solvent and kinds thereof, reaction temperature, pressure in the reaction, and the like. Accordingly, desirable reaction time cannot be said unconditionally, however, it is, for example, usually 1 minute to 24 hours, and preferably 3 minutes to 12 hours.

A series of products after the reaction represented by the scheme [ii-i] can be isolated by a general post-treatment operation and purification operation usually carried out in this field. Still more, the product may be isolated by filtration or washing of the reaction solution, as needed, and by carrying out recrystallization, distillation, column chromatography, and the like, of the residue obtained by concentration of the reaction solution.

The compound represented by the general formula ($B_3$—$X^a$), pertaining to the production method for the compound represented by the general formula (A) of the present invention, can be produced, for example, by a method shown in the following scheme [iii]. That is, among the compounds represented by the general formula ($B_3$—$X^a$), a compound, where $Q^1$ to $Q^3$ in the general formula ($B_3$—$X^a$) are the general formula ($b_2$), and $R^{19}$ represents an alkyl group having a tertiary alkyl at the binding site (a compound represented by the following general formula ($B_{3a}$—$X^a$)), may be synthesized, for example, by a reaction of a phosphine represented by the general formula (XII) and an alkylazide represented by the general formula (XIII), to obtain a compound represented by the general formula (XIV), and then by a reaction of the compound represented by the general formula (XIV) and a hydrogen halide represented by the general formula (VIII). In addition, a compound, where $Q^1$ to $Q^3$ in the general formula ($B_3$—$X^a$) are the general formula ($b_2$), and $R^{19}$ represents a hydrogen atom or an alkyl group having a primary or a secondary alkyl at the binding site (a compound represented by the following general formula ($B_{3b}$—$X^a$)), may be synthesized, for example, by refluxing with the addition of trimethylsilyl azide into the phosphine represented by the general formula (XII), and next by the addition of methanol to obtain a phosphazene represented by the general formula (XV), and still more by a reaction of the phosphazene represented by the general formula (XV) and an alkyl halide represented by the general formula (XVI). In addition, among the compounds represented by the general formula ($B_3$—$X^a$), a compound, where $Q^1$ to $Q^3$ in the general formula ($B_3$—$X^a$) are the general formula ($b_3$) (a compound represented by the following general formula ($B_{3c}$—$X^a$)), may be synthesized, for example, by a reaction of the phosphazene represented by the general formula (XV), synthesized by the above-described method, and a compound represented by the general formula (XVII), to obtain a compound represented by the general formula (XVIII), and then by a reaction of the compound represented by the general formula (XVIII) and the hydrogen halide represented by the general formula (VIII).

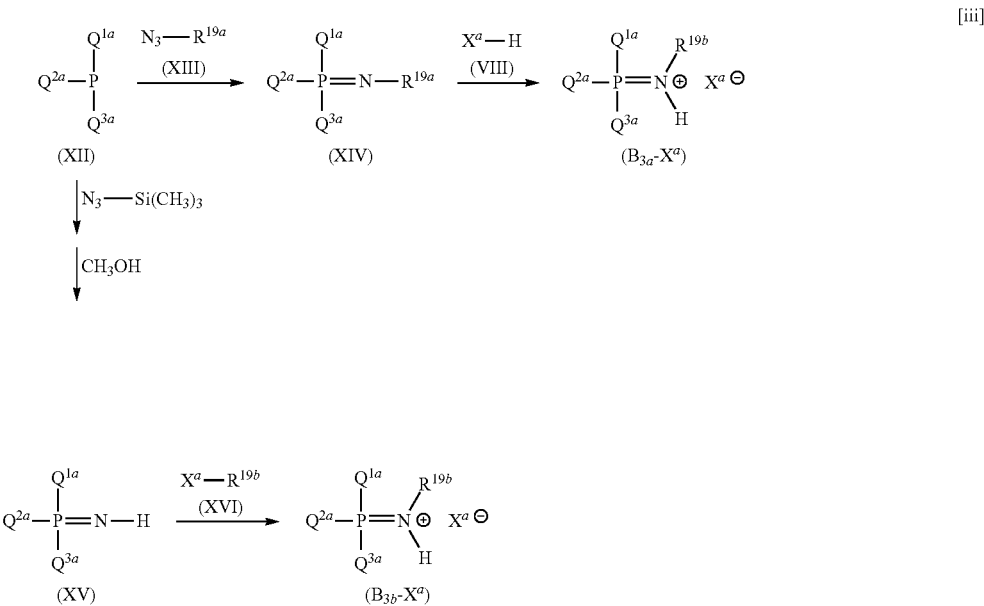

[iii]

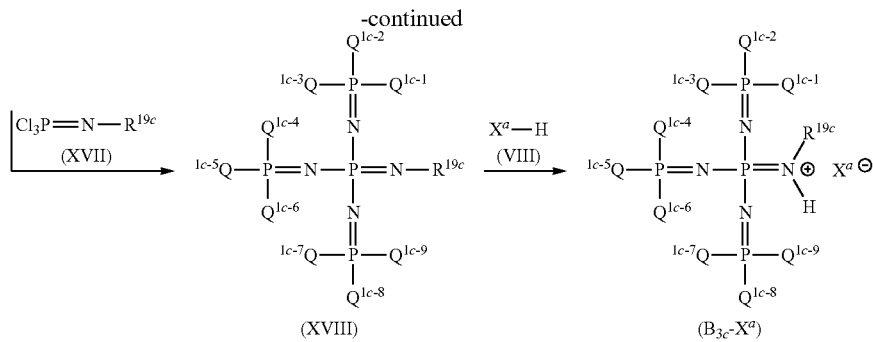

(in the scheme, $R^{19}$ represents an alkyl group having 4 to 12 carbon atoms, having a tertiary alkyl at the binding site; $R^{19b}$ represents a hydrogen atom or an alkyl group having 1 to 12 carbon atoms, having a primary or a secondary alkyl at the binding site; $R^{19c}$ represents an alkyl group having 1 to 12 carbon atoms; $Q^{1a}$ to $Q^{3a}$ and $Q^{1c-1}$ to $Q^{1c-9}$ each independently represent the general formula ($b_2$); $X^a$ and $X^{a-}$ are the same as described above, and in the general formulae (XII), (XIV) and (XVIII), number of hydrogen atoms bonding to the nitrogen atoms in the formula is 0 to 4, and in the general formulae (XV), ($B_{3a}$—$X^a$), ($B_{3b}$—$X^a$) and ($B_{3c}$—$X^a$), number of hydrogen atoms bonding to the nitrogen atoms in the formula is 1 to 5.

A specific example of each functional group ($R^{19c}$, $Q^{1a}$ to $Q^{3a}$, and $Q^{1c-1}$ to $Q^{1c-9}$) in the general formulae (XII) to (XVIII) and ($B_{3a}$—$X^a$) to ($B_{3c}$—$X^a$) includes the same as the specific example of corresponding each functional group ($R^{19}$ and $Q^1$ to $Q^3$) described in the general formula ($B_2$), and a preferable specific example also includes the same.

As the alkyl group having 4 to 12 carbon atoms, having a tertiary alkyl at a binding site, represented by $R^{19a}$ in the general formulae (XIII), (XIV) and ($B_{3a}$—$X^a$), a branched group having a tertiary alkyl at a binding site is preferable, and specifically includes, such as a tert-butyl group, a tert-pentyl group, a tert-hexyl group, a 3-methylpentane-3-yl group, a tert-heptyl group, a 3-methylhexane-3-yl group, a 3-ethylpentane-3-yl group, a tert-octyl group, a 3-methylheptane-3-yl group, a 3-ethylhexane-3-yl group, a 2,4,4-trimethylpentane-2-yl group, a tert-nonyl group, a tert-decyl group, a tert-undecyl group, a tert-dodecyl group, an adamanthyl group; among these, an alkyl group having 4 to 8 carbon atoms, having a tertiary alkyl at a binding site, such as a tert-butyl group, a tert-pentyl group, a tert-hexyl group, a 3-methylpentane-3-yl group, a tert-heptyl group, a 3-methylhexane-3-yl group, a 3-ethylpentane-3-yl group, a tert-octyl group, a 3-methylheptane-3-yl group, a 3-ethylhexane-3-yl group, a 2,4,4-trimethylpentane-2-yl group, is preferable; and among these, a tert-butyl group is more preferable.

The alkyl group having 1 to 12 carbon atoms, having a primary or a secondary alkyl at a binding site, represented by $R^1$ in the general formulae (XVI) and ($B_{3b}$—$X^a$), may be any of a straightchained, a branched, or a cyclic one, as long as having a primary or a secondary alkyl at a binding site, and specifically includes, for example, a methyl group, an ethyl group, an n-propyl group, an isopropyl group, an n-butyl group, an isobutyl group, a sec-butyl group, a cyclobutyl group, an n-pentyl group, an isopentyl group, a sec-pentyl group, a neopentyl group, a 2-methylbutyl group, a 1,2-dimethylpropyl group, a 1-ethylpropyl group, a cyclo-pentyl group, an n-hexyl group, an isohexyl group, a sec-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a neoheptyl group, a cycloheptyl group, an n-octyl group, an isooctyl group, a sec-octyl group, a neooctyl group, a 2-ethylhexyl group, a cyclooctyl group, an n-nonyl group, an isononyl group, a sec-nonyl group, a neononyl group, a cyclononyl group, an n-decyl group, an isodecyl group, a sec-decyl group, a neodecyl group, a cyclodecyl group, an n-undecyl group, a cycloundecyl group, an n-dodecyl group, a cyclododecyl group, and the like. Among these, an alkyl group having 1 to 8 carbon atoms, having a primary or a secondary alkyl at a binding site, such as a methyl group, an ethyl group, an n-propyl group, an isopropyl group, an n-butyl group, an isobutyl group, a sec-butyl group, a cyclobutyl group, an n-pentyl group, an isopentyl group, a sec-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a neoheptyl group, a cycloheptyl group, an n-octyl group, an isooctyl group, a sec-octyl group, a neooctyl group, a 2-ethylhexyl group, a cyclooctyl group, is preferable; and among these, an alkyl group having 1 to 4 carbon atoms, having a primary or a secondary alkyl at a binding site, such as a methyl group, an ethyl group, an n-propyl group, an isopropyl group, an n-butyl group, an isobutyl group, a sec-butyl group, a cyclobutyl group, is more preferable; and among these, a straight chained alkyl group having 1 to 4 carbon atoms, such as a methyl group, an ethyl group, an n-propyl group, an n-butyl group, is still more preferable; and among these, a methyl group is particularly preferable.

In the general formulae (XII), (XIV) and (XVIII), number of hydrogen atoms bonding to the nitrogen atoms in the formula, is an integer of 0 to 4, 0 to 2 is preferable, and 0 is more preferable.

Number of hydrogen atoms bonding to the nitrogen atoms in the general formulae (XV) and ($B_{3a}$—$X^a$) to ($B_{3c}$—$X^a$) is an integer of 1 to 5, 1 to 3 is preferable, and 1 is more preferable. It should be noted that number of hydrogen atoms shown here is always 1 or larger, because in the general formulae (XV) and ($B_{3a}$—$X^a$) to ($B_{3c}$—$X^a$), the nitrogen atoms in the formula already has one hydrogen atom.

As $R^{19a}$ in the general formulae (XIII), (XIV) and ($B_{3a}$—$X^a$), an alkyl group having 4 to 8 carbon atoms, and having a tertiary alkyl at a binding site is more preferable.

As $R^{19b}$ in the general formulae (XVI) and ($B_{3b}$—$X^a$), an alkyl group having 1 to 12 carbon atoms, and having a primary or a secondary alkyl at the binding site is more preferable.

As $R^{19c}$ in the general formulae (XVII), (XVIII) and ($B_{3c}$—$X^a$), an alkyl group having 1 to 8 carbon atoms is more preferable.

As the phosphine represented by the general formula (XII), pertaining to the production method for the compound represented by the general formula ($B_3$—$X^a$), the commercially available one, or the one synthesized as appropriate by a method known per se may be used. A specific example of the phosphine represented by the general formula (XII) includes tris(dimethylamino)phosphine, tris(diethylamino)phosphine, tris(di-n-propylamino)phosphine, tris(diisopropylamino)phosphine, tris(di-n-butylamino)phosphine, tris(diisobutylamino)phosphine, tris(di-sec-butylamino)phosphine, tris(di-tert-butylamino)phosphine, tris(dicyclobutylamino)phosphine, tris(N-aziridinyl)phosphine, tris(N-azetidinyl)phosphine, tris(N-pyrrolidinyl)phosphine, 2-diethylamino-1-methyl-1,3-diaza-2-phosphacyclohexane, 2-diethylamino-1,3-dimethyl-1,3-diaza-2-phosphacyclohexane, 2-tert-butylamino-1-methyl-1,3-diaza-2-phosphacyclohexane, 2-tert-butylamino-1,3-dimethyl-1,3-diaza-2-phosphacyclohexane, and the like.

As the alkylazide represented by the general formula (XIII), pertaining to the production method for the compound represented by the general formula ($B_3$—$X^a$), the commercially available one, or the one synthesized as appropriate by a method known per se may be used. A specific example of the alkylazide represented by the general formula (XIII) includes tert-butyl azide, tert-pentyl azide, tert-hexyl azide, 3-methylpentane-3-yl azide, tert-heptyl azide, 3-methylhexane-3-yl azide, 3-ethylpentane-3-yl azide, tert-octyl azide, 3-methylheptane-3-yl azide, 3-ethylhexane-3-yl azide, 2,4,4-trimethylpentane-2-yl azide, tert-nonyl azide, tert-decyl azide, tert-undecyl azide, tert-dodecyl azide, adamantyl azide, and the like.

As the alkyl halide represented by the general formula (XVI), pertaining to the production method for the compound represented by the general formula ($B_3$—$X^a$), the commercially available one, or the one synthesized as appropriate by a method known per se may be used. A specific example of the alkyl halide represented by the general formula (XVI) includes methyl chloride, methyl bromide, methyl iodide, ethyl chloride, ethyl bromide, ethyl iodide, propyl chloride, propyl bromide, propyl iodide, butyl chloride, butyl bromide, butyl iodide, pentyl chloride, pentyl bromide, pentyl iodide, hexyl chloride, hexyl bromide, hexyl iodide, heptyl chloride, heptyl bromide, heptyl iodide, octyl chloride, octyl bromide, octyl iodide, nonyl chloride, nonyl bromide, nonyl iodide, decyl chloride, decyl bromide, decyl iodide, undecyl chloride, undecyl bromide, undecyl iodide, dodecyl chloride, dodecyl bromide, dodecyl iodide, and the like. It should be noted that, in the specific example, the alkyl group in the alkyl halide is not limited to a normal-form; and a branched-type one such as sec-form, iso-form, neo-form, or a ring-type one such as cyclo-form, is also included in the specific example; but the alkyl group having a tertiary alkyl in a binding site, such as a tert-form, is excluded.

As the compound represented by the general formula (XVII), pertaining to the production method for the compound represented by the general formula ($B_3$—$X^a$), the commercially available one, or the one synthesized as appropriate by a method known per se may be used. Such a compound represented by the general formula (XVII) includes P,P-dichloro-N-methylphosphine imide, P,P-dichloro-N-ethylphosphine imide, P,P-dichloro-N-n-propylphosphine imide, P,P-dichloro-N-isopropylphosphine imide, P,P-dichloro-N-n-butylphosphine imide, P,P-dichloro-N-isobutylphosphine imide, P,P-dichloro-N-sec-butylphosphine imide, P,P-dichloro-N-tert-butylphosphine imide, P,P-dichloro-N-cyclobutylphosphine imide, P,P-dichloro-N-n-pentylphosphine imide, P,P-dichloro-N-isopentylphosphine imide, P,P-dichloro-N-sec-pentylphosphine imide, P,P-dichloro-N-tert-pentylphosphine imide, P,P-dichloro-N-neopentylphosphine imide, P,P-dichloro-N-2-methylbutylphosphine imide, P,P-dichloro-N-1,2-dimethylpropylphosphine imide, P,P-dichloro-N-1-ethylpropylphosphine imide, P,P-dichloro-N-cyclopentylphosphine imide, P,P-dichloro-N-n-hexylphosphine imide, P,P-dichloro-N-isohexylphosphine imide, P,P-dichloro-N-sec-hexylphosphine imide, P,P-dichloro-N-tert-hexylphosphine imide, P,P-dichloro-N-neohexylphosphine imide, P,P-dichloro-N-2-methylpentylphosphine imide, P,P-dichloro-N-1,2-dimethylbutylphosphine imide, P,P-dichloro-N-2,3-dimethylbutylphosphine imide, P,P-dichloro-N-1-ethylbutylphosphine imide, P,P-dichloro-N-cyclohexylphosphine imide, P,P-dichloro-N-n-heptylphosphine imide, P,P-dichloro-N-isoheptylphosphine imide, P,P-dichloro-N-sec-heptylphosphine imide, P,P-dichloro-N-tert-heptylphosphine imide, P,P-dichloro-N-neoheptylphosphine imide, P,P-dichloro-N-cycloheptylphosphine imide, P,P-dichloro-N-n-octylphosphine imide, P,P-dichloro-N-isooctylphosphine imide, P,P-dichloro-N-sec-octylphosphine imide, P,P-dichloro-N-tert-octylphosphine imide, P,P-dichloro-N-neooctylphosphine imide, P,P-dichloro-N-2-ethylhexylphosphine imide, P,P-dichloro-N-cyclooctylphosphine imide, and the like.

Use amount of the alkylazide represented by the general formula (XIII), in the production method for the compound represented by the general formula ($B_3$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of phosphines represented by the general formula (XII). When the use amount of the alkylazide is extremely low, yield of the compound represented by the general formula (XIV) could decrease. On the other hand, when the use amount of the alkylazide is extremely high, a problem such as impairing economic performance occurs.

Use amount of the hydrogen halide represented by the general formula (VIII), in the production method for the compound represented by the general formula ($B_3$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (XIV) or the general formula (XVIII). When the use amount of the hydrogen halide is extremely low, yield of the compound represented by the general formula ($B_3$—$X^a$) or the general formula ($B_{3b}$—$X^a$) could decrease. On the other hand, when the use amount of the hydrogen halide is extremely high, a problem such as impairing economic performance occurs.

Use amount of trimethylsilyl azide and methanol to be used in a reaction to obtain the phosphazene represented by the general formula (XV), in the production method for the compound represented by the general formula ($B_3$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of phosphines represented by the general formula (XII). When the use amount of trimethylsilyl azide and methanol is extremely low, yield of the phosphazene could decrease. On the other hand, when the use amount of trimethylsilyl azide and methanol is extremely high, a problem such as impairing economic performance occurs.

Use amount of the alkyl halide represented by the general formula (XVI), in the production method for the compound represented by the general formula ($B_3$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of phosphazenes represented by the general formula (XV). When the use amount of the alkyl halide is extremely low, yield of the compound represented by the general formula (X) could decrease. On the other hand, when the use amount of the alkyl halide is extremely high, a problem such as impairing economic performance occurs.

Use amount of the phosphazene represented by the general formula (XV) to be used in a reaction to obtain the compound represented by the general formula (XVIII), in the production method for the compound represented by the general formula ($B_3$—$X^a$), is not especially limited, as long as being a generally use amount in this field usually, and is, for example, usually 2.6 to 30 equivalents, preferably 2.8 to 10 equivalents, and more preferably 3 to 4 equivalents, relative to mole number of compounds represented by the general formula (XVII). When the use amount of the phosphazene is extremely low, yield of the compound represented by the general formula (XVIII) could decrease. On the other hand, when the use amount of the phosphazene is extremely high, a problem such as impairing economic performance occurs.

A series of reactions represented by the scheme [iii] is usually carried out in suitable organic solvent. A specific example of the organic solvent is not especially limited, as long as it is an organic solvent which does not react with the phosphine, the alkylazide, the hydrogen halide, trimethylsilyl azide, methanol, the phosphazene, the alkyl halide, and the compounds represented by the general formulae (XVII) and (XVIII), and includes the same as the specific example of the organic solvent represented by the scheme [i]. It should be noted that such an organic solvent may be used alone as one kind of the organic solvent, or may be used in combination of two or more kinds of the organic solvents. In addition, as such an organic solvent, the commercially available one may be used.

Use amount of the organic solvent is not especially limited, as long as being a generally use amount in this field usually, and is, for example, usually 0.01 to 500 mL, and preferably 0.1 to 100 mL, relative to 1 mmol of the phosphine represented by the general formula (XII), the compound represented by the general formula (XIV), the phosphazene represented by the general formula (XV), or the compound represented by the general formula (XVIII).

It is desirable that a series of reactions represented by the scheme [iii] are carried out under the following conditions (reaction temperature, pressure, reaction time).

It is desirable that temperature in the reaction (reaction temperature) of the phosphine represented by the general formula (XII) and the alkylazide represented by the general formula (XIII), is set at temperature where the phosphine and the alkylazide react in good efficiency, and the compound represented by the general formula (XIV) can be obtained in good yield. Specifically, the reaction temperature is, for example, usually −20 to 150° C., and preferably 0 to 80° C.

It is desirable that temperature in the reaction (reaction temperature) of the compound represented by the general formula (XIV) or the general formula (XVIII) and the hydrogen halide represented by the general formula (VIII), is set at temperature where the compound represented by the general formula (XIV) or the general formula (XVIII) and the hydrogen halide react in good efficiency, and the compound represented by the general formula ($B_{3a}$—$X^a$) or the general formula ($B_{3c}$—$X^a$) can be obtained in good yield. Specifically, the reaction temperature is, for example, usually −20 to 150° C., and preferably 0 to 80° C.

Temperature in the reaction (reaction temperature) of the phosphine represented by the general formula (XII) and trimethylsilyl azide may be temperature generally used in carrying out refluxing operation in this field usually, and it is desirable to be set at temperature where the phosphine and trimethylsilyl azide react in good efficiency, and the phosphazene represented by the general formula (XV) can be obtained in good yield. Specifically, the reaction temperature is, for example, usually 50 to 300° C., and preferably 100 to 200° C.

It is desirable that temperature in the reaction (reaction temperature) of the compound, obtained by a reaction of the phosphine and trimethylsilyl azide, and methanol is set at temperature where the compound, obtained by a reaction of the phosphine and trimethylsilyl azide, reacts with methanol in good efficiency, and the phosphazene represented by the general formula (XV) can be obtained in good yield. Specifically, the reaction temperature is, for example, usually −20 to 150° C., and preferably 0 to 80° C.

It is desirable that temperature in the reaction (reaction temperature) of the phosphazene represented by the general formula (XV) and the alkyl halide represented by the general formula (XVI) is set at temperature where the phosphazene and the alkyl halide react in good efficiency, and the compound represented by the general formula ($B_{3b}$—$X^a$) can be obtained in good yield. Specifically, the reaction temperature is, for example, usually 0 to 200° C., and preferably 20 to 150° C.

It is desirable that temperature in the reaction (reaction temperature) of the phosphazene represented by the general formula (XV) and the compound represented by the general formula (XVII) is set at temperature where the phosphazene and the compound represented by the general formula (XVII) react in good efficiency, and the compound represented by the general formula (XVIII) can be obtained in good yield. Specifically, the reaction temperature is, for example, usually −20 to 150° C., and preferably 0 to 80° C.

Pressure in a series of reactions represented by the scheme [iii] is not especially limited, as long as the series of reactions is carried out without delay, and the series of reactions may be carried out, for example, under normal pressure.

Reaction time in a series of reactions represented by the scheme [iii] may be influenced in some cases, by kinds of the phosphine, the alkylazide, the hydrogen halide, trimethylazide, methanol, the phosphazene, the alkyl halide, and the compounds represented by the general formulae (XVII) and (XVIII), use amount of such compounds, kinds of an organic solvent, reaction temperature, pressure in the reaction, and the like. Accordingly, desirable reaction time cannot be said unconditionally, however, it is, for example, usually 1 minute to 24 hours, and preferably 3 minutes to 12 hours.

A series of products after the reaction represented by the scheme [iii] can be isolated by a general post-treatment operation and purification operation usually carried out in this field. As a specific example of the isolation method, the product can be isolated, for example, as needed, by the addition of a non-polar solvent, such as diethyl ether and methylene chloride, into a reaction system, and by vacuum concentration of an organic layer. In addition, the product may be isolated by filtration or washing of the reaction solution, as needed, and by carrying out recrystallization, distillation, column chromatography, and the like, of the residue obtained by concentration of the reaction solution.

The compound represented by the general formula ($B_4$—$X^a$), pertaining to the production method for the compound represented by the general formula (A) of the present invention, can be produced, for example, by a method shown in the following scheme [iv]. That is, the compound represented by the general formula ($B_4$—$X^a$) may be synthesized, for example, by refluxing with the addition of trimethylsilyl azide into a phosphine represented by the general formula (XIX), and then by the addition of a compound represented by the general formula (XX) to obtain a compound represented by the general formula (XXI), and still more by a reaction of the compound represented by the general formula (XXI) and a compound represented by the general formula (XXII).

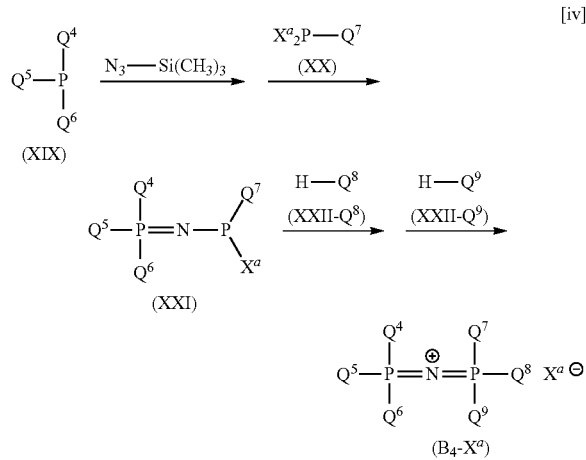

[iv]

(In the scheme, $Q^4$ to $Q^9$ and $X^a$ are the same as described above, and in the general formula ($B_4$—$X^a$), number of hydrogen atoms bonding to the nitrogen atoms in the formula is 0 to 4.)

In the general formula ($B_4$—$X^a$), number of hydrogen atoms bonding to the nitrogen atoms in the formula, is an integer of 0 to 4, 0 to 2 is preferable, and 0 is more preferable.

A specific example of the phosphine represented by the general formula (XIX), pertaining to the production method for the compound represented by the general formula ($B_4$—$X^a$), includes tris(dimethylamino)phosphine, tris(diethylamino)phosphine, tris(di-n-propylamino)phosphine, tris(diisopropylamino)phosphine, tris(di-n-butylamino)phosphine, tris(diisobutylamino)phosphine, tris(di-sec-butylamino) phosphine, tris(di-tert-butylamino)phosphine, tris(dicyclobutylamino)phosphine, and the like. It should be noted that, as such a phosphine represented by the general formula (XIX), the commercially available one, or the one synthesized as appropriate by a method known per se may be used.

A specific example of the compound represented by the general formula (XX), pertaining to the production method for the compound represented by the general formula ($B_4$—$X^a$), includes dichloro(dimethylamino)phosphine, dichloro (diethylamino)phosphine, dichloro(di-n-propylamino)phosphine, dichloro(diisopropylamino)phosphine, dichloro(di-n-butylamino)phosphine, dichloro(diisobutylamino) phosphine, dichloro(di-sec-butylamino)phosphine, dichloro (di-tert-butylamino)phosphine, dichloro (dicyclobutylamino)phosphine, dichlorophosphineimino tris (dimethylamino)phosphorane, dichlorophosphineimino tris (diethylamino)phosphorane, dichlorophosphineimino tris (di-n-propylamino)phosphorane, dichlorophosphineimino tris(diisopropylamino)phosphorane, dichlorophosphineimino tris(di-n-butylamino)phosphorane, dichlorophosphineimino tris(diisobutylamino)phosphorane, dichlorophosphineimino tris(di-sec-butylamino)phosphorane, dichlorophosphineimino tris(di-tert-butylamino)phosphorane, dichlorophosphineimino tris(dicyclobutylamino)phosphorane, and the like. It should be noted that, as such a compound represented by the general formula (XX), the commercially available one, or the one synthesized as appropriate by a method known per se may be used.

A specific example of the compounds represented by the general formulae (XXII-$Q^8$) and (XXII-$Q^9$), pertaining to the production method for the compound represented by the general formula ($B_4$—$X^a$), includes dimethylamine, diethylamine, di-n-propylamine, diisopropylamine, di-n-butylamine, diisobutylamine, di-sec-butylamine, di-tert-butylamine, dicyclobutylamine, tris(dimethylamino)phosphine imine, tris(diethylamino)phosphine imine, tris(di-n-propylamino)phosphine imine, tris(diisopropylamino)phosphine imine, tris(di-n-butylamino)phosphine imine, tris(diisobutylamino)phosphine imine, tris(di-sec-butylamino)phosphine imine, tris(di-tert-butylamino)phosphine imine, tris(dicyclobutylamino)phosphine imine. It should be noted that, as such a compounds represented by the general formulae (XXII-$Q^8$) and (XXII-$Q^9$), the commercially available one, or the one synthesized as appropriate by a method known per se may be used.

Use amount of trimethylsilyl azide to be used in a reaction to obtain the compound represented by the general formula (XXI), in the production method for the compound represented by the general formula ($B_4$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of phosphines represented by the general formula (XIX). When the use amount of trimethylsilyl azide is extremely low, yield of the compound represented by the general formula (XXI) could decrease. On the other hand, when the use amount of trimethylsilyl azide is extremely high, a problem such as impairing economic performance occurs.

Use amount of the compound represented by the general formula (XX), in the production method for the compound represented by the general formula ($B_4$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of phosphines represented by the general formula (XIX). When the use amount of the compound represented by the general formula (XX) is extremely low, yield of the compound represented by the general formula (XXI) could decrease. On the other hand, when the use amount of the compound represented by the general formula (XX) is extremely high, a problem such as impairing economic performance occurs.

Use amount of the compound represented by the general formula (XXII-$Q^8$), in the production method for the compound represented by the general formula ($B_4$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (XXI). When the use amount of the compound represented by the general formula (XXII-$Q^8$) is extremely low, yield of the compound represented by the general formula ($B_4$—$X^a$) could decrease. On the other hand, when the use amount of the compound represented by the general formula (XXII-$Q^8$) is extremely high, a problem such as impairing economic performance occurs.

Use amount of the compound represented by the general formula (XXII-$Q^9$), in the production method for the compound represented by the general formula ($B_4$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (XXI). When the use amount of the compound represented by the general formula (XXII-$Q^9$) is extremely low, yield of the compound represented by the general formula ($B_4$—$X^a$) could decrease. On the other hand, when the use amount of the compound represented by the general formula (XXII-$Q^9$) is extremely high, a problem such as impairing economic performance occurs.

In the production method for the compound represented by the general formula ($B_4$—$X^a$), in a reaction to obtain the compound represented by the general formula ($B_4$—$X^a$), when $Q^8$ and $Q^9$ in the scheme [iv] represent the same functional group, the compound represented by the general formula ($B_4$—$X^a$) may be obtained by one time reaction operation by the addition of the compound represented by the general formula (XXII-$Q^8$) and the compound represented by the general formula (XXII-$Q^9$) at the same time. In this case, use amount of each of the compounds represented by the general formulae (XXII-$Q^8$) and (XXII-$Q^9$) is similar to the use amount of the compound represented by the general formula (XXII-$Q^8$) described above, and preferable use amount also includes the same.

A series of reactions represented by the scheme [iv] may be carried out under solvent-free condition, or may be carried out in an organic solvent. A specific example of the organic solvent is not especially limited, as long as it is an organic solvent which does not react with the phosphine, trimethylsilyl azide, and the compounds represented by the general formulae (XX), (XXII-$Q^8$) and (XXII-$Q^9$), and includes the same as the specific example of the organic solvent represented by the scheme [i]. It should be noted that such an organic solvent may be used alone as one kind of the organic solvent, or may be used in combination of two or more kinds of the organic solvents. In addition, as such an organic solvent, the commercially available one may be used.

Use amount of the organic solvent is not especially limited, as long as being a generally use amount in this field usually, and is, for example, usually 0.01 to 500 mL, and preferably 0.1 to 100 mL, relative to 1 mmol of the phosphine represented by the general formula (XIX) or the compound represented by the general formula (XXI).

It is desirable that a series of reactions represented by the scheme [iv] are carried out under the following conditions (reaction temperature, pressure, reaction time).

Temperature in the reaction (reaction temperature) of the phosphine represented by the general formula (XIX) and trimethylsilyl azide may be temperature generally used in carrying out refluxing operation in this field usually, and it is desirable to be set at temperature where the phosphine and trimethylsilyl azide react in good efficiency, and the reaction product can be obtained in good yield. Specifically, the reaction temperature is, for example, usually 50 to 300° C., and preferably 100 to 200° C.

It is desirable that temperature in the reaction (reaction temperature) of the compound, obtained by a reaction of the phosphine and trimethylsilyl azide, and the compound represented by the general formula (XX) may be set at temperature where the compound, obtained by a reaction of the phosphine and trimethylsilyl azide, reacts with the compound represented by the general formula (XX) in good efficiency, and the compound represented by the general formula (XXI) can be obtained in good yield. Specifically, the reaction temperature is, for example, usually −20 to 150° C., and preferably 0 to 80° C.

It is desirable that temperature in the reaction (reaction temperature) of the compound represented by the general formula (XXI) and the compound represented by the general formula (XXII-$Q^8$) or (XXII-$Q^9$) may be set at temperature where the compound represented by the general formula (XXI) and the compound represented by the general formula (XXII-$Q^8$) or (XXII-$Q^9$) react in good efficiency, and the compound represented by the general formula ($B_4$—$X^a$) can be obtained in good yield. Specifically, the reaction temperature is, for example, usually −20 to 150° C., and preferably 0 to 80° C.

Pressure in a series of reactions represented by the scheme [iv] is not especially limited, as long as the series of reactions is carried out without delay, and the series of reactions may be carried out, for example, under normal pressure.

Reaction time in a series of reactions represented by the scheme [iv] may be influenced in some cases, by kinds of the phosphine, trimethylsilyl azide, and the compounds represented by the general formulae (XX), (XXII-$Q^8$) and (XXII-$Q^9$), use amount of such compounds, kinds of an organic solvent, reaction temperature, pressure in the reaction, and the like. Accordingly, desirable reaction time cannot be said unconditionally, however, it is, for example, usually 1 minute to 24 hours, and preferably 3 minutes to 12 hours.

A series of products after the reaction represented by the scheme [iv], can be isolated by a general post-treatment operation and purification operation usually carried out in this field. In addition, the product may be isolated by filtration or washing of the reaction solution, as needed, and by carrying out recrystallization, distillation, column chromatography, and the like, of the residue obtained by concentration of the reaction solution.

The compound represented by the general formula ($B_5$—$X^a$), pertaining to the production method for the compound represented by the general formula (A) of the present invention, can be produced, for example, by a method shown in the following scheme [v]. That is, among the compounds represented by the general formula ($B_5$—$X^a$), a compound, where $R^{30}$ in the general formula ($B_5$—$X^a$) represents the group represented by the general formula ($b_3$), and $R^{32}$, $R^{33}$ together with $R^{35}$ do not form an alkylene group having 5 to 10 carbon atoms which may contain a nitrogen atom (a compound represented by the following general formula ($B_{5a}$—$X^a$)), may be synthesized, for example, by a reaction of a phosphine represented by the general formula (XXIII) and a phosphonium azide represented by the general formula (XXIV). In addition, a compound, where $R^{32}$, $R^{33}$ together with $R^{35}$ in the general formula ($B_5$—$X^a$) form an alkylene group having 5 to 10 carbon atoms which may contain a nitrogen atom (a compound represented by the following general formula ($B_{5b}$—$X^a$)), may be synthesized, for example, by the addition of diethylamine into a phosphorus trihalide represented by the general formula (XXV), to obtain a compound represented by the general formula (XXVI), and then by a reaction of the compound represented by the general formula (XXVI) and a compound represented by the general formula (XXVII).

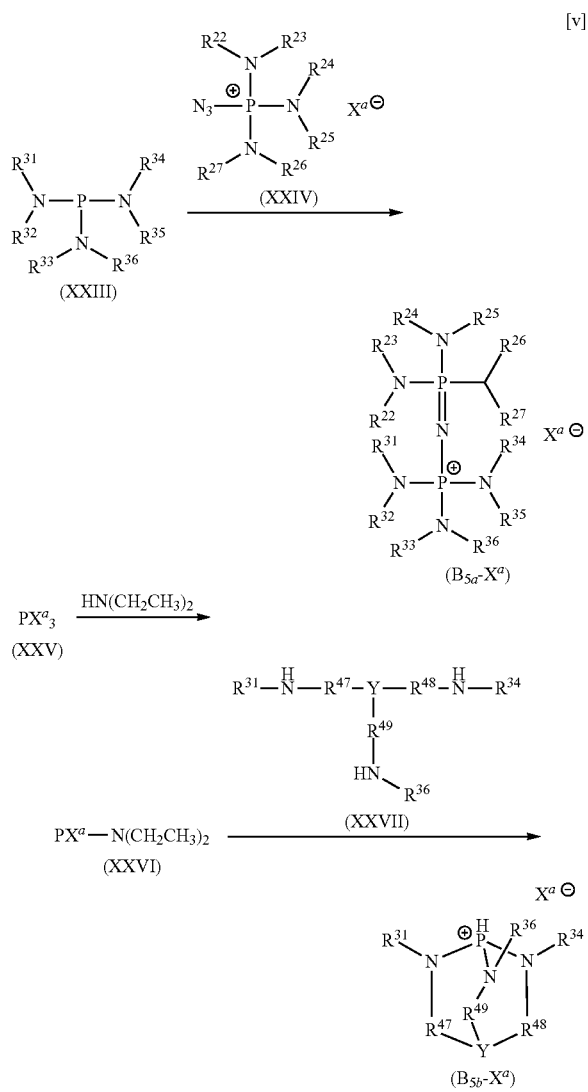

(In the scheme, $R^{22}$ to $R^{27}$, $R^{31}$ to $R^{36}$, $R^{47}$ to $R^{49}$, $X^a$ and Y are the same as described above, and in the general formulae ($B_{5a}$—$X^a$) and ($B_{5b}$—$X^a$), number of hydrogen atoms bonding to the nitrogen atoms in the formula is 0 to 4.)

In the general formulae ($B_{5a}$—$X^a$) and ($B_{5b}$—$X^a$), number of hydrogen atoms bonding to the nitrogen atoms in the formula, is an integer of 0 to 4, 0 to 2 is preferable, and 0 is more preferable.

As the phosphine represented by the general formula (XXIII), pertaining to the production method for the compound represented by the general formula ($B_5$—$X^a$), the commercially available one, or the one synthesized as appropriate by a method known per se may be used. A specific example of the phosphine represented by the general formula (XXIII) includes the same as the specific example of the phosphine represented by the general formula (XII), pertaining to the production method for the compound represented by the general formula ($B_3$—$X^a$).

As the phosphonium azide represented by the general formula (XXIV), pertaining to the production method for the compound represented by the general formula ($B_5$—$X^a$), the commercially available one, or the one synthesized as appropriate by a method known per se may be used. A specific example of the phosphonium azide represented by the general formula (XXIV) includes tris(dimethylamino)phosphonium azide chloride, tris(diethylamino)phosphonium azide chloride, tris(di-n-propylamino)phosphonium azide chloride, tris(diisopropylamino)phosphonium azide chloride, tris(di-n-butylamino)phosphonium azide chloride, tris(diisobutylamino)phosphonium azide chloride, tris(di-sec-butylamino)phosphonium azide chloride, tris(di-tert-butylamino)phosphonium azide chloride, tris(dicyclobutylamino)phosphonium azide chloride, and the like.

As the phosphorus trihalide represented by the general formula (XXV), pertaining to the production method for the compound represented by the general formula ($B_5$—$X^a$), the commercially available one, or the one synthesized as appropriate by a method known per se may be used. A specific example of the phosphorus trihalide represented by the general formula (XXV) includes phosphorus trichloride, phosphorus tribromide, phosphorus triiodide, and the like.

As the compound represented by the general formula (XXVII), pertaining to the production method for the compound represented by the general formula ($B_5$—$X^a$), the commercially available one, or the one synthesized as appropriate by a method known per se may be used. A specific example of the compound represented by the general formula (XXVII) includes tris(2-(N-methylamino)ethyl)amine, tris(2-(N-ethylamino)ethyl)amine, tris(2-(N-n-propylamino)ethyl)amine, tris(2-(N-isopropylamino)ethyl)amine, tris(2-(N-n-butylamino)ethyl)amine, tris(2-(N-isobutylamino)ethyl)amine, tris(2-(N-sec-butylamino)ethyl)amine, tris(2-(tert-butylamino)ethyl)amine, tris(2-(cyclobutylamino)ethyl)amine, tris(2-(N-methylamino)methyl)amine, tris(2-(N-methylamino)propyl)amine, tris(2-(N-methylamino)ethyl)methane, tris(2-(N-ethylamino)ethyl)methane, tris(2-(N-n-propylamino)ethyl)methane, tris(2-(N-isopropylamino)ethyl)methane, tris(2-(N-n-butylamino)ethyl)methane, tris(2-(N-isobutylamino)ethyl)methane, tris(2-(N-sec-butylamino)ethyl)methane, tris(2-(tert-butylamino)ethyl)methane, tris(2-(cyclobutylamino)ethyl)methane, tris(2-(N-methylamino)methyl)methane, tris(2-(N-methylamino)propyl) methane, and the like.

Use amount of the phosphonium azide represented by the general formula (XXIV), in the production method for the compound represented by the general formula ($B_5$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of phosphines represented by the general formula (XXIII). When the use amount of the phosphonium azide is extremely low, yield of the compound represented by the general formula ($B_{5a}$—$X^a$) could decrease. On the other hand, when the use amount of the phosphonium azide is extremely high, a problem such as impairing economic performance occurs.

Use amount of the diethylamine to be used in a reaction to obtain the compound represented by the general formula (XXVI), in the production method for the compound represented by the general formula ($B_5$—$X^a$), is not especially limited, as long as being a generally use amount in this field usually, and is, for example, usually 3.6 to 30 equivalents, preferably 3.8 to 10 equivalents, and more preferably 4 to 5 equivalents, relative to mole number of phosphorus trihalides represented by the general formula (XXV). When the use amount of the diethylamine is extremely low, yield of the compound represented by the general formula (XXVI) could decrease. On the other hand, when the use amount of the diethylamine is extremely high, a problem such as impairing economic performance occurs.

Use amount of the compound represented by the general formula (XXVII), in the production method for the compound represented by the general formula ($B_5$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (XXVI). When the use amount of the compound represented by the general formula (XXVII) is extremely low, yield of the compound represented by the general formula ($B_{5a}$—$X^a$) could decrease. On the other hand, when the use amount of the compound represented by the general formula (XXVII) is extremely high, a problem such as impairing economic performance occurs.

A series of reactions represented by the scheme [v] may be carried out under solvent-free condition, or may be carried out in an organic solvent. A specific example of the organic solvent is not especially limited, as long as it is an organic solvent which does not react with the phosphine, the phosphorus trihalide, diethylamine, and the compounds represented by the general formulae (XXIV) and (XXVII), and includes the same as the specific example of the organic solvent represented by the scheme [i]. It should be noted that such an organic solvent may be used alone as one kind of the organic solvent, or may be used in combination of two or more kinds of the organic solvents. In addition, as such an organic solvent, the commercially available one may be used.

Use amount of the organic solvent is not especially limited, as long as being a generally use amount in this field usually, and is, for example, usually 0.01 to 500 mL, and preferably 0.1 to 100 mL, relative to 1 mmol of the phosphine represented by the general formula (XXIII), the phosphorus trihalide represented by the general formula (XXV), or the compound represented by the general formula (XXVI).

It is desirable that a series of reactions represented by the scheme [v] are carried out under the following conditions (reaction temperature, pressure, reaction time).

Temperature in the reaction (reaction temperature) of the phosphine represented by the general formula (XXIII) and the compound represented by the general formula (XXIV) may be temperature generally used in carrying out refluxing operation in this field usually, and it is desirable to be set at temperature where the phosphine and the compound represented by the general formula (XXIV) react in good efficiency, and the compound represented by the general formula ($B_{5a}$—$X^a$) can be obtained in good yield. Specifically, the reaction temperature is, for example, usually −20 to 150° C., and preferably 0 to 80° C.

It is desirable that temperature in the reaction (reaction temperature) of the phosphorus trihalide represented by the general formula (XXV) and diethylamine, is set at temperature where the phosphorus trihalide and diethylamine react in good efficiency, and the compound represented by the general formula (XXVI) can be obtained in good yield. Specifically, the reaction temperature is, for example, usually −100 to 50° C., and preferably −80 to 20° C.

It is desirable that temperature in the reaction (reaction temperature) of the compound represented by the general formula (XXVI) and the compound represented by the general formula (XXVII), is set at temperature where the compound represented by the general formula (XXVI) and the compound represented by the general formula (XXVII) react in good efficiency, and the compound represented by the general formula ($B_{5b}$—$X^a$) can be obtained in good yield. Specifically, the reaction temperature is, for example, usually −20 to 150° C., and preferably 0 to 80° C.

Pressure in a series of reactions represented by the scheme [v] is not especially limited, as long as the series of reactions is carried out without delay, and the series of reactions may be carried out, for example, under normal pressure.

Reaction time in a series of reactions represented by the scheme [v] may be influenced in some cases, by kinds of the phosphine, the phosphorus trihalide, diethylamine, and the compounds represented by the general formulae (XXIV) and (XXVII), use amount of such compounds, kinds of an organic solvent, reaction temperature, pressure in the reaction and the like. Accordingly, desirable reaction time cannot be said unconditionally, however, it is, for example, usually 1 minute to 24 hours, and preferably 3 minutes to 12 hours.

A series of products after the reaction represented by the scheme [v] can be isolated by a general post-treatment operation and purification operation usually carried out in this field. In addition, the product may be isolated by filtration or washing of the reaction solution, as needed, and by carrying out recrystallization, distillation, column chromatography, and the like, of the residue obtained by concentration of the reaction solution.

The compound represented by the general formula ($B_6$—$X^a$), pertaining to the production method for the compound represented by the general formula (A) of the present invention, can be produced, for example, by a method shown in the following scheme [vi]. That is, the compound represented by the general formula ($B_6$—$X^a$) may be synthesized, for example, by a reaction of a phosphorus pentahalide represented by the general formula (XXVIII) and a compound represented by the general formula (XXIX).

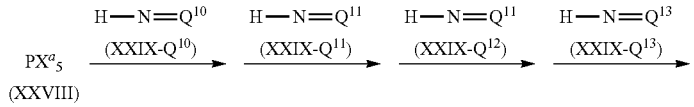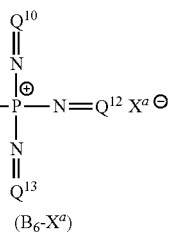

(In the scheme, $Q^{10}$ to $Q^{13}$ and $X^a$ are the same as described above, and in the general formula ($B_6$—$X^a$), number of hydrogen atoms bonding to the nitrogen atoms in the formula is 0 to 4.)

In the general formula ($B_6$—$X^a$), number of hydrogen atoms bonding to the nitrogen atoms in the formula, is an integer of 0 to 4, 0 to 2 is preferable, and 0 is more preferable.

As the phosphorus pentahalide represented by the general formula (XXVIII), pertaining to the production method for the compound represented by the general formula ($B_6$—$X^a$), the commercially available one, or the one synthesized as appropriate by a method known per se may be used. A specific example of the phosphorus pentahalide represented by the general formula (XXVIII) includes phosphorus pentachloride, phosphorus pentabromide, phosphorus pentaiodide, and the like.

As the compound represented by the general formula (XXIX), pertaining to the production method for the compound represented by the general formula ($B_6$—$X^a$), the commercially available one, or the one synthesized as appropriate by a method known per se may be used. A specific example of the compound represented by the general formula (XXIX) includes a guanidine derivative, such as 1,1,3,3-tetramethylguanidine, 1,1,3,3-tetraethylguanidine, 1,1,3,3-tetra-n-propylguanidine, 1,1,3,3-tetraisopropylguanidine, 1,1,3,3-tetra-n-butylguanidine, 1,1,3,3-tetraisobutylguanidine, 1,1,3,3-tetra-sec-butylguanidine, 1,1,3,3-tetra-tert-butylguanidine, 1,1,3,3-tetracyclobutylguanidine; a phosphine imine derivative, such as tris(dimethylamino)phosphine imine, tris(diethylamino)phosphine imine, tris(di-n-propylamino)phosphine imine, tris(diisopropylamino)phosphine imine, tris(di-n-butylamino)phosphine imine, tris(diisobutylamino)phosphine imine, tris(di-sec-butylamino)phosphine imine, tris(di-tert-butylamino)phosphine imine, tris(dicyclobutylamino)phosphine imine.

Use amount of the compound represented by the general formula (XXIX-$Q^{10}$), in the production method for the compound represented by the general formula ($B_6$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of compounds represented by the general formula (XXVIII). When the use amount of the compound represented by the general formula (XXIX-$Q^{10}$) is extremely low, yield of the compound represented by the general formula ($B_6$—$X^a$) could decrease. On the other hand, when the use amount of the compound represented by the general formula (XXIX-$Q^{10}$) is extremely high, a problem such as impairing economic performance occurs.

Use amount of the compound represented by the general formula (XXIX-$Q^{11}$), in the production method for the compound represented by the general formula ($B_6$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of the compound represented by the general formula (XXVIII). When the use amount of the compound represented by the general formula (XXIX-$Q^{11}$) is extremely low, yield of the compound represented by the general formula ($B_6$—$X^a$) could decrease. On the other hand, when the use amount of the compound represented by the general formula (XXIX-$Q^{11}$) is extremely high, a problem such as impairing economic performance occurs.

Use amount of the compound represented by the general formula (XXIX-$Q^{12}$), in the production method for the compound represented by the general formula ($B_6$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of the compound represented by the general formula (XXVIII). When the use amount of the compound represented by the general formula (XXIX-$Q^{12}$) is extremely low, yield of the compound represented by the general formula ($B_6$—$X^a$) could decrease. On the other hand, when the use amount of the compound represented by the general formula (XXIX-$Q^{12}$) is extremely high, a problem such as impairing economic performance occurs.

Use amount of the compound represented by the general formula (XXIX-$Q^{13}$), in the production method for the compound represented by the general formula ($B_6$—$X^a$), is not especially limited, as long as being a generally use amount in this field usually, and is, for example, usually 0.8 to 10 equivalents, preferably 0.9 to 5 equivalents, and more preferably 1 to 2 equivalents, relative to mole number of the compound represented by the general formula (XXVIII). When the use amount of the compound represented by the general formula (XXIX-$Q^{13}$) is extremely low, yield of the compound represented by the general formula ($B_6$—$X^a$) could decrease. On the other hand, when the use amount of the compound represented by the general formula (XXIX-$Q^{13}$) is extremely high, a problem such as impairing economic performance occurs.

In the production method for the compound represented by the general formula ($B_6$—$X^a$), in a reaction to obtain the compound represented by the general formula ($B_6$—$X^a$), when all of $Q^{10}$ to $Q^{13}$ in the scheme [vi] represent the same functional group, the compound represented by the general formula ($B_6$—$X^a$) may be obtained by one time reaction operation by the addition of the compounds represented by the general formulae (XXIX-$Q^{10}$) to (XXIX-$Q^{13}$) at the same time. In this case, use amount of each of the compounds represented by the general formulae (XXIX-$Q^{10}$) to (XXIX-$Q^{13}$) is similar to the use amount of the compound represented by the general formula (XXIX-$Q^{10}$) described above, and preferable use amount also includes the same.

A series of reactions represented by the scheme [vi] may be carried out under solvent-free condition, or may be carried out in an organic solvent. A specific example of the organic solvent is not especially limited, as long as it is an organic solvent which does not react with the phosphorus pentahalide, diethylamine, and the compounds represented by the general formulae (XXIX-$Q^{10}$) to (XXIX-$Q^{13}$), and includes the same as the specific example of the organic solvent represented by the scheme [i]. It should be noted that such an organic solvent may be used alone as one kind of the organic solvent, or may be used in combination of two or more kinds of the organic solvents. In addition, as such an organic solvent, the commercially available one may be used.

Use amount of the organic solvent is not especially limited, as long as being a generally use amount in this field usually, and is, for example, usually 0.01 to 500 mL, and preferably 0.1 to 100 mL, relative to 1 mmol of the phosphorus pentahalide represented by the general formula (XXVIII).

It is desirable that a series of reactions represented by the scheme [vi] are carried out under the following conditions (reaction temperature, pressure, reaction time).

It is desirable that temperature in the reaction (reaction temperature) of the phosphorus pentahalide represented by the general formula (XXVIII) and the compounds represented by the general formulae (XXIX-$Q^{10}$) to (XXIX-$Q^{13}$), is set at temperature where the phosphorus pentahalide and the compounds represented by the general formulae (XXIX-$Q^{10}$) to (XXIX-$Q^{13}$) react in good efficiency, and the compound represented by the general formula ($B_6$—$X^a$) can be obtained in good yield. Specifically, for example, usually at −50 to 50° C., and preferably at −30 to 0° C., the phosphorus pentahalide and the compounds represented by the general formulae (XXIX-$Q^{10}$) to (XXIX-$Q^{13}$) may be mixed, and then the reaction may be advanced at 50 to 200° C., and preferably at 100 to 180° C.

Pressure in a series of reactions represented by the scheme [vi] is not especially limited, as long as the series of reactions is carried out without delay, and the series of reactions may be carried out, for example, under normal pressure.

Reaction time in a series of reactions represented by the scheme [vi] may be influenced in some cases, by kinds of the phosphorus pentahalide and the compounds represented by the general formulae (XXIX-$Q^{10}$) to (XXIX-$Q^{13}$), use amount of such compounds, kinds of an organic solvent, reaction temperature, pressure in the reaction, and the like. Accordingly, desirable reaction time cannot be said unconditionally, however, it is, for example, usually 1 minute to 24 hours, and preferably 3 minutes to 12 hours.

A series of products after the reaction represented by the scheme [vi] can be isolated by a general post-treatment operation and purification operation usually carried out in this field. As a specific example of the isolation method, the product can be isolated, for example, as needed, by the addition of sodium methoxide into a reaction system and removal of volatile components under vacuum, then by dissolution of the residue into methylene chloride and filtration through sodium, and lastly by evaporation of the solvent under vacuum. In addition, the product may be isolated by filtration or washing of the reaction solution, as needed, and by carrying out recrystallization, distillation, column chromatography, and the like, of the residue obtained by concentration of the reaction solution.

The Base Generator of the Present Invention

The base generator of the present invention is a base generator comprising the compound represented by the general formula (A), and is a base generator which generates a base by irradiation of light (active energy rays) of, for example, UV rays, visible rays, infrared rays, X-rays, and the like, or by heating.

In the case where the base generator of the present invention generates a base by irradiation of light (active energy rays), the base generator of the present invention is capable of generating a base, by irradiation of active energy rays, having a wavelength of, particularly 100 to 780 nm, preferably a wavelength of 200 to 450 nm. Because the base generator of the present invention has an absorption wavelength region where molar absorption coefficient is high, in a region of a wavelength of 200 to 450 nm, it is capable of generating a base efficiently. In addition, as for the base generator of the present invention, a base generator showing absorption to active energy rays of at least one or more of i-rays, h-rays, and g-rays, among the wavelength regions, is preferable in view of general-purpose property.

In the case where the base generator of the present invention generates a base by heating, the base generator of the present invention is capable of generating a base using thermal energy by heating at particularly 150 to 400° C., preferably 250 to 350'C.

It is preferable that a temperature is higher than 150° C., when the weight of the base generator of the present invention is decreased by 5% from the initial weight, by heating (hereafter, it may be abbreviated as 5% weight decrease temperature). In preparing a cured film using the base generator of the present invention, baking and the like may be carried out, and when the 5% weight decrease temperature of the base generator is high, baking temperature can be set high, therefore, for example, residue of an organic solvent, contained in the base-reactive composition of the present invention described below, can be suppressed as low as possible, after baking. In this way, deterioration of contrast between an exposed part (cured part) and a non-exposed part (non-cured part), caused by remaining an organic solvent, can be suppressed.

The base generator of the present invention may contain an additive, other than the compounds represented by the general formula (A), for example, a sensitizer, a cross-linking agent, an organic solvent, and the like, in a range not to hinder the object and effect of the present invention. Such additives may be used alone as one kind of the additive, or may be used in combination of two or more kinds of the additives. It should be noted that, as such additives, those commercially available or those synthesized as appropriate by a method known per se may be used.

The Base-Reactive Composition of the Present Invention

The base-reactive composition of the present invention is a composition comprising the base generator of the present invention and a base-reactive compound.

The base-reactive compound contained in the base-reactive composition of the present invention is not especially limited, as long as it is a compound which reacts by an action of a strong base (guanidines, biguanides, phosphazenes or phosphoniums) generated from the base generator of the present invention, and is cured by cross-linking and the like. A specific example of the base-reactive compound includes, for example, an epoxy-based compound having at least one epoxy group, a silicon-based compound having at least one alkoxysilyl group or a silanol group, an isocyanate-based compound having at least one isocyanate group, a polyamic acid-based compound having at least one amide bond, and the like. Such a base-reactive compound may be used alone as one kind of the base-reactive compound, or may be used in combination of two or more kinds of the base-reactive compounds.

The epoxy-based compound (epoxy-based resin) may be any of a monomer, an oligomer or a polymer, and specifically includes, for example, diglycidyl ether, ethylene glycol diglycidyl ether, spiroglycol diglycidyl ether, diethylene glycol diglycidyl ether, propylene glycol diglycidyl ether, tripropylene glycol diglycidyl ether, butanediol diglycidyl ether, glycerin diglycidyl ether, glycidyl propoxy trimethoxysilane, allyl glycidyl ether, butyl glycidyl ether, neopentyl glycol diglycidyl ether, 1,6-hexanediol diglycidyl ether, phenyl glycidyl ether, cresyl glycidyl ether, alkylphenol glycidyl ether, bisphenol A diglycidyl ether, bisphenol F diglycidyl ether, bisphenol AD diglycidyl ether, biphenyl-based diglycidyl ether, 3,4-epoxycyclohexylmethyl-3',4'-epoxycyclohexane carboxylate, aliphatic diglycidyl ether, polyfunctional glycidyl ether, tertiary fatty acid monoglycidyl ether, polyethylene glycol diglycidyl ether, polypropylene glycol diglycidyl ether, polyglycidyl methacrylate, glycerin polyglycidyl ether, diglycerin polyglycidyl ether, trimethylol propane polyglycidyl ether, sorbitol polyglycidyl ether, and the like. Such an epoxy-based compound may be halogenated or hydrogenated. In addition, such an epoxy-based compound includes a derivative of the specific example. It should be noted that such an epoxy-based compound may be used alone as one kind of the epoxy-based compound, or may be used in combination of two or more kinds of the epoxy-based compounds. In addition, as such an epoxy-based compound, the commercially available one, or the one synthesized as appropriate by a method known per se may be used.

In the case where the epoxy-based compound (epoxy-based resin) is an oligomer or a polymer, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the base-reactive composition of the present invention could be insufficient. On the other hand, when the weight average molecular weight is over 30,000, viscosity of the epoxy-based compound (epoxy-based resin) itself increases, which not only deteriorates solubility but also could be difficult to provide a cured film having uniform surface and constant film thickness. It should be noted that weight average molecular weight is a value converted to standard polystyrene, measured by using gel permeation chromatography.

The silicon-based compound (silicon-based resin) may be any of a monomer, an oligomer or a polymer, and specifically includes, for example, an alkoxysilane compound or a silane coupling agent, and the like. A specific example of the alkoxysilane compound includes, for example, trimethylmethoxysilane, dimethyldimethoxysilane, methyltrimethoxysilane, tetramethoxysilane, trimethylethoxysilane, dimethyldiethoxysilane, methyltriethoxysilane, tetraethoxysilane, diphenyldimethoxysilane, phenyltrimethoxysilane, diphenyldiethoxysilane, phenyltriethoxysilane, hexyltrimethoxysilane, tetrapropoxysilane, tetrabutoxysilane, poly-3-(methyldimethoxysilane)propyl methacrylate, poly-3-(methyldiethoxysilane)propyl methacrylate, poly-3-(trimethoxysilyl)propyl methacrylate, poly-3-(triethoxysilyl)propyl methacrylate, and the like. Such an alkoxysilane compound may be used alone as one kind of the alkoxysilane compound, or may be used in combination of two or more kinds of the alkoxysilane compounds. It should be noted that, as such an alkoxysilane compound, the commercially available one, or the one synthesized as appropriate by a method known per se may be used.

A specific example of the silane coupling agent includes, for example, a vinylsilane, an acrylsilane, an epoxysilane, an aminosilane, and the like. A specific example of the vinylsilane includes, for example, vinyl trichlorosilane, vinyl tris(β-methoxyethoxy)silane, vinyl triethoxysilane, vinyl trimethoxysilane, and the like. A specific example of the acrylsilane includes, for example, γ-methacryloxypropyl trimethoxysilane, γ-methacryloxypropyl methyl dimethoxysilane, and the like. A specific example of the epoxysilane includes, for example, β-(3,4-epoxycyclohexyl)ethyl trimethoxysilane, γ-glycidoxypropyl trimethoxysilane, γ-glycidoxypropyl methyl diethoxysilane, and the like. A specific example of the aminosilane includes, for example, N-β-(aminoethyl)-γ-aminopropyl trimethoxysilane, N-β-(aminoethyl)-γ-aminopropyl methyl dimethoxysilane, γ-aminopropyl trimethoxysilane, N-phenyl-γ-aminopropyl trimethoxysilane, and the like. A specific example of other than the silane coupling agent includes, for example, γ-mercaptopropyl trimethoxysilane, γ-chloropropyl methyl dimethoxysilane, γ-chloropropyl methyl diethoxysilane, and the like. Such a silane coupling agent may be used alone as one kind of the silane coupling agent, or may be used in combination of two or more kinds of the silane coupling agents. It should be noted that, as such a silane coupling agent, the commercially available one, or the one synthesized as appropriate by a method known per se may be used.

In the case where the silicon-based compound (silicon-based resin) is an oligomer or a polymer, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the base-reactive composition of the present invention could be insufficient. On the other hand, when the weight average molecular weight is over 30,000, viscosity of the silicon-based compound (silicon-based resin) itself increases, which not only deteriorates solubility but also could be difficult to provide a cured film having uniform surface and constant film thickness. It should be noted that weight average molecular weight is a value converted to standard polystyrene, measured by using gel permeation chromatography.

A specific example of the isocyanate-based compound may be any of a monomer, an oligomer or a polymer, and specifically includes, for example, a monomer of an isocyanate-based compound, a dimer of an isocyanate-based compound, and the like. A preferable specific example of the isocyanate-based compound includes, for example, toluene-2,4-diisocyanate, toluene-2,6-diisocyanate, m-xylylene diisocyanate, hexahydro-m-xylylene diisocyanate, hexamethylene diisocyanate, isophorone diisocyanate, methylene diphenyl-4,4'-diisocyanate, polymethylene polyphenyl polyisocyanate, and the like. Such an isocyanate-based compound may be used alone as one kind of the isocyanate-based compound, or may be used in combination of two or more kinds of the isocyanate-based compounds. It should be noted that, as such an isocyanate-based compound, the commercially available one, or the one synthesized as appropriate by a method known per se may be used.

In the case where the isocyanate-based compound is an oligomer or a polymer, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the base-reactive composition of the present invention could be insufficient. On the other hand, when the weight average molecular weight is over 30,000, viscosity of the isocyanate-based compound itself increases, which not only deteriorates solubility but also could be difficult to provide a cured film having uniform surface and constant film thickness. It should be noted that weight average molecular weight is a value converted to standard polystyrene, measured by using gel permeation chromatography.

A specific example of the polyamic acid-based compound includes a polyamic acid-based compound known per se (polyamic acid-based resin), and the like, obtained by a reaction of an acid anhydride and a diamine. A preferable specific example of the polyamic acid-based compound includes, for example, a polyamic acid-based compound (polyamic acid-based resin) obtained by a reaction of tetracarboxylic dianhydride, such as pyromellitic dianhydride, naphthalene tetracarboxylic dianhydride, biphenyl ether tetracarboxylic dianhydride, benzophenone tetracarboxylic dianhydride, cyclopentane tetracarboxylic dianhydride, cyclohexane tetracarboxylic dianhydride, 4-(1,2-dicarboxyethyl)-1,2,3,4-tetrahydronaphthalene-1,2-dicarboxylic dianhydride, 5-(1,2-dicarboxyethyl)-3-methylcyclohexane-1,2-dicarboxylic dianhydride, with a diamine, such as phenylene diamine, diaminobiphenyl ether, diaminobenzophenone. Such a polyamic acid-based compound may be halogenated or hydrogenated. In addition, such a polyamic acid-based compound includes a derivative of the specific example. It should be noted that such a polyamic acid-based compound may be used alone as one kind of the polyamic acid-based compound, or may be used in combination of two or more kinds of the polyamic acid-based compounds. In addition, as such a polyamic acid-based compound, the commercially available one, or the one synthesized as appropriate by a method known per se may be used.

It is preferable to set weight average molecular weight of the polyamic acid-based compound at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the base-reactive composition of the present invention could be insufficient. On the other hand, when the weight average molecular weight is over 30,000, viscosity of the polyamic acid-based compound itself increases, which not only deteriorates solubility but also could be difficult to provide a cured film having uniform surface and constant film thickness. It should be noted that weight average molecular weight is a value converted to standard polystyrene, measured by using gel permeation chromatography.

Content of the base generator of the present invention contained in the base-reactive composition of the present invention is not especially limited, as long as being a generally use amount in this field usually, and it is, for example, usually 0.1 to 100% by weight, preferably 1 to 50% by weight, and more preferably 5 to 30% by weight, relative to weight of the base-reactive compound. When the content of the base generator is extremely low, curing of the base-reactive composition of the present invention could be insufficient. On the other hand, when the content of the base generator is extremely high, a problem such as impairing economic performance occurs.

A sensitizer may be added to the base-reactive composition of the present invention, when it is used as a photosensitive resin composition, to enhance sensitivity by widening a photosensitive wavelength region. Such a sensitizer is not especially limited, as long as it is the one generally used in this field usually. A preferable specific example of the sensitizer includes, for example, benzophenone, p,p'-tetramethyldiamino benzophenone, p,p'-tetraethyldiamino benzophenone, ketoprofen, 2-(9-oxoxanthene-2-yl)propionic acid, 2-chlorothioxanthone, 2-isopropylthioxanthone, 2,4-diethylthioxanthone, anthrone, benzanthrone, 3-methyl-1,3-diaza-1,9-benzanthrone, 9-ethoxyanthracene, 9,10-diphenylanthracene, 1,2-benzanthracene, anthracene, pyrene, perylene, phenothiazine, benzophenoxazine, benzil, acridine, acridine orange, acridine yellow, acridone, oxazine, benzoflavin, riboflavin, setoflavin-T, 9-fluorenone, 2-nitrofluorene, 2,3-benzofluorene, 5-nitroacenaphthene, acenaphthene, acetophenone, 3,4,5,6-dibenzophenanthrene, phenanthrene, 1,2-naphthoquinone, phylloquinone, 2-ethylanthraquinone, 2-tert-butylanthraquinone, 1,2-benzanthraquinone, anthraquinone, methylbenzoquinone, benzoquinone, 2-chloro-4-nitroaniline, 2,6-dichloro-4-nitroaniline, N-acetyl-p-nitroaniline, p-nitroaniline, N-acetyl-4-nitro-1-naphthylamine, picramide, dibenzalacetone, coumarin, 3,3'-carbonyl-bis(5,7-dimethoxycarbonylcoumarin), N-methylnifedipine, fluorescein, rhodamine, eosin, erythrosine, coronene, rose bengal, malachite green, basic blue 7, toluidine blue (basic blue 17), indigo, chlorophyll, tetraphenylporphyrin, phthalocyanine, tris(4-dimethylaminophenyl)isopropenyl, phylloquinone, bis(2,4,6-trimethylbenzoyl)phenylphosphine oxide, 2,4,6-triarylpyrylium, sodium 4-(1-naphthylazo)benzene sulfonate, bis(2,4,6-trimethylbenzoyl)phenylphosphine oxide, 1-[(4-phenylthio)phenyl]octane-1,2-dione 2-(O-benzoyloxime), 1-[9-ethyl-6-(2-methylbenzoyl)-9H-carbazole-3-yl]ethanone O-acetyloxime, 9-anthrylmethyl N,N-diethylcarbamate, 1-(9,10-dibutoxyanthracene-2-yl)ethyl piperidine-1-carboxylate, 1-(anthraquinone-2-yl)ethyl N,N-diethyl-1-carbamate, 1,2-diisopropyl-4,4,5,5-tetramethylbiguanidium 2-(3-benzoylphenyl)propionate, and the like. Such a sensitizer may be used alone as one kind of the sensitizer, or may be used in combination of two or more kinds of the sensitizers. It should be noted that, as such a sensitizer, the commercially available one, or the one synthesized as appropriate by a method known per se may be used.

Content of the sensitizer to be contained, as needed, in the base-reactive composition of the present invention, is not especially limited, as long as being a generally use amount in this field usually, and may be determined as appropriate, depending on the base generator or the base-reactive compound to be used, and sensitivity required. More specifically, when the sensitizer is contained, content of the sensitizer is preferably 1 to 30% by weight, and among these, more preferably 1 to 20% by weight, relative to total of the base-reactive composition. When the content of the sensitizer is below 1% by weight, sensitivity may not be enhanced sufficiently in some cases. On the other hand, when the content of the sensitizer is over 30% by weight, it may be excess to enhance sensitivity in some cases.

It is desirable that into the base-reactive composition of the present invention, a thiol-based compound or an acid anhydride is still more contained as a cross-linking agent.

The thiol-based compound is the one acting as a cross-linking agent which reacts with an epoxy group in the epoxy-based compound to cure the epoxy-based compound, in combined use with the epoxy-based compound, and the like. The thiol-based compound may be any of a monomer, an oligomer or a polymer, however, use of the thiol-based compound having two or more thiol groups is preferable, and a preferable specific example of the thiol-based compound includes the thiol-based compound having 2 to 5 thiol groups, such as ethylene glycol bis(3-mercaptobutyrate), butanediol bis(3-mercaptobutyrate), pentaerythritol tetrakis(3-mercaptobutyrate), dipentaerythritol hexakis(3-mercaptobutyrate), ethyleneglycol bis(3-mercaptoisobutyrate), butanediol bis(3-mercaptoisobutyrate), pentaerythritol tetrakis(3-mercaptoisobutyrate), dipentaerythritol hexakis(3-mercaptoisobutyrate), trimethylolpropane tris(3-mercaptoisobutyrate), tris[(3-mercaptopropionyloxy)ethyl]isocyanurate, pentaerythritol tetrakis(3-mercaptopropionate), dipentaerythritol hexa(3-mercaptopropionate), trimethylolpropane tris(3-mercaptopropionate), diethyleneglycol bis(3-mercaptopropionate), pentaerythritol tetrakis(3-mercaptobutyrate), 1,4-bis(3-mercaptobutyryloxy)butane, 1,3,5-tris(3-mercaptobutyloxyethyl)-1,3,5-triazine-2,4,6-(1H,3H,5H)-trione; liquid polymercaptane; polysulfide; and the like. Among these thiol-based compounds, in consideration of reactivity, and the like, and handling easiness, pentaerythritol tetrakis(3-mercaptopropionate), pentaerythritol tetrakis(3-mercaptobutyrate), tris[(3-mercaptopropionyloxy)ethyl]isocyanurate are preferable. Such a thiol-based compound may be used alone as one kind of the thiol-based compound, or may be used in combination of two or more kinds of the thiol-based compounds. It should be noted that, as such a thiol-based compound, the commercially available one, or the one synthesized as appropriate by a method known per se may be used.

In the case where the thiol-based compound is an oligomer or a polymer, it is preferable to set weight average molecular weight at 100 to 10,000, and more preferably at 200 to 5,000, in the viewpoint of heat resistance, coating property, solubility to an organic solvent, solubility to a developing solution, of the base-reactive composition of the present invention, and the like. When the weight average molecular weight is less than 100, strength of a cured film or a molded product obtained from the base-reactive composition of the present invention could be insufficient. On the other hand, when the weight average molecular weight is over 10,000, viscosity of the thiol-based compound itself increases, which not only deteriorates solubility but also could be difficult to provide a cured film having uniform surface and constant film thickness. It should be noted that weight average molecular weight is a value converted to standard polystyrene, measured by using gel permeation chromatography.

As content of the thiol-based compound, it is preferable to attain a ratio of equivalent of the thiol group (equivalent of an SH group)/equivalent of the epoxy group=0.3/1.7 to 1.7/0.3, and among these, it is more preferable to attain the ratio of 0.8/1.2 to 1.2/0.8, for example, relative to the epoxy-based compound in the base-reactive compound.

The acid anhydride is the one acting as a cross-linking agent to cure the epoxy-based compound by a reaction with an epoxy group in the epoxy-based compound, in combined use with the epoxy-based compound, and the like. The acid anhydride may be any of a monomer, an oligomer or a polymer, and a preferable specific example of the acid anhydride includes a mono-functional acid anhydride, such as phthalic anhydride, tetrahydrophthalic anhydride, hexahydrophthalic anhydride, methyltetrahydrophthalic anhydride, methylhexahydrophthalic anhydride, methylnadic anhydride, dodecylsuccinic anhydride, chlorendic anhydride; a bifunctional acid anhydride, such as pyromellitic dianhydride, benzophenone tetracarboxylic dianhydride, ethylene glycol bis(anhydrotrimellitate), methylcyclohexene tetracarboxylic dianhydride; a free acid anhydride, such as trimellitic anhydride, polyazelaic anhydride; and the like. Such an acid anhydride may be used alone as one kind of the acid anhydride, or may be used in combination of two or more kinds of the acid anhydrides. It should be noted that, as such an acid anhydride, the commercially available one, or the one synthesized as appropriate by a method known per se may be used.

In the case where the acid anhydride is an oligomer or a polymer, it is preferable to set weight average molecular weight at 100 to 10,000, and more preferably at 200 to 5,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the base-reactive composition of the present invention could be insufficient. On the other hand, when the weight average molecular weight is over 10,000, viscosity of the acid anhydride itself increases, which not only deteriorates solubility but also could be difficult to provide a cured film having uniform surface and constant film thickness. It should be noted that weight average molecular weight is a value converted to standard polystyrene, measured by using gel permeation chromatography.

As content of the acid anhydride, it is preferable to attain a ratio of equivalent of the acid anhydride group (equivalent of a —C(=O)OC(=O)— group)/equivalent of the epoxy group=0.3/2.7 to 2.0/1.0, and among these, it is more preferable to attain the ratio of 0.5/2.5 to 1.5/1.5, for example, relative to the epoxy-based compound in the base-reactive compound.

By containing the cross-linking agent in the base-reactive composition of the present invention, the base-reactive composition of the present invention is capable of suppressing shrinkage in curing, caused by homopolymerization of the base-reactive compound only, and more enhancing dimensional stability. In addition, by containing the cross-linking agent in the base-reactive composition of the present invention, it is capable of enhancing flexibility, water resistance, chemical resistance, adhesion between a resin and a substrate, resistance to curing hindrance caused by oxygen, and the like, of a resin after curing.

In the case of coating, and the like, of the base-reactive composition of the present invention onto a predetermined substrate, a composition containing an organic solvent may be desirable in some cases. By containing the organic solvent in the base-reactive composition, coating property can be enhanced and workability is improved. The organic solvent is not especially limited, as long as it is the one generally used in this field usually. A preferable specific example of the organic solvent includes a saturated or unsaturated aliphatic hydrocarbon-based solvent, such as pentane, hexane, heptane, octane, nonane, decane, tetrahydronaphthalene, menthane, squalene; an aromatic hydrocarbon-based solvent, such as benzene, toluene, ethylbenzene, styrene, xylene, diethylbenzene, trimethylbenzene; a halogen-based solvent, such as dichloromethane, trichloromethane (chloroform), tetrachloromethane (carbon tetrachloride); an ether-based solvent, such as diethyl ether, di-n-propyl ether, diisopropyl ether, methyl tert-butyl ether, di-n-butyl ether, di-tert-butyl ether, cyclopentyl methyl ether, tetrahydrofuran, 2-methyltetrahydrofuran, 1,4-dioxane; an alcohol-based solvent, such as methanol, ethanol, n-propanol, isopropanol, n-butanol, isobutanol, sec-butanol, tert-butanol, 2-methoxyethanol; a glycol ether-based solvent, such as ethylene glycol monomethyl ether, propylene glycol monomethyl ether (PGME), propylene glycol monoethyl ether, diethylene glycol monomethyl ether, dipropylene glycol monomethyl ether, dipropylene glycol monoethyl ether, ethylene glycol dimethyl ether, propylene glycol dimethyl ether, ethylene glycol diethyl ether, propylene glycol diethyl ether, diethylene glycol dimethyl ether, dipropylene glycol dimethyl ether, dipropylene glycol diethyl ether; a glycol ether acetate-based solvent, such as ethylene glycol monoethyl ether acetate, diethylene glycol monoethyl ether acetate, diethylene glycol monobutyl ether acetate, propylene glycol monomethyl ether acetate (PGMEA), propylene glycol monoethyl ether acetate, dipropylene glycol monomethyl ether acetate, dipropylene glycol monoethyl ether acetate; a ketone-based solvent, such as 2-propanone (acetone), 2-butanone (ethyl methyl ketone), diethyl ketone, 4-methyl-2-pentanone (methyl isobutyl ketone), cyclopentanone, cyclohexanone, cycloheptanone; an ester-based solvent, such as methyl acetate, ethyl acetate, n-propyl acetate, isopropyl acetate, isobutyl acetate, sec-butyl acetate, tert-butyl acetate, ethyl butyrate, isoamyl butyrate, ethyl lactate (EL), n-propyl lactate, isopropyl lactate, isobutyl lactate, sec-butyl lactate, tert-butyl lactate, isoamyl lactate, γ-butyrolactone, butyl stearate; an amide-based solvent, such as N,N-dimethylformamide, N,N-dimethylacetamide, 1-methyl-2-pyrrolidinone (N-methylpyrrolidone), 1,3-dimethyl-2-imidazolidinone (dimethylethyleneurea); a nitrile-based solvent, such as acetonitrile; and the like. It should be noted that such an organic solvent may be used alone as one kind of the organic solvent, or may be used in combination of two or more kinds of the organic solvents. In addition, as such an organic solvent, the commercially available one may be used.

Content of the organic solvent to be contained, as needed, in the base-reactive composition of the present invention is not especially limited, as long as being a generally use amount in this field usually, and may be selected as appropriate so as to attain uniform coating, for example, in forming a layer of the base-reactive composition by coating the base-reactive composition onto a predetermined substrate, and is, for example, usually 0.01 to 50 mL, preferably 0.05 to 30 mL, and more preferably 0.1 to 10 mL, relative to 1 g of the base-reactive compound.

In the base-reactive composition of the present invention, such additives, besides the above-described additives, may also be contained as, for example, fillers, pigments, dyes, leveling agents, antifoaming agents, antistatic agents, pH adjusting agents, dispersing agents, dispersing aids, surface modifiers, plasticizers, plasticizing accelerators, anti-sagging agents, curing accelerators, and the like, in a range not to hinder the object and effect of the present invention. Such additives may be used alone as one kind of the additive, or may be used in combination of two or more kinds of the additives. It should be noted that, as such additives, those commercially available, or those synthesized as appropriate by a method known per se may be used.

To form a pattern using the base-reactive composition of the present invention, for example, the composition is dissolved in an organic solvent to prepare coating liquid, and thus prepared coating liquid is coated on a suitable solid surface, such as a substrate, and dried to form a coated film. Then after generating a base by carrying out pattern exposure to the coated film formed, heating treatment is carried out under the predetermined condition, so as to promote a polymerization reaction of the base-reactive compound contained in the base-reactive composition.

The base-reactive composition of the present invention progresses a polymerization reaction even at room temperature by irradiation of active energy rays, because of containing the base generator of the present invention, however, it is preferable to be subjected to a baking (heating) treatment to progress the polymerization reaction efficiently. Condition of the baking (heating) treatment may be determined as appropriate depending on irradiation (exposure) energy, kinds of a strong base (guanidines, biguanides, phosphazenes or phosphoniums) generating from the base generator to be used, kinds of a base-reactive compound, such as an epoxy-based compound and a silicon-based compound, however, it is preferable that baking (heating) temperature is set within a range of 50° C. to 150° C., and more preferably within a range of 60° C. to 130° C. In addition, it is preferable that baking (heating) time is set at 10 seconds to 60 minutes, and more preferably at 60 seconds to 30 minutes. A substrate formed with the coated film after irradiation of active energy rays and heating treatment, as needed, is immersed into a solvent (developing solution) which creates difference of solubility between an exposed part and a non-exposed part, and is developed, then a pattern can be obtained.

As for a coating method of the base-reactive composition of the present invention onto a substrate, a baking method, an irradiation method of active energy rays, a development method or the like, which are carried out in the pattern formation, a method known per se may be adopted as appropriate.

By containing the base generator of the present invention and the base-reactive compound, the base-reactive composition of the present invention explained above induces a polymerization reaction of the base-reactive compound using the strong base (guanidines, biguanides, phosphazenes or phosphoniums) generated from the base generator, as an initiator, by operation of irradiation of light (active energy rays), heating, and the like, and is thus not only capable of promoting curing of the base-reactive compound effectively but also storing itself in a stable state without decreasing performance, even in storage for a long period of time, without carrying out curing operation. The base-reactive composition of the present invention exerting such effect can be used suitably, for example, as a curing material, a resist material (pattern formation material) and the like.

When the base-reactive composition of the present invention is used as a curing material, a molded product formed after curing operation is widely used as members of a field, where characteristics such as heat resistance, dimensional stability, insulation property and the like are said effective, for example, as constituent members of a coating material, printing ink, a color filter, a film for a flexible display, a semiconductor device, electronics parts, an interlayer insulating film, a wiring coating film, an optical circuit, optical circuit parts, an antireflective film, a hologram, optical members or a construction material, and provides a printed matter, a color filter, a film for a flexible display, a semiconductor device, electronics parts, an inter-layer insulating film, a wiring coating film, an optical circuit, optical circuit parts, an antireflective film, a hologram, optical members or construction members, and the like. In addition, when the base-reactive composition of the present invention is used as a resist material (pattern formation material), the pattern or the like, formed after pattern formation operation, is provided with heat resistance and insulation property, and can be used effectively, for example, as a color filter, a film for a flexible display, electronics parts, a semiconductor device, an interlayer insulating film, a wiring coating film, an optical circuit, optical circuit parts, an antireflective film, other optical members or electronics members.

—The Compound Represented by the General Formula (A-a) of the Present Invention—

The compound represented by the following general formula (A-a) is a compound having property as a radical generator as well as property as a base generator, among the compounds represented by the general formula (A) of the present invention.

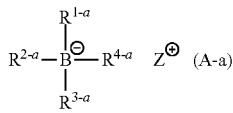

(wherein $R^{1-a}$ represents an alkyl group having 1 to 12 carbon atoms or an alkenyl group having 2 to 12 carbon atoms, $R^{2-a}$ to $R^{4-a}$ each independently represent an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms, and $Z^+$ is the same as described above.)

A specific example of each functional group in $R^{1-a}$ to $R^{4-a}$ in the general formula (A-a) includes the same as the specific example of corresponding each functional group described in $R^1$ to $R^4$ in the general formula (A), and a preferable specific example also includes the same.

As $R^{1-a}$ in the general formula (A-a), an alkyl group having 1 to 12 carbon atoms is more preferable.

As $R^{2-a}$ to $R^{4-a}$ in the general formula (A-a), the one where all of $R^{2-a}$ to $R^{4-a}$ are the same phenyl group, which may be substituted with a halogen atom, an alkyl group having 1 to 6 carbon atoms, an alkoxy group having 1 to 6 carbon atoms, or an alkylthio group having 1 to 6 carbon atoms, is more preferable.

A combination of $R^{1-a}$ to $R^{4-a}$ in the general formula (A-a) includes a combination where $R^{1-a}$ represents an alkyl group having 1 to 12 carbon atoms, $R^{2-a}$ to $R^{4-a}$ each independently represent an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms; and a combination where $R^{1-a}$ represents an alkenyl group having 2 to 12 carbon atoms, $R^{2-a}$ to $R^{4-a}$ each independently represent an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms.

A specific example of the borate-based anion in the compound represented by the general formula (A-a) includes the anion represented by the formulae (A-1) to (A-7), (A-17), (A-18) and (A-32).

Still more, a specific example of the compound represented by the general formula (A-a) includes, for example, the compound represented by the formulae (1) to (5).

The Radical Generator of the Present Invention

The radical generator of the present invention is a radical generator comprising the compound represented by the general formula (A-a) of the present invention, and a radical generator which generates a radical by irradiation of light (active energy rays) of, for example, UV rays, visible rays, infrared rays, X-rays, and the like, or by heating.

In the case where the radical generator of the present invention generates a radical by irradiation of light (active energy rays), the radical generator of the present invention is capable of generating a radical, by irradiation of active energy rays, having a wavelength of, particularly 100 to 780 nm, preferably 200 to 450 nm. Because the radical generator of the present invention has an absorption wavelength region where molar absorption coefficient is high, in a region of a wavelength of 200 to 450 nm, it is capable of generating a radical efficiently. In addition, as for the radical generator of the present invention, a radical generator showing absorption to active energy rays of at least one or more of i-rays, h-rays, and g-rays, among the wavelength regions, is preferable in view of general-purpose property.

In addition, the radical generator of the present invention can also be used as a radical generator in a resist peeling agent in a surface treatment process of a semiconductor, and by using a composition containing the radical generator of the present invention, residue of a resist layer or residue of an antireflective film layer, remaining after processing of the surface of a semiconductor provided with an antireflective film and the like, can be removed efficiently.

In use for such an object, the radical generator of the present invention may be used in accordance with the content described, for example, in a WO2009/110582 publication, and also as for use amount thereof, other materials to be present together, or use amount of the materials may be selected as appropriate in accordance with the content described in the publication.

Still more, the radical generator of the present invention can also be used as a catalyst in a carbon-carbon bond forming reaction using a radical reaction.

In use for such an object, the radical generator of the present invention may be used in accordance with the content described, for example, in a JP-A-11-5033 publication, and also as for use amount thereof, other materials to be present together, or use amount of the materials may be selected as appropriate in accordance with the content described in the publication.

Additionally, the radical generator of the present invention is capable of forming a polythioether by progressing sequential polymerization, by irradiation of light (active energy rays) of UV rays, visible rays, infrared rays, X-rays and the like, or by heating, for example, in the presence of a thiol-based compound and a compound having a carbon-carbon double bond.

The thiol-based compound is not especially limited, as long as it is a compound generally used in this field usually. A preferable specific example of the thiol-based compound includes the same as the specific example of the thiol-based compound to be used in the base-reactive composition of the present invention. Such a thiol-based compound may be used alone as one kind of the thiol-based compound, or may be used in combination of two or more kinds of the thiol-based compounds. It should be noted that, as such a thiol-based compound, the commercially available one, or the one synthesized as appropriate by a method known per se may be used.

A specific example of the compound having the carbon-carbon double bond, is not especially limited, as long as it is a compound generally used in this field usually, and includes, besides the one described in, for example, a JP-A-2014-28938 publication, a JP-A-2007-291313 publication, and the like; maleimide derivatives, such as N,N'-1,3-phenylene dimaleimide, N,N'-1,4-phenylene dimaleimide, N,N',N''-1,3,5-phenylene trimaleimide, 4,4'-bismaleimide diphenylmethane, 1,2-bismaleimideethane, 1,6-bismaleimidehexane, bis(3-ethyl-5-methyl-4-maleimidephenyl)methane; an olefin compound having two or more double bonds, such as 1,3-butadiene, 1,3-pentadiene, 1,4-pentadiene, isoprene, 1,4-hexadiene, 1,5-hexadiene, 2,4-hexadiene, 2-methyl-1,4-pentadiene, 2,3-dimethyl-1,3-butadiene, 1,4-heptadiene, 1,5-heptadiene, 1,6-heptadiene, 2-methyl-1,5-hexadiene, 1,7-octadiene, 2,5-dimethyl-1,5-hexadiene, 1,5-cyclooctadiene, 1,8-nonadiene, 1,9-decadiene, 1,10-undecadiene, 1,11-dodecadiene, 1,12-tridecadiene, 1,13-tetradecadiene, tetraallyloxyethane, 1,3-divinylbenzene, 1,4-divinylbenzene, 1,3,5-trivinylbenzene, 1,3-diisopropenylbenzene, 1,4-diisopropenylbenzene, 1,3,5-triisopropenylbenzene, 3,3'-divinylbiphenyl, 3,4'-divinylbiphenyl, 4,4'-divinylbiphenyl, 4,4'-diisopropenylbiphenyl, 2,6-diisopropenylnaphthalene; an allyl compound such as a compound having two allyl groups (for example, diethylene glycol diallyl ether, diallyl hexahydrophthalate, diallyl chlorendate, 1,2-bis(vinylphenyl)ethane, and the like), a compound having three allyl groups (for example, triallyl trimellitate, 2,4,6-tris(allyloxy)-1,3,5-triazine, triallyl isocyanurate, trially phosphate, 2,4,6-tris(allylthio)-1,3,5-triazine, and the like), a compound having four or more allyl groups (for example, tetraallyl pyromellitate, and the like); and the like.

As content of the compound having the carbon-carbon double bond, it is preferable to attain, for example, a ratio of equivalent of the thiol group in the thiol-based compound (equivalent of an SH group)/equivalent of the carbon-carbon double bond=0.3/1.7 to 1.7/0.3, and among these, it is more preferable to attain the ratio of 0.8/1.2 to 1.2/0.8.

The Radical-Reactive Composition of the Present Invention

The radical-reactive composition of the present invention is a composition comprising the radical generator of the present invention and a radical-reactive compound.

The radical-reactive compound contained in the radical-reactive composition of the present invention is not especially limited, as long as it induces a polymerization reaction and is cured by an action of a radical generated by the radical generator. The radical-reactive compound may be a compound having at least one radically polymerizable ethylenic unsaturated bond, and a preferable specific example of the radical-reactive compound includes an unsaturated carboxylic acid, such as acrylate, methacrylate, allylate, itaconic acid, crotonic acid, isocrotonic acid, maleic acid; a radical-reactive compound, such as ester, urethane, amide, amide anhydride, acid amide, acrylonitrile, styrene, unsaturated polyester, unsaturated polyether, unsaturated polyamide, unsaturated polyurethane; and the like. Such a radical-reactive compound may be used alone as one kind of the radical-reactive compound, or may be used in combination of two or more kinds of the radical-reactive compounds.

The acrylate may be any of a monomer, an oligomer or a polymer, and specifically includes, for example, mono-functional alkyl acrylates, mono-functional ether-group-containing acrylates, mono-functional carboxyl-containing acrylates, bifunctional acrylates, tri- or more-functional acrylates, and the like. Such an acrylate may be halogenated or hydrogenated. In addition, such an acrylate includes also a derivative of the specific example. It should be noted that, such an acrylate may be used alone as one kind of the acrylate, or in combination of two or more kinds of the acrylates. In addition, as such an acrylate, the commercially available one, or the one synthesized as appropriate by a method known per se may be used.

A specific example of the mono-functional alkyl acrylates includes methyl acrylate, ethyl acrylate, propyl acrylate, isopropyl acrylate, butyl acrylate, isoamyl acrylate, hexyl acrylate, 2-ethylhexyl acrylate, octyl acrylate, decyl acrylate, lauryl acrylate, stearyl acrylate, isobornyl acrylate, cyclohexyl acrylate, dicyclopentenyl acrylate, dicyclopentenyloxyethyl acrylate, benzyl acrylate, and the like.

A specific example of the mono-functional ether-group-containing acrylates includes 2-methoxyethyl acrylate, 1,3-butylene glycol methyl ether acrylate, butoxyethyl acrylate, methoxytriethylene glycol acrylate, methoxypolyethylene glycol #400 acrylate, methoxydipropylene glycol acrylate, methoxytripropylene glycol acrylate, methoxypolypropylene glycol acrylate, ethoxydiethylene glycol acrylate, ethylcarbitol acrylate, 2-ethylhexylcarbitol acrylate, tetrahydrofurfuryl acrylate, phenoxyethyl acrylate, phenoxydiethylene glycol acrylate, phenoxypolyethylene glycol acrylate, cresylpolyethylene glycol acrylate, p-nonylphenoxyethyl acrylate, p-nonylphenoxypolyethylene glycol acrylate, glycidyl acrylate, and the like.

A specific example of the mono-functional carboxyl-containing acrylates includes β-carboxyethyl acrylate, succinic acid monoacryloyloxyethyl ester, ω-carboxypolycaprolactone monoacrylate, 2-acryloyloxyethyl hydrogen phthalate, 2-acryloyloxypropyl hydrogen phthalate, 2-acryloyloxypropyl hexahydro hydrogen phthalate, 2-acryloyloxypropyl tetrahydro hydrogen phthalate, and the like.

A specific example of the other mono-functional acrylates not included in the mono-functional alkyl acrylates, the mono-functional ether-group-containing acrylates and the mono-funmctional carboxyl-containing acrylates, includes N,N-dimethylaminoethyl acrylate, N,N-dimethylaminopropyl acrylate, morpholinoethyl acrylate, trimethylsiloxyethyl acrylate, diphenyl-2-acryloyloxyethyl phosphate, 2-acryloyloxyethyl acid phosphate, caprolactone modified 2-acryloyloxyethyl acid phosphate, and the like.

A specific example of the bifunctional acrylates includes 1,4-butanediol diacrylate, 1,6-hexanediol diacrylate, ethylene glycol diacrylate, diethylene glycol diacrylate, triethylene glycol diacrylate, tetraethylene glycol diacrylate, diethylene glycol #200 diacrylate, polyethylene glycol #300 diacrylate, polyethylene glycol #400 diacrylate, polyethylene glycol #600 acrylate, dipropylene glycol diacrylate, tripropylene glycol diacrylate, tetrapropylene glycol diacrylate, polypropylene glycol #400 diacrylate, polypropylene glycol #700 diacrylate, neopentyl glycol diacrylate, neopentyl glycol PO-modified diacrylate, hydroxypivalic acid neopentylglycol ester diacrylate, caprolactone adduct of hydroxypivalic acid neopentyl glycol ester diacrylate, 1,6-hexanediol bis(2-hydroxy-3-acryloyloxypropyl)ether, bis(4-acryloxypolyethoxyphenyl)propane, 1,9-nonanediol diacrylate, pentaerythritol diacrylate, pentaerythritol diacrylate monostearate, pentaerythritol diacrylate monobenzoate, bisphenol-A diacrylate, EO-modified bisphenol-A diacrylate, PO-modified bisphenol-A diacrylate, hydrogenated bisphenol-A diacrylate, EO-modified hydrogenated bisphenol-A diacrylate, PO-modified hydrogenated bisphenol-A diacrylate, bisphenol-F diacrylate, EO-modified bisphenol-F diacrylate, PO-modified bisphenol-F diacrylate, EO-modified tetrabromobisphenol-A diacrylate, tricyclodecane dimethylol diacrylate, isocyanuric acid EO-modified diacrylate, and the like.

A specific example of the tri- or more-functional acrylates includes glycerin PO-modified triacrylate, trimethylol propane triacrylate, trimethylol propane EO-modified triacrylate, trimethylol propane PO-modified triacrylate, isocyanuric acid EO-modified triacrylate, isocyanuric acid EO-modified ε-caprolactone-modified triacrylate, 1,3,5-triacryloyl hexahydro-s-triazine, pentaerythritol triacrylate, dipentaerythritol triacrylate tripropionate, pentaerythritol tetraacrylate, dipentaerythritol tetraacrylate, dipentaerythritol pentaacrylate monopropionate, dipentaerythritol hexaacrylate, tetramethylol methane tetraacrylate, oligoester tetraacrylate, tris(acryloyloxy) phosphate, and the like.

In the case where the acrylate is an oligomer or a polymer, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the radical composition could be insufficient. On the other hand, when the weight average molecular weight is over 30,000, viscosity of the acrylate itself increases, which not only deteriorates solubility but also could be difficult to provide a cured film having uniform surface and constant film thickness. It should be noted that weight average molecular weight is a value converted to standard polystyrene, measured by using gel permeation chromatography.

The methacrylate may be any of a monomer, an oligomer or a polymer, and specifically includes, for example, mono-functional alkyl methacrylates, mono-functional ether-group-containing methacrylates, mono-functional carboxyl-containing methacrylates, bifunctional methacrylates, tri- or more-functional methacrylates, and the like. Such a methacrylate may be halogenated or hydrogenated. In addition, such a methacrylate includes a derivative of the specific example. It should be noted that such a methacrylate may be used alone as one kind of the methacrylate, or may be used in combination of two or more kinds of the methacrylates. In addition, as such a methacrylate, the commercially available one, or the one synthesized as appropriate by a method known per se may be used.

A specific example of the mono-functional alkyl methacrylates includes methyl methacrylate, ethyl methacrylate, propyl methacrylate, isopropyl methacrylate, butyl methacrylate, isoamyl methacrylate, hexyl methacrylate, 2-hexyl methacrylate, 2-ethylhexyl methacrylate, octyl methacrylate, decyl methacrylate, lauryl methacrylate, stearyl methacrylate, isobornyl methacrylate, cyclohexyl methacrylate, dicyclopentenyl methacrylate, dicyclopentenyloxyethyl methacrylate, benzyl methacrylate, and the like.

A specific example of the mono-functional ether-group-containing methacrylates includes 2-methoxyethyl methacrylate, 1,3-butyleneglycol methylether methacrylate, butoxyethyl methacrylate, methoxytriethylene glycol methacrylate, methoxypolyethylene glycol #400 methacrylate, methoxydipropylene glycol methacrylate, methoxytripropylene glycol methacrylate, methoxypolypropylene glycol methacrylate, ethoxydiethylene glycol methacrylate, 2-ethylhexylcarbitol methacrylate, tetrahydrofurfuryl methacrylate, phenoxyethyl methacrylate, phenoxydiethylene glycol methacrylate, phenoxypolyethylene glycol methacrylate, cresylpolyethylene glycol methacrylate, p-nonylphenoxyethyl methacrylate, p-nonylphenoxypolyethylene glycol methacrylate, glycidyl methacrylate, and the like.

A specific example of the mono-functional carboxyl-containing methacrylates includes β-carboxyethyl methacrylate, succinic acid mono-methacryloyloxyethyl ester, ω-carboxypolycaprolactone monomethacrylate, 2-methacryloyloxyethyl hydrogen phthalate, 2-methacryloyloxypropyl hydrogen phthalate, 2-methacryloyloxypropyl hexahydro hydrogen phthalate, 2-methacryloyloxypropyl tetrahydro hydrogen phthalate, and the like.

A specific example of the other mono-functional methacrylates, not included in the mono-functional alkyl methacrylates, the mono-functional ether-group-containing methacrylates and the mono-functional carboxyl-containing methacrylates, includes dimethylaminomethyl methacrylate, N,N-dimethylaminoethyl methacrylate, N,N-dimethylaminopropyl methacrylate, morpholinoethyl methacrylate, trimethylsiloxyethyl methacrylate, diphenyl-2-methacryloyloxyethyl phosphate, 2-methacryloyloxyethyl acid phosphate, caprolactone-modified 2-methacryloyloxyethyl acid phosphate, and the like.

A specific example of the bifunctional methacrylates includes 1,4-butanediol dimethacrylate, 1,6-hexanediol dimethacrylate, ethylene glycol dimethacrylate, diethylene glycol dimethacrylate, triethylene glycol dimethacrylate, tetraethylene glycol dimethacrylate, polyethylene glycol #200 dimethacrylate, polyethylene glycol #300 dimethacrylate, polyethylene glycol #400 dimethacrylate, polyethylene glycol #600 dimethacrylate, dipropylene glycol dimethacrylate, tripropylene glycol dimethacrylate, tetrapropylene glycol dimethacrylate, polypropylene glycol #400 dimethacrylate, polypropylene glycol #700 dimethacrylate, neopentyl glycol dimethacrylate, neopentyl glycol PO-modified dimethacrylate, hydroxypivalic acid neopentyl glycol ester dimethacrylate, caprolactone adduct of hydroxypivalic acid neopentyl glycol ester dimethacrylate, 1,6-hexanediol bis(2-hydroxy-3-methacryloyloxypropyl)ether, 1,9-nonanediol dimethacrylate, pentaerythritol dimethacrylate, pentaerythritol dimethacrylate monostearate, pentaerythritol dimethacrylate monobenzoate, 2,2-bis(4-methacryloxypolyethoxyphenyl)propane, bisphenol-A dimethacrylate, EO-modified bisphenol-A dimethacrylate, PO-modified bisphenol-A dimethacrylate, hydrogenated bisphenol-A dimethacrylate, EO-modified hydrogenated bisphenol-A dimethacrylate, PO-modified hydrogenated bisphenol-A dimethacrylate, bisphenol-F dimethacrylate, EO-modified bisphenol-F dimethacrylate, PO-modified bisphenol-F dimethacrylate, EO-modified tetrabromobisphenol-A dimethacrylate, tricyclodecane dimethylol dimethacrylate, isocyanuric acid EO-modified dimethacrylate, and the like.

A specific example of the tri- or more-functional methacrylates includes glycerin PO-modified trimethacrylate, trimethylol ethane trimethacrylate, trimethylol propane trimethacrylate, trimethylol propane EO-modified trimethacrylate, trimethylol propane PO-modified trimethacrylate, isocyanuric acid EO-modified trimethacrylate, isocyanuric acid EO-modified ε-caprolactone-modified trimethacrylate, 1,3,5-trimethacryloyl hexahydro-s-triazine, pentaerythritol trimethacrylate, dipentaerythritol trimethacrylate tripropionate, pentaerythritol tetramethacrylate, dipentaerythritol pentamethacrylate monopropionate, dipentaerythritol hexamethacrylate, tetramethylol methane tetramethacrylate, oligoester tetramethacrylate, tris(methacryloyloxy)phosphate, and the like.

In the case where the methacrylate is an oligomer or a polymer, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the radical-reactive composition could be insufficient. On the other hand, when the weight average molecular weight is over 30,000, viscosity of the methacrylate itself increases, which not only deteriorates solubility but also could be difficult to provide a cured film having uniform surface and constant film thickness. It should be noted that weight average molecular weight is a value converted to standard polystyrene, measured by using gel permeation chromatography.

The allylate may be any of a monomer, an oligomer or a polymer, and specifically includes, for example, allyl glycidyl ether, diallyl phthalate, triallyl trimellitate, isocyanuric acid triallylate, and the like. Such an allylate may be halogenated or hydrogenated. In addition, such an allylate includes a derivative of the specific example. It should be noted that such an allylate may be used alone as one kind of the allylate, or may be used in combination of two or more kinds of the allylates. In addition, as such an allylate, the commercially available one, or the one synthesized as appropriate by a method known per se may be used.

In the case where the allylate is an oligomer or a polymer, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the radical-reactive composition could be insufficient. On the other hand, when the weight average molecular weight is over 30,000, viscosity of the allylate itself increases, which not only deteriorates solubility but also could be difficult to provide a cured film having uniform surface and constant film thickness. It should be noted that weight average molecular weight is a value converted to standard polystyrene, measured by using gel permeation chromatography.

The acid amide may be any of a monomer, an oligomer or a polymer, and specifically includes, for example, acrylamide, N-methylol acrylamide, diacetone acrylamide, N,N-dimethylacrylamide, N,N-diethylacrylamide, N-isopropylacrylamide, acryloylmorpholine, methacrylamide, N-methylol methacrylamide, diacetone methacrylamide, N,N-dimethyl methacrylamide, N,N-diethyl methacrylamide, N-isopropyl methacrylamide, methacryloyl morpholine, and the like. Such an acid amide may be halogenated or hydrogenated. In addition, such an acid amide includes a derivative of the specific example. It should be noted that such an acid amide may be used alone as one kind of the acid amide, or may be used in combination of two or more kinds of the acid amides. In addition, as such an acid amide, the commercially available one, or the one synthesized as appropriate by a method known per se may be used.

In the case where the acid amide is an oligomer or a polymer, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the radical-reactive composition could be insufficient. On the other hand, when the weight average molecular weight is over 30,000, viscosity of the acid amide itself increases, which not only deteriorates solubility but also could be difficult to provide a cured film having uniform surface and constant film thickness. It should be noted that weight average molecular weight is a value converted to standard polystyrene, measured by using gel permeation chromatography.

The styrens may be any of a monomer, an oligomer or a polymer, and specifically includes, for example, styrene, p-methylstyrene, p-methoxystyrene, p-tert-butoxystyrene, p-tert-butoxycarbonylstyrene, p-tert-butoxycarbonyloxystyrene, 2,4-diphenyl-4-methyl-1-pentene, and the like. Such styrenes may be halogenated or hydrogenated. In addition, such styrenes include a derivative of the specific example. It should be noted that such styrenes may be used alone as one kind of the styrenes, or may be used in combination of two or more kinds of the styrenes. In addition, as such styrenes, those commercially available, or those synthesized as appropriate by a method known per se may be used.

In the case where the styrenes are oligomers or polymers, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the radical-reactive composition could be insufficient. On the other hand, when the weight average molecular weight is over 30,000, viscosity of the styrenes themselves increases, which not only deteriorates solubility but also could be difficult to provide a cured film having uniform surface and constant film thickness. It should be noted that weight average molecular weight is a value converted to standard polystyrene, measured by using gel permeation chromatography.

A specific example of the other vinyl compound, not included in the unsaturated carboxylic acid, the acid amide and the styrene, includes vinyl acetate, vinyl monochloroacetate, vinyl benzoate, vinyl pivalate, vinyl butyrate, vinyl laurate, divinyl adipate, vinyl methacrylate, vinyl crotonate, vinyl 2-ethylhexanoate, N-vinylcarbazole, N-vinylpyrrolidone, and the like.

In the case where the vinyl compound is an oligomer or a polymer, it is preferable to set weight average molecular weight at 100 to 30,000, and more preferably at 200 to 20,000, in the viewpoint of heat resistance, coating property, solubility to an organic solvent, solubility to a developing solution of the base-reactive composition of the present invention, and the like. When the weight average molecular weight is less than 100, strength of a cured film or a molded product obtained from the radical-reactive composition could be insufficient. On the other hand, when the weight average molecular weight is over 30,000, viscosity of the vinyl compound itself increases, which not only deteriorates solubility but also could be difficult to provide a cured film having uniform surface and constant film thickness. It should be noted that weight average molecular weight is a value converted to standard polystyrene, measured by using gel permeation chromatography.

Content of the radical generator of the present invention contained in the radical-reactive composition, is not especially limited, as long as being a generally use amount in this field usually, and is, for example, usually 0.1 to 100% by weight, preferably 1 to 50% by weight, and more preferably 5 to 30% by weight, relative to weight of the radical-reactive compound. When the content of the radical generator of the present invention is extremely low, curing of the radical-reactive composition could be insufficient. On the other hand, when the content of the radical generator of the present invention is extremely high, such a problem such as impairing economic performance occurs.

A sensitizer may be added to the radical-reactive composition, when it is used as a photosensitive resin composition, to enhance sensitivity by widening a photosensitive wavelength region. Such a sensitizer is not especially limited, as long as it is the one generally used in this field usually. A preferable specific example of the sensitizer includes the same as the specific example of the sensitizer to be used in the base-reactive composition of the present invention. Such a sensitizer may be used alone as one kind of the sensitizer, or may be used in combination of two or more kinds of the sensitizers. It should be noted that, as such a sensitizer, the commercially available one, or the one synthesized as appropriate by a method known per se may be used.

Content of the sensitizer to be contained, as needed, in the radical-reactive composition, is not especially limited, as long as being a generally use amount in this field usually, and may be determined as appropriate, depending on the radical generator or the radical-reactive compound to be used, and sensitivity required. More specifically, when the sensitizer is contained, content of the sensitizer is preferably 1 to 30% by weight, and among these, more preferably 1 to 20% by weight, relative to total of the base-reactive composition. When the content of the sensitizer is below 1% by weight, sensitivity may not be enhanced sufficiently in some cases. On the other hand, when the content of the sensitizer is over 30% by weight, it may be excess to enhance sensitivity in some cases.

In the case of coating, and the like, of the radical-reactive composition onto a predetermined substrate, a composition containing an organic solvent may be desirable in some cases. By containing the organic solvent in the radical-reactive composition, coating property can be enhanced and workability is improved. The organic solvent is not especially limited, as long as it is the one generally used in this field usually. A preferable specific example of the organic solvent includes the same as the specific example of the organic solvent to be used in the base-reactive composition of the present invention. It should be noted that such an organic solvent may be used alone as one kind of the organic solvent, or may be used in combination of two or more kinds of the organic solvents. In addition, as such an organic solvent, the commercially available one may be used.

Content of the organic solvent to be contained, as needed, in the radical-reactive composition is not especially limited, as long as being a generally use amount in this field usually, and may be selected as appropriate so as to attain uniform coating, for example, in forming a layer of the radical-reactive composition by coating the radical-reactive composition onto a predetermined substrate, and is, for example, usually 0.01 to 50 mL, preferably 0.05 to 30 mL, and more preferably 0.1 to 10 mL, relative to 1 g of the radical-reactive composition.

In the radical-reactive composition, besides the above-described additives, additives may also be contained, for example, pigments; dyes; polymerization inhibitors, such as cupferron, N-nitrosophenylhydroxyl amine aluminum salt, p-methoxyphenol, hydroquinone, alkyl substituted hydroquinone, catechol, tert-butylcatechol, phenothiazine; curing accelerators and chain transfer catalysts, such as amines (for example, N-phenylglycine, triethanolamine, N,N-diethylaniline, and the like), thiols, disulfides, thiones, O-acylthiohydroxamate, N-alkyloxypyridinethiones; deoxygenating agents and reducing agents, such as phosphine, phosphonate, phosphate; antifogging agents; antifading agents; antihalation agents; fluorescent brightening agents; surfactants; coloring agents; bulking agents; plasticizing agents; flame retardants; antioxidants; ultraviolet absorbing agents; blowing agents; fungicides; antistatic agents; magnetic substances or additives to impart a variety of other characteristics; diluting solvent; and the like; in a range not to hinder the object and effect of the present invention. Such additives may be used alone as one kind of the additive, or may be used in combination of two or more kinds of the additives. It should be noted that, as such additives, those commercially available, or those synthesized as appropriate by a method known per se may be used.

To form a pattern using the radical-reactive composition, for example, the composition is dissolved in an organic solvent to prepare coating liquid, and thus prepared coating liquid is coated on a suitable solid surface, such as a substrate, and dried to form a coated film. Then after generating a radical by carrying out pattern exposure to the coated film formed, a polymerization reaction of the radical-reactive compound contained in the radical-reactive composition may be promoted.

As for a coating method of the radical-reactive composition of the present invention onto a substrate, an irradiation method of active energy rays, a development method and the like, which is carried out in the pattern formation, a method known per se may be adopted as appropriate.

In addition, by still more containing a base-reactive compound in the radical-reactive composition of the present invention, the radical-reactive composition of the present invention can be cured by "a hybrid curing reaction", where a radical curing reaction and an anion curing reaction are combined. That is, because the radical generator of the present invention is capable of generating a radical and a base at the same time by, for example, irradiation of active energy rays or heating, in the case of containing the base-reactive compound in the radical-reactive composition of the present invention, two types of curing reactions can be carried out at the same time; a radical curing reaction of a radical generated from the radical generator of the present invention with the radical-reactive compound, and an anion curing reaction of a base generated from the radical generator of the present invention with the base-reactive compound.

In the case of carrying out pattern formation using the hybrid curing reaction, a composition containing, for example, the radical generator of the present invention, the radical-reactive compound and the base-reactive compound, is dissolved in an organic solvent to prepare coating liquid, and thus prepared coating liquid is coated on a suitable solid surface, such as a substrate, and dried to form a coated film. Then after generating a radical and a base at the same time by carrying out pattern exposure to the coated film formed, and carrying out heating treatment under the predetermined condition, a radical curing reaction in the radical-reactive compound, and an anion curing reaction in the base-reactive compound may be promoted at the same time.

The radical-reactive compound, the base-reactive compound, the organic solvent and other substance to be present together, in the hybrid curing reaction, are not especially limited, as long as they are those generally used in this field usually, and may be selected as appropriate in accordance with the content described in the base-reactive composition of the present invention and the radical-reactive composition of the present invention.

As for a coating method of the radical-reactive composition of the present invention onto the substrate, an irradiation method of active energy rays, a development method, and the like, which are carried out in the pattern formation, a method known per se may be adopted as appropriate.

By containing the radical generator of the present invention and the radical-reactive compound, the radical-reactive composition of the present invention explained above induces the polymerization reaction of the radical-reactive compound using a radical generated from the radical generator, as an initiator, by operation of irradiation of light (active energy rays), heating, and the like, and is capable of promoting curing of the radical-reactive compound effectively. The radical-reactive composition of the present invention exerting such effect can be used suitably, for example, as a curing material, a resist material (pattern formation material), and the like.

When the radical-reactive composition of the present invention is used as the curing material, a molded product formed after curing operation is widely used as members of a field where characteristics such as heat resistance, dimensional stability and insulation property are said effective, for example, as constituent members of a coating material, printing ink, a color filter, a film for a flexible display, a semiconductor device, electronics parts, an inter-layer insulating film, a wiring coating film, an optical circuit, optical circuit parts, an antireflective film, a hologram, optical members or a construction material; and provides a printed matter, a color filter, a film for a flexible display, a semiconductor device, electronics parts, an inter-layer insulating film, a wiring coating film, an optical circuit, optical circuit parts, an antireflective film, a hologram, optical members or construction members, and the like. In addition, when the base-reactive composition of the present invention is used as a resist material (pattern formation material), the pattern and the like, formed after pattern formation operation, is provided with heat resistance and insulation property, and can be used effectively, for example, as a color filter, a film for a flexible display, electronics parts, a semiconductor device, an interlayer insulating film, a wiring coating film, an optical circuit, optical circuit parts, an antireflective film, other optical members or electronics members.

EXAMPLES

Explanation on the present invention will be given specifically below, based on Examples and Comparative Examples, however, the present invention should not be limited to these Examples.

Synthesis Example 1

Synthesis of 1,2-diisopropyl-4,4,5,5-tetramethylbiguanide

Into 11.9 g of 1,1,3,3-tetramethylguanidine (10.3 mmol; produced by Wako Pure Chemical Industries, Ltd.), 13.1 g of N,N'-diisopropylcarbodiimide (10.3 mmol; produced by Wako Pure Chemical Industries, Ltd.) was added and stirred under heating at 100° C. for 2 hours. After completion of the reaction, hexane was added into the reaction solution and cooled down to 5° C., and the resulting crystal was filtrated to obtain 9.88 g of 1,2-diisopropyl-4,4,5,5-tetramethylbiguanide (white powder, yield: 39%). Measurement of $^1$H-NMR, and a structural formula of 1,2-diisopropyl-4,4,5,5-tetramethylbiguanide are shown below. $^1$H-NMR (400 MHz, CDCl$_3$) δ (ppm): 1.10 (12H, d), 2.78 (12H, s), 3.38 (2H, q)

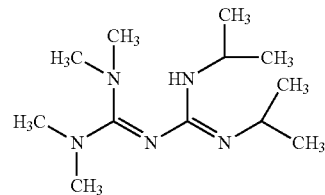

Synthesis Example 2

Synthesis of 1,2-dicyclohexyl-4,4,5,5-tetramethylbiguanide carbonate

Into 12.2 g of 1,1,3,3-tetramethylguanidine (106 mmol; produced by Wako Pure Chemical Industries, Ltd.), 10.9 g of N,N'-dicyclohexylcarbodiimide (53 mmol; produced by Wako Pure Chemical Industries, Ltd.) was added and stirred under heating at 100° C. for 2 hours. After completion of the reaction, the reaction solution was concentrated under reduced pressure to remove 1,1,3,3-tetramethylguanidine, and then 20 mL of acetone and 2 mL of water were added to the resulting residue, dry ice was put in, and the resulting crystal was filtrated to obtain 8.44 g of 1,2-dicyclohexyl-4,4,5,5-tetramethylbiguanide carbonate (white powder, yield: 45%). Measurement of $^1$H-NMR and $^{13}$C-NMR, and a structural formula of 1,2-dicyclohexyl-4,4,5,5-tetramethylbiguanide carbonate are shown below. $^1$H-NMR (400 MHz, D$_2$O) δ (ppm): 1.22-1.80 (20H, brm), 2.86 (12H, s), 3.02 (2H, m) $^{13}$C-NMR (400 MHz, CD$_3$OD) δ (ppm): 26.1, 34.1, 40.1, 52.4, 158.0, 161.2, 164.4

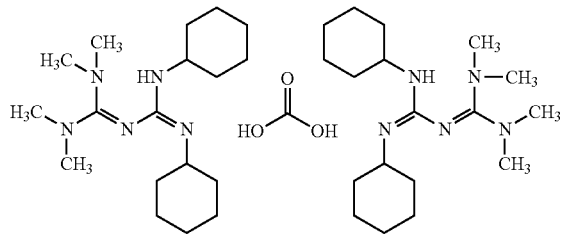

Synthesis Example 3

Synthesis of 1,3-dimethyl-2-(N',N',N'',N''-tetramethylguanidino)-4,5-dihydro-3H-imidazolium chloride Into 3.38 g of 2-chloro-1,3-dimethylimidazolinium chloride (20 mmol; produced by Wako Pure Chemical Industries, Ltd.), 20 mL of dichloromethane and 20 mL of tetrahydrofuran (THF) were added and cooled down to 5° C., then 4.6 g of 1,1,3,3-tetramethylguanidine (40 mmol; produced by Wako Pure Chemical Industries, Ltd.) was added into that and stirred at 60° C. for 1.5 hour. After completion of the reaction, 30 mL of acetone was added to the reaction solution, and a salt precipitated was removed by filtration. The resulting organic layer was concentrated under reduced pressure to obtain 4.76 g of 1,3-dimethyl-2-(N',N',N'',N''-tetramethylguanidino)-4,5-dihydro-3H-imidazolium chloride (white powder, yield: 96%). Measurement of $^1$H-NMR, and a structural formula of 1,3-dimethyl-2-(N',N',N'',N''-tetramethylguanidino)-4,5-dihydro-3H-imidazolium chloride are shown below.

$^1$H-NMR (400 MHz, D$_2$O) δ (ppm): 2.86 (6H, s), 3.04 (12H, s), 3.88 (4H, d)

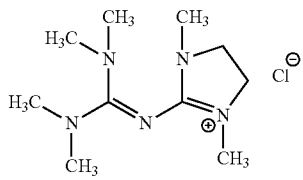

Synthesis Example 4

Synthesis of tetrakis(tetramethylguanidino)phosphonium hydrochloride

Tetrakis(tetramethylguanidino)phosphonium hydrochloride was synthesized in accordance with a method described in a German patent application No. 102006010034 publication.

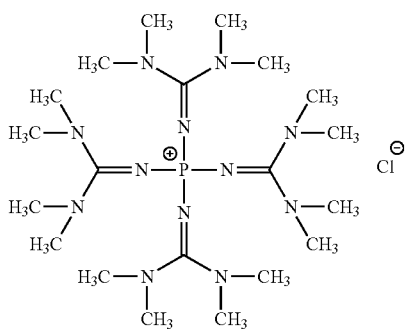

Synthesis Example 5

Synthesis of Lithium p Tolylethynyl Triphenyl Borate

Into 1.16 g of 4-ethynyltoluene (10 mmol; produced by Wako Pure Chemical Industries, Ltd.), 20 mL of THF was added and cooled down to 5° C., then 6.25 mL of a 1.6 M hexane solution of n-butyl lithium (10 mmol; produced by Wako Pure Chemical Industries, Ltd.) was added into that and stirred at 5° C. for 0.5 hour. Subsequently, 2.42 g of triphenyl borane (10 mmol; produced by Sigma-Aldrich Co., LLC.) was added and reacted at room temperature for 1 hour. After completion of the reaction, 30 mL of water was added to the reaction solution, and the water layer was washed with toluene twice. The resulting water layer was concentrated under reduced pressure to obtain 1.76 g of lithium p-tolylethynyl triphenylborate (white powder, yield: 48%). Measurement of $^1$H-NMR, and a structural formula of lithium p-tolylethynyl triphenylborate are shown below.

$^1$H-NMR (400 MHz, D$_2$O) δ (ppm): 2.19 (3H, s), 6.98 (3H, t), 7.06-7.12 (8H, m), 7.28 (2H, d), 7.40 (6H, d)

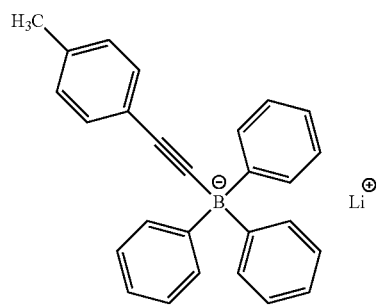 [SMILES: Cc1ccc(C#C[B-](c2ccccc2)(c2ccccc2)c2ccccc2)cc1 ; [Li+]]

Synthesis Example 6

Synthesis of 1,2-bis(2,6-diisopropylphenyl)-4,4,5,5-tetramethyl biguanide

Into 3.18 g of 1,1,3,3-tetramethylguanidine (27.6 mmol; produced by Wako Pure Chemical Industries, Ltd.), 13.1 g of bis(2,6-diisopropylphenyl)carbodiimide (27.6 mmol; produced by Tokyo Chemical Industry Co., Ltd.) was added and stirred at 25° C. for 30 minutes. After completion of the reaction, hexane was added into the reaction solution and cooled down to 5° C., and the resulting crystal was filtrated to obtain 10.20 g of 1,2-bis(2,6-diisopropylphenyl)-4,4,5,5-tetramethyl biguanide (white powder, yield: 77%). Measurement of $^1$H-NMR, and a structural formula of 1,2-bis(2,6-diisopropylphenyl)-4,4,5,5-tetramethyl biguanide are shown below. $^1$H-NMR (400 MHz, CDCl$_3$) δ (ppm): 1.00-1.29 (24H, m), 2.81 (12H, s), 3.43 (4H, m), 7.07-7.26 (6H, m)

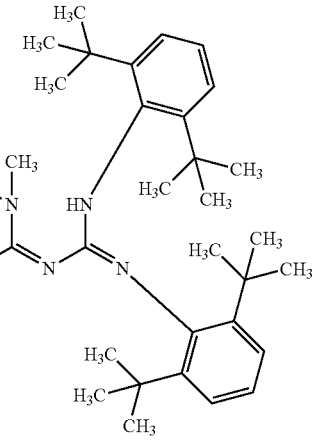

Synthesis Example 7

Synthesis of 1-cyclohexyl-3-(4-nitrophenyl)carbodiimide

Into 10.0 g of 4-nitrophenyl isothiocyanate (55.5 mmol; produced by Wako Pure Chemical Industries, Ltd.), 40 mL of acetonitrile was added and cooled down to 5° C., then 5.50 g of cyclohexylamine (55.5 mmol; produced by Wako Pure Chemical Industries, Ltd.) was added into that and stirred for 1 hour. After completion of the reaction, the crystal of thiourea generated was filtrated to isolate 14.75 g (42.6 mmol). 5.0 g (17.9 mmol) of the resulting thiourea was suspended in ethyl acetate, and 3.62 g of triethylamine (35.8 mmol; produced by Wako Pure Chemical Industries, Ltd.) and 2.50 g of iodine (19.7 mmol; produced by Wako Pure Chemical Industries, Ltd.) were added and stirred at 25° C. for 1 hour. After completion of the reaction, the crystal generated was filtrated and purified using silica gel column chromatography to obtain 1.17 g of 1-cyclohexyl-3-(4-nitrophenyl)carbodiimide (pale yellow oil, yield: 27%). Measurement of $^1$H-NMR, and a structural formula of 1-cyclohexyl-3-(4-nitrophenyl)carbodiimide are shown below.

$^1$H-NMR (400 MHz, CDCl$_3$) δ (ppm): 1.24-1.58 (8H, m), 1.75-1.79 (2H, m), 3.59-3.63 (1H, m), 7.14 (2H, d), 8.16 (2H, d)

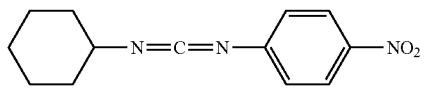

Synthesis Example 8

Synthesis of 1-cyclohexyl-3-(4-nitrophenyl)-4,4,5,5-tetramethyl biguanide

Into 0.55 g of 1,1,3,3-tetramethylguanidine (4.8 mmol; produced by Wako Pure Chemical Industries, Ltd.), 20 mL of toluene and 1.17 g of 1-cyclohexyl-3-(4-nitrophenyl) carbodiimide (4.8 mmol), obtained in Synthesis Example 7, were added and stirred at 25° C. for 1 hour. After completion of the reaction, the crystal generated in the reaction solution was filtrated to isolate and obtain 1.73 g of 1-cyclohexyl-3-(4-nitrophenyl)-4,4,5,5-tetramethyl biguanide (brown oil, yield: 100%). Measurement of $^1$H-NMR, and a structural formula of 1-cyclohexyl-3-(4-nitrophenyl)-4,4,5,5-tetramethyl biguanide are shown below.

$^1$H-NMR (400 MHz, CDCl$_3$) δ (ppm): 1.12-1.24 (3H, m), 1.34-1.43 (2H, m), 1.59-1.62 (3H, m), 1.68-1.73 (2H, m), 2.54 (12H, s), 3.78 (1H, brm), 4.48 (1H, brm), 6.76 (2H, d), 8.02 (2H, d)

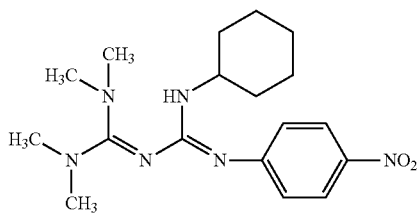

Example 1

Synthesis of 1,5,7-triazabicyclo[4.4.0]deca-5-enium triphenyl(n-butyl)borate (Compound Represented by the Formula (1))

Into 8 mL of 10% hydrochloric acid, 0.68 g of 1,5,7-triazabicyclo[4.4.0]deca-5-ene (5.0 mmol; produced by Sigma Aldrich Co., Ltd.) was dissolved, and 7.65 g (5.0 mmol) of a 20% aqueous solution of lithium triphenyl(n-butyl) borate (produced by Hokko Chemical Industry Co., Ltd.) was added to the solution and stirred at room temperature for 30 minutes. After completion of the reaction, ethyl acetate was added to the reaction solution for extraction, and the organic layer was washed with water and then concentrated under reduced pressure to obtain 1.53 g of 1,5,7-triazabicyclo[4.4.0]deca-5-enium triphenyl(n-butyl)borate (white powder, yield: 69%). Measurement of $^1$H-NMR, and a structural formula of 1,5,7-triazabicyclo[4.4.0]deca-5-enium triphenyl(n-butyl)borate are shown below.

$^1$H-NMR (400 MHz, CDCl$_3$) δ (ppm): 0.81 (3H, t), 1.07-1.09 (4H, m), 1.25-1.29 (2H, m), 1.67-1.71 (4H, m), 2.68-2.72 (4H, m), 2.95-3.20 (4H, m), 3.20 (2H, brs), 6.90 (3H, t), 7.07-7.11 (6H, m), 7.25-7.50 (6H, m)

(1)

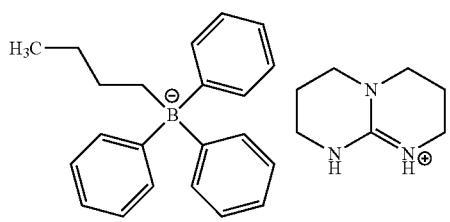

Example 2

Synthesis of 1,2-diisopropyl-4,4,5,5-tetramethylbiguanidium triphenyl(n-butyl)borate (Compound Represented by the Formula (2))

Into 2 mL of 10% hydrochloric acid, 1.32 g (5.0 mmol) of 1,2-diisopropyl-4,4,5,5-tetramethylbiguanide obtained in Synthesis Example 1 was dissolved, and 7.65 g of a 20% aqueous solution of lithium triphenyl(n-butyl) borate (5.0 mmol; produced by Hokko Chemical Industry Co., Ltd.) was added into the solution and stirred at room temperature for 30 minutes. After completion of the reaction, ethyl acetate was added to the reaction solution for extraction, and the organic layer was washed with water and then concentrated under reduced pressure to obtain 2.07 g of 1,2-diisopropyl-4,4,5,5-tetramethylbiguanidium triphenyl(n-butyl)borate (white powder, yield: 76%). Measurement of $^1$H-NMR, and a structural formula of 1,2-diisopropyl-4,4,5,5-tetramethylbiguanidium triphenyl(n-butyl)borate are shown below.

$^1$H-NMR (400 MHz, CDCl$_3$) δ (ppm): 0.80 (3H, t), 1.02 (12H, d), 1.03-1.19 (4H, brm), 1.26-1.48 (2H, m), 1.42 (1H, s), 2.67 (12H, s), 3.17 (2H, brs), 3.91 (1H, brs), 6.89 (3H, t), 7.03-7.07 (6H, m), 7.45-7.47 (6H, m)

(2)

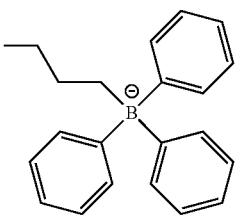

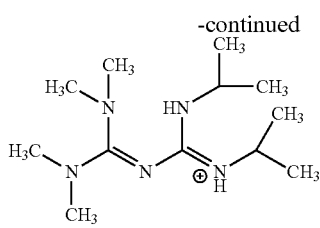

Example 3

Synthesis of 1,2-dicyclohexyl-4,4,5,5-tetramethylbiguanidium triphenyl(n-butyl)borate (Compound Represented by the Formula (3))

Into 2 mL of 10% hydrochloric acid, 1.41 g (2.0 mmol) of 1,2-dicyclohexyl-4,4,5,5-tetramethylbiguanide carbonate obtained in Synthesis Example 2 was dissolved, and 6.12 g of a 20% aqueous solution of lithium triphenyl(n-butyl) borate (4.0 mmol; produced by Hokko Chemical Industry Co., Ltd.) was added to the solution and stirred at room temperature for 30 minutes. After completion of the reaction, ethyl acetate was added to the reaction solution for extraction, and the organic layer was washed with water and then concentrated under reduced pressure to obtain 1.83 g of 1,2-dicyclohexyl-4,4,5,5-tetramethylbiguanidium triphenyl (n-butyl)borate (white powder, yield: 73%). Measurement of $^1$H-NMR, and a structural formula of 1,2-dicyclohexyl-4,4,5,5-tetramethylbiguanidium triphenyl(n-butyl)borate are shown below.

$^1$H-NMR (400 MHz, CDCl$_3$) δ (ppm): 0.81 (3H, t), 1.02 (2H, m), 1.03-1.14 (12H, brm), 1.27-1.30 (2H, m), 1.50-1.70 (10H, brm), 2.75 (12H, s), 2.76-2.78 (3H, brm), 4.37 (1H, brs), 6.87 (3H, t), 7.04-7.08 (6H, m), 7.44-7.46 (6H, m)

(3)

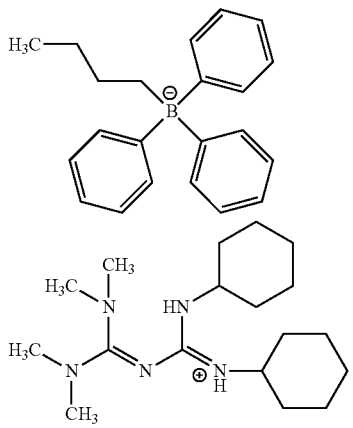

Example 4

Synthesis of 1,3-dimethyl-2-(N',N',N'',N''-tetramethylguanidino)-4,5-dihydro-3H-imidazolium triphenyl(n-butyl)borate (Compound Represented by the Formula (4))

Into 7.65 g of a 20% aqueous solution of lithium triphenyl(n-butyl) borate (5.0 mmol; produced by Hokko Chemical Industry Co., Ltd.), 1.23 g (5.0 mmol) of 1,3-dimethyl-2-(N',N',N'',N''-tetramethylguanidino)-4,5-dihydro-3H-imidazolium chloride obtained in Synthesis Example 3 was added, and stirred at room temperature for 30 minutes. After completion of the reaction, ethyl acetate was added to the reaction solution for extraction, and the organic layer was washed with water and then concentrated under reduced pressure to obtain 1.94 g of 1,3-dimethyl-2-(N',N',N'',N''-tetramethylguanidino)-4,5-dihydro-3H-imidazolium triphenyl(n-butyl)borate (white powder, yield: 74%). Measurement of $^1$H-NMR, and a structural formula of 1,3-dimethyl-2-(N',N',N'',N''-tetramethylguanidino)-4,5-dihydro-3H-imidazolium triphenyl(n-butyl)borate are shown below.

$^1$H-NMR (400 MHz, CDCl$_3$) δ (ppm): 0.80 (3H, t), 1.02-1.29 (6H, brm), 2.45 (6H, s), 2.66 (12H, s), 3.03 (4H, s), 6.82 (6H, t), 7.02 (6H, t), 7.42 (6H, brm)

(4)

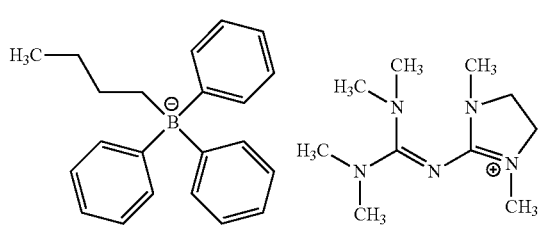

Example 5

Synthesis of tetrakis(tetramethylguanidino)phosphonium triphenyl(n-butyl)borate (Compound Represented by the Formula (5))

Into 7.65 g of a 20% aqueous solution of lithium triphenyl(n-butyl) borate (5.0 mmol; produced by Hokko Chemical Industry Co., Ltd.), 2.61 g (5.0 mmol) of tetrakis(tetramethylguanidino)phosphoniumn chloride obtained in Synthesis Example 4 was added, and stirred at room temperature for 30 minutes. After completion of the reaction, ethyl acetate was added to the reaction solution for extraction, and the organic layer was washed with water and then concentrated under reduced pressure to obtain 2.91 g of tetrakis(tetramethylguanidino)phosphonium triphenyl(n-butyl)borate (white powder, yield: 74%). Measurement of $^1$H-NMR, and a structural formula of tetrakis(tetramethylguanidino)phosphonium triphenyl(n-butyl)borate are shown below.

$^1$H-NMR (400 MHz, CDCl$_3$) δ (ppm): 0.80 (3H, t), 1.02-1.29 (6H, brm), 2.76 (48H, s), 6.84 (3H, t), 7.01-7.04 (6H, m), 7.44-7.46 (6H, brm)

(5)

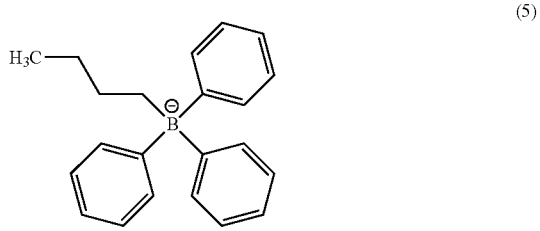

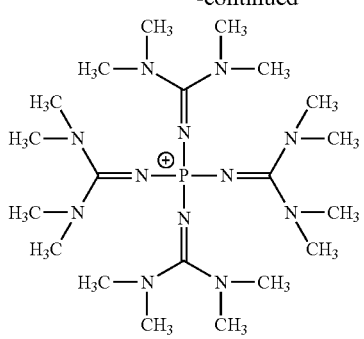

Example 6

Synthesis of
1,2-diisopropyl-4,4,5,5-tetramethylbiguanidium
p-tolylethynyl triphenylborate (Compound
Represented by the Formula (6))

Into 1 mL of 10% hydrochloric acid, 0.48 g (2.0 mmol) of 1,2-diisopropyl-4,4,5,5-tetramethylbiguanide obtained in Synthesis Example 1 was dissolved, and 0.72 g (2.0 mmol) of lithium p-tolylethynyl triphenylborate obtained in Synthesis Example 5 was added to the solution and stirred at room temperature for 30 minutes. After completion of the reaction, ethyl acetate was added to the reaction solution for extraction, and the organic layer was washed with water and then concentrated under reduced pressure to obtain 0.96 g of 1,2-diisopropyl-4,4,5,5-tetramethylbiguanidium p tolylethynyl triphenylborate (white powder, yield: 80%). Measurement of $^1$H-NMR, and a structural formula of 1,2-diisopropyl-4,4,5,5-tetramethylbiguanidium p tolylethynyl triphenylborate are shown below.

$^1$H-NMR (400 MHz, CDCl$_3$) δ (ppm): 0.85 (12H, d), 2.28 (3H, s), 2.46 (12H, s), 3.04 (2H, brm), 4.89 (1H, brs), 6.91 (3H, t), 6.99 (2H, d), 7.06 (6H, t), 7.32 (2H, d), 7.60 (6H, d)

(6)

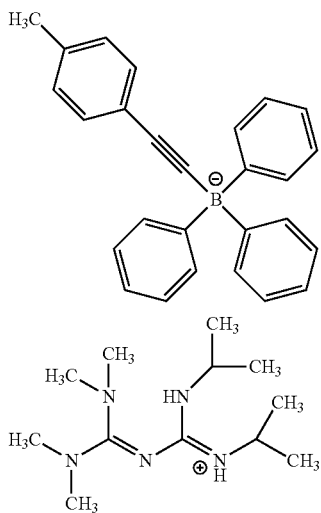

Example 7

Synthesis of
tetrakis(tetramethylguanidino)phosphonium
p-tolylethynyl triphenylborate (Compound
Represented by the Formula (7))

Into 0.82 g (2.2 mmol) of lithium p tolylethynyl triphenylborate obtained in Synthesis Example 4, 1.04 g (2.0 mmol) of tetrakis(tetramethylguanidino)phosphonium chloride obtained in Synthesis Example 3 was added, and stirred at room temperature for 30 minutes. After completion of the reaction, ethyl acetate was added to the reaction solution for extraction, and the organic layer was washed with water and then concentrated under reduced pressure to obtain 1.48 g of tetrakis(tetramethylguanidino)phosphonium p-tolylethynyl triphenylborate (white powder, yield: 89%). Measurement of $^1$H-NMR, and a structural formula of tetrakis(tetramethylguanidino)phosphonium p-tolylethynyl triphenylborate are shown below.

$^1$H-NMR (400 MHz, CDCl$_3$) δ (ppm): 2.25 (3H, t), 2.73 (48H, s), 6.89-6.95 (5H, m), 7.03 (6H, t), 7.35 (2H, d), 7.57 (6H, d)

(7)

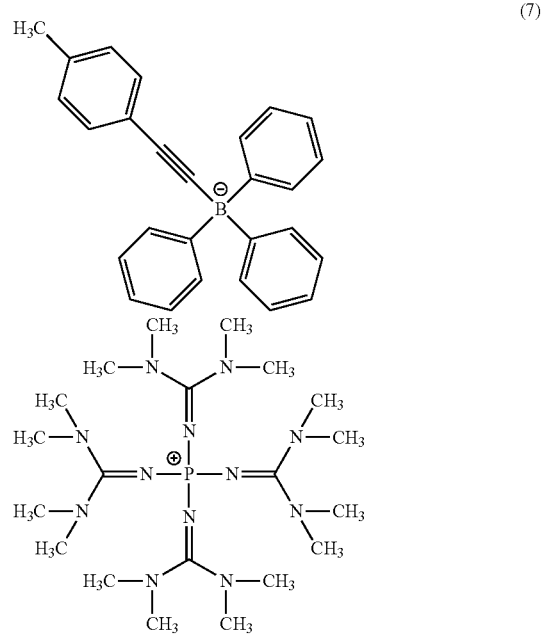

Example 8

Synthesis of 1,2-bis(2,6-diisopropylphenyl)-4,4,5,5-
tetramethylbiguanidium triphenyl(n-butyl)borate
(Compound Represented by the Formula (8))

Into 0.7 mL of 36.5% hydrochloric acid, 3.00 g (6.28 mmol) of 1,2-bis(2,6-diisopropylphenyl)-4,4,5,5-tetramethylbiguanide obtained in Synthesis Example 6 was dissolved, and 9.61 g of a 20% aqueous solution of lithium triphenyl (n-butyl)borate (6.28 mmol; produced by Hokko Chemical Industry Co., Ltd.) was added into the solution and stirred at room temperature for 30 minutes. After completion of the reaction, dichloromethane was added to the reaction solution for extraction, and the organic layer was washed with water and then concentrated under reduced pressure to obtain 3.76 g of 1,2-bis(2,6-diisopropylphenyl)-4,4,5,5-tetramethylbiguanidium triphenyl(n-butyl) borate (white powder, yield: 77%). Measurement of ¹H-NMR, and a structural formula of 1,2-bis(2,6-diisopropylphenyl)-4,4,5,5-tetramethylbiguanidium triphenyl(n-butyl) borate are shown below.

¹H-NMR (400 MHz, CDCl₃) δ (ppm): 0.76-1.41 (30H, m), 2.53 (12H, s), 2.93 (2H, m), 3.24 (2H, m), 6.78 (3H, t), 6.79 (6H, t), 7.15 (2H, d), 7.25-7.35 (3H, m), 7.43-7.50 (7H, m)

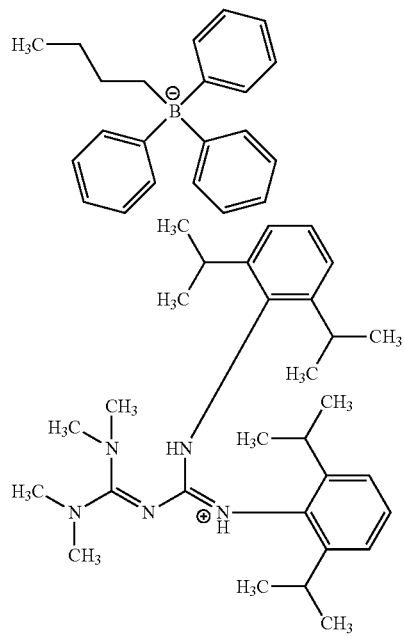

(8)

Example 9

Synthesis of 1-cyclohexyl-3-(4-nitrophenyl)-4,4,5,5-tetramethylbiguanidium triphenyl(n-butyl)borate (Compound Represented by the Formula (9))

Into 0.49 mL of 36.5% hydrochloric acid, 1.73 g (4.8 mmol) of 1-cyclohexyl-3-(4-nitrophenyl)-4,4,5,5-tetramethylbiguanide obtained in Synthesis Example 8 was dissolved, and 7.0 g of a 20% aqueous solution of lithium triphenyl (n-butyl) borate (4.8 mmol, produced by Hokko Chemical Industry Co., Ltd.) was added into the solution and stirred at room temperature for 1 hour. After completion of the reaction, dichloromethane was added to the reaction solution for extraction, and the organic layer was washed with water and then concentrated under reduced pressure to obtain 3.03 g of 1-cyclohexyl-3-(4-nitrophenyl)-4,4,5,5-tetramethylbiguanidium triphenyl(n-butyl)borate (yellow powder, yield: 96%). Measurement of ¹H-NMR, and a structural formula of 1-cyclohexyl-3-(4-nitrophenyl)-4,4,5,5-tetramethylbiguanidium triphenyl(n-butyl)borate are shown below.

¹H-NMR (400 MHz, CDCl₃) δ (ppm): 0.78 (3H, t), 0.93-1.03 (4H, m), 1.23-1.30 (7H, m), 1.75-1.82 (5H, m), 2.45 (12H, s), 3.34 (1H, brm), 4.59 (1H, d), 5.20 (1H, brs), 6.48 (2H, d), 6.90 (3H, t), 7.03 (6H, t), 7.47 (2H, d), 8.04 (2H, d)

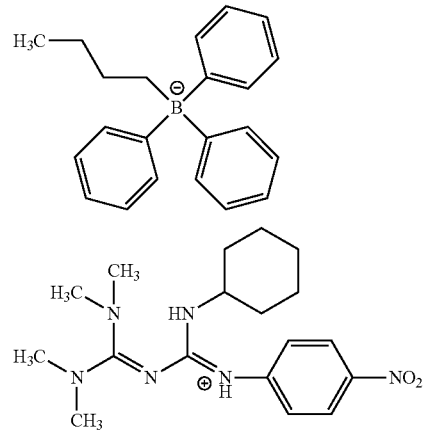

(9)

Comparative Example 1

Synthesis of 1,5,7-triazabicyclo[4.4.0]deca-5-enium tetraphenylborate (Compound Represented by the Formula (101))

In accordance with a method described in J. Am. Chem. Soc., 130, 8130 (2008), 1,5,7-Triazabicyclo[4.4.0]deca-5-enium tetraphenylborate was synthesized.

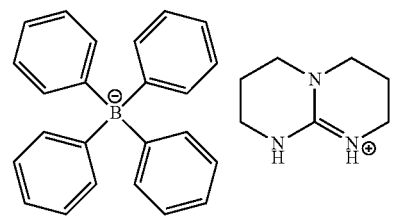

(101)

Comparative Example 2

Synthesis of 1,2-diisopropyl-4,4,5,5-tetramethylbiguanidium tetraphenylborate (Compound Represented by the Formula (102))

Except for using sodium tetraphenylborate instead of a 20% aqueous solution of lithium triphenyl(n-butyl)borate of Example 2 (produced by Hokko Chemical Industry Co., Ltd.), 1,2-Diisopropyl-4,4,5,5-tetramethylbiguanidium tetraphenylborate was synthesized (white powder, yield: 75%) by a similar operation as in Example 2. Measurement of ¹H-NMR, and a structural formula of 1,2-diisopropyl-4,4,5,-5-tetramethylbiguanidium tetraphenylborate are shown below.

¹H-NMR (400 MHz, CDCl₃) δ(ppm): 0.96 (12H, d), 2.68 (12H, s), 3.18 (2H, m), 3.92 (2H, d), 6.94 (4H, t), 7.05-7.08 (8H, m), 7.41-7.43 (8H, m)

(102)

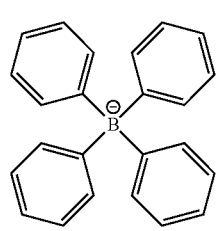 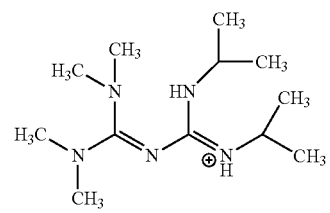

Comparative Example 3

Synthesis of 1,2-dicyclohexyl-4,4,5,5-tetramethylbiguanidium tetraphenylborate (Compound Represented by the Formula (103))

Except for using sodium tetraphenylborate instead of a 20% aqueous solution of lithium triphenyl(n-butyl)borate of Example 3 (produced by Hokko Chemical Industry Co., Ltd.), 1,2-Dicyclohexyl-4,4,5,5-tetramethylbiguanidium tetraphenylborate was synthesized (white powder, yield: 67%) by a similar operation as in Example 3. Measurement of $^1$H-NMR, and a structural formula of 1,2-dicyclohexyl-4,4,5,5-tetramethylbiguanidium tetraphenylborate are shown below.

$^1$H-NMR (400 MHz, CDCl$_3$) δ (ppm): 0.98-0.98 (10H, m), 1.44-1.69 (10H, m), 2.68 (12H, s), 2.68 (2H, brm), 4.03 (2H, brs), 6.92 (4H, t), 7.04-7.08 (8H, m), 7.25-7.41 (8H, m)

(103)

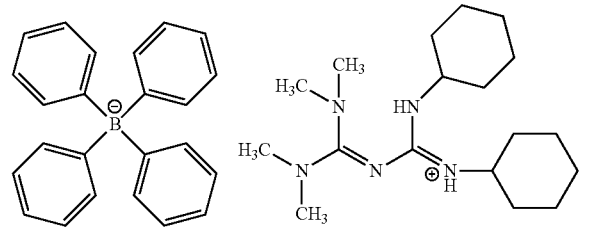

Comparative Example 4

Synthesis of Tetrakis(Tetramethylguanidino)Phosphonium Tetraphenylborate (Compound Represented by the Formula (104))

Except for using sodium tetraphenylborate instead of a 20% aqueous solution of lithium triphenyl(n-butyl)borate of Example 5 (produced by Hokko Chemical Industry Co., Ltd.), Tetrakis(tetramethylguanidino)phosphonium tetraphenylborate was synthesized (white powder, yield: 75%) by a similar operation as in Example 5. Measurement of $^1$H-NMR, and a structural formula of tetrakis(tetramethylguanidino)phosphonium tetraphenylborate are shown below.

$^1$H-NMR (400 MHz, CDCl$_3$) δ (ppm): 2.75 (48H, s), 6.88 (4H, t), 7.02-7.06 (8H, m), 7.41-7.46 (6H, m)

(104)

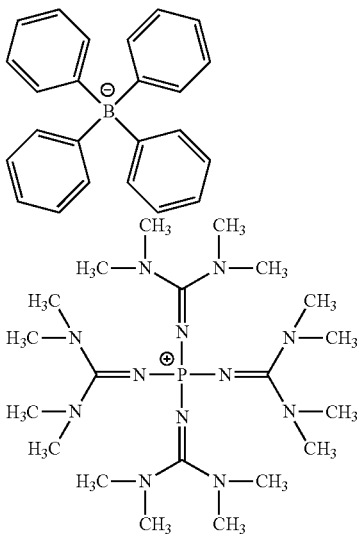

Comparative Example 5

Synthesis of 1,5,7-triazabicyclo[4.4.0]deca-5-enium 2-(3-benzoylphenyl)propionate (Compound Represented by the Formula (201))

In accordance with a method described in a JP-A-2011-80032 publication, 1,5,7-Triazabicyclo[4.4.0]deca-5-enium 2-(3-benzoylphenyl)propionate was synthesized.

(201)

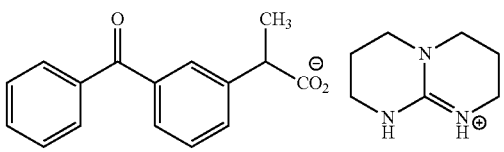

Comparative Example 6

Synthesis of 1,2-diisopropyl-4,4,5,5-tetramethylbiguanidium 2-(3-benzoylphenyl)propionate (Compound Represented by the Formula (202))

Into 30 mL of acetone, 7.62 g of ketoprofen (30.0 mmol, produced by Hamari Chemicals, Ltd.), and 7.24 g (30.0 mmol) of 1,2-diisopropyl-4,4,5,5-tetramethylbiguanide obtained in Synthesis Example 1 were dissolved, and stirred at room temperature for 10 minutes. After completion of the reaction, the reaction solution was concentrated under reduced pressure, and the resulting residue was washed with hexane and then dried under reduced pressure to obtain 14.86 g of 1,2-diisopropyl-4,4,5,5-tetramethylbiguanidium 2-(3-benzoylphenyl)propionate (white wax-like solid, yield: 100%). Measurement of $^1$H-NMR, and a structural formula of 1,2-diisopropyl-4,4,5,5-tetramethylbiguanidium 2-(3-benzoylphenyl)propionate are shown below.

$^1$H-NMR (400 MHz, CDCl$_3$) δ (ppm): 1.10 (12H, d), 1.53 (3H, d), 2.82 (12H, s), 3.26 (2H, q), 3.70 (1H, t), 7.35 (1H, t), 7.44 (1H, t), 7.52-7.60 (2H, m), 7.74 (1H, d), 7.80 (1H, d), 7.89 (1H, s), 9.97 (1H, brs)

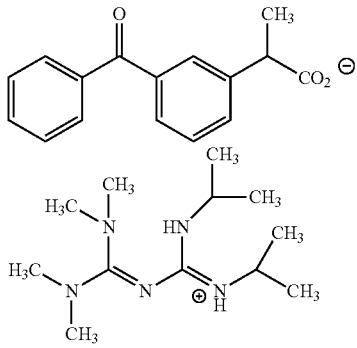

(202)

Comparative Example 7

Synthesis of 1,1-dimethylbiguanidium triphenyl(n-butyl)borate (Compound Represented by the Formula (301))

Into 1.5 g of a 20% aqueous solution of lithium triphenyl (n-butyl)borate (5.0 mmol; produced by Hokko Chemical Industry Co., Ltd.), 0.82 g of 1,1-dimethylbiguanide hydrochloride (5.0 mmol; produced by Wako Pure Chemical Industries, Ltd.) was added, and stirred at room temperature for 1 hour. After completion of the reaction, ethyl acetate was added to the reaction solution for extraction, and the organic layer was washed with water and then concentrated under reduced pressure to obtain 1.56 g of 1,1-dimethylbiguanidium triphenyl(n-butyl)borate (white powder, yield: 72%). Measurement of $^1$H-NMR, and a structural formula of 1,1-dimethylbiguanidium triphenyl(n-butyl)borate are shown below.

$^1$H-NMR (400 MHz, CDCl$_3$) δ (ppm): 0.74 (3H, t), 0.93-1.03 (4H, m), 1.18 (2H, m), 2.91 (6H, s), 6.53 (3H, s), 6.73 (3H, t), 6.88 (6H, t), 7.18 (8H, d)

(301)

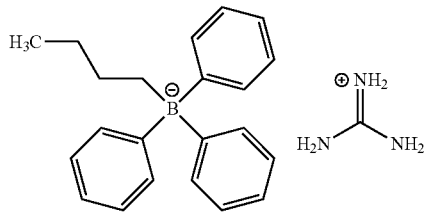

Comparative Example 8

Synthesis of guanidinium triphenyl(n-butyl)borate (Compound Represented by the Formula (302))

Into 1.5 g of a 20% aqueous solution of lithium triphenyl (n-butyl)borate (5.0 mmol; produced by Hokko Chemical Industry Co., Ltd.), 0.47 g of guanidinium chloride (5.0 mmol; produced by Wako Pure Chemical Industries, Ltd.) was added, and stirred at room temperature for 1 hour. After completion of the reaction, ethyl acetate was added to the reaction solution for extraction, and the organic layer was washed with water and then concentrated under reduced pressure to obtain 1.66 g of guanidinium triphenyl(n-butyl) borate (white powder, yield: 92%). Measurement of $^1$H-NMR, and a structural formula of guanidinium triphenyl (n-butyl)borate are shown below.

$^1$H-NMR (400 MHz, d-DMSO) δ (ppm): 0.74 (3H, t), 0.76-0.90 (4H, m), 1.18 (2H, m), 6.70 (3H, t), 6.88 (6H, t), 7.18 (6H, d)

(302)

Comparative Example 9

Synthesis of aminoguanidinium triphenyl(n-butyl)borate (Compound Represented by the Formula (303))

Into 5 mL of 10% hydrochloric acid, 0.68 g of aminoguanidine bicarbonate (5.0 mmol, produced by Wako Pure Chemical Industries, Ltd.) was dissolved, and 1.5 g of a 20% aqueous solution of lithium triphenyl(n-butyl) borate (5.0 mmol, produced by Hokko Chemical Industry Co., Ltd.) was added into the solution and stirred at room temperature for 1 hour. After completion of the reaction, ethyl acetate was added to the reaction solution for extraction, and the organic layer was washed with water and then concentrated under reduced pressure to obtain 1.55 g of aminoguanidinium triphenyl(n-butyl)borate (white powder, yield: 82%). Measurement of $^1$H-NMR, and a structural formula of aminoguanidinium triphenyl(n-butyl)borate are shown below.

$^1$H-NMR (400 MHz, d-DMSO) δ (ppm): 0.74 (3H, t), 0.76-0.88 (4H, m), 1.69 (2H, m), 4.65 (1H, brs), 6.71 (3H, t), 6.86 (6H, t), 7.18 (6H, d)

(303)

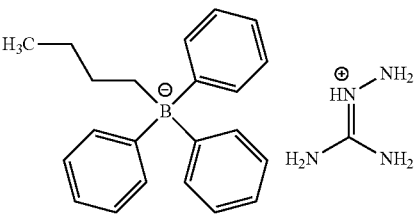

Comparative Example 10

Synthesis of 1,3-dimethyl-2-(N,N',N'',N'''-tetramethylguanidino)-4,5-dihydro-3H-imidazolium triphenyl (n-butyl)borate (Compound Represented by the Formula (105))

Except for using sodium tetraphenylborate instead of a 20% aqueous solution of lithium triphenyl(n-butyl)borate of Example 4 (produced by Hokko Chemical Industry Co., Ltd.), 1,3-Dimethyl-2-(N',N',N'',N''-tetramethylguanidino)-4,5-dihydro-3H-imidazolium triphenyl(n-butyl)borate was synthesized (white powder, yield: 49%) by a similar operation as in Example 4. Measurement of $^1$H-NMR, and a structural formula of 1,3-dimethyl-2-(N',N',N'',N''-tetramethylguanidino)-4,5-dihydro-3H-imidazolium triphenyl(n-butyl)borate are shown below.

$^1$H-NMR (400 MHz, CDCl$_3$) δ (ppm): 0.80 (3H, t), 1.02-1.29 (6H, brm), 2.45 (6H, s), 2.66 (12H, s), 3.03 (4H, s), 6.82 (6H, t), 7.02 (6H, t), 7.42 (6H, brm)

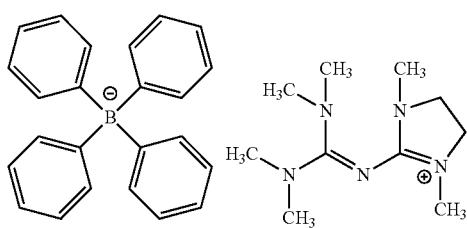

(105)

Experiment Example 1

Solubility Tests to Organic Solvents and a Base-Reactive Compound

The compounds (base generators) obtained in Examples 1 to 9, and the compounds (base generators) obtained in Comparative Examples 1 to 4 and 7 to 10 were each weighed out 0.1 g, and into these compounds, various kinds of organic solvents {propyleneglycol monomethylether acetate (PGMEA), ethyl lactate (EL)} or a base-reactive compound {neopentylglycol diglycidyl ether (SR-NPG); produced by Sakamoto Yakuhin Kogyo Co., Ltd.} were added gradually at room temperature to confirm visually solubility of the compounds (base generators) to the organic solvents and the base-reactive compound. The case where the compounds (base generators) were dissolved into less than 1 mL of the addition amount of the organic solvents or the base-reactive compound was evaluated as [++]; the case where the compounds (base generators) were dissolved into not less than 1 mL and less than 5 mL thereof was evaluated as [+]; the case where the compounds (base generators) were dissolved into not less than 5 mL and less than 10 mL thereof was evaluated as [−]; and the case where the compounds (base generators) were dissolved only into not less than 10 mL thereof was evaluated as [−−]. Results of solubility are shown in Table 3.

TABLE 3

| Example | Compound | PGMEA | EL | SR-NPG |
|---|---|---|---|---|
| Example 1 | Compound represented by formula (1) | + | + | ++ |
| Example 2 | Compound represented by formula (2) | + | + | ++ |
| Example 3 | Compound represented by formula (3) | + | + | ++ |
| Example 4 | Compound represented by formula (4) | + | + | + |
| Example 5 | Compound represented by formula (5) | + | + | + |
| Example 6 | Compound represented by formula (6) | − | − | + |
| Example 7 | Compound represented by formula (7) | − | − | + |
| Example 8 | Compound represented by formula (8) | + | + | + |
| Example 9 | Compound represented by formula (9) | + | + | + |
| Comp. Ex. 1 | Compound represented by formula (101) | − | − | − |
| Comp. Ex. 2 | Compound represented by formula (102) | − | − | + |
| Comp. Ex. 3 | Compound represented by formula (103) | − | − | + |
| Comp. Ex. 4 | Compound represented by formula (104) | −− | −− | −− |
| Comp. Ex. 7 | Compound represented by formula (301) | + | + | + |
| Comp. Ex. 8 | Compound represented by formula (302) | −− | −− | −− |
| Comp. Ex. 9 | Compound represented by formula (303) | −− | −− | −− |
| Comp. Ex. 10 | Compound represented by formula (105) | −− | −− | −− |

Experiment Example 2

Storage Stability Tests to a Base-Reactive Compound

The compounds (base generators) obtained in Examples 1 to 9, and the compounds (base generators) obtained in Comparative Examples 1 to 10 were each weighed out 0.1 g, and these compounds were dissolved into 2 g of a base-reactive compound {neopentylglycol diglycidyl ether (SR-NPG); produced by Sakamoto Chemicals Co., Ltd.}, and stored them for 1 week in a thermostatic chamber maintained at 40° C. The case where there was no viscosity change before and after storage (the one showing good storage stability) was evaluated as [○]; the case where viscosity was increased two times or more (the one showing poor storage stability) was evaluated as [x]; and the case where evaluation was not possible due to no dissolution was evaluated as [−]. Results are shown in Table 4.

TABLE 4

| Example | Compound | Storage stability in epoxy |
|---|---|---|
| Example 1 | Compound represented by formula (1) | ○ |
| Example 2 | Compound represented by formula (2) | ○ |
| Example 3 | Compound represented by formula (3) | ○ |
| Example 4 | Compound represented by formula (4) | ○ |
| Example 5 | Compound represented by formula (5) | ○ |
| Example 6 | Compound represented by formula (6) | ○ |
| Example 7 | Compound represented by formula (7) | ○ |
| Example 8 | Compound represented by formula (8) | ○ |
| Example 9 | Compound represented by formula (9) | ○ |
| Comp. Ex. 1 | Compound represented by formula (101) | — |
| Comp. Ex. 2 | Compound represented by formula (102) | ○ |
| Comp. Ex. 3 | Compound represented by formula (103) | ○ |
| Comp. Ex. 4 | Compound represented by formula (104) | — |
| Comp. Ex. 5 | Compound represented by formula (201) | X |
| Comp. Ex. 6 | Compound represented by formula (202) | X |
| Comp. Ex. 7 | Compound represented by formula (301) | ○ |
| Comp. Ex. 8 | Compound represented by formula (302) | — |
| Comp. Ex. 9 | Compound represented by formula (303) | — |
| Comp. Ex. 10 | Compound represented by formula (105) | — |

Experiment Example 3

Exposure Curing Tests Using a Bisphenol-A-Based Diglycidyl Ether Oligomer and a Multi-Functional Thiol The compounds (base generators) obtained in Examples 1 to 9, and the compounds (base generators) obtained in Comparative Examples 1 to 10 were each weighed out 10 mg, and also 1 mg of 2-isopropylthioxanthone was weighed, as a sensitizer, and after these compounds and the sensitizer were dissolved by warming into 100 mg of a bisphenol-A-based diglycidyl ether oligomer (trade name: jER® 828; produced by Mitsubishi Chemical Corp.), they were mixed into 70 mg of pentaerythritol tetrakis(3-mercaptobutyrate) (trade name: KarenzMT® PE1; produced by Showa Denko K.K.). The resulting sample was bar-coated on a glass plate, and the coated film was cured by irradiation of UV rays (active energy rays) for 30 seconds, using a UV ray irradiation light source apparatus REX-250 (manufactured by Asahi Spectra Co., Ltd.) having specific exposure intensity, and using a filter BP365, and then heating at 90° C. for 5 minutes. Hardness of the coated film was evaluated by a pencil hardness test method, and the case where pencil hardness attained 4H or higher was evaluated as [○]; the case where the unexposed part and the exposed part were cured at the same time was evaluated as [x]; and the case where evaluation was not possible due to no dissolution was evaluated as [–]. Evaluation results are shown in Table 5. It should be noted that the UV ray irradiation light source apparatus, REX-250 (manufactured by Asahi Spectra Co., Ltd.) is the one which irradiates light (active energy rays) having a wavelength of 240 to 440 nm. In addition, the filter BP365 is the one which absorbs light (active energy rays) having a wavelength of shorter than 365 nm and transmits only light (active energy rays) having a wavelength of 365 nm or longer.

TABLE 5

| Example | Compound | Curing performance |
|---|---|---|
| Example 1 | Compound represented by formula (1) | ○ |
| Example 2 | Compound represented by formula (2) | ○ |
| Example 3 | Compound represented by formula (3) | ○ |
| Example 4 | Compound represented by formula (4) | ○ |
| Example 5 | Compound represented by formula (5) | ○ |
| Example 6 | Compound represented by formula (6) | ○ |
| Example 7 | Compound represented by formula (7) | ○ |
| Example 8 | Compound represented by formula (8) | ○ |
| Example 9 | Compound represented by formula (9) | ○ |
| Comp. Ex. 1 | Compound represented by formula (101) | — |
| Comp. Ex. 2 | Compound represented by formula (102) | — |
| Comp. Ex. 3 | Compound represented by formula (103) | — |
| Comp. Ex. 4 | Compound represented by formula (104) | — |
| Comp. Ex. 5 | Compound represented by formula (201) | X |
| Comp. Ex. 6 | Compound represented by formula (202) | X |
| Comp. Ex. 7 | Compound represented by formula (301) | X |
| Comp. Ex. 8 | Compound represented by formula (302) | — |
| Comp. Ex. 9 | Compound represented by formula (303) | — |
| Comp. Ex. 10 | Compound represented by formula (105) | — |

Experiment Example 4

Exposure Curing Tests Using an Aliphatic Epoxy Monomer and a Multi-Functional Thiol The compounds (base generators) obtained in Examples 1 to 9, and the compounds (base generators) obtained in Comparative Examples 1 to 10 were each weighed out 10 mg, and also 2 mg of 2-isopropylthioxanthone was weighed, as a sensitizer, and after these compounds and the sensitizer were dissolved by warming into 100 mg of 3,4-epoxycyclohexylmethyl 3',4'-epoxycyclohexanecarboxylate (trade name: CEL2021P, produced by Daicel Corp.), which is an alicyclic epoxy monomer, they were mixed into 100 mg of pentaerythritol tetrakis(3-mercaptobutyrate) (trade name: KarenzMT® PE1, produced by Showa Denko K.K.). The resulting sample was bar-coated on a glass plate, and the coated film was cured by irradiation of UV rays (active energy rays) for 30 seconds, using a UV ray irradiation light source apparatus REX-250 (manufactured by Asahi Spectra Co., Ltd.) having specific exposure intensity, and using a filter BP365, and then heating at 120° C. for 5 minutes. Hardness of the coated film was evaluated by a pencil hardness test method, and the case where pencil hardness attained 4H or higher was evaluated as [○]; the case where the unexposed part and the exposed part were cured at the same time was evaluated as [x]; and the case where evaluation was not possible due to no dissolution was evaluated as [–]. Evaluation results are shown in Table 6.

TABLE 6

| Example | Compound | Curing performance |
|---|---|---|
| Example 1 | Compound represented by formula (1) | ○ |
| Example 2 | Compound represented by formula (2) | ○ |
| Example 3 | Compound represented by formula (3) | ○ |
| Example 4 | Compound represented by formula (4) | ○ |
| Example 5 | Compound represented by formula (5) | ○ |
| Example 6 | Compound represented by formula (6) | — |
| Example 7 | Compound represented by formula (7) | — |
| Example 8 | Compound represented by formula (8) | ○ |
| Example 9 | Compound represented by formula (9) | ○ |
| Comp. Ex. 1 | Compound represented by formula (101) | — |
| Comp. Ex. 2 | Compound represented by formula (102) | — |
| Comp. Ex. 3 | Compound represented by formula (103) | — |
| Comp. Ex. 4 | Compound represented by formula (104) | — |
| Comp. Ex. 5 | Compound represented by formula (201) | X |
| Comp. Ex. 6 | Compound represented by formula (202) | X |
| Comp. Ex. 7 | Compound represented by formula (301) | — |
| Comp. Ex. 8 | Compound represented by formula (302) | — |
| Comp. Ex. 9 | Compound represented by formula (303) | — |
| Comp. Ex. 10 | Compound represented by formula (105) | — |

Results of Experiment Examples 1 to 4 are summarized in Table 7.

TABLE 7

| Example | Compound | PGMEA | EL | SR-NPG | Storage stability in epoxy | Curing performance of general-purpose epoxy Aromotic ring-type | Curing performance of general-purpose epoxy Alicyclic-type |
|---|---|---|---|---|---|---|---|
| Example 1 | formula (1) | + | + | ++ | ○ | ○ | ○ |
| Example 2 | formula (2) | + | + | ++ | ○ | ○ | ○ |
| Example 3 | formula (3) | + | + | ++ | ○ | ○ | ○ |
| Example 4 | formula (4) | + | + | + | ○ | ○ | ○ |
| Example 5 | formula (5) | + | + | + | ○ | ○ | ○ |
| Example 6 | formula (6) | − | − | + | ○ | ○ | − |
| Example 7 | formula (7) | − | − | + | ○ | ○ | − |
| Example 8 | formula (8) | + | + | + | ○ | ○ | ○ |
| Example 9 | formula (9) | + | + | + | ○ | ○ | ○ |
| Comp. Ex. 1 | formula (101) | − | − | − | − | − | − |
| Comp. Ex. 2 | formula (102) | − | − | + | ○ | − | − |
| Comp. Ex. 3 | formula (103) | − | − | + | ○ | − | − |
| Comp. Ex. 4 | formula (104) | −− | −− | −− | − | − | − |
| Comp. Ex. 5 | formula (201) | | | | x | x | x |
| Comp. Ex. 6 | formula (202) | | | | x | x | x |
| Comp. Ex. 7 | formula (301) | + | + | + | ○ | x | − |
| Comp. Ex. 8 | formula (302) | −− | −− | −− | − | − | − |
| Comp. Ex. 9 | formula (303) | −− | −− | −− | − | − | − |
| Comp. Ex. 10 | formula (105) | −− | −− | −− | − | − | − |

It has been understood, from Table 7, that the compounds (base generators) obtained in Comparative Examples 1 and 4 have poor solubility to organic solvents generally used in this field, and thus they have low general versatility. In addition, it has been understood that the compounds (base generators) obtained in Comparative Examples 1 and 4 have poor solubility to the base-reactive compound and thus they need to be dissolved in an organic solvent, however, as described above, they also have poor solubility to the organic solvents generally used in this field, and thus they are compounds (base generators) being poor in versatility. Next, the compounds (base generators) obtained in Comparative Examples 5 and 6 have poor storage stability in a mixed state with the base-reactive compound, therefore viscosity thereof increased by progress of a reaction, even in an unexposed state. Accordingly, it has been understood that the base generators of Comparative Examples 5 and 6 are difficult to be stored for a long period of time in a mixed state with the base-reactive compound, and they are compounds (base generators) being inconvenient such as requiring combination of both just before carrying out curing, and requiring quick use. It has been understood that the compounds (base generators) obtained in Comparative Examples 1 to 4 and 10 are the compounds (base generators) having low solubility to a general-purpose epoxy monomer, such as an epoxy oligomer having an aromatic ring or an alicyclic epoxy monomer. It has been understood that the compound (base generator) obtained in Comparative Example 7 has a cation structure where number of hydrogen atoms in $R^{11}$ to $R^{18}$ in the general formula ($B_2$) is 3 or more, therefore it has low basicity of a base generated from the compound (base generator), and thus it is not capable of efficiently accelerating a reaction between a base-reactive compound, such as an epoxy, and a multi-functional thiol. It has been understood that the compounds (base generators) obtained in Comparative Examples 8 and 9 generally have low solubility due to not having a substituent on guanidine, and thus they are compounds (base generators) being poor in versatility that cannot be dissolved in the organic solvents generally used in this field, or the base-reactive compound such as an epoxy.

It has been understood, from Table 7, as against the results of the Comparative Examples 1 to 10, that the compounds (base generators) of the present invention have all of performances of solubility to the organic solvents, storage stability in a mixed state with the base-reactive compound, and high curing performance that is capable of easily curing the base-reactive compound in the base-reactive composition. Accordingly, it has been understood that the compounds (base generators) of the present invention are those having superior performance both in view of usage and in view of storage.

Experiment Example 5

Exposure Curing Tests Using a Bisphenol-A-Based Diglycidyl Ether Oligomer and an Acid Anhydride The compounds (base generators) obtained in Examples 1 to 9, and the compounds (base generators) obtained in Comparative Examples 1 to 10 were each weighed out 10 mg, and also 2 mg of 2-isopropylthioxanthone was weighed, as a sensitizer, and after these compounds and the sensitizer were dissolved into 100 mg of a bisphenol-A-based diglycidyl ether oligomer (trade name: jER® 828; produced by Mitsubishi Chemical Corp.) by warming at 40° C., and cooled down to room temperature, 60 mg of methyl-5-norbornene-2,3-dicarboxylic anhydride (produced by Wako Pure Chemical Industries, Ltd.) was mixed into them. The resulting sample was bar-coated on a glass plate, and the coated film was cured by irradiation of UV rays (active energy rays) for 60 seconds onto the coated film, using a UV ray irradiation light source apparatus REX-250 (manufactured by Asahi Spectra Co., Ltd.), and using a filter BP405, and then heating at 120° C. for 7 minutes. Hardness of the coated film was evaluated by a pencil hardness test method, and the case where pencil hardness attained 4H or higher was evaluated as [○]; the case where the unexposed part and the exposed part were cured at the same time was evaluated as [x]; and the case where evaluation was not possible due to no dissolution was evaluated as [−]. Evaluation results are shown in Table 8. It should be noted that the filter BP405 is the one which absorbs light (active energy rays) having a wavelength of shorter than 405 nm and transmits only light (active energy rays) having a wavelength of 405 nm or longer.

TABLE 8

| Example | Compound | Curing performance |
|---|---|---|
| Example 1 | Compound represented by formula (1) | ○ |
| Example 2 | Compound represented by formula (2) | ○ |
| Example 3 | Compound represented by formula (3) | ○ |
| Example 4 | Compound represented by formula (4) | ○ |
| Example 5 | Compound represented by formula (5) | ○ |
| Example 6 | Compound represented by formula (6) | ○ |
| Example 7 | Compound represented by formula (7) | ○ |
| Example 8 | Compound represented by formula (8) | ○ |
| Example 9 | Compound represented by formula (9) | ○ |
| Comp. Ex. 1 | Compound represented by formula (101) | — |
| Comp. Ex. 2 | Compound represented by formula (102) | — |
| Comp. Ex. 3 | Compound represented by formula (103) | — |
| Comp. Ex. 4 | Compound represented by formula (104) | — |
| Comp. Ex. 5 | Compound represented by formula (201) | x |
| Comp. Ex. 6 | Compound represented by formula (202) | x |
| Comp. Ex. 7 | Compound represented by formula (301) | x |
| Comp. Ex. 8 | Compound represented by formula (302) | — |
| Comp. Ex. 9 | Compound represented by formula (303) | — |
| Comp. Ex. 10 | Compound represented by formula (105) | — |

It has been understood, from results of Experiment Example 5, that the compounds (base generators) of the present invention are capable of using an acid anhydride in combination, as a cross-linking agent. On the other hand, it has been understood that the compounds (base generators) obtained in Comparative Examples 1 to 4 and 8 to 10 are compounds (base generators) having low solubility to a general-purpose epoxy monomer, such as an epoxy oligomer having an aromatic ring. In addition, it has been understood that the compounds (base generators) obtained in Comparative Examples 5 and 6 are poor in versatility due to being unable to use an acid anhydride in combination, because curing at an exposed part and a non-exposed part proceeds at the same time when heated at 120° C. after exposure, and it is not capable of providing contrast between the exposed part and the non-exposed part. Still more, it has been understood that the compound (base generator) obtained in Comparative Example 7 has a cation structure where number of hydrogen atoms in $R^{11}$ to $R^{18}$ in the general formula $(B_2)$ is 3 or more, therefore it has low basicity of a base generated from the compound (base generator), and thus it is not capable of efficiently accelerating a reaction between the base-reactive compound, such as an epoxy, and an acid anhydride.

Experiment Example 6

Investigation on Sensitizers

Exposure evaluation was carried out similarly as in Experiment Example 3, except for using the compound obtained in Example 1, as the base generator, using various kinds of sensitizers shown in the following Tables 9 and 10, as the sensitizers, and not using a filter or using BP365, BP405 or BP435 as the filter, in Experiment Example 3. Hardness of the coated film was evaluated by a pencil hardness test method, and the case where pencil hardness attained 4H or higher was evaluated as [○]; and the case where pencil hardness was below 4H (curing was not occurred) was evaluated as [x]. Evaluation results are shown in Table 9. It should be noted that the filter BP435 is the one which absorbs light (active energy rays) having a wavelength of shorter than 435 nm and transmits only light (active energy rays) having a wavelength of 435 nm or longer.

TABLE 9

| Sensitizer | Product name (Maker) | Filter | | | |
|---|---|---|---|---|---|
| | | Non | 365BP | 405BP | 436BP |
| Non | — | x | x | x | x |
| Phenothiazine structure | Phenothiazine (produced by Wako Pure Chem. Ind.) | ○ | ○ | x | x |
| Coumarin structure | Coumarin (produced by Wako Pure Chem. Ind.) | ○ | ○ | x | x |
| Ketoprofen structure | Ketoprofen (produced by Wako Pure Chem. Ind.) | ○ | x | x | x |
| 2-(9-oxoxanthene-2-yl)propionic acid structure | 2-(9-oxoxanthene-2-yl)propionic acid (produced by Toyko Chem. Ind. Co.) | ○ | ○ | x | x |

TABLE 9-continued

| Sensitizer | Product name (Maker) | Filter | | | |
|---|---|---|---|---|---|
| | | Non | 365BP | 405BP | 436BP |
| (diethylthioxanthone structure) | diethtylthioxanthone (produced by Wako Pure Chem. Ind.) | ○ | ○ | ○ | x |
| (acridone structure) | Acridone (produced by Wako Pure Chem. Ind.) | ○ | ○ | ○ | x |
| (2-methylbenzoquinone structure) | 2-methylbenzoquinone (produced by Wako Pure Chem. Ind.) | ○ | ○ | ○ | ○ |
| (Vitamin B$_2$ structure) | Vitamine B$_2$ (produced by Wako Pure Chme. Ind.) | ○ | ○ | ○ | ○ |
| (Vitamin K$_1$ structure) | Vitamine K$_1$ (produced by Wako Pure Chem. Ind.) | ○ | ○ | ○ | ○ |
| (Michler's ketone structure) | Michler's ketone (produced by Wako Pure Chem. Ind.) | ○ | ○ | ○ | x |

TABLE 10
| Sensitizer | Product name (Maker) | Filter | | | |
|---|---|---|---|---|---|
| | | Non | 365BP | 405BP | 436BP |
| 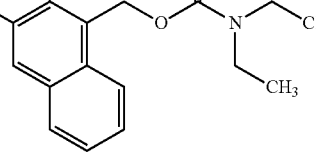 | WPBG-018 (produced by Wako Pure Chem. Ind.) | ○ | ○ | x | x |
| 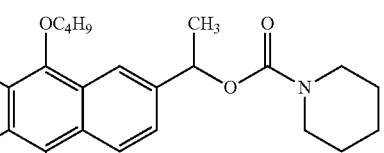 | WPBG-054 (produced by Wako Pure Chem. Ind.) | ○ | ○ | ○ | x |
| 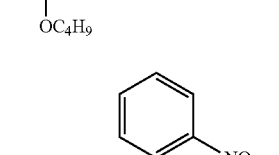 | WPBG-130 (produced by Wako Pure Chem. Ind.) | ○ | ○ | ○ | x |
| 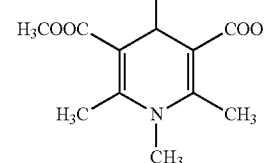 | WPBG-266 (produced by Wako Pure Chem. Ind.) | ○ | x | x | x |
| 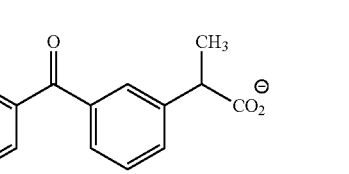 | WPBG-294 (produced by Wako Pure Chem. Ind.) | ○ | ○ | ○ | x |
| 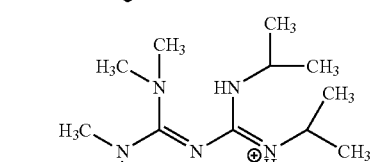 | Irgacure 819 (produced by BASF) | ○ | ○ | ○ | ○ |

TABLE 10-continued

| Sensitizer | Product name (Maker) | Filter | | | |
|---|---|---|---|---|---|
| | | Non | 365BP | 405BP | 436BP |
| 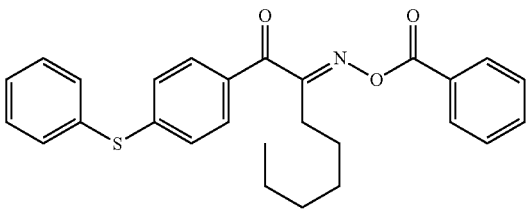 [SMILES: CCCCCC/C(=N\OC(=O)c1ccccc1)C(=O)c1ccc(Sc2ccccc2)cc1] | Irgacure OXE 01 (produced by BASF) | ○ | ○ | ○ | x |
| 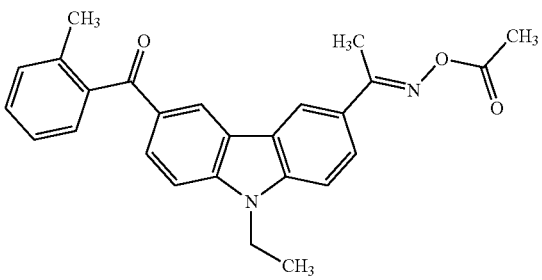 [SMILES: CCn1c2ccc(C(=O)c3ccccc3C)cc2c2cc(/C(C)=N/OC(C)=O)ccc21] | Irgacure OXE 02 (produced by BASF) | ○ | ○ | ○ | x |
| 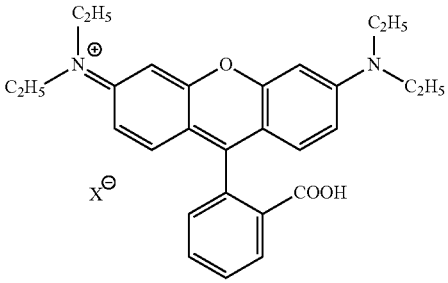 | Rhodamine derivative (produced by Wako Pure Chem. Ind.) | ○ | ○ | ○ | ○ |
| 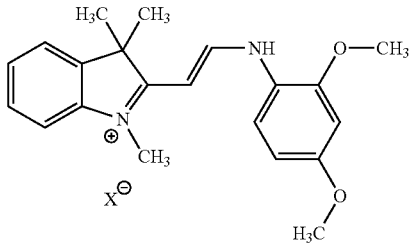 | Basic Yellow derivative (produced by Wako Pure Chem. Ind.) | ○ | ○ | ○ | ○ |
| 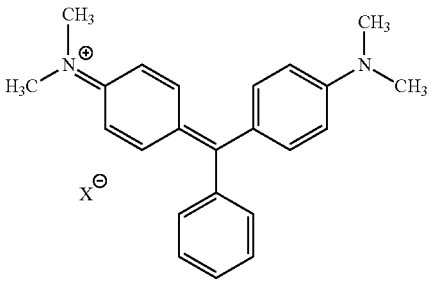 | Malachite Green derivative (produced by Wako Pure Chem. Ind.) | ○ | ○ | ○ | ○ |
| 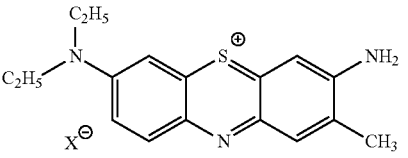 | Toluidine Blue derivative (produced by Wako Pure Chem. Ind.) | ○ | ○ | ○ | ○ |

TABLE 10-continued

| Sensitizer | Product name (Maker) | Filter | | | |
|---|---|---|---|---|---|
| | | Non | 365BP | 405BP | 436BP |
| (structure shown) | Basic Blue 7 derivative (produced by Toyko Chem. Ind. Co.) | ○ | ○ | ○ | ○ |

It has been understood, from results of Experiment Example 6, that the compounds (base generators) of the present invention enhance photosensitivity in a long wavelength, by using various sensitizers in combination. On the other hand, various sensitizers shown in Table 9 were used in combination for the compounds represented by the formulae (201) and (202), however, photosensitivity in a long wavelength was not exhibited at all, and sensitization was not exhibited. Accordingly, it has been understood that the compounds (base generators) of the present invention are capable of enhancing photosensitivity in a long wavelength by the combined use of various sensitizers, and thus they are useful compounds (base generators).

In addition, in the case of a borate-based photo base generator introduced with a sensitizing unit at a cation part, disclosed in JP-A-2003-212856 and WO2009/122664, it generally tends to have poor solubility and was difficult to make directly dissolved into a monomer. Still more, the borate-based photo base generator had such a problem as decreasing amount of a base occupying per one molecule due to increasing molecular weight of the photo base generator itself by introduction of a sensitizer group, or as hindering light transmission to the deep part of a film due to remaining of the sensitizer group of equal mole to a base generated in the system. Additionally, the borate-based photo base generator had a limited skeleton introducible as the sensitizing unit, therefore it is difficult to using an ion-type sensitizer such as having a dye skeleton in combination.

On the contrary, from results of Experiment Example 6, it has been understood that the compounds (base generators) of the present invention are capable of also generating two different kinds of bases in the system, because not only capable of formulating the borate unit and the sensitizer in an arbitrary ratio, but also capable of using a conventional photo base generator already having absorption in a long wavelength in combination. In addition, it has also been understood that they are capable of extending photosensitive wavelength up to a visible-ray region or an infrared region, because they are capable of using a coloring matter having a complicated structure in combination. Additionally, in the case of using some coloring matters as the sensitizer, curing to the deep part can be expected due to effect of optical quenching by light.

Experiment Example 7

Radical UV Curing Tests Using Acrylates

Each 10 mg of the compounds obtained in Examples 1 to 9, and 1 mg of 9-anthrylmethyl N,N-diethylcarbamate (trade name: WPBG-018; produced by Wako Pure Chemical Industries, Ltd.) as a sensitizer, were weighed out and dissolved into 100 mg of dipentaerythritol hexaacrylate (trade name: KAYARAD DPHA; produced by Nippon Kayaku Co., Ltd.) by warming at 40° C. In addition, 1 mg of only 9-anthrylmethyl N,N-diethylcarbamate (trade name: WPBG-018; produced by Wako Pure Chemical Industries, Ltd.) was added and dissolved into 100 mg of dipentaerythritol hexaacrylate (trade name: KAYARAD DPHA; produced by Nippon Kayaku Co., Ltd.) by warming at 40° C. The resulting sample was bar-coated on a glass plate, and the coated film was cured by irradiation of UV rays (active energy rays) at room temperature for 30 seconds on the coated film, using a UV ray irradiation light source apparatus REX-250 (manufactured by Asahi Spectra Co., Ltd.), and using a filter BP365. Hardness of the coated film was evaluated by a pencil hardness test method, and the case where pencil hardness attained 4H or higher was evaluated as [○]; and the case where pencil hardness was below 4H (curing was not occurred) was evaluated as [x]. Evaluation results are shown in Table 11.

TABLE 11

| Example | Compound | Curing performance of acrylate |
|---|---|---|
| Example 1 | Compound represented by formula (1) | ○ |
| Example 2 | Compound represented by formula (2) | ○ |
| Example 3 | Compound represented by formula (3) | ○ |
| Example 4 | Compound represented by formula (4) | ○ |
| Example 5 | Compound represented by formula (5) | ○ |
| Example 6 | Compound represented by formula (6) | X |
| Example 7 | Compound represented by formula (7) | X |
| Example 8 | Compound represented by formula (8) | ○ |
| Example 9 | Compound represented by formula (9) | ○ |
| — | WPBG-018 only | X |

Experiment Example 8

A UV Curing Test Using a Thiol-Ene Reaction 0.18 g of the compound obtained in Example 2, 0.10 g of 9-anthrylmethyl N,N-diethylcarbamate (trade name: WPBG-018; produced by Wako Pure Chemical Industries, Ltd.) as a sensitizer, and 3 mg of an N-nitrosophenyl hydroxylamine aluminum salt (trade name: Q-1301; produced by Wako Pure Chemical Industries, Ltd.) as a polymerization inhibitor, were dissolved into acetone, and then 2.49 g of 2,4,6-tris(allyloxy)-1,3,5-triazine (produced by Wako Pure Chemical Industries, Ltd.) and 5.52 g of pentaerythritol tetrakis(3-mercaptobutyrate) (trade name: KarenzMT® PE1; produced by Showa Denko K.K.) were mixed therein. The resulting sample was bar-coated on a glass plate, and the coated film was cured by irradiation of UV rays (active energy rays) onto the coated film at room temperature for 10 seconds, using a UV ray irradiation light source apparatus REX-250 (manufactured by Asahi Spectra Co., Ltd.), and using a filter BP365. Hardness of the coated film was evaluated by a pencil hardness test method, and the hardness was 3H or higher.

Experiment Example 9

A Hybrid UV Curing Test Using a Photo-Sol-Gel Reaction and a Thiol-Ene Reaction 0.18 g of the compound obtained in Example 2, 0.10 g of ketoprofen (produced by Wako Pure Chemical Industries, Ltd.) as a sensitizer, and 3 mg of an N-nitrosophenyl hydroxylamine aluminum salt (trade name: Q-1301; produced by Wako Pure Chemical Industries, Ltd.) as a polymerization inhibitor, were dissolved into acetone, and then 1.9 g of (3-mercaptopropyl)trimethoxysilane (produced by Wako Pure Chemical Industries, Ltd.) and 0.27 g of ion-exchanged water were added therein and stirred at room temperature for 1 hour, and still more, 0.79 g of 2,4,6-tris (allyloxy)-1,3,5-triazine (produced by Wako Pure Chemical Industries, Ltd.) was added and mixed. The resulting sample was bar-coated on a glass plate, pre-baking of the coated film prepared at 80° C. for 1 minute, and then the coated film was cured by irradiation of UV rays (active energy rays) onto the coated film for 10 seconds, using a UV ray irradiation light source apparatus REX-250 (manufactured by Asahi Spectra Co., Ltd.). Hardness of the coated film was evaluated by a pencil hardness test method, and the hardness was 4H or higher.

It has been understood, from results of Experiment Example 7, that the compounds obtained in Examples 6 and 7, as well as WPBG-018, as the sensitizer, are not capable of generating a radical, and was thus not capable of inducing a polymerization reaction (curing), however, the compounds (the radical generators) represented by the general formula (A-a) of the present invention can be applied also to radical polymerization of an alkene, such as an acrylate, by generation of a radical. In addition, from results of Experiment Example 8, the compounds were applicable also to UV curing by the thiol-ene reaction by generation of a radical under the co-presence of a thiol compound and an ene compound. Still more, as shown in Experiment Example 9, the compounds were applicable also to a curing system using, in combination, a sol-gel method by a base, and the thiol-ene reaction by a radical. Therefore, it has been understood that the compounds, because of being capable of generating a base and a radical at the same time, can be used also as a hybrid curing agent for hybrid UV curing by combination of a radical UV curing and an anion UV curing, which has conventionally been difficult.

Experiment Example 10

Heat Resistance Tests

The compounds (base generators) obtained in Examples 1 to 9 were each weighed out 10 mg, and as for these compounds, weight change was measured, when they were heated from 30° C. to 500° C. under a temperature increasing rate of 10° C./min., using TG-DTA2000SA (manufactured by BRUKER AXS CO., Ltd.), to calculate "5% weight loss initiation temperature" of each of the compounds (base generators). Thus calculated temperature was used as decomposition initiation temperature to evaluate heat resistance of these compounds (base generators). Results thereof are shown in Table 12.

TABLE 12

| Example | Compound | TG-DTA Decomposition Initiation Temperature (° C.) |
|---|---|---|
| Example 1 | Compound represented by formula (1) | 176 |
| Example 2 | Compound represented by formula (2) | 186 |
| Example 3 | Compound represented by formula (3) | 203 |
| Example 4 | Compound represented by formula (4) | 280 |
| Example 5 | Compound represented by formula (5) | 318 |
| Example 6 | Compound represented by formula (6) | 185 |
| Example 7 | Compound represented by formula (7) | 300 |
| Example 8 | Compound represented by formula (8) | 171 |
| Example 9 | Compound represented by formula (9) | 223 |

It has been understood, from results of Experiment Example 10, that the compounds (base generators) of the present invention are compounds all having the decomposition initiation temperature of over 150° C., and thus they are relatively stable to heat. Accordingly, it has been understood that, in the case of using the base generators of the present invention, temperature in baking can be set high, therefore, there is advantage in that not only an organic solvent having high boiling point can be used, but also residue of the organic solvent can be suppressed as low as possible, after baking. That is, deterioration of contrast between an exposed part (cured part) and a non-exposed part (non-cured part), caused by remaining organic solvent, can be suppressed.

Experiment Example 11

A Michael Addition-Type UV Curing Test Using a Multi-Functional Acrylate and a Multi-Functional Thiol 10 mg of the compound obtained in Example 6, and 2 mg of 9-anthrylmethyl N,N-diethylcarbamate (trade name: WPBG-018; produced by Wako Pure Chemical Industries, Ltd.) as a sensitizer, were weighed out and dissolved by warming into γ-butyrolactone, and then 100 mg of pentaerythritol triacrylate (trade name: Light Acrylate PE-3A; produced by Kyoeisha Chemical Co., Ltd.) and 141 mg of pentaerythritol tetrakis(3-mercaptobutyrate) (trade name: KarenzMT® PE1; produced by Showa Denko K.K.) were mixed therein. The resulting sample was bar-coated on a glass plate, and the coated film was cured by irradiation of UV rays (active energy rays) onto the coated film for 10 seconds, using a UV ray irradiation light source apparatus REX-250 (manufactured by Asahi Spectra Co., Ltd.), and using a filter BP365, and then heating at 80° C. for 10 minutes. Hardness of the coated film was evaluated by a pencil hardness test method, and the hardness was 3H or higher.

It has been understood, from results of Experiment Examples 5 and 7, that a combination of the compound obtained in Example 6 and WPBG-018 as the sensitizer, generates selectively only a base by UV irradiation and does not generate a radical. That is, the compound, wherein at least one group among $R^1$ to $R^4$ in the general formula (A) has "an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms" (hereafter it may be abbreviated as the arylalkynyl compound of the present invention), like the compound obtained in Example 6, is capable of generating selectively only a base by UV irradiation. In addition, it has been understood, from result of Experiment Examples 11, that the arylalkynyl compound of the present invention is applicable to anion UV curing by Michael addition reaction of a thiol and an acrylate. Accordingly, the arylalkynyl compound of the present invention is capable of adjusting reaction ratio of an acrylate and a thiol to 1:1, because it is able to carry out an anion curing reaction between a thiol and an acrylate without generating a radical polymerization reaction by an acrylate alone like in Experiment Example 7, by carrying out UV irradiation. That is, because the arylalkynyl compound of the present invention generates selectively only a base by UV irradiation, it is applicable to anion UV curing, where reaction ratio of the acrylate and the thiol is adjusted to 1:1, whose control has conventionally been difficult.

Because of containing a thiol, such a UV cured resin of an acrylate and a thiol generally has high various performances, such as dimensional stability, flexibility, water resistance, chemical resistance, adhesion between a resin and a substrate, resistance to curing hindrance caused by oxygen, of the resin, as compared with a cured resin of an acrylate only, and thus can be a useful material. In addition, it is preferable in view of creating a novel material, because in Michael addition reaction of an acrylate and a thiol, a multi-functional acrylate, as a starting material, is easily available, whereas in a thiol-ene reaction of an allyl compound polymerizable by a radical, and a thiol, a multi-functional allyl compound, as a starting material, is generally difficult in availability.

INDUSTRIAL APPLICABILITY

The compound represented by the general formula (A) of the present invention and the base generator of the present invention are those generating a strong base (guanidines, biguanides, phosphazenes or phosphoniums) by operation of irradiation of light (active energy rays) or heating, and the like, and on the other hand, they are those having no reaction with a base-reactive compound, even in the case of storage for a long period of time in a mixed state of the compound (base generator) and a base-reactive composition, such as an epoxy-based compound, because of low nucleophilicity of the borate part of the anion. Accordingly, the compound represented by the general formula (A) of the present invention and the base generator of the present invention are useful as a base generator, which is capable of enhancing storage stability without decreasing performance thereof, even in the case of storage of a composition containing the compound (base generator) and a base-reactive compound, for a long period of time.

The base-reactive composition of the present invention is a composition containing the base generator of the present invention, as described above, and in carrying out curing operation, it is capable of effectively advancing curing of a base-reactive compound, by using a strong base (guanidines, biguanides, phosphazenes or phosphoniums) generated from the base generator in the composition as an initiator, as well as capable of being stored in a stable state without decreasing performance as a base-reactive composition, even in the case of storage for a long period of time, and thus it is useful as, for example, a coating material, printing ink, a dental material, an optical material, such as a resist, an electronics material, and the like.

The invention claimed is:

1. A compound represented by the following general formula (A):

(A)

wherein $R^1$ represents an alkyl group having 1 to 12 carbon atoms; an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms; an alkenyl group having 2 to 12 carbon atoms; a 2-furylethynyl group; a 2-thiophenylethynyl group; or a 2,6-dithianyl group; $R^2$ to $R^4$ each independently represent an alkyl group having 1 to 12 carbon atoms; an arylalkynyl group having 8 to 16 carbon atoms which may be substituted with a halogen atom, an alkyl group having 1 to 6 carbon atoms, an alkoxy group having 1 to 6 carbon atoms, or an alkylthio group having 1 to 6 carbon atoms; an aryl group having 6 to 14 carbon atoms which may be substituted with a halogen atom, an alkyl group having 1 to 6 carbon atoms, an alkoxy group having 1 to 6 carbon atoms, or an alkylthio group having 1 to 6 carbon atoms; a furanyl group; a thienyl group; or an N-alkyl-substituted pyrrolyl group; and $Z^+$ represents an ammonium cation having a biguanidium group.

2. The compound according to claim 1, wherein the ammonium cation having the biguanidium group, represented by $Z^+$ in the general formula (A), is an ammonium cation having a biguanidium group represented by the following general formula ($B_2$)

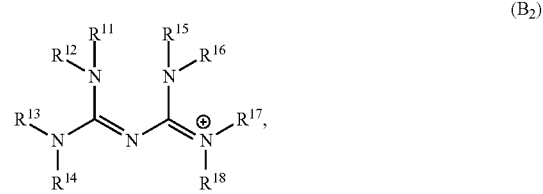

($B_2$)

wherein $R^{11}$ to $R^{15}$ and $R^{18}$ each independently represent a hydrogen atom or an alkyl group having 1 to 12 carbon atoms, $R^{16}$ and $R^{17}$ each independently represent a hydrogen atom, an alkyl group having 1 to 12 carbon atoms, or an aryl group having 6 to 14 carbon atoms which may be substituted with a nitro group, an alkyl group having 1 to 6 carbon atoms, an alkoxy group having 1 to 6 carbon atoms, an alkylthio group having 1 to 6 carbon atoms, or a dialkylamino group having 1 to 12 carbon atoms; $R^{16}$ together with $R^{17}$ may form an alkylene group having 2 to 4 carbon atoms, and number of hydrogen atoms among $R^{11}$ to $R^{18}$ is 0 to 2.

3. The compound according to claim 1, wherein $R^1$ in the general formula (A) is an alkyl group having 1 to 12 carbon atoms, or a phenylethynyl group which may be substituted with a halogen atom, an alkyl group having 1 to 6 carbon atoms, an alkoxy group having 1 to 6 carbon atoms, or an alkylthio group having 1 to 6 carbon atoms, and all of $R^2$ to $R^4$ are the same phenyl group which may be substituted with a halogen atom, an alkyl group having 1 to 6 carbon atoms, an alkoxy group having 1 to 6 carbon atoms, or an alkylthio group having 1 to 6 carbon atoms.

4. The compound according to claim 2, wherein, in the compound represented by the general formula ($B_2$), $R^{11}$ to $R^{14}$ each independently represent an alkyl group having 1 to 12 carbon atoms, $R^{15}$ and $R^{18}$ each independently represent a hydrogen atom or an alkyl group having 1 to 12 carbon atoms, and $R^{16}$ and $R^{17}$ each independently represent an alkyl group having 1 to 12 carbon atoms, or a phenyl group substituted with only a nitro group or only an alkyl group having 1 to 6 carbon atoms, or $R^{16}$ together with $R^{17}$ may form an alkylene group having 2 to 4 carbon atoms.

5. The compound according to claim 1, wherein the ammonium cation having the biguanidium group, represented by $Z^+$ in the general formula (A), is an ammonium cation having a biguanidium group represented by one of the following formula (B-4), (B-5), (B-6), (B-17), and (B-18):

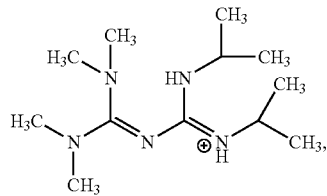
(B-4)

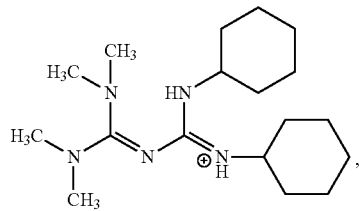
(B-5)

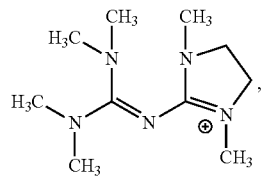
(B-6)

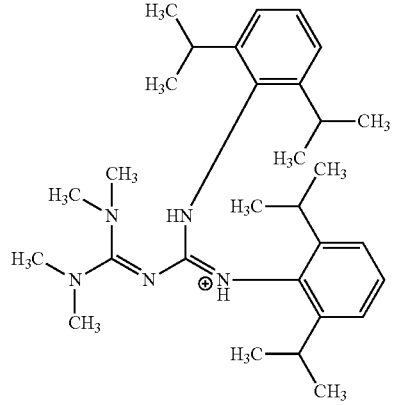
(B-17)

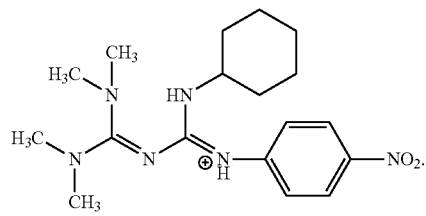
(B-18)

6. A base generator comprising the compound according to claim 1.

7. A base-reactive composition comprising the base generator according to claim 6 and a base-reactive compound.

8. The base-reactive composition according to claim 7, wherein the composition further comprises a sensitizer.

9. The base-reactive composition according to claim 7, wherein the composition further comprises an organic solvent.

10. The base-reactive composition according to claim 7, wherein the base-reactive compound is selected from the group consisting of an epoxy-based compound, a silicon-based compound, an isocyanate-based compound, and a polyamic acid-based compound.

* * * * *